United States Patent [19]
Gallatin et al.

[11] Patent Number: 5,728,533
[45] Date of Patent: Mar. 17, 1998

[54] HUMAN $\beta_2$ INTEGRIN $\alpha$SUBUNIT

[75] Inventors: W. Michael Gallatin, Mercer Island; Monica Van der Vieren, Seattle, both of Wash.

[73] Assignee: ICOS Corporation, Bothell, Wash.

[21] Appl. No.: 485,618

[22] Filed: Jun. 7, 1995

Related U.S. Application Data

[63] Continuation-in-part of Ser. No. 362,652, Dec. 21, 1994, which is a continuation-in-part of Ser. No. 286,889, Aug. 5, 1994, Pat. No. 5,470,953, which is a continuation-in-part of Ser. No. 173,497, Dec. 23, 1993, Pat. No. 5,437,958.

[51] Int. Cl.$^6$ .................. C12Q 1/00; G01N 33/53; C07K 14/00; A61K 35/14

[52] U.S. Cl. .................. 435/7.1; 435/7.8; 530/350; 530/380

[58] Field of Search .................. 435/7.1, 7.8; 530/350, 530/380; 536/22.1, 23.1, 23.4, 23.8

[56] References Cited

U.S. PATENT DOCUMENTS

| 4,271,139 | 6/1981 | Hart ........................... 436/531 |
| 4,568,649 | 2/1986 | Bertoglio-Matte ........... 436/534 |

OTHER PUBLICATIONS

Adams, et al., "Experimental graft arteriosclerosis: II. Immunocytochemical analysis of lesion development," *Transplantation*, 56:794–799 (1993).

Adams, et al., "Experimental graft arteriosclerosis: 1. The Lewis-to-F-444 Allograft Model," *Transplantation*, 53:1115–1119 (1992).

Anderson, et al., "Exact Definition of Species–specific and Cross–reactive Epitopes of the 65–kilodalton Protein of *Mycobacterium leprae* Using Synthetic Peptides", *J. Immunol.* 141:607–613 (1988).

Arfors, et al., "A monoclonal antibody to the membrane glycoprotein complex CD18 inhibits polymorphonuclear leukocyte accumulation and plasma leakage in vivo," *Blood* 69:338–340 (1987).

Arnaout, "Structure and function of the leukocyte adhesion molecules CD11/CD18," *Blood* 75:1037–1050 (1990).

Berman, et al., "Biosynthesis and function of membrane bound and secreted forms of recombinant CD11b/CD18 (Mac–1)," *J. Cell. Biochem* 52:183–195 (1993).

Burnett, et al., "The IgA heavy–chain gene family in rabbits: cloning and sequence analysis of 13 C$\alpha$ genes," *Embo J.* 8:4041–4047 (1989).

Capecchi, "Altering the genome by homologous recombination," *Science* 244:1288–1292 (1989).

Chang, et al., "A general method for facilitating heterodimeric pairing between two proteins: Application to expression of $\alpha$ and $\beta$ T–cell receptor extracellular segments", *Proc.Natl.Acad.Sci* (USA) 91:11408–11412 (1994).

Collins, "The HL–60 Promyelocytic Leukemia Cell Line: Proliferation, Differentiation, and Cellular Oncogene Expression", *Blood* 70:1233–1244 (1987).

Corbi, et al., "cDNA cloning and complete primary structure of the $\alpha$ subunit of a leukocyte adhesion glycoprotein, p150,95," *Embo J.* 6:4023–4028 (1987).

Corbi, et al., "The human leukocyte adhesion glycoprotein Mac–1 (complement receptor type 3, CD11b $\alpha$ subunit," *J.Bio.Chem.* 263:12403–12411 (1988).

Cromartie, et al., "Arthritis in rats after systemic injection of Streptococcal cells or cell walls." *J.Exp.Med.* 146:1585–1602 (1977).

Chisaka, et al., "Developmental defects of the ear, cranial nerves and hindbrain resulting from targeted disruption of the mouse homeobox gene Hox–1.6," *Nature* 355:516–520 (1992).

Dana, et al., "Deficiency of a surface membrane glycoprotein (Mo1) in man," *J.Clin.Invest.* 73:153–159 (1984).

Diamond, et al., "The I domain is a major recognition site on the leukocyte integrin Mac–1 (CD11b/CD18) for four distinct adhesion ligands," *J.Cell, Biol.* 120:1031–1043 (1993).

Danilenko, et al., "Canine leukocyte cell adhesion molecules (LeuCAMS): characterization of the CD11/CD18 family," *Tissue Antigens* 40:13–21 (1992).

Deng, et al., "Location of crossovers during gene targeting with insertion and replacement vectors," *Mol.Cell.Biol.* 13:2134–2140 (1993).

Frohman, "RACE: Rapid amplification of cDNA ends" in *PCR Protocols: A Guide to Methods and Applications*, Innis, et al. (eds.) Academic press:New York (1990) pp. 28–38.

Greve, et al., "The major human rhinovirus receptor is ICAM–1," *Cell* 56:839–847 (1989).

Hanenberg et al., "Macrophage infiltration precedes and is a prerequisite for lymphocytic insulitis in pancreatic islets of prediabetic BB rats," *Diatetologia* 32:126–134 (1989).

Hart and Greenwald, "Scintillation proximity assay (SPA)—a new method of immunoassay", *Molecular Immunol.* 16:265–267, (1979).

Hart and Greenwald, "Scintillation proximity assay of antigen–antibody binding kinetics: concise communication," *J.Nuc.Med* 20:1062–1065 (1979).

Hildreth & Orentas, "Involvement of a leukocyte adhesion receptor (LFA–1) in HIV–induced syncytium formation," *Science* 244:1075–1078 (1989).

Huitinga, et al., "Treatment with anti–CR3 antibodies ED7 and ED8 suppresses experimental allergic encephalomyelitis in Lewis rats," *Eur.J.Immunol* 23:709–715 (1993).

(List continued on next page.)

*Primary Examiner*—Karen C. Carlson
*Attorney, Agent, or Firm*—Marshall, O'Toole, Gerstein, Murray & Borun

[57] ABSTRACT

DNA encoding a novel human $\beta_2$ integrin $\alpha$ subunit polypeptide, designated $\alpha_d$, is disclosed along with methods and materials for production of the same by recombinant procedures. Fusion proteins are also disclosed which include extracellular $\alpha_d$ protein fragments, $\alpha_d$ I domain fragments or full length $\alpha_d$ polypeptides and human immunoglobulin constant regions. Binding molecules specific for $\alpha_d$ are also disclosed as useful for modulating the biological activities of $\alpha_d$. DNA from other species which show homology to human $\alpha_d$ encoding sequences are also disclosed.

3 Claims, 4 Drawing Sheets

OTHER PUBLICATIONS

Hynes, "Integrins, Versatility, Modulation, and Signaling in Cell Adhesion", *Cell* 69:11–25 (1992).

Jutila, et al., "In vivo distribution and characterization of two novel mononuclear phagocyte differentiation antigens in mice," *J.Leukocyte Biol.* 54:30–39 (1993).

Karin and Richards, "Human metallothionein genes—primary structure of the metallothionein–II gene and a related processed protein," *Nature* 299:797–802 (1982).

Kishimoto, et al., "Heterogeneous mutations in the β subunit common to the LFA–1, Mac–1 and p150,95 glycoproteins cause leukocyte adhesion deficiency," *Cell* 50:193–202 (1987).

Kishimoto, et al., "Cloning of the β subunit of the leukocyte adhesion proteins: homology to an extracellular matrix receptor defines a novel supergene family," *Cell* 48:681–690 (1987).

Kröncke, et al., "Activated Macrophages Kill Pancreatic Syngeneic Islet Cells Via Arginine–Dependant Nitric Oxide Generation", *Biochemical and Biophysical Research Communications*, 175:752–758 (1991).

Landis, et al., "A novel LFA–1 activation epitope maps to the I domain," *J.Cell.Biol.* 120:1519–1527 (1993).

Larson, et al., "Primary structure of the leukocyte function–associated molecular–1 α subunit: an integrin with an embedded domain defining a protein superfamily," *J.Cell. Biol.* 108:703–712 (1989).

Larson and Springer, "Structure and function of leukocyte integrins," *Immunol.Rev.* 114:181–217 (1990).

Letvin, et al., "Conservation of myeloid surface antigens on primary granulocytes," *Blood* 61:408–410 (1983).

MacMicking, et al., "Altered Responses to Bacterial Infection and Endotoxic Shock in Mice Lacking Inducible Nitric Oxide Synthase", *Cell* 81:641–650 (1995).

McCabe, "Production of single–stranded DNA by asymmetric PCR," in *PCR Protocols: A Guide to Methods and Applications*, Innis et al. (ed) Academic Press: New York (1990) pp. 76–83.

Merrill, et al., "Microglial Cell Cytotoxicity of Oligodendrocytes Is Mediated through Nitric Oxide", *Jour. of Immunol.* 151:2132–2141 (1993).

Metlay, et al., "The distinct leukocyte integrins of mouse spleen dendritic cells as identified with new hamster monoclonal antibodies," *J.Exp.Med.* 171:1753–1771 (1990).

Michishita, et al., "A novel divalent cation–binding site in the A domain of the β2 integrin CR3 (CD11b/CD18) is essential for ligand binding," *Cell* 72:857–867 (1993).

Moore, et al., "Canine leukocyte integrins: characterization of a CD18 homologue," *Tissue Antigens* 36:211–220 (1990).

Mulligan, et al., "Tissue injury caused by deposition of immune complexes is L–arginine dependent", *Proc.Natl.Acad.Sci.* (USA) 88:6338–6342 (1991).

Nourshargh, et al., "Accumulation of [111]In–neutrophils in rabbit skin in allergic and non–allergic inflammatory reactions in vivo," *J.Immunol.* 142:3193–3198 (1989).

Patarroyo, et al., "Leukocyte–cell adhesion: a molecular process fundamental in leukocyte physiology," *Immunol.Rev.* 114:67–108 (1990).

Price, et al., "In vivo inhibition of neutrophil function in the rabbis using monoclonal antibody to CD18, " *J.Immunol.* 139:4174–4177 (1987).

Randi and Hogg, "I domain of $β_2$ integrin lymphocyte function–associated antigen–1 contains a binding site for ligand intercellular adhesion molecule–1," *J.Biol.Chem.* 269:12395–12398 (1994).

Rojiani et al., "In vitro interaction of a polypeptide homologous to human Ro/SS–A antigen (calreticulin) with a highly conserved amino acid sequence in the cytoplasmic domain of integrin α subunits," *Biochemistry* 30:9859–9866 (1991).

Rosenfeld, et al., "Fatty streak initiation in watanabe heritable hyperlipemic and comparably hypercholesterolemic fat–fed rabbits" *Arteriosclerosis* 7:9–23 (1987).

Rosenfeld, et al., "Fatty streak expansion and maturation in watanabe heritable hyperlipemic and hypercholesterolemic fat–fed rabbits" *Arteriosclerosis* 7:24–34 (1987).

Sambrook, et al., (eds), "Immobilization of Bacteriophage λ plaques on nitrocellulose filters or nylon membranes" in *Molecular Cloning: a laboratory manual*, Cold Spring Harbor Press:ColdSring Harbor, NY (1989) p. 2.110.

Sanchez–Madrid, et al., "A human leukocyte differentiation antigen family with distinct α–subunits and a common βsubunit," *J.Exp.Med.* 154:1785–1803 (1981).

Schneiderman, et al., "Expression of 12 rabbit IgA Cα genes as chimeric rabbit–mouse IgA antibodies," *Proc.Natl.Acad..Sci.* (USA) 86:7561–7565 (1989).

Schwab, et al., "Pro–and anti–inflammatory roles of interleukin–1 recurrence of bacterial cell wall–induced arthritis in rats," *Infection and Immunity* 59:4436–4442 (1991).

Searle, et al., "Regulation, linkage, and sequence of mouse metallothionein I and II genes," *Mol.Cell.Biol.* 4:1221–1230 (1984).

Shaw, et al., "Molecular cloning of the human mucosal lymphocyte integrin $α^E$ subunit," *J.Biol.Chem.* 269:6016–6025 (1994).

Smith, et al., "Cooperative interactions of LFA–1 and Mac–1 with intercellular adhesion molecular–1 in facilitating adherence and transendothelial migration of human neutrophils in vitro," *J.Clin.Invest.* 83:2008–2017 (1989).

Springer, "Adhesion molecules of the immune system," *Nature* 346:425–434 (1990).

Tamura, et al., "Epithelial integrin$α_6β_4$: complete primary structure of $α_6$ and variant forms of $β_4$," *J.Cell.Biol.* 111:1593–1604 (1990).

Ueda, et al., "Identification of the complement iC3b binding site in the β2 integrin CR3 (CD11b/CD18)," *Proc.Natl.Acad.Sci.* (USA) 91:10680–10684 (1994).

Varshney, et al., "Structure, organization, and regulation of human metallothionein $I_F$ gene: differential and cell–type-specific expression in response to heavy metals and glucocoriticoids," *Mol.Cell.Biol.* 6:26–36 (1986).

Yamada, et al., "Mucosal injury and inflammation in a model of chronic granulomatous colitis in rats," *Gastroenterology* 104:759–771 (1993).

Zhou, et al., "Differential ligand binding specificities of recombinant CD11b/CD8 integrin I–domain" *J.Biol.Chem.* 269:17075–17079 (1994).

Vazeux et al. "Cloning & Characterization of a new intercellular" *Nature* 360: pp. 485–488 Dec. 3, 1992.

|  |  |  |  |  |  |
|---|---|---|---|---|---|
| αD    | TF-GT--VLL | LSVLASYHGF | NLDVEEPTIF | QEDAGGFGQS | VVQFGGSRLV | 47 |
| CD11B | MA-LR--VLL | LTALTLCHGF | NLDTENAMTF | QENARGFGQS | VVQLQGSRVV | 47 |
| CD11C | MTRTRAALLL | FTALATSLGF | NLDTEELTAF | RVDSAGFGDS | VVQYANSWVV | 50 |

| αD    | VGAPLEVVAA | NQTGRLYDCA | AATGMCQPIP | LHIRPEAVNM | SLGLTLAAST | 97 |
| CD11B | VGAPQEIVAA | NQRGSLYQCD | YSTGSCEPIR | LQVPVEAVNM | SLGLSLAATT | 97 |
| CD11C | VGAPQKIIAA | NQIGGLYQCG | YSTGACEPIG | LQVPPEAVNM | SLGLSLASTT | 100 |

| αD    | NGSRLLACGP | TLHRVCGENS | YSKGSCLLLG | SR-WEIIQTV | PDATPECPHQ | 146 |
| CD11B | SPPQLLACGP | TVHQTCSENT | YVKGLCFLFG | SNLRQQPQKF | PEALRGCPQE | 147 |
| CD11C | SPSQLLACGP | TVHHECGRNM | YLTGLCFLLG | PT--QLTQRL | PVSRQECPRQ | 148 |

| αD    | EMDIVFLIDG | SGSIDQNDFN | QMKGFVQAVM | GQFEGTDTLF | ALMQYSNLLK | 196 |
| CD11B | DSDIAFLIDG | SGSIIPHDFR | RMKEFVSTVM | EQLKKSKTLF | SLMQYSEEFR | 197 |
| CD11C | EQDIVFLIDG | SGSISSRNFA | TMMNFVRAVI | SQFQRPSTQF | SLMQFSNKFQ | 198 |

| αD    | IHFTFTQFRT | SPSQQSLVDP | IVQLKGLTFT | ATGILTVVTQ | LFHHKNGARK | 246 |
| CD11B | IHFTFKEFQN | NPNPRSLVKP | ITQLLGRTHT | ATGIRKVVRE | LFNITNGARK | 247 |
| CD11C | THFTFEEFRR | TSNPLSLLAS | VHQLQGFTYT | ATAIQNVVHR | LFHASYGARR | 248 |

| αD    | SAKKILIVIT | DGQKYKDPLE | YSDVIPQAEK | AGIIRYAIGV | GHAFQGPTAR | 296 |
| CD11B | NAFKILVVIT | DGEKFGDPLG | YEDVIPEADR | EGVIRYVIGV | GDAFRSEKSR | 297 |
| CD11C | DAIKILIVIT | DGKKEGDSLD | YKDVIPMADA | AGIIRYAIGV | GLAFQNRNSW | 298 |

FIGURE 1A

|        |            |            |            |            |            |     |
|--------|------------|------------|------------|------------|------------|-----|
| αD     | QELNTISSAP | PQDHVFKVDN | FAALGSIQKQ | LQEKIYAVEG | TQSRASSSFQ | 346 |
| CD11B  | QELNTIASKP | PRDHVFQVNN | FEALKTIQNQ | LREKIFAIEG | TQTGSSSSFE | 347 |
| CD11c  | KELNDIASKP | SQEHIFKVED | FDALKDIQNQ | LKEKIFAIEG | TETISSSSFE | 348 |
|        |            |            |            |            |            |     |
| αD     | HEMSQEGFST | ALTMDGLFLG | AVGSFSWSGG | AFLYPPNMSP | TFINMSQENV | 396 |
| CD11B  | HEMSQEGFSA | AITSNGPLLS | TVGSYDWAGG | VFLYTSKEKS | TFINMTRVDS | 397 |
| CD11c  | LEMAQEGFSA | VFTPDGPVLG | AVGSFTWSGG | AFLYPPNMSP | TFINMSQENV | 398 |
|        |            |            |            |            |            |     |
| αD     | DMRDSYLGYS | TELALWKGVQ | NLVLGAPRYQ | HTGKAVIFTQ | VSRQWRKKAE | 446 |
| CD11B  | DMNDAYLGYA | AAIILRNRVQ | SLVLGAPRYQ | HIGLVAMFRQ | NTGMWESNAN | 447 |
| CD11c  | DMRDSYLGYS | TELALWKGVQ | SLVLGAPRYQ | HIGKAVIFIQ | VSRQWRMKAE | 448 |
|        |            |            |            |            |            |     |
| αD     | VTGTQIGSYF | GASLCSVDVD | SDGSTDLILI | GAPHYYEQTR | GGQVSVCPLP | 496 |
| CD11B  | VKGTQIGAYF | GASLCSVDVD | SNGSTDLVLI | GAPHYYEQTR | GGQVSVCPLP | 497 |
| CD11c  | VIGTQIGSYF | GASLCSVDVD | TDGSTDLVLI | GAPHYYEQTR | GGQVSVCPLP | 498 |
|        |            |            |            |            |            |     |
| αD     | RGQRVQWQCD | AVLRGEQGHP | WGRFGAALTV | LGDVNEDKLI | DVAIGAPGEQ | 546 |
| CD11B  | RGQRARWQCD | AVLYGEQGQP | WGRFGAALTV | LGDVNGDKLT | DVAIGAPGEE | 547 |
| CD11c  | RGWRRWW-CD | AVLYGEQGHP | WGRFGAALTV | LGDVNGDKLT | DVVIGAPGEE | 547 |
|        |            |            |            |            |            |     |
| αD     | ENRGAVYLFH | GASESGISPS | HSQRIASSQL | SPRLQYFGQA | LSGGQDLTQD | 596 |
| CD11B  | DNRGAVYLFH | GTSGSGISPS | HSQRIAGSKL | SPRLQYFGQS | LSGGQDLTMD | 597 |
| CD11c  | ENRGAVYLFH | GVLGPSISPS | HSQRIAGSQL | SSRLQYFGQA | LSGGQDLTQD | 597 |

FIGURE 1B

```
αD     GLMDLAVGAR GQVLLLRSLP VLKVGVAMRF SPVEVAKAVY RCWEEKPSAL   646
CD11b  GLVDLTVGAQ GHVLLLRSQP VLRVKAIMEF NPREVARHVF ECNDQVVKGK   647
CD11c  GLVDLAVGAR GQVLLLRTRP VLWVGVSMQF IPAEIPRSAF ECREQVVSEQ   647

αD     EAGDATVCLT IQKSSLDQL- -GDIQSSVRF DLALDPGRLT SRAIFNETKN   694
CD11b  EAGEVRVCLH VQKSTRDRLR EGQIQSVVTY DLALDSGRPH SRAVFNETKN   697
CD11c  TLVQSNICLY IDKRSKNLLG SRDLQSSVTL DLALAPGRLS PRAIFQETKN   697

αD     PTLTTRKTLG LGIHCETLKL LLPDCVEDVV SPIILHLNFS LVREPIPSPQ   744
CD11b  STRRQTQVLG LTQTCETLKL QLPNCIEDPV SPIVLRLNFS LVGTPLSAFG   747
CD11c  RSLSRVRVLG LKAHCENFNL LLPSCVEDSV IPIILRLNFT LVGKPLLAFR   747

αD     NLRPVLAVGS QDLFTASLPF EKNCGQDGLC EGDLGVTLSF SGLQTLTVGS   794
CD11b  NLRPVLAEDA QRLFTALFPF EKNCGNDNIC QDDLSITFSF MSLDCLVVGG   797
CD11c  NLRPMLAALA QRYFTASLPF EKNCGADHIC QDNLGISFSF PGLKSLLVGS   797

αD     SLELNVIVTV WNAGEDSYGT VVSLYYPAGL SHRRVSGAQK QPHQSALRLA   844
CD11b  PREFNVTVTV RNDGEDSYRT QVTFFFPLDL SYRKVSTLQN QRSQRSWRLA   847
CD11c  NLELNAEVMV WNDGEDSYGT TITFSHPAGL SYRYVAEGQK QGQLRSLHLT   847

αD     CETVPTED-- EGLRSSRCSV NHPIFHEGSN GTFIVTFDVS Y----KATLG   888
CD11b  CESASSTEVS GALKSTSCSI NHPIFPENSE ----VTFNIT FDVDSKASLG   893
CD11c  CCSA-PVGSQ GTW-STSCRI NHLIFRGGAQ ----ITFLAT FDVSPKAVGL   891
```

FIGURE 1C

| | | | | | |
|---|---|---|---|---|---|
| αD    | DRMLMRASAS | SENNKASSSK | ATFQLELPVK | YAVYTMISRQ | EESTKYFNFA | 938 |
| CD11B | NKLLLKANVT | SENNMPRTNK | TEFQLELPVK | YAVYMVVTSH | GVSTKYLNFT | 943 |
| CD11C | DRLLIANVS  | SENNIPRTSK | TIFQLELPVK | YAVYIVVSSH | EQFTKYLNFS | 941 |

| | | | | | |
|---|---|---|---|---|---|
| αD    | TS-DEKKMKE | AEHRYRVNNL | SQRDLAISIN | FWVPVLLNGV | AVWDVVMEAP | 987 |
| CD11B | AS-ENTS-RV | MQHQYQVSNL | GQRSLPISLV | FLVPVRLNQT | VIWDRPQVTF | 991 |
| CD11C | ESEEKES-HV | AMHRYQVNNL | GQRDLPVSIN | FWVPVELNQE | AVWMDVEVSH | 990 |

| | | | | | |
|---|---|---|---|---|---|
| αD    | SQSLP--CVS | ERKPPQHSDF | LTQISRSPML | DCSIADCLQF | RCDVPSFSVQ | 1035 |
| CD11B | SENLSSTCHT | KERLPSHSDF | LAELRKAPVV | NCSIAVCQRI | QCDIPFFGIQ | 1041 |
| CD11C | PQNPSLRCSS | EKIAPPASDF | LAHIQKNPVL | DCSIAGCLRF | RCDVPSFSVQ | 1040 |

| | | | | | |
|---|---|---|---|---|---|
| αD    | EELDFTLKGN | LSFGWVRETL | QKKVLVVSVA | EITFDTSVYS | QLPGQEAFMR | 1085 |
| CD11B | EEFNATLKGN | LSFDWYIKTS | HNHLLIVSTA | EILFNDSVFT | LLPGQGAFVR | 1091 |
| CD11C | EELDFTLKGN | LSFGWVRQIL | QKKVSVVSVA | EIIFDTSVYS | QLPGQEAFMR | 1090 |

| | | | | | |
|---|---|---|---|---|---|
| αD    | AQMENVLEED | EVYNAIPIIM | GSSVGALLLL | ALITATLYKL | GFFKRHYKEM | 1135 |
| CD11B | SQTETKVEPF | EVPNPLPLIV | GSSVGGLLLL | ALITAALYKL | GFFKRQYKDM | 1141 |
| CD11C | AQTITVLEKY | KVHNPIPLIV | GSSIGGLLLL | ALITAVLYKV | GFFKRQYKEM | 1140 |

| | | |
|---|---|---|
| αD    | LEDKPED--- | -----TATFS | GDDFSCVAPN VPLS | 1161 |
| CD11B | M---SEG--- | -----GP--P | GAE----PQ       | 1153 |
| CD11C | M---EEANGQ | IAPENGT--Q | TPS----PP SEK   | 1163 |

FIGURE 1D

HUMAN β₂ INTEGRIN αSUBUNIT

This application is a continuation-in-part of U.S. application Ser. No. 08/362,652, filed Dec. 21, 1994, which is pending, which is a continuation-in-part of U.S. application Ser. No. 08/286,889, filed Aug. 5, 1994, now U.S. Pat. No. 5,470,953, which in turn is a continuation-in-part of U.S. application Ser. No. 08/173,497, filed Dec. 23, 1993, now U.S. Pat. No. 5,437,958.

FIELD OF THE INVENTION

The present invention relates to the cloning and expression of polynucleotides encoding a novel human β₂ integrin α subunit, designated $\alpha_d$, which is structurally related to the known human β₂ integrin α subunits, CD11a, CD11b and CD11c. The present invention also relates to polynucleotides isolated from other species which show homology to human $\alpha_d$ encoding sequences.

BACKGROUND OF THE INVENTION

The integrins are a class of membrane-associated molecules which actively participate in cellular adhesion. Integrins are transmembrane heterodimers comprising an α subunit in noncovalent association with a β subunit. To date, at least fourteen α subunits and eight β subunits have been identified [reviewed in Springer, *Nature* 346:425–434 (1990)]. The β subunits are generally capable of association with more than one α subunit and the heterodimers sharing a common β subunit have been classified as subfamilies within the integrin population.

One class of human integrins, restricted to expression in white blood cells, is characterized by a common β₂ subunit. As a result of this cell-specific expression, these integrins are commonly referred to as the leukocyte integrins, Leu-CAMs or leukointegrins. Because of the common β₂ subunit, an alternative designation of this class is the β₂ integrins. The β subunit (CD18) has previously been isolated in association with one of three distinct α subunits, CD11a, CD11b or CD11c. The isolation of a cDNA encoding human CD18 is described in Kishimoto, et al., *Cell* 48:681–690 (1987). In official WHO nomenclature, the heterodimeric proteins are referred to as CD11a/CD18, CD11b/CD18, and CD11c/CD18; in common nomenclature they are referred to as LFA-1, Mac-1 or Mo1 and p150,95 or LeuM5, respectively [Cobbold, et al., in *Leukocyte Typing III*, McMichael (ed), Oxford Press, p.788 (1987)]. The human β₂ integrin α subunits CD11a, CD11b and CD11c have been demonstrated to migrate under reducing condition in electrophoresis with apparent molecular weights of approximately 180 kD, 155 kD and 150 kD, respectively, and DNAs encoding these subunits have been cloned [CD11a, Larson, et al., *J. Cell Biol.* 108:703–712 (1989); CD11b, Corbi, et al., *J. Biol. Chem.* 263:12403–12411 (1988) and CD11c, Corbi, et al. *EMBO J.* 6:4023–4028 (1987)]. Putative homologs of the human β₂ integrin α and β chains, defined by approximate similarity in molecular weight, have been variously identified in other species including monkeys and other primates [Letvin, et al., *Blood* 61:408–410 (1983)], mice [Sanchez-Madrid, et al., *J. Exp. Med.* 154:1517 (1981)], and dogs [Moore, et al., *Tissue Antigens* 36:211–220 (1990)].

The absolute molecular weights of presumed homologs from other species have been shown to vary significantly [see, e.g., Danilenko et al., *Tissue Antigens* 40:13–21 (1992)], and in the absence of sequence information, a definitive correlation between human integrin subunits and those identified in other species has not been possible.

Moreover, variation in the number of members in a protein family has been observed between different species. Consider, for example, that more IgA isotypes have been isolated in rabbits than in humans [Burnett, et al., *EMBO J.* 8:4041–4047 (1989) and Schneiderman, et al., *Proc. Natl. Acad. Sci. (USA)* 86:7561–7565 (1989)]. Similarly, in humans, at least six variants of the metallothionine protein have been previously identified [Karin and Richards, *Nature* 299:797–802 (1982) and Varshney, et al., *Mol. Cell. Biol.* 6:26–37, (1986)], whereas in the mouse, only two such variants are in evidence [Searle, et al., *Mol. Cell. Biol.* 4:1221–1230 (1984)]. Therefore, existence of multiple members of a protein family in one species does not necessarily imply that corresponding family members exist in another species.

In the specific context of β₂ integrins, in dogs it has been observed that the presumed canine β₂ counterpart to the human CD18 is capable of dimer formation with as many as four potentially distinct α subunits [Danilenko, et al., supra]. Antibodies generated by immunizing mice with canine splenocytes resulted in monoclonal antibodies which immunoprecipitated proteins tentatively designated as canine homologs to human CD18, CD11a, CD11b and CD11c based mainly on similar, but not identical, molecular weights. Another anti-canine splenocyte antibody, Ca11.8H2, recognized and immunoprecipitated a fourth α-like canine subunit also capable of association with the β₂ subunit, but having a unique molecular weight and restricted in expression to a subset of differentiated tissue macrophages.

Antibodies generated by immunization of hamsters with murine dendritic cells resulted in two anti-integrin antibodies [Metlay, et al., *J. Exp. Med.* 171:1753–1771 (1990)]. One antibody, 2E6, immunoprecipitated a predominant heterodimer with subunits having approximate molecular weights of 180 kD and 90 kD in addition to minor bands in the molecular weight range of 150–160 kD. The second antibody, N418, precipitated another apparent heterodimer with subunits having approximate molecular weights of 150 kD and 90 Kd. Based on cellular adhesion blocking studies, it was hypothesized that antibody 2E6 recognized a murine counterpart to human CD18. While the molecular weight of the N418 antigen suggested recognition of a murine homolog to human CD11c/CD18, further analysis indicated that the murine antigen exhibited a tissue distribution pattern which was inconsistent with that observed for human CD11c/CD18.

The antigens recognized by the canine Ca11.8H2 antibody and the murine N418 antibody could represent a variant species (e.g., a glycosylation or splice variant) of a previously identified canine or murine α subunit. Alternatively, these antigens may represent unique canine and murine integrin α subunits. In the absence of specific information regarding primary structure, these alternatives cannot be distinguished.

In humans, CD11a/CD18 is expressed on all leukocytes. CD11b/CD18 and CD11c/CD18 are essentially restricted to expression on monocytes, granulocytes, macrophages and natural killer (NK) cells, but CD11c/CD18 is also detected on some B-cell types. In general, CD11a/CD18 predominates on lymphocytes, CD11b/CD18 on granulocytes and CD11c/CD18 on macrophages [see review, Arnaout, *Blood* 75:1037–1050 (1990)]. Expression of the α chains, however, is variable with regard to the state of activation and differentiation of the individual cell types [See review, Larson and Springer, *Immunol. Rev.* 114:181–217 (1990).]

The involvement of the β₂ integrins in human immune and inflammatory responses has been demonstrated using monoclonal antibodies which are capable of blocking $\beta_2$ integrin-associated cell adhesion. For example, CD11a/CD18, CD11b/CD18 and CD11c/CD18 actively participate in natural killer (NK) cell binding to lymphoma and adenocarcinoma cells [Patarroyo, et al., *Immunol. Rev.* 114:67–108 (1990)], granulocyte accumulation [Nourshargh, et al., *J. Immunol.* 142:3193–3198 (1989)], granulocyte-independent plasma leakage [Arfors, et al., *Blood* 69:338–340 (1987)], chemotactic response of stimulated leukocytes [Arfors, et at., supra] and leukocyte adhesion to vascular endothelium [Price, et al., *J. Immunol.* 139:4174–4177 (1987) and Smith, et al., *J. Clin. Invest.* 83:2008–2017 (1989)]. The fundamental role of $\beta_2$ integrins in immune and inflammatory responses is made apparent in the clinical syndrome referred to as leukocyte adhesion deficiency (LAD), wherein clinical manifestations include recurrent and often life threatening bacterial infections. LAD results from heterogeneous mutations in the $\beta_2$ subunit [Kishimoto, et al., *Cell* 50:193–202 (1987)] and the severity of the disease state is proportional to the degree of the deficiency in $\beta_2$ subunit expression. Formation of the complete integrin heterodimer is impaired by the $\beta_2$ mutation [Kishimoto, et al., supra].

Interestingly, at least one antibody specific for CD18 has been shown to inhibit human immunodeficiency virus type-1 (HIV-1) syncytia formation in vitro, albeit the exact mechanism of this inhibition is unclear [Hildreth and Orentas, *Science* 244:1075–1078 (1989)]. This observation is consistent with the discovery that a principal counter-receptor of CD11a/CD18, ICAM-1, is also a surface receptor for the major group of rhinovirus serotypes [Greve, et al., *Cell* 56:839 (1989)].

The significance of $\beta_2$ integrin binding activity in human immune and inflammatory responses underscores the necessity to develop a more complete understanding of this class of surface proteins. Identification of yet unknown members of this subfamily, as well as their counterreceptors, and the generation of monoclonal antibodies or other soluble factors which can alter biological activity of the $\beta_2$ integrins will provide practical means for therapeutic intervention in $\beta_2$ integrin-related immune and inflammatory responses.

BRIEF DESCRIPTION OF THE INVENTION

In one aspect, the present invention provides novel purified and isolated polynucleotides (e.g., DNA and RNA transcripts, both sense and anti-sense strands) encoding a novel human $\beta_2$ integrin $\alpha$ subunit, $\alpha_d$, and variants thereof (i.e., deletion, addition or substitution analogs) which possess binding and/or immunological properties inherent to $\alpha_d$. Preferred DNA molecules of the invention include cDNA, genomic DNA and wholly or partially chemically synthesized DNA molecules. A presently preferred polynucleotide is the DNA as set forth in SEQ ID NO: 1, encoding the polypeptide of SEQ ID NO: 2. Also provided are recombinant plasmid and viral DNA constructions (expression constructs) which include $\alpha_d$ encoding sequences, wherein the $\alpha_d$ encoding sequence is operatively linked to a homologous or heterologous transcriptional regulatory element or elements.

Also provided by the present invention are isolated and purified mouse and rat polynucleotides which exhibit homology to polynucleotides encoding human $\alpha_d$. A preferred mouse polynucleotide is set forth in SEQ ID NO: 52; a preferred rat polynucleotide is set forth in SEQ ID NO: 54.

As another aspect of the invention, prokaryotic or eukaryotic host cells transformed or transfected with DNA sequences of the invention are provided which express $\alpha_d$ polypeptide or variants thereof. Host cells of the invention are particularly useful for large scale production of $\alpha_d$ polypeptide, which can be isolated from either the host cell itself or from the medium in which the host cell is grown. Host cells which express $\alpha_d$ polypeptide on their extracellular membrane surface are also useful as immunogens in the production of $\alpha_d$-specific antibodies. Preferably, host cells transfected with $\alpha_d$ will be co-transfected to express a $\beta_2$ integrin subunit in order to allow surface expression of the heterodimer.

Also provided by the present invention are purified and isolated $\alpha_d$ polypeptides, fragments and variants thereof. Preferred $\alpha_d$ polypeptides are as set forth in SEQ ID NO: 2. Novel $\alpha_d$ products of the invention may be obtained as isolates from natural sources, but, along with $\alpha_d$ variant products, are preferably produced by recombinant procedures involving host cells of the invention. Completely glycosylated, partially glycosylated and wholly de-glycosylated forms of the $\alpha_d$ polypeptide may be generated by varying the host cell selected for recombinant production and/or post-isolation processing. Variant $\alpha_d$ polypeptides of the invention may comprise water soluble and insoluble $\alpha_d$ polypeptides including analogs wherein one or more of the amino acids are deleted or replaced: (1) without loss, and preferably with enhancement, of one or more biological activities or immunological characteristics specific for $\alpha_d$; or (2) with specific disablement of a particular ligand/receptor binding or signalling function. Fusion polypeptides are also provided, wherein $\alpha_d$ amino acid sequences are expressed contiguously with amino acid sequences from other polypeptides. Such fusion polypeptides may possess modified biological, biochemical, and/or immunological properties in comparison to wild-type $\alpha_d$. Analog polypeptides including additional amino acid (e.g., lysine or cysteine) residues that facilitate multimer formation are contemplated.

Also comprehended by the present invention are polypeptides and other non-peptide molecules which specifically bind to $\alpha_d$. Preferred binding molecules include antibodies (e.g., monoclonal and polyclonal antibodies), counterreceptors (e.g., membrane-associated and soluble forms) and other ligands (e.g., naturally occurring or synthetic molecules), including those which competitively bind $\alpha_d$ in the presence of $\alpha_d$ monoclonal antibodies and/or specific counterreceptors. Binding molecules are useful for purification of $\alpha_d$ polypeptides and identifying cell types which express $\alpha_d$. Binding molecules are also useful for modulating (i.e., inhibiting, blocking or stimulating) of in vivo binding and/or signal transduction activities of $\alpha_d$.

Assays to identify $\alpha_d$ binding molecules are also provided, including immobilized ligand binding assays, solution binding assays, scintillation proximity assays, di-hybrid screening assays, and the like.

In vitro assays for identifying antibodies or other compounds that modulate the activity of $\alpha_d$ may involve, for example, immobilizing $\alpha_d$ or a natural ligand to which $\alpha_d$ binds, detectably labelling the nonimmobilized binding partner, incubating the binding partners together and determining the effect of a test compound on the amount of label bound wherein a reduction in the label bound in the presence of the test compound compared to the amount of label bound in the absence of the test compound indicates that the test agent is an inhibitor of $\alpha_d$ binding.

Another type of assay for identifying compounds that modulate the interaction between $\alpha_d$ and a ligand involves immobilizing $\alpha_d$ or a fragment thereof on a solid support coated (or impregnated with) a fluorescent agent, labelling the ligand with a compound capable of exciting the fluorescent agent, contacting the immobilized $\alpha_d$ with the labelled ligand in the presence and absence of a putative modulator compound, detecting light emission by the fluorescent agent, and identifying modulating compounds as those compounds that affect the emission of light by the fluorescent agent in comparison to the emission of light by the fluorescent agent in the absence of a modulating compound. Alternatively, the $\alpha_d$ ligand may be immobilized and $\alpha_d$ may be labelled in the assay.

Yet another method contemplated by the invention for identifying compounds that modulate the interaction between $\alpha_d$ and a ligand involves transforming or transfecting appropriate host cells with a DNA construct comprising a reporter gene under the control of a promoter regulated by a transcription factor having a DNA-binding domain and an activating domain, expressing in the host cells a first hybrid DNA sequence encoding a first fusion of part or all of $\alpha_d$ and either the DNA binding domain or the activating domain of the transcription factor, expressing in the host cells a second hybrid DNA sequence encoding part or all of the ligand and the DNA binding domain or activating domain of the transcription factor which is not incorporated in the first fusion, evaluating the effect of a putative modulating compound on the interaction between $\alpha_d$ and the ligand by detecting binding of the ligand to $\alpha_d$ in a particular host cell by measuring the production of reporter gene product in the host cell in the presence or absence of the putative modulator, and identifying modulating compounds as those compounds altering production of the reported gene product in comparison to production of the reporter gene product in the absence of the modulating compound. Presently preferred for use in the assay are the lexA promoter, the lexA DNA binding domain, the GAL4 transactivation domain, the lacZ reporter gene, and a yeast host cell.

A modified version of the foregoing assay may be used in isolating a polynucleotide encoding a protein that binds to $\alpha_d$ by transforming or transfecting appropriate host cells with a DNA construct comprising a reporter gene under the control of a promoter regulated by a transcription factor having a DNA-binding domain and an activating domain, expressing in the host cells a first hybrid DNA sequence encoding a first fusion of part or all of $\alpha_d$ and either the DNA binding domain or the activating domain of the transcription factor, expressing in the host cells a library of second hybrid DNA sequences encoding second fusions of part or all of putative $\alpha_d$ binding proteins and the DNA binding domain or activating domain of the transcription factor which is not incorporated in the first fusion, detecting binding of an $\alpha_d$ binding protein to $\alpha_d$ in a particular host cell by detecting the production of reporter gene product in the host cell, and isolating second hybrid DNA sequences encoding $\alpha_d$ binding protein from the particular host cell.

Hybridoma cell lines which produce antibodies specific for $\alpha_d$ are also comprehended by the invention. Techniques for producing hybridomas which secrete monoclonal antibodies are well known in the art. Hybridoma cell lines may be generated after immunizing an animal with purified $\alpha_d$, variants of $\alpha_d$ or cells which express $\alpha_d$ or a variant thereof on the extracellular membrane surface. Immunogen cell types include cells which express $\alpha_d$ in vivo, or transfected prokaryotic or eukaryotic cell lines which normally do not normally express $\alpha_d$ in vivo.

The value of the information contributed through the disclosure of the DNA and amino acid sequences of $\alpha_d$ is manifest. In one series of examples, the disclosed $\alpha_d$ cDNA sequence makes possible the isolation of the human $\alpha_d$ genomic DNA sequence, including transcriptional control elements for the genomic sequence. Identification of $\alpha_d$ allelic variants and heterologous species (e.g., rat or mouse) DNAs is also comprehended. Isolation of the human $\alpha_d$ genomic DNA and heterologous species DNAs can be accomplished by standard DNA/DNA hybridization techniques, under appropriately stringent conditions, using all or part of the $\alpha_d$ cDNA sequence as a probe to screen an appropriate library. Alternatively, polymerase chain reaction (PCR) using oligonucleotide primers that are designed based on the known cDNA sequence can be used to amplify and identify genomic $\alpha_d$ DNA sequences. Synthetic DNAs encoding the $\alpha_d$ polypeptide, including fragments and other variants thereof, may be produced by conventional synthesis methods.

DNA sequence information of the invention also makes possible the development, by homologous recombination or "knockout" strategies [see, e.g., Kapecchi, *Science* 244:1288–1292 (1989)], to produce rodents that fail to express a functional $\alpha_d$ polypeptide or that express a variant $\alpha_d$ polypeptide. Such rodents are useful as models for studying the activities of $\alpha_d$ and $\alpha_d$ modulators in vivo.

DNA and amino acid sequences of the invention also make possible the analysis of $\alpha_d$ epitopes which actively participate in counterreceptor binding as well as epitopes which may regulate, rather than actively participate in, binding. Identification of epitopes which may participate in transmembrane signal transduction is also comprehended by the invention.

DNA of the invention is also useful for the detection of cell types which express $\alpha_d$ polypeptide. Standard DNA/RNA hybridization techniques which utilize $\alpha_d$ DNA to detect $\alpha_d$ RNA may be used to determine the constitutive level of $\alpha_d$ transcription within a cell, as well as changes in the level of transcription in response to internal or external agents. Identification of agents which modify transcription and/or translation of $\alpha_d$ can, in turn, be assessed for potential therapeutic or prophylactic value. DNA of the invention also makes possible in situ hybridization of $\alpha_d$ DNA to cellular RNA to determine the cellular localization of $\alpha_d$ specific messages within complex cell populations and tissues.

DNA of the invention is also useful for identification of non-human polynucleotide sequences which display homology to human $\alpha_d$ sequences. Possession of non-human $\alpha_d$ DNA sequences permits development of animal models (including, for example, transgenic models) of the human system.

As another aspect of the invention, monoclonal or polyclonal antibodies specific for $\alpha_d$ may be employed in immunohistochemical analysis to localize $\alpha_d$ to subcellular compartments or individual cells within tissues. Immunohistochemical analyses of this type are particularly useful when used in combination with in situ hybridization to localize both $\alpha_d$ mRNA and polypeptide products of the $\alpha_d$ gene.

Identification of cell types which express $\alpha_d$ may have significant ramifications for development of therapeutic and prophylactic agents. It is anticipated that the products of the invention related to $\alpha_d$ can be employed in the treatment of diseases wherein macrophages are an essential element of the disease process. Animal models for many pathological conditions associated with macrophage activity have been described in the art. For example, in mice, macrophage recruitment to sites of both chronic and acute inflammation is reported by Jutila, et al., *J. Leukocyte Biol.* 54:30–39 (1993). In rats, Adams, et al., [*Transplantation* 53:1115–1119(1992) and *Transplantation* 56:794–799 (1993)] describe a model for graft arteriosclerosis following heterotropic abdominal cardiac allograft transplantation. Rosenfeld, et al., [*Arteriosclerosis* 7:9–23 (1987) and *Arteriosclerosis* 7:24–34 (1987)] describe induced atherosclerosis in rabbits fed a cholesterol supplemented diet. Hanenberg, et al., [*Diabetologia* 32:126–134 (1989)] report the spontaneous development of insulin-dependent diabetes in BB rats. Yamada et al., [*Gastroenterology* 104:759–771 (1993)] describe an induced inflammatory bowel disease, chronic granulomatous colitis, in rats following injections of streptococcal peptidoglycan-polysaccharide polymers. Cromartie, et al., [*J. Exp. Med.* 146:1585–1602 (1977)] and Schwab, et al., [*Infection and Immunity* 59:4436–4442 (1991)] report that injection of streptococcal cell wall protein into rats results in an arthritic condition characterized by inflammation of peripheral joints and subsequent joint destruction. Finally, Huitinga, et al., [*Eur. J. Immunol* 23:709–715 (1993) describe experimental allergic encephalomyelitis, a model for multiple sclerosis, in Lewis rats. In each of these models, $\alpha_d$ antibodies, other $\alpha_d$ binding proteins, or soluble forms of $\alpha_d$ are utilized to attenuate the disease state, presumably through inactivation of macrophage activity.

Pharmaceutical compositions for treatment of these and other disease states are provided by the invention. Pharmaceutical compositions are designed for the purpose of inhibiting interaction between $\alpha_d$ and its ligand(s) and include various soluble and membrane-associated forms of $\alpha_d$ (comprising the entire $\alpha_d$ polypeptide, or fragments thereof which actively participate in $\alpha_d$ binding), soluble and membrane-associated forms of $\alpha_d$ binding proteins (including antibodies, ligands, and the like), intracellular or extracellular modulators of $\alpha_d$ binding activity, and/or modulators of $\alpha_d$ and/or $\alpha_d$-ligand polypeptide expression, including modulators of transcription, translation, post-translational processing and/or intracellular transport.

The invention also comprehends methods for treatment of disease states in which $\alpha_d$ binding, or localized accumulation of cells which express $\alpha_d$, is implicated, wherein a patient suffering from said disease state is provided an amount of a pharmaceutical composition of the invention sufficient to modulate levels of $\alpha_d$ binding or to modulate accumulation of cell types which express $\alpha_d$. The method of treatment of the invention is applicable to disease states such as, but not limited to, Type I diabetes, atherosclerosis, multiple sclerosis, asthma, psoriasis, lung inflammation, acute respiratory distress syndrome and rheumatoid arthritis.

BRIEF DESCRIPTION OF THE DRAWING

Numerous other aspects and advantages of the present invention will be apparent upon consideration of the following description thereof, reference being made to the drawing wherein:

FIG. 1A through 1D comprises an alignment of the human amino acid sequences of CD11b (SEQ ID NO: 3), CD11c (SEQ ID NO: 4) and $\alpha_d$ (SEQ ID NO: 2).

DETAILED DESCRIPTION OF THE INVENTION

The present invention is illustrated by the following examples relating to the isolation of a cDNA clone encoding $\alpha_d$ from a human spleen cDNA library. More particularly, Example 1 illustrates the use of anti-canine $\alpha_{TM1}$ antibody in an attempt to detect a homologous human protein. Example 2 details purification of canine $\alpha_{TM1}$ and N-terminal sequencing of the polypeptide to design oligonucleotide primers for PCR amplification of the canine $\alpha_{TM1}$ gene. Example 3 addresses large scale purification of canine $\alpha_{TM1}$ for internal sequencing in order to design additional PCR primers. Example 4 describes use of the PCR and internal sequence primers to amplify a fragment of the canine $\alpha_{TM1}$ gene. Example 5 addresses cloning of the human $\alpha_d$-encoding cDNA sequence. Example 6 describes Northern blot hybridization analysis of human tissues and cells for expression of $\alpha_d$ mRNA. Example 7 details the construction of human $\alpha_d$ expression plasmids and transfection of COS cells with the resulting plasmids. Example 8 addresses ELISA analysis of $\alpha_d$ expression in transfected COS cells. Example 9 describes FACS analysis of COS cells transfected with human $\alpha_d$ expression plasmids. Example 10 addresses immunoprecipitation of CD18 in association with $\alpha_d$ in co-transfected COS cells. Example 11 relates to stable transfection of $\alpha_d$ expression constructs in Chinese hamster ovary cells. Example 12 addresses CD 18-dependent binding of $\alpha_d$ to the intercellular adhesion molecule, ICAM-R. Example 13 describes scintillation proximity screening assays to identify inhibitors of $\alpha_d$ ligand/anti-ligand binding interactions. Example 14 addresses construction of expression plasmids which encode soluble forms of $\alpha_d$. Example 15 relates to production of $\alpha_d$-specific monoclonal antibodies. Example 16 describes analysis of $\alpha_d$ tissue distribution using polyclonal anti-serum. Example 17 describes isolation of rat cDNA sequences which show homology to human $\alpha_d$ gene sequences. Example 18 relates to construction of rat $\alpha_d$ I domain expression plasmids, including I domain/IgG fusion proteins, and production of monoclonal antibodies to I domain fusion proteins. Example 19 addresses isolation of mouse cDNA sequences which show homology to human $\alpha_d$ gene sequences. Example 20 describes isolation of additional mouse $\alpha_d$ cDNA clones used to confirm sequence analysis. Example 21 relates to in situ hybridization analysis of various mouse tissues to determine tissue and cell specific expression of the putative mouse homolog to human $\alpha_d$. Example 22 describes generation of expression constructs which encode the putative mouse homolog of human $\alpha_d$. Example 23 addresses design of a "knock-out" mouse wherein the gene encoding the putative mouse homolog of human $\alpha_d$ is disrupted. Example 24 describes isolation of rabbit cDNA clones which show homology to human $\alpha_d$ encoding sequences. Example 25 describes animal models of human disease states wherein modulation of $\alpha_d$ is assayed for therapeutic capabilities.

EXAMPLE 1

Attempt to Detect a Human Homolog of Canine $\alpha_{TM1}$

The monoclonal antibody Ca11.8H2 [Moore, et al., supra] specific for canine $\alpha_{TM1}$ was tested for cross-reactivity on human peripheral blood leukocytes in an attempt to identify a human homolog of canine $\alpha_{TM1}$. Cell preparations (typically $1\times10^6$ cells) were incubated with undiluted hybridoma supernatant or a purified mouse IgG-negative control antibody (10 µg/ml) on ice in the presence of 0.1% sodium azide. Monoclonal antibody binding was detected by subsequent incubation with FITC-conjugated horse anti-mouse IgG (Vector Laboratories, Burlingame, Calif.) at 6 µg/ml. Stained cells were fixed with 2% w/v paraformaldehyde in phosphate buffered saline (PBS) and were analyzed with a Facstar Plus fluorescence-activated cell sorter (Becton Dickinson, Mountain View, Calif.). Typically, 10,000 cells were analyzed using logarithmic amplification for fluorescence intensity.

The results indicated that Ca11.8H2 did not cross-react with surface proteins expressed on human peripheral blood leukocytes, while the control cells, neoplastic canine peripheral blood lymphocytes, were essentially all positive for $\alpha_{TM1}$.

Because the monoclonal antibody Ca11.8H2 specific for the canine α subunit did not cross react with a human homolog, isolation of canine $\alpha_{TM1}$ DNA was deemed a necessary prerequisite to isolate a counterpart human gene if one existed.

EXAMPLE 2

Affinity Purification Of Canine $\alpha_{TM1}$ For N-Terminal Sequencing

Canine $\alpha_{TM1}$ was affinity purified in order to determine N-terminal amino acid sequences for oligonucleotide probe/primer design. Briefly, anti-$\alpha_{TM1}$ monoclonal antibody Ca11.8H2 was coupled to Affigel 10 chromatographic resin (BioRad, Hercules, Calif.) and protein was isolated by specific antibody-protein interaction. Antibody was conjugated to the resin, according to the BioRad suggested protocol, at a concentration of approximately 5 mg antibody per ml of resin. Following the conjugation reaction, excess antibody was removed and the resin blocked with three volumes of 0.1M ethanolamine. The resin was then washed with thirty column volumes of phosphate buffered saline (PBS).

Twenty-five grams of a single dog spleen were homogenized in 250 ml of buffer containing 0.32M sucrose in 25 mM Tris-HCl, Ph 8.0, with protease inhibitors. Nuclei and cellular debris were pelleted with centrifugation at 1000 g for 15 minutes. Membranes were pelleted from the supernatant with centrifugation at 100,000 g for 30 minutes. The membrane pellet was resuspended in 200 ml lysis buffer (50 mM NaCl, 50 mM borate, pH 8.0, with 2% NP-40) and incubated for 1 hour on ice. Insoluble material was then pelleted by centrifugation at 100,000 g for 60 minutes. Ten milliliters of the cleared lysate were transferred to a 15 ml polypropylene tube with 0.5 ml Ca11.8H2-conjugated Affigel 10 resin described above. The tube was incubated overnight at 4° C. with rotation and the resin subsequently washed with 50 column volumes D-PBS. The resin was then transferred to a microfuge tube and boiled for ten minutes in 1 ml Laemmli (non-reducing) sample buffer containing 0.1M Tris-HCl, pH 6.8, 2% SDS, 20% glycerol and 0.002% bromophenol blue. The resin was pelleted by centrifugation and discarded; the supernatant was treated with $\frac{1}{15}$ volume β-mercaptoethanol (Sigma, St. Louis, Mo.) and run on a 7% polyacrylamide gel. The separated proteins were transferred to Immobilon PVDF membrane (Millipore, Bedford, Mass.) as follows.

The gels were washed once in deionized, Millipore-filtered water and equilibrated for 15–45 minutes in 10 mM 3-[cyclohexylamino]-1-propanesulfonic acid (CAPS) transfer buffer, pH 10.5, with 10% methanol. Immobilon membranes were moistened with methanol, rinsed with filtered water, and equilibrated for 15–30 minutes in CAPS transfer buffer. The initial transfer was carried out using a Biorad transfer apparatus at 70 volts for 3 hours. The Immobilon membrane was removed after transfer and stained in filtered 0.1% R250 Coomassie stain for 10 minutes. Membranes were destained in 50% methanol/10% acetic acid three times, ten minutes each time. After destaining, the membranes were washed in filtered water and air-dried.

Protein bands of approximately 150 kD, 95 kD, 50 kD and 30 kD were detected. Presumably the 50 kD and 30 kD bands resulted from antibody contamination. N-terminal sequencing was then attempted on both the 150 kD and 95 kD bands, but the 95 kD protein was blocked, preventing sequencing. The protein band of 150 kD was excised from the membrane and directly sequenced with an Applied Biosystems (Foster City, Calif.) Model 473A protein sequencer according to the manufacturer's instructions. The resulting amino acid sequence is set in SEQ ID NO: 5 using single letter amino acid designations.

FNLDVEEPMVFQ  (SEQ ID NO: 5)

The identified sequence included the FNLD sequence characteristic of α subunits of the integrin family [Tamura, et al., *J. Cell. Biol.* 111:1593–1604 (1990)].

Primer Design and Attempt to Amplify Canine $\alpha_{TM1}$ Sequences

From the N-terminal sequence information, three oligonucleotide probes were designed for hybridization: a) "Tommer," a fully degenerate oligonucleotide; b) "Patmer," a partially degenerate oligonucleotide; and c) "Guessmer," a nondegenerate oligonucleotide based on mammalian codon usage. These probes are set out below as SEQ ID NOS: 6, 7 and 8, respectively. Nucleic acid symbols are in accordance with 37 C.F.R. §1.882 for these and all other nucleotide sequences herein.

| | |
|---|---|
| 5'-TTYAAYYTGGAYGTNGARGARCCNAT-GGTNTTYCA-3' | (SEQ ID NO: 6) |
| 5'-TTCAACCTGGACGTGGAGGAGCCCAT-GGTGTTCCAA-3' | (SEQ ID NO: 7) |
| 5'-TTCAACCTGGACGTNGAASANCCCAT-GGTCTTCCAA-3' | (SEQ ID NO: 8) |

Based on sequencing data, no relevant clones were detected using these oligonucleotides in several low stringency hybridizations to a canine spleen/peripheral blood macrophage cDNA library cloned into λZAP (Stratagene, La Jolla, Calif.).

Four other oligonucleotide primers, designated 5'Deg, 5'Spec, 3'Deg and 3'Spec (as set out in SEQ ID NOS: 9, 10, 11 and 12, respectively, wherein Deg indicates degenerate and Spec indicates non-degenerate) were subsequently designed based on the deduced N-terminal sequence for attempts to amplify canine $\alpha_{TM1}$ sequences by PCR from phage library DNA purified from plate lysates of the Stratagene library described above.

| | |
|---|---|
| 5'-TTYAAYYTNGAYGTNGARGARCC-3' | (SEQ ID NO: 9) |
| 5'-TTYAAYYTGGACGTNGAAGA-3' | (SEQ ID NO: 10) |
| 5'-TGRAANACCATNGGYTC-3' | (SEQ ID NO: 11) |
| 5'-TTGGAAGACCATNGGYTC-3' | (SEQ ID NO: 12) |

The $\alpha_{TM1}$ oligonucleotide primers were paired with T3 or T7 vector primers, as set out in SEQ ID NOS: 13 and 14, respectively, which hybridize to sequences flanking the polylinker region in the Bluescript phagemid found in λZAP.

| | |
|---|---|
| 5'-ATTAACCCTCACTAAAG-3' | (SEQ ID NO: 13) |
| 5'-AATACGACTCACTATAG-3' | (SEQ ID NO: 14) |

The PCR amplification was carried out in Taq buffer (Boehringer Mannheim, Indianapolis, Ind.) containing magnesium with 150 ng of library DNA, 1 μg of each primer, 200 μM dNTPs and 2.5 units Taq polymerase (Boehringer Mannheim) and the products were separated by electrophoresis on a 1% agarose gel in Tris-Acetate-EDTA (TAE) buffer with 0.25 µg/ml ethidium bromide. DNA was transferred to a Hybond (Amersham, Arlington Heights, Ill.) membrane by wicking overnight in 10× SSPE. After transfer, the immobilized DNA was denatured with 0.5M NaOH with 0.6M NaCl, neutralized with 1.0M Tris-HCl, pH 8.0, in 1.5M NaCl, and washed with 2× SSPE before UV crosslinking with a Stratalinker (Stratagene) crosslinking apparatus. The membrane was incubated in prehybridization buffer (5× SSPE, 4× Denhardts, 0.8% SDS, 30% formamide) for 2 hr at 50° C. with agitation.

Oligonucleotide probes 5'Deg, 5'Spec, 3'Deg and 3'Spec (SEQ ID NOS: 9, 10, 11 and 12, respectively) were labeled using a Boehringer Mannheim kinase buffer with 100–300 µCi $\lambda P^{32}$-dATP and 1–3 units of polynucleotide kinase for 1–3 hr at 37° C. Unincorporated label was removed with Sephadex G-25 fine (Pharmacia, Piscataway, N.J.) chromatography using 10 mM Tris-HCl, pH 8.0, 1 mM EDTA (TE) buffer and the flow-through added directly to the prehybridization solution. Membranes were probed for 16 hr at 42° C. with agitation and washed repeatedly, with a final stringency wash of 1× SSPE/0.1% SDS at 50° for 15 min. The blot was then exposed to Kodak X-Omat AR film for 1–4 hours at −80° C.

The oligonucleotides 5'Deg, 5'Spec, 3'Deg and 3'Spec only hybridized to PCR products from the reactions in which they were used as primers and failed to hybridize as expected to PCR products from the reactions in which they were not used as primers. Thus, it was concluded that none of the PCR products were specific for $\alpha_{TM1}$ because no product hybridized with all of the appropriate probes.

EXAMPLE 3

Large Scale Affinity Purification Of Canine $\alpha_{TM1}$ For Internal Sequencing In order to provide additional amino acid sequence for primer design, canine $\alpha_{TM1}$ was purified for internal sequencing. Three sections of frozen spleen (approximately 50 g each) and frozen cells from two partial spleens from adult dogs were used to generate protein for internal sequencing. Fifty grams of spleen were homogenized in 200–300 ml borate buffer with a Waring blender. The homogenized material was diluted with 1 volume of buffer containing 4% NP-40, and the mixture then gently agitated for at least one hour. The resulting lysate was cleared of large debris by centrifugation at 2000 g for 20 min, and then filtered through either a Corning (Corning, N.Y.) prefilter or a Corning 0.8 micron filter. The lysate was further clarified by filtration through the Corning 0.4 micron filter system.

Splenic lysate and the antibody-conjugated Affigel 10 resin described in Example 2 were combined at a 150:1 volume ratio in 100 ml aliquots and incubated overnight at 4° C. with rocking. The lysate was removed after centrifugation at 1000 g for 5 minutes, combined with more antibody-conjugated Affigel 10 resin and incubated overnight as above. The absorbed resin aliquots were then combined and washed with 50 volumes D-PBS/0.1% Tween 20 and the resin transferred to a 50 ml Biorad column. Adsorbed protein was eluted from the resin with 3–5 volumes of 0.1M glycine (pH 2.5); fractions of approximately 900 µl were collected and neutralized with 100 µl 1M Tris buffer, pH 8.0. Aliquots of 15 µl were removed from each fraction and boiled in an equal volume of 2×Laemmli sample buffer with 1/15 volume 1M dithiothreitol (DTF). These samples were electrophoresed on 8% Novex (San Diego, Calif.) polyacrylamide gels and visualized either by Coomassie stain or by silver stain using a Daiichi kit (Enprotech, Natick, Mass.) according to the manufacturer's suggested protocol. Fractions which contained the largest amounts of protein were combined and concentrated by vacuum. The remaining solution was diluted by 50% with reducing Laemmli sample buffer and run on 1.5 mm 7% polyacrylamide gels in Tris-glycine/SDS buffer. Protein was transferred from the gels to Immobilon membrane by the procedure described in Example 2 using the Hoefer transfer apparatus.

The protein bands corresponding to came $\alpha_{TM1}$ were excised from 10 PVDF membranes and resulted in approximately 47 µg total protein. The bands were destained in 4 ml 50% methanol for 5 minutes, air dried and cut into 1×2 mm pieces. The membrane pieces were submerged in 2 ml 95% acetone at 4° C. for 30 minutes with occasional vortexing and then air dried.

Prior to proteolytic cleavage of the membrane bound protein, 3 mg of cyanogen bromide (CNBr) (Pierce, Rockford, Ill.) were dissolved in 1.25 ml 70% formic acid. This solution was then added to a tube containing the PVDF membrane pieces and the tube incubated in the dark at room temperature for 24 hours. The supernatant (S1) was then removed to another tube and the membrane pieces washed with 0.25 ml 70% formic acid. This supernatant (S2) was removed and added to the previous supernatant (S1). Two milliliters of Milli Q water were added to the combined supernatants (S1 and S2) and the solution lyophilized. The PVDF membrane pieces were dried under nitrogen and extracted again with 1.25 ml 60% acetonitrile, 0.1% tetrafluoroacetic acid (TFA) at 42° C. for 17 hours. This supernatant (S3) was removed and the membrane pieces extracted again with 1.0 ml 80% acetonitrile with 0.08% TFA at 42° C. for 1 hour. This supernatant (S4) was combined with the previous supernatants (S1, S2 and S3) and vacuum dried.

The dried CNBr fragments were then dissolved in 63 µl 8M urea, 0.4M $NH_4HCO_3$. The fragments were reduced in 5 µl 45 mM dithiothreitol (DTT) and subsequently incubated at 50° C. for 15 minutes. The solution was then cooled to room temperature and the fragments alkylated by adding 5 µl 100 mM iodoacetamide (Sigma, St. Louis, Mo.). Following a 15 minute incubation at room temperature, the sample was diluted with 187 µl Milli Q water to a final urea concentration of 2.0M. Trypsin (Worthington, Freehold, N.J.) was then added at a ratio of 1:25 (w:w) of enzyme to protein and the protein digested for 24 hours at 37° C. Digestion was terminated with addition of 30 µl TFA.

The protein fragments were then separated with high performance liquid chromatography (HPLC) on a Waters 625 LC system (Millipore, Milford, Mass.) using a 2.1×250 mm, 5 micron Vydac C-18 column (Vydac, Hesperia, Calif.) equilibrated in 0.05% TFA and HPLC water (buffer A). The peptides were eluted with increasing concentration of 80% acetonitrile in 0.04% TFA (buffer B) with a gradient of 38–75% buffer B for 65–95 minutes and 75–98% buffer B for 95–105 minutes. Peptides were fractionated at a flow rate of 0.2 ml/minute and detected at 210 nm.

Following fractionation, the amino acid sequence of the peptides was analyzed by automated Edman degradation performed on an Applied Biosystems Model 437A protein sequencer using the manufacturer's standard cycles and the Model 610A Data Analysis software program, Version 1.2.1. All sequencing reagents were supplied by Applied Biosystems. The amino acid sequences of seven of the eight internal fragments are set out below wherein "X" indicates the identity of the amino acid was not certain.

| | |
|---|---|
| VFQEXGAGFGQ | (SEQ ID NO: 15) |
| LYDXVAATGLXQPI | (SEQ ID NO: 16) |
| PLEYXDVIPQAE | (SEQ ID NO: 17) |
| FQEGFSXVLX | (SEQ ID NO: 18) |
| TSPTFIXMSQENVD | (SEQ ID NO: 19) |
| LVVGAPLEVVAVXQTGR | (SEQ ID NO: 20) |
| LDXKPXDTA | (SEQ ID NO: 21) |

Primer Design

One internal amino acid sequence (set out in SEQ ID NO: 22) obtained was then used to design a fully degenerate oligonucleotide primer, designated p4(R) as set out in SEQ ID NO: 23.

| | |
|---|---|
| FGEQFSE | (SEQ ID NO: 22) |
| 5'-RAANCCYTCYTGRAAACTYTC-3' | (SEQ ID NO: 23) |

EXAMPLE 4

PCR Cloning Of A Canine $\alpha_{TM1}$ Fragment

The 5' portion of the canine $\alpha_{TM1}$ gene was amplified from double-stranded canine splenic cDNA by PCR.

A. Generation of Double Stranded Canine Spleen cDNA

One gram of frozen material from a juvenile dog spleen was ground in liquid nitrogen on dry ice and homogenized in 20 ml RNA-Stat 60 buffer (Tel-Test B, Inc, Friendswood, Tex.). Four ml chloroform were added, and the solution extracted by centrifugation at 12,000 g for 15 minutes. RNA was precipitated from the aqueous layer with 10 ml ethanol. Poly A$^+$ RNA was then selected on Dynal Oligo dT Dynabeads (Dynal, Oslo, Norway). Five aliquots of 100 µg total RNA were combined and diluted with an equal volume of 2× binding buffer (20 mM Tris-HCl, pH 7.5, 1.0M LiCl, 1 mM EDTA, 0.1% SDS). RNA was then incubated 5 minutes with the Oligo dT Dynabeads (1.0 ml or 5 mg beads for all the samples). Beads were washed with buffer containing 10 mM Tris-HCl, pH 7.5, 0.15M LiCl, 1 mM EDTA and 0.1% SDS, according to the manufacturer's suggested protocol prior to elution of poly A$^+$ mRNA with 2 mM EDTA, pH 7.5. Double-stranded cDNA was then generated using the eluted poly A$^+$ mRNA and the Boehringer Mannheim cDNA Synthesis Kit according to the manufacturer's suggested protocol.

B. Isolation of a Partial Canine $\alpha_{TM1}$ cDNA

Oligonucleotide primers 5'Deg (SEQ ID NO: 9) and p4(R) (SEQ ID NO: 23) were employed in a standard PCR reaction using 150 ng double-stranded cDNA, 500 ng of each primer, 200 µM dNTPs and 1.5 units Taq polymerase (Boehringer Mannheim) in Taq buffer (Boehringer Mannheim) with magnesium. The resulting products (1 µl of the original reaction) were subjected to a second round of PCR with the same primers to increase product yield. This band was eluted from a 1% agarose gel onto Schleicher & Schuell (Keene, N.H.) NA45 paper in a buffer containing 10 mM Tris-HCl, 1 pH 8, 1 mM EDTA, 1.5M NaCl at 65° C., precipitated, and ligated into the pCR™II vector (Invitrogen, San Diego, Calif.) using the TA cloning kit (Invitrogen) and the manufacturer's suggested protocol. The ligation mixture was transformed by electroporation into XL-1 Blue bacteria (Stratagene). One clone, 2.7, was determined to contain sequences corresponding to $\alpha_{TM1}$ peptide sequences which were not utilized in design of the primers.

Sequencing was performed with an Applied Biosystems 373A DNA sequencer (Foster City, Calif.) with a Dye-deoxy terminator cycle sequence kit (ABI) in which fluorescent-labeled dNTPs were incorporated in an asymmetric PCR reaction [McCabe, "Production of Single Stranded DNA by Asymmetric PCR," in *PCR Protocols: A Guide to Methods and Applications*, Innis, et al. (eds.) pp. 76–83 Academic Press: New York (1990)] as follows. Samples were held at 96° C. for 4 minutes and subjected to 25 cycles of the step sequence: 96° C., for 15 seconds; 50° C. for 1 second; 60° C. for 4 minutes. Sequence data was automatically downloaded into sample files on the computer that included chromatogram and text files. The sequence of the entire insert of clone 2.7 is set out in SEQ ID NO: 24.

Attempts to isolate the full length canine $\alpha_{TM1}$ cDNA from the Stratagene library (as described in Example 2) were unsuccessful. Approximately 1×10$^6$ phage plaques were screened by hybridization under low stringency conditions using 30% formamide with clone 2.7 as a probe, but no positive clones resulted. Attempts to amplify relevant sequences downstream from those represented in clone 2.7 using specific oligonucleotides derived from clone 2.7 or degenerate primers based on amino acid sequence from other peptide fragments paired with a degenerate oligonucleotide based on the conserved α subunit amino acid motif GFFKR [Tamura, et al., supra] were also unsuccessful.

Example 5

Cloning Of A Putative Human Homolog Of Canine $\alpha_{TM1}$

To attempt the isolation of a human sequence homologous to canine $\alpha_{TM1}$ the approximately 1 kb canine $\alpha_{TM1}$ fragment from clone 2.7 was used as a probe. The probe was generated by PCR under conditions described in Example 2 using NT2 (as set out in SEQ ID NO: 25) and p4(R) (SEQ ID NO: 3) primers.

| | |
|---|---|
| 5'-GTNTTYCARGARGAYGG-3' | (SEQ ID NO: 25) |

The PCR product was purified using the Qiagen (Chatsworth, Ga.) Quick Spin kit and the manufacturer's suggested protocol. The purified DNA (200 ng) was labeled with 200 µCi α$^{32}$PdCTP using the Boehringer Mannheim Random Prime Labelling kit and the manufacturer's suggested protocol. Unincorporated isotope was removed with Sephadex G25 (fine) gravity chromatography. The probe was denatured with 0.2N NaOH and neutralized with 0.4M Tris-HCl, pH 8.0, before use.

Colony lifts on Hybond filters (Amersham) of a human spleen cDNA library in pCDNA/Amp (Invitrogen, San Diego, Calif.) were prepared. The filters were initially denatured and neutralized as described in Example 2 and subsequently incubated in a prehybridization solution (8 ml/filter) with 30% formamide at 50° C. with gentle agitation for 2 hours. Labeled probe as described above was added to this solution and incubated with the filters for 14 hours at 42° C. The filters were washed twice in 2× SSC/0.1% SDS at 37° C. and twice in 2× SSC/0.1% SDS at 50° C. Final stringency washes were 1× SSC/0.1% SDS, twice at 65° C. (1× SSC is 150 mM NaCl, 15 mM sodium citrate, pH 7.0). Filters were exposed to Kodak X-Omat AR film for six hours with an intensifying screen. Colonies giving signals on duplicate lifts were streaked on LB medium with magnesium (LBM)/carbenicillin plates and incubated overnight at 37° C. Resulting streaked colonies were lifted with Hybond filters and these filters were treated as above. The filters were hybridized under more stringent conditions with the 1 kb probe from clone 2.7, labeled as previously described, in a 50% formamide hybridization solution at 50° C. for 3 hours. Probed filters were washed with a final stringency of 0.1×SSC/0.1% SDS at 65° C. and exposed to Kodak X-Omat AR film for 2.5 hours at −80° C. with an intensifying screen. Positive colonies were identified and cultured in LBM/carbenicillin medium overnight. DNA from the cultures was prepared using the Promega Wizard miniprep kit according to the manufacturer's suggested protocol and the resulting DNA was sequenced.

The initial screening resulted in 18 positive clones, while the secondary screening under more stringent hybridization conditions produced one positive clone which was designated 19A2. The DNA and deduced amino acid sequences of the human $\alpha_d$ clone 19A2 are set out in SEQ ID NOS: 1 and 2, respectively.

Characteristics of The Human $\alpha_d$ cDNA and Predicted Polypeptide

Clone 19A2 encompasses the entire coding region for the mature protein, plus 48 bases (16 amino acid residues) of the 5' upstream signal sequence and 241 bases of 3' untranslated sequence which do not terminate in a polyadenylation sequence. The core molecular weight of the mature protein is predicted to be around 125 kD. The extracellular domain is predicted to encompass approximately amino acid residues 17 through 1108 of SEQ ID NO: 2. This extracellular region is contiguous with about a 20 amino acid region homologous to the human CD11c transmembrane region (residues 1109 through 1128 of SEQ ID NO: 2). The cytoplasmic domain comprises approximately 30 amino acids (about residues 1129 through 1161 of SEQ ID NO: 2). The protein also contains a region (around residues 150 through 352) of approximately 202 amino acids homologous to the I (insertion) domain common to CD11a, CD11b and CD11c [Larson and Springer, supra], $\alpha_E$ [Shaw, et al., *J. Biol. Chem.* 269:6016–6025 (1994)] and in VLA-1 and VLA-2, [Tamura, et al., supra]. The I domain in other integrins has been shown to participate in ICAM binding [Landis, et al., *J. Cell. Biol.* 120:1519–1527 (1993); Diamond, et al., *J. Cell. Biol.* 120:1031–1043 (1993)], suggesting that $\alpha_d$ may also bind members of the ICAM family of surface molecules. This region has not been demonstrated to exist in any other integrin subunits.

The deduced amino acid sequence of $\alpha_d$ shows approximately 36% identity to that of CD11a, approximately 60% identity to CD11b and approximately 66% identity to CD11c. An alignment of amino acid sequences for (CD11b SEQ ID NO: 3), CD11c (SEQ ID NO: 4) and $\alpha_d$ (SEQ ID NO: 2) is presented in FIG. 1.

The cytoplasmic domains of $\alpha$ subunits in $\beta_2$ integrins are typically distinct from one another within the same species, while individual $\alpha$ subunits show high degrees of homology across species boundaries. Consistent with these observations, the cytoplasmic region of $\alpha_d$ differs markedly from CD11a, CD11b, and CD11c except for a membrane proximal GFFKR amino acid sequence which has been shown to be conserved among all $\alpha$ integrins [Rojiani, et al., *Biochemistry* 30:9859–9866 (1991)]. Since the cytoplasmic tail region of integrins has been implicated in "inside out" signaling and in avidity regulation [Landis et al., supra], it is possible that $\alpha_d$ interacts with cytosolic molecules distinct from those interacting with CD11a, CD11b, and CD11c, and, as a result, participates in signaling pathways distinct from those involving other $\beta_2$ integrins.

The extracellular domain of $\alpha_d$ contains a conserved DGSGS amino acid sequence adjacent the I-domain; in CD11b, the DGSGS sequence is a metal-binding region required for ligand interaction [Michishita, et al. *Cell* 72:857–867 (1993)]. Three additional putative cation binding sites in CD11b and CD11c are conserved in the $\alpha_d$ sequence at amino acids 465–474, 518–527, and 592–600 in clone 19A2 (SEQ ID NO: 1). The $\alpha_d$ I-domain is 36%, 62%, and 57% identical to the corresponding regions in CD11a, CD11b, and CD11c, respectively, and the relatively low sequence homology in this region suggests that $\alpha_d$ may interact with a set of extracellular proteins distinct from proteins with which other known $\beta_2$ integrins interact. Alternatively, the affinity of $\alpha_d$ for known $\beta_2$ integrin ligands, for example, ICAM-1, ICAM-2 and/or ICAM-R, may be distinct from that demonstrated for the other $\beta_2$ integrin/ICAM interactions. [See Example 12.]

Isolation of additional human $\alpha_d$ cDNA clones for sequence verification

In order to confirm the DNA sequence encoding human $\alpha_d$, additional human cDNAs were isolated by hybridization from a human splenic oligo dt-primed cDNA library (Invitrogen) in pcDNA/Amp (described in Example 5) which was size selected by agarose gel electrophoresis for cDNA greater than 3 kb in length. The probe for hybridization was derived from a 5' region of $\alpha_d$ as described below. Hybridization conditions were the same as described above for the isolation of the initial human $\alpha_d$ clone, except that following hybridization, filters were washed twice in 2× SSC/0.1% SDS at room temperature and once in 2× SSC/0.1% SDS at 42° C. Filters were exposed to Kodak X-Omat AR film overnight.

The 5' $\alpha_d$ hybridization probe was generated by PCR from the 19A2 clone using primers CD11c 5' For (SEQ ID NO: 94) and CD11c 5' Rev (SEQ ID NO: 95) under the following conditions. Samples were held at 94° C. for four minutes and subjected to 30 cycles of the temperature step sequence i) 94° C., for 15 seconds; ii) 5° C., for 30 seconds; and iii) 72° C., for 1 minute in a Perkin-Elmer 9600 thermocycler.

CD11c 5' For: (5')CTGGTCTGGAGGTGCC-
TTCCTG(3')                                   (SEQ ID NO: 94)

CD11c 5' Rev: (5')CCTGAGCAGGAGCACC-
TGGCC(3')                                    (SEQ ID NO: 95)

The amplification product was purified using the BioRad (Hercules, Calif.) Prep-A-Gene kit according to manufacturer's suggested protocol. The resulting 5' $\alpha_d$ probe was approximately 720 bases long, corresponding to the region from nucleotide 1121 to nucleotide 1839 in SEQ ID NO: 1. The purified DNA (approximately 50 ng) was labeled with $^{32}$P-dCTP using a Boehringer Mannheim (Indianapolis, Ind.) Random Prime Labeling kit according to manufacturer's suggested protocol. Unincorporated isotope was removed using Centrisep Spin Columns (Princeton Separations, Adelphia, N.J.) according to manufacturer's suggested protocol. Labeled probe was added to the filters in a prehybridization solution containing 45% formamide and incubation allowed to proceed overnight at 50° C. Following incubation, the filters were washed as described above.

Thirteen colonies gave signals on duplicate lifts. Positive colonies were picked from master plates, diluted in LBM and carbenicillin (100 µg/ml) and plated at varying dilutions onto Hybond (Amersham) filters. Duplicate filters were hybridized with the same solution from the primary hybridization and following hybridization, the filters were washed at a final stringency of 2× SSC/0.1% SDS at 42° C. and exposed to film.

Ten of the originally identified thirteen positive colonies were confirmed in the secondary screen. Of these ten clones, two (designated A7.Q and A8.Q) were sequenced and determined to encode human $\alpha_d$. Clone A7.Q was found to be approximately 2.5 kb in length, including a 5' leader, part of a coding region, and an additional 60 bases of 5' untranslated sequence. The incomplete coding region was determined to have resulted from an aberrantly spliced intron region at corresponding nucleotide 2152 of SEQ ID NO: 1. Clone A8.Q was determined to be approximately 4 kb in length, spanning the entire $\alpha_d$ coding region and also including an intron sequence at corresponding base 305 of SEQ ID NO: 1. In comparison to the originally isolated $\alpha_d$ clone (SEQ ID NO: 1), one difference was observed in that both A7.Q and A8.Q clones were determined to have a three base CAG codon insertion occurring at base 1495. Sequences for clones A7.Q AND A8.Q are set out in SEQ ID NOs: 96 and 97, respectively, and a composite human sequence derived from clones A7.Q and A8.Q, and its corresponding deduced amino acid sequence, are set out in SEQ ID NOs: 98 and 99, respectively.

EXAMPLE 6

Northern Analysis of Human $\alpha_d$ Expression in Tissues

In order to determine the relative level of expression and tissue specificity of $\alpha_d$, Northern analysis was performed using fragments from clone 19A2 as probes. Approximately 10 μg of total RNA from each of several human tissues or cultured cell lines were loaded on a formaldehyde agarose gel in the presence of 1 μg of ethidium bromide. After electrophoresis at 100 V for 4 hr, the RNA was transferred to a nitrocellulose membrane (Schleicher & Schuell) by wicking in 10× SSC overnight. The membrane was baked 1.5 hr at 80° C. under vacuum. Prehybridization solution containing 50% formamide in 3-(N-morpholino)propane sulfonic acid (MOPS) buffer was used to block the membrane for 3 hr at 42° C. Fragments of clone 19A2 were labeled with the Boehringer Mannheim Random Prime kit according to the manufacturer's instructions including both $\alpha P^{32}dCTP$ and $\alpha P^{32}dTTP$. Unincorporated label was removed on a Sephadex G25 column in TE buffer. The membrane was probed with $1.5 \times 10^6$ counts per ml of prehybridization buffer. The blot was then washed successively with 2× SSC/0.1% SDS at room temperature, 2× SSC/0.1% SDS at 42° C., 2× SSC/0.1% SDS at 50° C., 1× SSC/0.1% SDS at 50° C., 0.5× SSC/0.1% SDS at 50° C. and 0.1× SSC/0.1% SDS at 50° C. The blot was then exposed to film for 19 hr.

Hybridization using a BstXI fragment from clone 19A2 (corresponding to nucleotides 2011 to 3388 in SEQ ID NO: 1) revealed a weak signal in the approximately 5 kb range in liver, placenta, thymus, and tonsil total RNA. No signal was detected in kidney, brain or heart samples. The amount of RNA present in the kidney lane was minimal, as determined with ethidium bromide staining.

When using a second fragment of clone 19A2 (encompassing the region from bases 500 to 2100 in SEQ ID NO: 1), RNA transcripts of two different sizes were detected in a human multi-tissue Northern (MTN) blot using polyA$^+$ RNA (Clontech). An approximately 6.5 kb band was observed in spleen and skeletal muscle, while a 4.5 kb band was detected in lung and peripheral blood leukocytes. The variation in sizes observed could be caused by tissue specific polyadenylation, cross reactivity of the probe with other integrin family members, or hybridization with alternatively spliced mRNAs.

Northern analysis using a third fragment from clone 19A2, spanning nucleotides 2000 to 3100 in SEQ ID NO: 1, gave results consistent with those using the other clone 19A2 fragments.

RNA from three myeloid lineage cell lines was also probed using the fragments corresponding to nucleotides 500 to 2100 and 2000 to 3100 in SEQ ID NO:1. A THP-1 cell line, previously stimulated with PMA, gave a diffuse signal in the same size range (approximately 5.0 kb), with a slightly stronger intensity than the tissue signals. RNA from unstimulated and DMSO-stimulated HL-60 cells hybridized with the $\alpha_d$ probe at the same intensity as the tissue samples, however. PMA treatment seemed to increase the signal intensity. Since PMA and DMSO drive HL-60 cell differentiation toward monocyte/macrophage and granulocyte pathways, respectively, this result suggests enhanced $\alpha_d$ expression in monocyte/macrophage cell types. U937 cells expressed the $\alpha_d$ message and this signal did not increase with PMA stimulation. No band was detected in Molt, Daudi, H9, JY, or Jurkat cells.

EXAMPLE 7

Transient Expression of Human $\alpha_d$ Constructs

A. Generation of expression constructs

The human clone 19A2 lacks an initiating methionine codon and possibly some of the 5' signal sequence. Therefore, in order to generate a human expression plasmid containing 19A2 sequences, two different strategies were used. In the first, two plasmids were constructed in which signal peptide sequences derived from genes encoding either CD11b or CD11c were spliced into clone 19A2 to generate a chimeric $\alpha_d$ sequence. In the second approach, a third plasmid was constructed in which an adenosine base was added at position 0 in clone 19A2 to encode an initiating methionine.

The three plasmids contained different regions which encoded the 5' portion of the $\alpha_d$ sequence or the chimeric $\alpha_d$ sequence. The $\alpha_d$ region was PCR amplified (see conditions in Example 2) with a specific 3' primer BamRev (set out below in SEQ ID NO: 26) and one of three 5' primers. The three 5' primers contained in sequence: (1) identical non-specific bases at positions 1–6 allowing for digestion, an EcoRI site from positions 7–12 and a consensus Kozak sequence from positions 13–18; (2) a portion of the CD11b (primer ER1B) or CD11c (primer ER1C) signal sequence, or an adenosine (primer EL1D); and (3) an additional 15–17 bases specifically overlapping 5' sequences from clone 19A2 to allow primer annealing. Primers ER1B, ER1C or ER1D are set out in SEQ ID NOS: 27, 28 or 29, respectively, where the initiating methionine codon is 6underlined and the EcoRI site is double underlined.

| | |
|---|---|
| 5'-CCACTGTCAGGATGCCCGTG-3' | (SEQ ID NO: 26) |
| 5'-AGTTACGAATTCGCCACC ATGGCTCTACGGGTGCTTCTTCTG-3' | (SEQ ID NO: 27) |
| 5'-AGTTACGAATTCGCCACC ATGACTCGGACTGTGCTTCTTCTG-3' | (SEQ ID NO: 28) |
| 5'-AGTTACGAATTCGCCACCATGACCTT-CGGCACTGTG-3' | (SEQ ID NO: 29) |

The resulting PCR product was digested with EcoRI and BamHI.

All three plasmids contained a common second $\alpha_d$ region (to be inserted immediately downstream from the 5' region described in the previous paragraph) including the 3' end of the $\alpha_d$ clone. The second $\alpha_d$ region, which extended from nucleotide 625 into the XbaI site in the vector 3' polylinker region of clone 19A2, was isolated by digestion of clone 19A2 with BamHI and XbaI.

Three ligation reactions were prepared in which the 3' $\alpha_d$ BamHI/XbaI fragment was ligated to one of the three 5' $\alpha_d$ EcoRI/BamHI fragments using Boehringer Mannheim ligase buffer and T4 ligase (1 unit per reaction). After a 4 hour incubation at 14° C., an appropriate amount of vector pcDNA.3 (Invitrogen) digested with EcoRI and XbaI was added to each reaction with an additional unit of ligase. Reactions were allowed to continue for another 14 hours. One tenth of the reaction mixture was then transformed into competent XL-1 Blue cells. The resulting colonies were cultured and the DNA isolated as in Example 5. Digestion with EcoRI identified three clones which were positive for that restriction site, and thus, the engineered signal sequences. The clones were designated pATM.B1 (CD11b/$\alpha_d$, from primer ER1B), pATM.C10 (CD11c/$\alpha_d$, from primer ER1C) and pATM.D12 (adenosine/$\alpha_d$ from primer ER1d). The presence of the appropriate signal sequences in each clone was verified by nucleic acid sequencing.

B. Transfection of COS Cells

Expression from the $\alpha_d$ plasmids discussed above was effected by cotransfection of COS cells with the individual plasmids and a CD18 expression plasmid, pRC.CD18. As a positive control, COS cells were also co-transfected with the plasmid pRC.CD18 and a CD11a expression plasmid, pDC.CD11A.

Cells were passaged in culture medium (DMEM/10% FBS/pen-strep) into 10 cm Corning tissue culture-treated petri dishes at 50% confluency 16 hours prior to transfection. Cells were removed from the plates with Versene buffer (0.5 mM NaEDTA in PBS) without trypsin for all procedures. Before transfection, the plates were washed once with serum-free DMEM. Fifteen micrograms of each plasmid were added to 5 ml transfection buffer (DMEM with 20 µg/ml DEAE-Dextran and 0.5 mM chloroquine) on each plate. After 1.5 hours incubation at 37° C., the cells were shocked for 1 minute with 5 ml DMEM/10% DMSO. This DMSO solution was then replaced with 10 ml/plate culture medium.

Resulting transfectants were analyzed by ELISA, FACS, and immunoprecipitation as described in Examples 8, 9, and 10.

EXAMPLE 8

ELISA Analysis of COS Transfectants

In order to determine if the COS cells co-transfected with CD18 expression plasmid pRC.CD18 and an $\alpha_d$ plasmid expressed $\alpha_d$ on the cell surface in association with CD18, ELISAs were performed using primary antibodies raised against CD18 (e.g., TS1/18 purified from ATCC HB203). As a positive control, ELISAs were also performed on cells co-transfected with the CD18 expression plasmid and a CD11a expression plasmid, pDC.CD11A. The primary antibodies in this control included CD18 antibodies and anti-CD11a antibodies (e.g., TS1/22 purified from ATCC HB202).

For ELISA, cells from each plate were removed with Versene buffer and transferred to a single 96-well flat-bottomed Corning tissue culture plate. Cells were allowed to incubate in culture media 2 days prior to assay. The plates were then washed twice with 150 µl/well D-PBS/0.5% teleost skin gelatin (Sigma) solution. This buffer was used in all steps except during the development. All washes and incubations were performed at room temperature. The wells were blocked with gelatin solution for 1 hour. Primary antibodies were diluted to 10 µg/ml in gelatin solution and 50 µl were then added to each well. Triplicate wells were set up for each primary antibody. After 1 hour incubation, plates were washed 3× with 150 µl/well gelatin solution. Secondary antibody (goat anti-mouse Ig/HRP-Fc specific [Jackson, West Grove, Pa.]) at a 1:3500 dilution was added at 50 µl/well and plates were incubated for 1 hour. After three washes, plates were developed for 20 minutes with 100 µl/well o-phenyldiamine (OPD) (Sigma) solution (1 mg/ml OPD in citrate buffer) before addition of 50 µl/well 15% sulfuric acid.

Analysis of transfectants in the ELISA format with anti-CD18 specific antibodies revealed no significant expression above background in cells transfected only with the plasmid encoding CD18. Cells co-transfected with plasmid containing CD11a and CD18 showed an increase in expression over background when analyzed with CD18 specific antibodies or with reagents specific for CD11a. Further analysis of cells co-transfected with plasmids encoding CD18 and one of the $\alpha_d$ expression constructs (pATM.C10 or pATM.D12) revealed that cell surface expression of CD18 was rescued by concomitant expression of $\alpha_d$. The increase in detectable CD18 expression in COS cells transfected with pATM.C10 or pATM.D12 was comparable to that observed in co-transfected CD11a/CD18 positive control cells.

EXAMPLE 9

FACS Analysis of COS Transfectants

For FACS analysis, cells in petri dishes were fed with fresh culture medium the day after transfection and allowed to incubate 2 days prior to the assay. Transfectant cells were removed from the plates with 3 ml Versene, washed once with 5 ml FACS buffer (DMEM/2% FBS/0.2% sodium azide) and diluted to 500,000 cells/sample in 0.1 ml FACS buffer. Ten microliters of either 1 mg/ml FITC-conjugated CD18, CD11a, or CD11b specific antibodies (Becton Dickinson) or 800 µg/ml CFSE-conjugated murine 23F2G (anti-CD18) (ATCC HB11081) were added to each sample. Samples were then incubated on ice for 45 minutes, washed 3× with 5 ml/wash FACS buffer and resuspended in 0.2 ml FACS buffer. Samples were processed on a Becton Dickinson FACscan and the data analyzed using Lysys II software (Becton Dickinson).

COS cells transfected with CD18 sequences only did not stain for CD18, CD11a or CD11b. When co-transfected with CD11a/CD18, about 15% of the cells stained with antibodies to CD11a or CD18. All cells transfected with CD18 and any $\alpha_d$ construct resulted in no detectable staining for CD11a and CD11b. The pATM.B1, pATM.C10 and pATM.D12 groups stained 4%, 13% and 8% positive for CD18, respectively. Fluorescence of the positive population in the CD11a/CD18 group was 4-fold higher than background. In comparison, the co-transfection of $\alpha_d$ constructs with the CD18 construct produced a positive population that showed a 4- to 7-fold increase in fluorescence intensity over background.

EXAMPLE 10

Biotin-Labeled Immunoprecipitation of Human $\alpha_d$/CD18 Complexes from Co-transfected COS Cells Immunoprecipitation was attempted on cells co-transfected with CD18 and each of the $\alpha_d$ expression plasmids separately described in Example 7 in order to determine if $\alpha_d$ could be isolated as part of the $\alpha\beta$ heterodimer complex characteristic of integrins.

Transfected cells (1–3×10$^8$ cells/group) were removed from petri dishes with Versene buffer and washed 3 times in 50 ml/group D-PBS. Each sample was labeled with 2 mg Sulpho-NHS Biotin (Pierce, Rockford, Ill.) for 15 minutes at room temperature. The reaction was quenched by washing 3 times in 50 ml/sample cold D-PBS. Washed cells were resuspended in 1 ml lysis buffer (1% NP40, 50 mM Tris-HCl, pH 8.0, 0.2M NaCl, 2 mM $Ca^{++}$, 2 mM $Mg^{++}$, and protease inhibitors) and incubated 15 minutes on ice. Insoluble material was pelleted by centrifugation at 10,000 g for 5 minutes, and the supernatant removed to fresh tubes. In order to remove material non-specifically reactive with mouse immunoglobulin, a pre-clearance step was initially performed. Twenty-five micrograms of mouse immunoglobulin (Cappel, West Chester, Pa.) was incubated with supernatants at 4° C. After 2.5 hr, 100 μl (25 μg) rabbit anti-mouse Ig conjugated Sepharose (prepared from Protein A Sepharose 4B and rabbit anti-mouse IgG, both from Zymed, San Francisco, Calif.) was added to each sample; incubation was continued at 4° C. with rocking for 16 hours. Sepharose beads were removed from the supernatants by centrifugation. After pre-clearance, the supernatants were then treated with 20 μg anti-CD18 antibody (TS1.18) for 2 hours at 4° C. Antibody/antigen complexes were isolated from supernatants by incubation with 100 μl/sample rabbit anti-mouse/Protein A-sepharose preparation described above. Beads were washed 4 times with 10 mM HEPES, 0.2M NaCl, and 1% Triton-X 100. Washed beads were pelleted and boiled for 10 minutes in 20 μl 2× Laemmli sample buffer with 2% β-mercaptoethanol. Samples were centrifuged and run on an 8% prepoured Novex polyacrylamide gel (Novex) at 100 V for 30 minutes. Protein was transferred to nitrocellulose membranes (Schleicher & Schuell) in TBS-T buffer at 200 mAmps for 1 hour. Membranes were blocked for 2 hr with 3% BSA in TBS-T. Membranes were treated with 1:6000 dilution of Strep-avidin horse radish peroxidase (POD) (Boehringer Mannheim) for 1 hour, followed by 3 washes in TBS-T. The Amersham Enhanced Chemiluminescence kit was then used according to the manufacturer's instructions to develop the blot. The membrane was exposed to Hyperfilm MP (Amersham) for 0.5 to 2 minutes.

Immunoprecipitation of CD18 complexes from cells transfected with pRC.CD18 and either pATM.B1, pATM.C10 or pATM.D12 revealed surface expression of a heterodimeric species consisting of approximately 100 kD β chain, consistent with the predicted size of CD18, and an α chain of approximately 150 kD, corresponding to $\alpha_d$.

EXAMPLE 11

Stable Transfection of Human $\alpha_d$ in Chinese Hamster Ovary Cells

To determine whether $\alpha_d$ is expressed on the cell surface as a heterodimer in association with CD18, cDNAs encoding each chain were both transiently and stably transfected into a cell line lacking both $\alpha_d$ and CD18.

For these experiments, $\alpha_d$ cDNA was augmented with additional leader sequences and a Kozak consensus sequence, as described in Example 7, and subcloned into expression vector pcDNA3. The final construct, designated pATM.D12, was co-transfected with a modified commercial vector, pDC 1. CD18 encoding human CD18 into dihydrofolate reductase (DHFR)⁻ Chinese hamster ovary (CHO) cells. The plasmid pDC1.CD18 encodes a DHFR⁺ marker and transfectants can be selected using an appropriate nucleoside-deficient medium. The modifications which resulted in pDC1.CD18 are as follows.

The plasmid pRC/CMV (Invitrogen) is a mammalian expression vector with a cytomegalovirus promoter and ampicillin resistance marker gene. A DHFR gene from the plasmid pSC1190-DHFR was inserted into pRC/CMV 5' of the SV40 origin of replication. In addition, a polylinker from the 5' region of the plasmid pHF2G-DHF was ligated into the pRC/CMV/DHFR construct, 3' to the DHFR gene. CD18 encoding sequences are subsequently cloned into the resulting plasmid between the 5' flanking polylinker region and the bovine growth hormone poly A encoding region.

Surface expression of CD18 was analyzed by flow cytometry using the monoclonal antibody TS1/18. Heterodimer formation detected between $\alpha_d$ and CD18 in this cell line was consistent with the immunoprecipitation described in Example 10 with transient expression in COS cells.

EXAMPLE 12

Human $\alpha_d$ binds to ICAM-R in a CD18-dependent fashion

In view of reports that demonstrate interactions between the leukocyte integrins and intercellular adhesion molecules (ICAMs) which mediate cell-cell contact [Hynes, Cell 69:11–25 (1992)], the ability of CHO cells expressing $\alpha_d$/CD18 to bind ICAM-1, ICAM-R, or VCAM-1 was assessed by two methods.

In replicate assays, soluble ICAM-1, ICAM-R, or VCAM-1 IgG1 fusion proteins were immobilized on plastic and the ability of $\alpha_d$/CD18 CHO transfected cells to bind the immobilized ligand was determined. Transfected cells were labeled internally with calcein, washed in binding buffer (RPMI with 1% BSA), and incubated in either buffer only (with or without 10 ng/ml PMA) or buffer with anti-CD18 monoclonal antibodies at 10 μg/ml. Transfected cells were added to 96-well Immulon 4 microtiter plates previously coated with soluble ICAM-1/IgG1, ICAM-R/IgG1 or VCAM-1/IgG1 fusion protein, or bovine serum albumin (BSA) as a negative control. Design of the soluble forms of these adhesion molecules is described and fully disclosed in co-pending and co-owned U.S. patent application Ser. No. 08/102,852, filed Aug. 5, 1993. Wells were blocked with 1% BSA in PBS prior to addition of labeled cells. After washing the plates by immersion in PBS with 0.1% BSA for 20 minutes, total fluorescence remaining in each well was measured using a Cytofluor 2300 (Millipore, Milford, Mass.).

In experiments with immobilized ICAMs, $\alpha_d$/CD18 co-transfectants consistently showed a 3–5 fold increase in binding to ICAM-R/IgG1 wells over BSA coated wells. The specificity and CD18-dependence of this binding was demonstrated by the inhibitory effects of anti-CD18 antibody TS 1/18. The binding of cells transfected with CD11a/CD18 to ICAM-1/IgG1 wells was comparable to the binding observed with BSA coated wells. CD11a/CD18 transfected cells showed a 2–3 fold increase in binding to ICAM-1/IgG1 wells only following pretreatment with PMA. PMA treatment of $\alpha_d$/CD18 transfectants did not affect binding to ICAM-1/IgG1 or ICAM-R/IgG1 wells. No detectable binding of $\alpha_d$/CD18 transfectants to VCAM-1/IgG1 wells was observed.

Binding of $\alpha_d$/CD18-transfected cells to soluble ICAM-1/IgG1, ICAM-R/IgG1, or VCAM-1/IgG1 fusion proteins was determined by flow cytometry. Approximately one million $\alpha_d$/CD18-transfected CHO cells (grown in spinner flasks for higher expression) per measurement were suspended in 100 μl binding buffer (RPMI and 1% BSA) with or without 10 μg/ml anti-CD18 antibody. After a 20 minute incubation at room temperature, the cells were washed in binding buffer and soluble ICAM-1/IgG1 or ICAM-R/IgG1 fusion protein was added to a final concentration of 5 μg/ml. Binding was allowed to proceed for 30 minute at 37° C., after which the cells were washed three times and resuspended in 100 μl binding buffer containing FITC-conjugated sheep anti-human IgG1 at a 1:100 dilution. After a 30 minute incubation, samples were washed three times and suspended in 200 μl binding buffer for analysis with a Becton Dickinson FACScan.

Approximately 40–50% of the $\alpha_d$/CD18 transfectants indicated binding to ICAM-R/IgG1, but no binding to ICAM-1/IgG1 or VCAM-1/IgG1 proteins. Pretreatment of transfected cells with PMA has no effect on $\alpha_d$/CD18 binding to either ICAM-1/IgG1, ICAM-R/IgG1 or VCAM-1/IgG1, which was consistent with the immobilized adhesion assay. Binding by ICAM-R was reduced to background levels after treatment of $\alpha_d$/CD18 transfectants with anti-CD 18 antibody TS1/18.

The collective dam from these two binding assays illustrate that $\alpha_d$/CD18 binds to ICAM-R and does so preferentially as compared to ICAM-1 and VCAM-1. The $\alpha_d$/CD18 binding preference for ICAM-R over ICAM-1 is opposite that observed with CD11a/CD18 and CD11b/CD18. Thus modulation of $\alpha_d$/CD18 binding may be expected to selectively affect normal and pathologic immune function where ICAM-R plays a prominent role. Moreover, results of similar assays, in which antibodies immunospecific for various extracellular domains of ICAM-R were tested for their ability to inhibit binding of ICAM-R to $\alpha_d$/CD18 transfectants, indicated that $\alpha_d$/CD18 and CD11a/CD18 interact with different domains of ICAM-R.

The failure of CD11a/CD18 to bind ICAM-1/IgG1 or ICAM-R/IgG1 in solution suggests that the affinity of binding between CD11a/CD18 and ICAM-1 or ICAM-R is too low to permit binding in solution. Detection of $\alpha_d$/CD18 binding to ICAM-R/IgG1, however, suggests an unusually high binding affinity.

$\alpha_d$ Binding to iC3b

Complement component C3 can be proteolytically cleaved to form the complex iC3b, which initiates the alternative pathway of complement activation and leads ultimately to cell-mediated destruction of a target. Both CD11b and CD11c have been implicated in iC3b binding and subsequent phagocytosis of iC3b-coated particles. A peptide fragment in the CD11b I domain has recently been identified as the site of iC3b interaction [Ueda, et al., *Proc. Natl. Acad. Sci.* (USA) 91:10680–10684 (1994)]. The region of iC3b binding is highly conserved in CD11b, CD11c, and $\alpha_d$, suggesting an $\alpha_d$/iC3b binding interaction.

Binding of $\alpha_d$ to iC3b is performed using transfectants or cell lines naturally expressing $\alpha_d$ (for example, PMA-stimulated HL60 cells) and iC3b-coated sheep red blood cells (sRBC) in a rosette assay [Dana, et al., *J. Clin. Invest.* 73:153–159 (1984)]. The abilities of $\alpha_d$/CD18 CHO transfectants, VLA4-CHO transfectants (negative control) and PMA-stimulated HL60 cells (positive control) to form rosettes are compared in the presence and absence of an anti-CD18 monoclonal antibody (for example TS1/18.1).

EXAMPLE 13

Screening by Scintillation Proximity Assay

Specific inhibitors of binding between the $\alpha_d$ ligands of the present invention and their binding partners ($\alpha_d$ ligand/anti-ligand pair) may be determined by a variety of means, such as scintillation proximity assay techniques as generally described in U.S. Pat. No. 4,271,139, Hart and Greenwald, *Mol. Immunol.* 12:265–267 (1979), and Hart and Greenwald, *J. Nuc. Med.* 20:1062–1065 (1979), each of which is incorporated herein by reference.

Briefly, one member of the $\alpha_d$ ligand/anti-ligand pair is bound to a solid support either directly or indirectly. Indirect capture would involve a monoclonal antibody, directly bound to the support, which recognizes a specific epitope at the C-terminus of the soluble integrin β chain protein. This epitope would be either the hemagglutinin protein or the mycobacterial IIIE9 epitope [Anderson, et al., *J. Immunol.* 141:607–613 (1988). A fluorescent agent is also bound to the support. Alternatively, the fluorescent agent may be integrated into the solid support as described in U.S. Pat. No. 4,568,649, incorporated herein by reference. The non-support bound member of the $\alpha_d$ ligand/anti-ligand pair is labeled with a radioactive compound that emits radiation capable of exciting the fluorescent agent. When the ligand binds the radiolabeled anti-ligand, the label is brought sufficiently close to the support-bound fluorescer to excite the fluorescer and cause emission of light. When not bound, the label is generally too distant from the solid support to excite the fluorescent agent, and light emissions are low. The emitted light is measured and correlated with binding between the ligand and the anti-ligand. Addition of a binding inhibitor to the sample will decrease the fluorescent emission by keeping the radioactive label from being captured in the proximity of the solid support. Therefore, binding inhibitors may be identified by their effect on fluorescent emissions from the samples. Potential anti-ligands to $\alpha_d$ may also be identified by similar means.

EXAMPLE 14

Soluble Human $\alpha_d$ Expression Constructs

The expression of full-length, soluble human $\alpha_d$/CD 18 heterodimeric protein provides easily purified material for immunization and binding assays. The advantage of generating soluble protein is that it can be purified from supernatants rather than from cell lysates (as with full-length membrane-bound $\alpha_d$/CD18); recovery in therefore improved and impurities reduced.

The soluble $\alpha_d$ expression plasmid was constructed as follows. A nucleotide fragment corresponding to the region from bases 0 to 3161 in SEQ ID NO: 1, cloned into plasmid pATM.D12, was isolated by digestion with HindIII and AatII. A PCR fragment corresponding to bases 3130 to 3390 in SEQ ID NO: 1, overlapping the HindIII/AatII fragment and containing an addition MluI restriction site at the 3' terminus, was amplified from pATM.D12 with primers sHAD.5 and sHAD.3 set out in SEQ ID NOS: 30 and 31, respectively.

| | |
|---|---|
| 5'-TTGCTGACTGCCTGCAGTTC-3' | (SEQ ID NO: 30) |
| 5'-GTTCTGACGCGTAATGGCATTGTAG-ACCTCGTCTTC-3' | (SEQ ID NO: 31) |

The PCR amplification product was digested with AatII and MluI and ligated to the HindIII/AatII fragment. The resulting product was ligated into HindIII/MluI-digested plasmid pDC 1.s.

This construct is co-expressed with soluble CD18 in stably transfected CHO cells, and expression is detected by autoradiographic visualization of immunoprecipitated CD 18 complexes derived from $^{35}$S-methionine labeled cells. The construct is also co-expressed with CD18 in 293 cells [Bennan, et al., *J. Cell. Biochem.* 52:183–195 (1993)].

Soluble full-length $\alpha_d$ construct

In order to facilitate expression and purification of an intact $\alpha_d$/CD18 heterodimer, soluble $\alpha_d$ and CD18 expression plasmids will be constructed to include a "leucine zipper" fusion sequence which should stabilize the heterodimer during purification [Chang, et al., *Proc. Natl. Acad.*

Sci. (USA), 91:11408–11412 (1994)]. Briefly, DNA encoding the acidic and basic amino acid strands of the zipper have been generated by primer annealing using oligonucleotides described in Chang, et al. The DNA sequences have been further modified to include additional MluI and Xba 1 restriction sites at the 5' and 3' ends, respectively, of the DNA to facilitate subcloning into $\alpha_d$ or CD18 expression constructs previously described. In addition, sequences representing either hemagglutinin protein or a polyhistidine sequence have been added, as well as a stop codon inserted after the XbaI site. The hemagglutinin or polyhistidine sequences are incorporated to facilitate affinity purification of the expressed protein. Sequences encoding the basic strand of the zipper are incorporated on the plasmid vector expressing CD18; the acidic strand is inserted on the α chain construct. Upon expression of the modified $\alpha_d$ and CD18 proteins in a host cell, it is presumed that interaction between the acidic and basic strands of the zipper structure will stabilize the heterodimer and permit isolation of the intact $\alpha_d$/CD18 molecule by affinity purification as described above.

Soluble Human $\alpha_d$ I Domain Expression Constructs

It has previously been reported that the I domain in CD11a can be expressed as an independent structural unit that maintains ligand binding capabilities and antibody recognition [Randi and Hogg, *J. Biol. Chem.* 269: 12395–12398 (1994); Zhout, et al., *J. Biol. Chem.* 269:17075–17079 (1994); Michishita, et al., *Cell* 72:857–867 (1993)]. To generate a soluble fusion protein comprising the $\alpha_d$ I domain and human IgG4, the $\alpha_d$ I domain is amplified by PCR using primers designed to add flanking BamHI and XhoI restriction sites to facilitate subcloning. These primers are set out in SEQ ID NOS: 32 and 33 with restriction sites underlined.

5'-ACGTATGCA<u>GGATCC</u>CATCAAGAGATGG-ACATCGCT-3' (SEQ ID NO: 32)

5'-ACTGCATGT<u>CTCGAG</u>GCTGAAGCCTTC-TTGGGACATC-3' (SEQ ID NO: 33)

The C nucleotide immediately 3' to the BamHI site in SEQ ID NO: 32 corresponds to nucleotide 435 in SEQ ID NO: 1; the G nucleotide 3' to the XhoI site in SEQ ID NO: 33 is complementary to nucleotide 1067 in SEQ ID NO: 1. The amplified I domain is digested with the appropriate enzymes, the purified fragment ligated into the mammalian expression vector pDCs and the prokaryotic expression vector pGEX-4T-3 (Pharmacia) and the I domain fragment sequenced. The fusion protein is then expressed in COS, CHO or *E. coil* cells transfected or transformed with an appropriate expression construct.

Given the affinity of $\alpha_d$ for ICAM-R, expression of the $\alpha_d$ I domain may be of sufficient affinity to be a useful inhibitor of cell adhesion in which $\alpha_d$ participates.

Analysis of Human $\alpha_d$ I Domain/IgG4 Fusion Proteins

Protein was resolved by SDS-PAGE under reducing and non-reducing conditions and visualized by either silver staining or Coomassie staining. Protein was then transferred to Immobilon PVDF membranes and subjected to Western blot analysis using anti-human IgG monoclonal antibodies or anti-bovine Ig monoclonal antibodies.

Protein detected was determined to migrate at about 120 kD under non-reducing conditions and at about 45 kD under reducing conditions. Minor bands were also detected on non-reducing gels at approximately 40–50 kD which were reactive with the anti-human, but not anti-bovine, antibodies. A 200 kD minor band was determined to be bovine Ig by Western blot.

Binding Assays Using I Domain Expression Products

The ability of the I domain to specifically recognize ICAM-R/IgG chimeric protein was tested in an ELISA format. Serial dilutions of $\alpha_d$ I domain IgG4 fusion protein (I$\alpha_d$/IgG4) in TBS were incubated with ICAM-1/IgG, ICAM-R/IgG, VCAM-1/IgG, or an irrelevant IgG1 myeloma protein immobilized on Immulon IV RIA/EIA plates. CD11a I domain/IgG chimeric protein and human IgG4/kappa myeloma protein were used as negative controls. Bound IgG4 was detected with the biotinylated anti-IgG4 monoclonal antibody HP6023 followed by addition of strepavidin-peroxidase conjugate and development with substrate o-phenyldiamine.

In repeated assays, no binding of the CD11a/IgG4 protein or the IgG4 myeloma protein was detected with any of the immobilized proteins. The I$\alpha_d$/IgG4 protein did not bind to fish skin gelatin or bovine serum albumin blocking agents, human IgG1, or ICAM-1/IgG. A two to three fold increase in binding signal over background was detected in ICAM-R/IgG protein coated wells using 1–5 µg/ml concentrations of I$\alpha_d$/IgG4 protein. The signal in VCAM-1/IgG protein coated wells was 7–10 fold higher than background. In previous assays, $\alpha_d$/CD18 transfected CHO cells did not bind VCAM-1/IgG protein, suggesting that VCAM-1 binding may be characteristic of isolated I domain amino acid sequences.

Additional $\alpha_d$ I domain constructs

Additional $\alpha_d$ I domain constructs are generated in the same fashion as the previous construct, but incorporating more amino acids around the $\alpha_d$ I domain. Specific constructs include: i) sequences from exon 5 (amino acids 127–353 in SEQ ID NO: 2), preceding the current construct, ii) the EF-hand repeats (amino acids 17–603 in SEQ ID NO: 2) following the I domain, and iii) the alpha chain truncated at the transmembrane region (amino acids 17–1029 in SEQ ID NO: 2), with an IgG4 tail for purification and detection purposes. These constructs are ligated into either the mammalian expression vector pDCS1 or the prokaryotic expression vector pGEX-4T-3 (Pharmacia) and the I domain sequenced. The fusion proteins are then be expressed in COS, CHO, or *E. coli* cells transformed or transfected with an appropriate expression construct. Protein are purified on a ProSepA column (Bioprocessing Limited, Durham, England), tested for reactivity with the anti-IgG4 monoclonal antibody HP6023 and visualized on polyacrylamide gels with Coomassie staining.

In order to construct an expression plasmid for the entire $\alpha_d$ polypeptide, pATM.D12, described supra, is modified to express an $\alpha_d$-IgG4 fusion protein by the following method. IgG4 encoding DNA is isolated from the vector pDCS 1 by PCR using primers which individually incorporate a 5' AatII restriction site (SEQ ID NO: 89) and a 3' XbaI restriction site (SEQ ID NO: 90).

5'-CGCTGTGACGTCAGAGTTGAGTCCAAA-TATGG-3' (SEQ ID NO: 89)

5'-GGTGACACTATAGAATAGGGC-3' (SEQ ID NO: 90)

Plasmid pATM.D12 is digested with AatII and XbaI, and the appropriately digested and purified IgG4 PCR product ligated into the linear vector.

EXAMPLE 15

Production of Human $\alpha_d$-Specific Antibodies

A. Production of Monoclonal Antibodies

1. Transiently transfected cells from Example 7 were washed three times in Dulbecco's phosphate buffered saline (D-PBS) and injected at 5×10⁶ cells/mouse into Balb/c mice with 50 μg/mouse muramyl dipeptidase (Sigma) in PBS. Mice were injected two more times in the same fashion at two week intervals. The pre-bleed and immunized serum from the mice were screened by FACS analysis as outlined in Example 9 and the spleen from the mouse with the highest reactivity to cells transfected with $\alpha_d$/CD18 was fused. Hybridoma culture supernatants were then screened separately for lack of reactivity against COS cells transfected with CD11a/CD18 and for reactivity with cells co-transfected with an $\alpha_d$ expression plasmid and CD18.

This method resulted in no monoclonal antibodies.

2. As an alternative for production of monoclonal antibodies, soluble $\alpha_d$ I domain/IgG4 fusion protein was affinity purified from supernatant of stably transfected CHO cells and used to immunize Balb/c mice as described above. Hybridomas were established and supernatants from these hybridomas were screened by ELISA for reactivity against $\alpha_d$ I domain fusion protein. Positive cultures were then analyzed for reactivity with full length $\alpha_d$/CD18 complexes expressed on CHO transfectants.

Mouse 1908 received three initial immunizations of $\alpha_d$/CD18 transfected CHO cells and two subsequent boosts with soluble $\alpha_d$/CD18 heterodimer. Two final immunizations included 50 μg/mouse $\alpha_d$ I domain/IgG4 fusion protein. The fusion produced 270 IgG-producing wells. Supernatant from 45 wells showed at least 7-fold higher binding to I$\alpha_d$/IgG4 fusion protein than to human IgG4 by ELISA. None of the supernatants reacted to $\alpha_d$/CD18 transfected CHO cells as determined by FACS analysis.

To determine whether the supernatants were able to recognize integrin alpha subunit proteins in another context, fresh frozen splenic sections were stained with supernatants from 24 of the 45 wells. Three supernatants were determined to be positive: one stained large cells in the red pulp, while two others stained scattered cells in the red pulp and also trabeculae.

These supernatants were further analyzed by their ability to immunoprecipitate biotinylated CD18 complexes from either $\alpha_d$/CD18 transfected CHO cells or PMA-stimulated HL60 cells. Fusion wells with supernatants that recognized protein in detergent lysates (which should not be as conformationally constrained as protein expressed as heterodimers) were selected for further subcloning. Monoclonal antibodies which recognize protein in detergent may be more useful in immunoprecipitation of heterodimeric complexes from transfectants, tissues, and cell lines.

3. As another alternative to monoclonal antibody production, CD18 complexes were immunoprecipitated from human spleen lysates with the anti-CD 18 monoclonal antibody 23F2G after preclearance of CD11a/CD 18 (using monoclonal antibody TS2/4) and CD11b/CD18 (using monoclonal antibody Mo-1). Five Balb/c mice, ten to twelve weeks old, were immunized by subcutaneous injection with approximately 30 μg of resulting protein in complete Freund's adjuvant on day 0, followed by two boosts of 30 ug immunogen/mouse on days 28 and 43 in incomplete Freund's adjuvant. Test sera were drawn ten days following the final boost and reactivity was assessed by using 1:500 dilution of each serum to detect 1 μg/lane immunogen in a Western blot. Sera from three mice detected bands of approximately 95 and 150 kD; no signal was seen in lanes treated with a 1:50 dilution of preimmune sera. The 150 kD band was presumed to represent $\alpha_d$ in an in vivo glycosylation state. In addition, all post immune sera immunoprecipitated protein from lysates of biotinylated $\alpha_d$/CD18 CHO cells that migrated at appropriate molecular weights on SDS-PAGE to represent the heterodimer. From these results, mouse #2212 was selected and was further immunized by intraperitoneal injection on day 64 with 30 μg immunogen in PBS. The mouse was sacrificed four days later, and the spleen was sterilely removed.

A single-cell suspension was formed by grinding the spleen between the frosted ends of two glass microscope slides submerged in serum-free RPMI 1640 supplemented with 2 mM L-glutamine, 1 mM sodium pyruvate, 100 units/ml penicillin, and 100 μg/ml streptomycin (RPMI) (Gibco, Canada). The cell suspension was filtered through a sterile 70-mesh Nitex cell strainer (Becton Dickinson, Parsippany, N.J.), and the filtrate washed twice by centrifugation at 200×g for 5 minutes. The resulting pellet was resuspended in 20 ml serum-free RPMI. Thymocytes taken from three naive Balb/c mice were prepared in a similar manner.

Prior to fusion, NS-1 myeloma cells, kept in log phase in RPMI with 10% Fetalclone serum (FBS) (Hyclone Laboratories, Inc., Logan, Utah) for three days prior to fusion, were pelleted by centrifugation at 200×g for 5 minutes, washed twice as described in the foregoing paragraph, and counted. Approximately 2×10⁸ spleen cells were combined with 4×10⁷ NS-1 cells, and the resulting mixture pelleted by centrifugation at 200×g. The supernatant was discarded. The cell pellet dislodged by tapping the tube and 2 ml of 50% PEG 1500 in 75 mM Hepes (pH 8.0, 37° C.) (Boehringer Mannheim) was added over the course of one minute with stirring. An additional 14 ml of serum-free RPMI was subsequently added over the next seven minutes, followed by immediate addition of 16 ml RPMI. The resulting mixture was centrifuged at 200×g for 10 minutes and the supernatant was discarded. The pellet was resuspended in 200 ml RPMI containing 15% FBS, 100 mM sodium hypoxanthine, 0.4 mM aminopterin, 16 mM thymidine (HAT) (Gibco), 25 units/ml IL-6 (Boehringer Mannheim) and 1.5×10⁶ thymocytes/ml, and dispensed into ten 96-well flat bottom tissue culture plates (Corning, United Kingdom) at 200 μl/well. Cells were fed on days 2, 4, and 6 days post-fusion by aspirating approximately 100 μl from each well with an 18 G needle (Becton Dickinson), and adding 100 μl/well plating medium described above, except containing 10 units/ml IL-6 and lacking thymocytes.

On day 7–10 post-fusion, supernatant from each well was screened by antibody capture ELISA, testing for the presence of mouse IgG. Immulon 4 plates (Dynatech, Cambridge, Mass.) were coated with 50 μl/well goat antimouse IgA, IgG, or IgM (Organon Teknika) diluted 1:5000 in 50 mM carbonate buffer, pH 9.6, at 4° C. Plates were washed 3× X with PBS containing 0.5% Tween 20 (PBST) and 50 μl culture supernatant from each well was added. After incubation at 37° C. for 30 minutes, wells were washed with PBST as above, and 50 μl of horseradish peroxidase conjugated goat anti-mouse IgG(fc) (Jackson ImmunoResearch, West Grove, Penn.) diluted 1:3500 in PBST was added to each well. Plates were incubated as above, washed 4× with PBST and 100 μl substrate, consisting of 1 mg/ml o-phenylene diamine (Sigma) and 0.1 μl/ml 30% $H_2O_2$ in 100 mM Citrate, pH 4.5, was added. The color reaction was stopped after five minutes with addition of 50 μl 15% $H_2SO_4$. Absorbance at 490 nm was determined for each well using a plate reader (Dynatech).

Hybridomas were further characterized as follows. Supernatants from IgG-producing cultures were analyzed by flow cytometry for reactivity to $\alpha_d$/CD18-transformed CHO cells but not to JY cells (a B-cell line positive for LFA-1, but not other $\alpha_2$ integrins as observed in previous in-house staining experiments). Briefly, 5×10$^5$ $\alpha_d$/CD18-transformed CHO or $\alpha_d$/CD18⁻ JY cells were suspended in 50 µl RPMI containing 2% FBS and 10 mM NaN$_3$ (FACS buffer). Individual cell suspensions were added to 50 µl IgG positive hybridoma culture supernatant in wells of 96-well round bottomed plates (Corning). After a 30 minute incubation on ice, cells were washed twice by pelleting in a clinical centrifuge, supernatant from each well was discarded, and pellets resuspended in 200–300 µl FACS buffer. The last wash was replaced with 50 µl/well of a 1:100 dilution of a F(ab')$_2$ fragment of sheep anti-mouse IgG (H+L)-FITC conjugate (Sigma, St. Louis, Me.) prepared in FACS Buffer. After incubation as described above, cells were washed twice with Dulbecco's PBS (D-PBS) supplemented with 10 mM NAN3, and finally resuspended in D-PBS containing 1% paraformaldehyde. Samples were then transferred to polystyrene tubes for flow cytometric analysis (FACS) with a Becton Dickinson FACsan analyzer.

The fusion yielded four cultures deemed positive by both criteria. When the secondary screen was repeated on expanded supernatants approximately four days later, three of the four cultures remained positive. The three wells, designated 169A, 169B, 169D were cloned two to three times, successively, by doubling dilution in RPMI, 15% FBS, 100 mM sodium hypoxanthine, 16 mM thymidine, and 10 units/ml IL-6. Wells of clone plates were scored visually after four days and the number of colonies in the least dense wells were recorded. Selected wells of the each cloning were assayed by FACS after 7–10 days. Activity was found in two of the cultures, 169A and 169B. In the final cloning, positive wells containing single colonies were expanded in RPMI with 11% FBS. Antibody from clonal supernatants of 169A and 169B were isotyped using IsoStrip kit (Boehringer Mannheim) according to manufacturer instructions and found to be of the IgG1 isotype.

Immunoprecipitation of $\alpha_d$/CD18 complexes from CHO transfectants and PMA-stimulated HL60 cells was used as a tertiary screen for specificity. Hybridomas 169A and 169B precipitated appropriate bands from CHO lines, and a single α chain species of 150–160 kD from HL60 cells as determined by SDS-PAGE. Hybridomas 169A and 169B were deposited May 31, 1995 with the American Type Culture Collection, 12301 Parklawn Drive, Rockville, Md. 20852 and assigned Accession Numbers HB11907 and HB11906, respectively.

4. As another alternative, monoclonal antibodies are generated as follows. Affinity purified $\alpha_d$/CD18 heterodimeric protein from detergent lysates of stably transfected CHO cells is used with 50 µg/ml muramyl dipeptidase to immunize Balb/c mice as described above. Mice receive three immunizations before serum reactivity against $\alpha_d$/CD18 is determined by immunoprecipitation of biotinylated complexes in the CHO transfectants. Hybridomas from positive animals are established according to standard protocols, after which hybridoma cultures are selected by flow cytometry using $\alpha_d$/CD18 transfectants. CD11a/CD18 transfectants are utilized to control for CD18-only reactivity.

5. As another alternative for monoclonal antibody production, Balb/c mice undergo an immunization/immunosuppression protocol designed to reduce reactivity to CHO cell determinants on transfectants used for immunization. This protocol involves immunization with untransfected CHO cells and subsequent killing of CHO-reactive B-cell blasts with cyclophosphamide treatment. After three rounds of immunization and cyclophosphamide treatment are performed, the mice are immunized with $\alpha_d$/CD18 CHO transfected cells as described above.

6. As another alternative, CD18 complexes from detergent lysates of PMA stimulated HL60 cells are enriched by preclearance as described above. Other β2 integrins are cleared on the same columns. Immunization with the resulting complexes, hybridoma production, and screening protocols are performed as described supra.

B. Production of Polyclonal Sera

Purified $\alpha_d$ I domain/IgG4 chimera (Example 14) was used to generate polyclonal anti-serum in rabbits. The $\alpha_d$ I domain/IgG4 antigen was injected at 100 µg/rabbit initially in complete Freund's adjuvant, followed by three boosts with the same amount of protein in incomplete Freund's adjuvant. Test bleeds were assayed after the third and fourth injections. Rabbit immunoglobulin (Ig) was purified from the serum on a protein A-sepharose column and precleared of anti-human IgG reactivity on a human IgG/Affigel 10 column. Reactivity by ELISA to the I domain chimera, but not to human IgG, was used to confirm complete preclearance.

The precleared polyclonal sera was used to immunoprecipitate protein from detergent lysates of surface-biotinylated CHO cells previously transfected with $\alpha_d$ and CD18 expression vectors. Immunoprecipitation was carried out by the method previously described in Example 10. The precleared sera recognized a protein complex of the same molecular weight as that precipitated by anti-CD18 monoclonal antibody TS1.18. In addition, the sera recognized a single band of appropriate size in a Western blot of CD18 complexes from $\alpha_d$/CD18 transfected CHO cells. Affinity purified integrins CD11a/CD18, CD11b/CD18, and VLA4 from human spleen were not recognized by the rabbit polyclonal sera. The sera failed to react with $\alpha_d$-transfected CHO cells in solution, as determined by flow cytometry. It was therefore concluded that the polyclonal rabbit sera was only capable of recognizing denatured $\alpha_d$ I domain/IgG4 proteins.

In an attempt to produce polyclonal antisera against $\alpha_d$/CD18, a mouse was immunized 3 times with $\alpha_d$ transfected CHO cells (D6.CHO, $\alpha_d$/CD18) with adjuvant peptide and once with purified $\alpha_d$/CD18 heterodimer. A final boost included only $\alpha_d$/CD18 heterodimer. Approximately 100 µl immunized serum was precleared by addition of approximately 10$^8$ LFA-1-transfected CHO cells for 2 hours at 4° C. The resulting serum was assayed for $\alpha_d$ reactivity at dilutions of 1/5000, 1/10000, 1/20000 and 1/40000 on normal human spleen. The polyclonal antibody was reactive at a dilution of 1/20000, while a 1/40000 dilution stained very weakly.

EXAMPLE 16

Analysis of $\alpha_d$ distribution

Tissue distribution of $\alpha_d$/CD18 was determined using polyclonal anti-serum generated as described in Example 15.

Purified rabbit polyclonal antibody was used at concentrations ranging between 120 ng/ml and 60 µg/ml for immunocytochemical analysis of frozen human spleen sections. Sections of 6 micron thickness were layered onto Superfrost Plus Slides (VWR) and stored at −70° C. Prior to use, slides were removed from −70° C. and placed at 55° C. for 5 minutes. Sections were then fixed in cold acetone for 2 minutes and air dried. Sections were blocked in a solution containing 1% BSA, 30% normal human sera and 5% normal rabbit sera for 30 minutes at room temperature. Primary antibody was applied to each section for 1 hour at room temperature. Unbound antibody was removed by washing the slides 3 times in TBS buffer for 5 minutes per wash. Next, a rabbit anti-mouse IgG link antibody was applied to each section in the same TBS buffer. A mouse alkaline phosphatase anti-alkaline phosphatase (APAAP) antibody, incubated for 30 minutes at room temperature, was used to detect the second antibody. Slides were then washed 3 times in TBS buffer. Fast Blue substrate (Vector Labs) was applied and color development stopped by immersion in water. Slides were counterstained in Nuclear Fast Red (Sigma) and rinsed in water before mounting with Aqua Mount (Baxter). Staining was detected in the splenic red pulp with this reagent, but not with an irrelevant rabbit polyclonal Ig preparation or the unpurified preimmune serum from the same animal.

Once mouse serum was determined to have specific $\alpha_d$ reactivity, it was used to stain various lymphoid and non-lymphoid tissues. Monoclonal antibodies recognizing CD18, CD11a, CD11b, and CD11c were used in the same experiment as controls. Staining of normal spleen sections with $\alpha_d$ polyclonal sera, and monoclonal antibodies to CD11a, CD11b, CD11c, and CD18 revealed the following results. The pattern observed with $\alpha_d$ polyclonal sera did not display the same pattern of labeling as CD11a, CD11b, CD11c, or CD18. There is a distinct pattern of labeling with some cells located in the marginal zone of the white pulp and a distinct labeling of cells peripheral to the marginal zone. This pattern was not observed with the other antibodies. Individual cells scattered throughout the red pulp were also labeled which may or may not be the same population or subset seen with CD11a and CD18.

Labeling with CD11c did display some cells staining in the marginal zone, but the antibody did not show the distinct ring pattern around the white pulp when compared to $\alpha_d$ polyclonal sera, nor did labeling in the red pulp give the same pattern of staining as $\alpha_d$ polyclonal sera.

Therefore, the labeling pattern seen with $\alpha_d$ polyclonal serum was unique compared to that seen using antibodies to the other β2 integrins (CD11a, CD11b, CD11c, and CD18), and suggests that the in vivo distribution of $\alpha_d$ in man is distinct from that of other 62 2 integrins.

Characterization of Human $\alpha_d$ Expression With Monoclonal Antibodies

Antibodies secreted by hybridomas 169A and 169B were used to analyze human $\alpha_d$ expression in frozen tissue sections by immunocytochemistry and on cell lines and peripheral blood leukocytes by flow cytometry. Hybridoma supernatants used in both sets of experiments were undiluted.

Tissue Staining

All stains were carried out as described above, except for liver sections which were stained in the following manner. After acetone fixation, sections were quenched in 1% $H_2O_2$ and 1% sodium azide in TBS for 15 minutes at room temperature. After primary antibody staining, a rabbit anti-mouse antibody directly conjugated to peroxidase was applied for 30 minutes at room temperature. Slides were washed 3 times in TBS buffer. A swine anti-rabbit antibody, directly conjugated to peroxidase, was incubated for 30 minutes at room temperature to detect the second antibody. Slides were then washed 3 times in TBS buffer and AEC substrate (Vector Labs) was applied and to allow color development. Slides were counterstained with Hematoxylin Gill's No. 2 (Sigma), and subsequently rinsed in water before dehydration and mounting.

In spleen sections, the majority of expression was localized to the splenic red pulp on cells identified by morphology as granulocytes and macrophages. A large number of granulocytes were stained, while only a subset of macrophages gave signal. A small number of follicular dendritic cells in the white pulp also were weakly stained by the $\alpha_d$ antibodies. CD11a and CD18 staining was detected throughout the red and white pulp. CD11c staining was more pronounced in large cells presumed to be macrophages in the splenic white pulp and in the marginal zone surrounding the white pulp; diffuse staining in the red pulp was also noted. CD11b appeared to have distribution overlapping with but not identical to $\alpha_d$ in the red pulp, with no white pulp involvement.

Integrin expression in normal and (rheumatoid) arthritic synovial tissue was compared. Minimal staining with all anti-integrin antibodies (including antibodies specifically immunoreactive with CD11a, CD11b, CD11c, CD18, as well as $\alpha_d$) was noted in normal tissue, with a widespread distribution on resident cells, presumably macrophages. In the inflamed synovium, expression of all integrins was more localized to cells clustered around lymphatic vessels. While $\alpha_d$ and CD11b expression patterns were similar, CD11c did not appear to be as strongly expressed and was restricted to a subset of leukocytes.

In the dog, CD11b, but not $\alpha_d$, expression was observed on liver macrophages, or Kuppfer cells. Staining of normal human liver sections (as previously described for staining of dog liver section, supra) confirmed the conservation of this staining pattern in humans. In addition, CD11c was detected at low levels. In sections from a hepatitis patient, all leukointegrin staining was higher than observed on normal liver, while $\alpha_d$ expression was detected on macrophages and granulocytes in these samples.

Minimal staining of normal human colon sections was observed with anti-$\alpha_d$ antibodies; hint smooth muscle staining and leukocyte staining was observed. All leukointegrins were detected at higher levels in sections from patients with Crohn's disease.

Normal lung showed a limited number of weakly $\alpha_d$-positive cells; these were determined by morphology to be macrophages and neutrophils. In lung tissue from a patent with emphysema, $\alpha_d$ staining was observed on neutrophils and on marophages containing hemisiderin, an iron-containing pigment, indicating red cell engulfment by these cells.

Sections of normal brain and plaque lesions from patients with multiple sclerosis (MS) were examined for integrin expression. In normal brain, $\alpha_d$ staining was less intense than that of CD11a, CD11b, and CD11c, and restricted to cells typed as microglial cells by morphology and CD68 staining. CD11b positive cells were located surrounding vessels and throughout the tissue. CD11c$^+$ cells appeared to be located within vessels, whereas $\alpha_d^+$ cells surrounded the vessels. In MS tissue sections, $\alpha_d$ expression was found on both microglial cells and on a non-macrophage leukocyte subset; $\alpha_d^+$ cells were located within plaque lesions, as well as throughout the cortex. The $\alpha_d$ signal was equivalent in intensity to CD11c, but lower than that of CD11b.

Both thoracic aorta and abdominal aorta sections from PDAY (Pathobiological Determinants of Atherosclerosis in Youth, LSU Medical Center) tissue samples were analyzed with anti-leukointegrin and anti-CAM antibodies. The lesions examined were consistent with aortic fatty streaks which consisted of subintimal aggregates of large foam cells (mostly macrophages with ingested lipid) and infiltrates of smaller leukocytes. Single label studies with monoclonal antibodies specific for $\alpha_d$ and the other β$_2$ integrin α chains (CD11a, CD11b, and CD11c), plus a macrophage marker (CD68) revealed that the majority of lipid-laden macrophages expressed a moderate level of $\alpha_d$ and CD18, while expressing CD11a and CD11c at weak or weak to moderate levels, respectively. CD11b was faintly expressed, and then by only a subset of macrophages.

Double label studies were conducted to determine the relative localization of $\alpha_d$ and ICAM-R antigens in the aortic sections. Since foam cells in these sections stained with the antibody Ham 56, specific for a macrophage marker, but not with antibodies to smooth muscle actin, it was determined that the foam cells were not derived from subintimal smooth muscle cells. CD68 positive macrophages expressing $\alpha_d$ were surrounded by and interspersed with small ICAM-R positive leukocytes. There appeared to be a limited number of small leukocytes which were CD68 negative but stained with both $\alpha_a$ and ICAM-R antibodies.

Distribution of $\alpha_d$ in normal tissues appeared to be on resident leukocytes in a pattern overlapping with but not identical to that of CD11b and CD11c, two other leukointegrin $\alpha$ chains which have previously been characterized as having restricted leukocyte distribution. Cellular morphology indicated that $\alpha_d$ staining is largely confined to macrophages and granulocytes, with limited lymphocyte staining. Generally, tissue inflammation appeared to increase the number and types of leukocytes observed in a particular tissue, along with increased staining of leukointegrins, including $\alpha_d$. Since the cellular and spatial distribution of the leukointegrins was not identical in pathologic tissues, it was inferred that distinct functions and ligands exist for each family member, including $\alpha_d$, in specific contexts.

Interestingly, $\alpha_d$ expression in early atherosclerotic lesions appeared to be more pronounced than that of CD11a, CD11b, and CD11c, suggesting that $\alpha_d$ may play a central role in the establishment of these lesions. The apposed distribution of $\alpha_d$ and ICAM-R positive cells, supported by evidence suggesting an interaction between $\alpha_d$ and ICAM-R, suggests that $\alpha_d$ may be involved in leukocyte recruitment or activation at early stages in these lesions.

Cell Line and Peripheral Blood Leukocyte Staining

The antibodies 169A and 169B stained a promyeolmonocytic cell line, HL60, by FACS. Surface expression of $\alpha_d$ in these cells is negatively affected by PMA stimulation, which is reported to induce differentiation along a macrophage pathway, but is unaffected by DMSO, which induces granulocyte differentiation [Collins, et al., Blood 70:1233-1244 (1987)]. The FACS profiles of 169A and 169B were antithetical with PMA stimulation to those observed with anti-CD11b and anti-CD11c monoclonal antibodies. A monocyte cell line, THP-1, also exhibited weak staining with 169A and 169B. In addition, a subset of cells in the lymphocyte and monocyte gates of peripheral blood leukocytes appeared to be weakly positive by FACS. A subset of peripheral blood monocytes stained weakly with 169A and 169B, while B lymphocytes were found to have no surface expression of $\alpha_d$. The CD8$^+$ subset of T lymphocytes was $\alpha_d^+$. In addition, antibodies 169A and 169B failed to detect antigen on the B cell lines, JY, Ramos, a basophilic line, KU812, and T cell lines, Jurkat, SKW, and Molt 16.

In light of the results with HL60 cells, granulocytes were isolated from peripheral blood by ficoll/hypaque gradient centrifugation and subsequent red blood cells lysis. All preparations were found to be >90% PMNs by visualization of nuclear morphology in acetic acid. Separate populations were stimulated for 30 minutes with 50 ng/ml PMA or $10^{-8}$M formyl peptide (fMLP) to release potential intracellular integrin stores. Unstimulated populations exhibited low, but significant expression of 169A and 169B antigens over an IgG1 control, with a detectable increase observed upon stimulation. On PMNs, levels of $\alpha_d$ and CD11c surface expression were more similar than that observed on HL60 cells. The antibody 169B was used subsequently to precipitate a heterodimeric molecule from a detergent lysate of biotinylated PMNs with subunit sizes of approximately 150 and 95 kD appropriate to $\alpha_d$ and CD18, respectively.

The presence of $\alpha_d$ on PMNs could not be anticipated from the information known about canine $\alpha_d$ expression. Canine neutrophils, unlike their human counterparts, express the T helper cell marker CD4, and also integrin VLA-4, and therefore may have different ligands and functions in the dog than in the human.

EXAMPLE 17

Isolation of Rat cDNA Clones

In view of the existence of both canine and human $\alpha_d$ subunits, attempts were made to isolate homologous genes in other species, including rat (this example) and mouse (Example 17, infra).

A partial sequence of a rat cDNA showing homology to the human $\alpha_d$ gene was obtained from a rat splenic λgt10 library (Clontech). The library was plated at $2 \times 10^4$ pfu/plate onto 150 mm LBM/agar plates. The library was lifted onto Hybond membranes (Amersham), denatured 3 minutes, neutralized 3 minutes and washed 5 minutes with buffers as described in standard protocols [Sambrook, et al., *Molecular Cloning: a laboratory manual*, p.2.110]. The membranes were placed immediately into a Stratalinker (Stratagene) and the DNA crosslinked using the autocrosslinking setting. The membranes were prehybridized and hybridized in 30% or 50% formamide, for low and high stringency conditions, respectively. Membranes were initially screened with a $^{32}$P-labeled probe generated from the human $\alpha_d$ cDNA, corresponding to bases 500 to 2100 in clone 19A2 (SEQ ID NO: 1). The probe was labeled using Boehringer Mannheim's Random Prime Kit according to manufacturer's suggested protocol. Filters were washed with 2× SSC at 55° C.

Two clones, designated 684.3 and 705.1, were identified which showed sequence homology to human $\alpha_d$, human CD11b, and human CD11c. Both clones aligned to the human $\alpha_d$ gene in the 3' region of the gene, starting at base 1871 and extending to base 3012 for clone 684.3, and bases 1551 to 3367 for clone 705.1.

In order to isolate a more complete rat sequence which included the 5' region, the same library was rescreened using the same protocol as employed for the initial screening, but using a mouse probe generated from clone A1160 (See Example 17, infra). Single, isolated plaques were selected from the second screening and maintained as single clones on LBM/agar plates. Sequencing primers 434FL and 434FR (SEQ ID NOS: 34 and 35, respectively) were used in a standard PCR protocol to generate DNA for sequencing.

5'-TATAGACTGCTGGGTAGTCCCCAC-3' (SEQ ID NO: 34)

5'-TGAAGATTGGGGGTAAATAACAGA-3' (SEQ ID NO: 35)

DNA from the PCR was purified using a Quick Spin Column (Qiagen) according to manufacturer's suggested protocol.

Two clones, designated 741.4 and 741.11, were identified which overlapped clones 684.3 and 705.1; in the overlapping regions, clones 741.1 and 741.11 were 100% homologous to clones 684.3 and 705.1. A composite rat cDNA having homology to the human $\alpha_d$ gene is set out in SEQ ID NO: 36; the predicted amino acid sequence is set forth in SEQ ID NO: 37.

Cloning of the 5' end of Rat $\alpha_d$

A 5' cDNA fragment for the rat $\alpha_d$ gene was obtained using a Clonetech rat spleen RACE cloning kit according to manufacturer's suggested protocol. The gene specific oligonucleotides used were designated 741.11#2R and 741.2#1R (SEQ ID NOS: 59 and 58, respectively).

5'-CCAAAGCTGGCTGCATCCTCTC-3'  (SEQ ID NO: 59)

5'-GGCCTTGCAGCTGGACAATG-3'  (SEQ ID NO: 58)

Oligo 741.11#2R encompasses base pairs 131-152 in SEQ ID NO: 36, in the reverse orientation and 741.2#1R encompasses bases pairs 696-715 in SEQ ID NO: 36, also in the reverse orientation. A primary PCR was carried out using the 3'-most oligo, 741.2#1R. A second PCR followed using oligo 741.1 1#2R and DNA generated from the primary reaction. A band of approximately 300 base pairs was detected on a 1% agarose gel.

The secondary PCR product was ligated into plasmid pCRTAII (Invitrogen) according to manufacturer's suggested protocol. White (positive) colonies were picked and added to 100 μl LBM containing 1 μl of a 50 mg/ml carbenicillin stock solution and 1 μl M13 K07 phage culture in individual wells in a round bottom 96 well tissue culture plate. The mixture was incubated at 37° C. for 30 minutes to one hour. Following the initial incubation period, 100 μl of LBM (containing 1 μl of 50 mg/ml carbenicillin and a 1:250 dilution of a 10 mg/ml kanamycin stock solution) were added and the incubation was continued overnight at 37° C.

Using a sterile 96 well metal transfer prong, supernatant from the 96 well plate was transferred to four Amersham Hybond nylon filters. The filters were denatured, neutralized and cross linked by standard protocols. The filters were prehybridized in 20 mls of prehybridization buffer (5× SSPE; 5× Denhardts; 1% SDS; 50 ugs/ml denatured salmon sperm DNA) at 50° C. for several hours while shaking.

Oligo probes 741.11#1 and 741.11#1R (SEQ ID NOS: 56 and 57, respectively), encompassing base pairs 86-105 (SEQ ID NO: 36) in the forward and reverse orientation respectively, were labeled as follows.

5'-CCTGTCATGGGTCTAACCTG-3'  (SEQ ID NO: 56)

5'-AGGTTAGACCCATGACAGG-3'  (SEQ ID NO: 57)

Approximately 65 ng oligo DNA in 12 μl dH₂O was heated to 65° C. for two minutes. Three μl of 10 mCi/ml λ-$^{32}$P-ATP were added to the tube along with 4 μl 15× Kinase Buffer (Gibco) and 1 μl T4 DNA Kinase (Gibco). The mixture was incubated at 37° C. for 30 minutes. Following incubation, 16 μl of each labeled oligo probe were added to the prehybridization buffer and filters and hybridization was continued overnight at 42° C. The filters were washed three times in 5× SSPE; 0.1% SDS for 5 minutes per wash at room temperature, and autoradiographed for 6 hours. Positive clones were expanded and DNA purified using the Magic Mini Prep Kit (Promega) according to manufacturer's suggested protocol. Clone 2F7 was selected for sequencing and showed 100% homology to clone 741.11 in the overlapping region. The complete rat $\alpha_d$ nucleic acid sequence is set out in SEQ ID NO: 54; the amino acid sequence is set out in SEQ ID NO: 55.

Characteristics of the Rat cDNA and Amino Acid Sequences

Neither nucleic acid nor amino acid sequences have previously been reported for rat α subunits in β₂ integrins. However sequence comparisons to reported human β₂ integrin α subunits suggests that the isolated rat clone and its predicted amino acid sequence are most closely related to $\alpha_d$ nucleotide and amino acid sequences.

At the nucleic acid level, the isolated rat cDNA clone shows 80% identity in comparison to the human $\alpha_d$ cDNA; 68% identity in comparison to human CD11b; 70% identity in comparison to human CD11c; and 65% identity in comparison to mouse CD11b. No significant identity is found in comparison to human CD11a and to mouse CD11a.

At the amino acid level, the predicted rat polypeptide encoded by the isolated cDNA shows 70% identity in comparison to human $\alpha_d$ polypeptide; 28% identity in comparison to human CD11a; 58% identity in comparison to human CD11b; 61% identity in comparison to human CD11c; 28% identity in comparison to mouse CD11a; and 55% identity in comparison to mouse CD11b.

EXAMPLE 18

Production and Characterization of Rodent $\alpha_d$-Specific Antibodies

A. Antibodies against Rat $\alpha_d$ I domain/Hu IgG4 Fusion Proteins

In view of the fact that the I domain of human β₂ integrins has been demonstrated to participate in ligand binding, it was assumed that the same would be true for rat $\alpha_d$ protein. Monoclonal antibodies immunospecific for the rat $\alpha_d$ I domain may therefore be useful in rat models of human disease states wherein $\alpha_d$ binding is implicated.

Oligos "rat alpha-DI5" (SEQ ID NO: 87) and "rat alpha-DI3" (SEQ ID NO: 88) were generated from the rat $\alpha_d$ sequence corresponding to base pairs 469-493 and base pairs 1101-1125 (in the reverse orientation), respectively, in SEQ ID NO: 54. The oligos were used in a standard PCR reaction to generate a rat $\alpha_d$ DNA fragment containing the I domain spanning base pairs 459-1125 in SEQ ID NO: 54. The PCR product was ligated into vector pCRTAII (Invitrogen) according to manufacturer's suggested protocol. A positive colony was selected and expanded for DNA purification using a Qiagen (Chatswoth, Ga.) Midi Prep kit according to manufacturer's protocol. The DNA was digested with XhoI and BglII in a standard restriction enzyme digest and a 600 base pair band was gel purified which was subsequently ligated into pDCS1/HuIgG4 expression vector. A positive colony was selected, expanded and DNA purified with a Quiagen Maxi Prep Kit.

COS cells were plated at half confluence on 100 mm culture dishes and grown overnight at 37° C. in 7% CO₂. Cells were rinsed once with 5 ml DMEM. To 5 ml DMEM, 50 μl DEAE-Dextran, 2 μl chloroquine and 15 μg rat $\alpha_d$ I domain/HuIgG4 DNA described above was added. The mixture was added to the COS cells and incubated at 37° C. for 3 hours. Media was then removed and 5 ml 10% DMSO in CMF-PBS was added for exactly one minute. The cells were gently rinsed once with DMEM. Ten ml DMEM containing 10% FBS was added to the cells and incubation continued overnight at 37° C. in 7% CO₂. The next day, media was replaced with fresh media and incubation continued for three additional days. The media was harvested and fresh media was added to the plate. After three days, the media was collected again and the plates discarded. The procedure was repeated until 2 liters of culture supernatant were collected.

Supernatant collected as described above was loaded onto a Prosep-A column (Bioprocessing Limited) and protein purified as described below.

The column was initially washed with 15 column volumes of Wash Buffer containing 35 mM Tris and 150 mM NaCl, pH 7.5. Supernatant was loaded at a slow rate of less than approximately 60 column volumes per hour. After loading, the column was washed with 15 column volumes of Wash Buffer, 15 column volumes of 0.55M diethanolamine, pH 8.5, and 15 column volumes 50 mM citric acid, pH 5.0. Protein was eluted with 50 mM citric acid, pH 3.0. Protein was neutralized with 1.0M Tris, pH 8.0, and dialyzed in sterile PBS.

The rat $\alpha_d$ I domain protein was analyzed as described in Example 14. The detected protein migrated in the same manner as observed with human I domain protein.

B. Production of Monoclonal Antibodies to Rat $\alpha_d$ I Domain/HuIgG4 Fusion Proteins Mice were individually immunized with 50 μg purified rat $\alpha_d$ I domain/HuIgG4 fusion protein previously emulsified in an equal volume of Freunds Complete Adjuvant (FCA) (Sigma). Approximately 200 μl of the antigen/adjuvant preparation was injected at 4 sites in the back and flanks of each of the mice. Two weeks later the mice were boosted with an injection of 100 μl rat $\alpha_d$ I domain/HuIgG4 antigen (50 μg/mouse) previously emulsified in an equal volume of Freunds Incomplete Adjuvant (FIA). After two additional weeks, the mice were boosted with 50 μg antigen in 200 μl PBS injected intravenously.

To evaluate serum titers in the immunized mice, retro-orbital bleeds were performed on the animals ten days following the third immunization. The blood was allowed to clot and serum isolated by centrifugation. The serum was used in an immunoprecipitation on biotinylated (BIP) rat splenocytes. Serum from each mouse immunoprecipitated protein bands of expected molecular weight for rat $\alpha_d$ and rat CD18. One mouse was selected for the fusion and was boosted a fourth time as described above for the third boost.

The hybridoma supernatants were screened by antibody capture, described as follows. Immulon 4 plates (Dynatech, Cambridge, Mass.) were coated at 4° C. with 50 μl/well goat anti-mouse IgA, IgG or IgM (Organon Teknika) diluted 1:5000 in 50 mM carbonate buffer, pH 9.6. Plates were washed 3× with PBS containing 0.05% Tween 20 (PBST) and 50 μl culture supernatant was added. After incubation at 37° C. for 30 minutes, and washing as described above, 50 μl horseradish peroxidase-conjugated goat anti-mouse IgG9 (Fc) (Jackson ImmunoResearch, West Grove, Pa.) diluted 1:3500 in PBST was added. Plates were incubated as described above and washed 4× with PBST. Immediately thereafter, 100 μl substrate, containing 1 mg/ml o-phenylene diamine (Sigma) and 0.1 μl/ml 30% $H_2O_2$ in 100 mM citrate, pH4.5, was added. The color reaction was stopped after 5 minutes with the addition of 50 μl 15% $H_2SO_4$. Absorbance at 490 nm was read on a Dynatech plate reader.

Supernatant from antibody-containing wells was also analyzed by ELISA with immobilized rat $\alpha_d$ I domain/HuIgG4 fusion protein. An ELISA with HuIgG4 antibody coated plates served as a control for reactivity against the IgG fusion partner. Positive wells were selected for further screening by BIP on rat splenocyte lysates using techniques described below.

C. Production of Polyclonal Sera To Rat $\alpha_d$ I domain/HuIgG4 Fusion Protein Two rabbits were prebled prior to immunization with 100 μg purified rat $\alpha_d$ I domain/HuIgG4 fusion protein in complete Freund's adjuvant. Injections were repeated at the same dose every three weeks in incomplete Freunds adjuvant (IFA). After three injections the rabbits were test bled and the collected sera used in a standard immunoprecipitation on rat splenocyte lysates. It was determined that sera from both rabbits were immunoreactive with rat $\alpha_d$. The rabbits were boosted again with 100 ug antigen in IFA, and the collected sera assayed for increased immunoreactivity with rat $\alpha_d$ by immunoprecipitation. The animals were given a final boost and 10 days later, bled out and sera collected.

Rat $\alpha_d$ Histology

Rabbit polyclonal sera generated against rat $\alpha_d$ "I" domain was used in immunohistochemical staining of rat tissue sections by the technique described in Example 16. The staining pattern detected on frozen and on parafin embedded rat spleen sections was essentially identical to that observed with the antibodies against human $\alpha_d$, with staining individual cells throughout the red pulp. The staining pattern differed from that observed with monoclonal antibodies against rat CD11a, CD11b and CD18. In addition, a positive staining pattern was seen in the thymus on individual cells throughout the cortex. Neither of these tissue gave any signal when stained with the rabbit preimmune sera.

D. Analysis of Antibody Specificity

Rats were sacrificed by asphyxiation with $CO_2$ and spleens were removed using standard surgical techniques. Splenocytes were harvested by gently pushing the spleen through a wire mesh with a 3 cc syringe plunger in 20 mls RPMI. Cells were collected into a 50 ml conical tube and washed in the appropriate buffer.

Cells were washed three times in cold D-PBS and resuspended at a density of $10^8$ to $10^9$ cells in 40 ml PBS. Four mg of NHS-Biotin (Pierce) was added to the cell suspension and the reaction was allowed to continue for exactly 15 minutes at room temperature. The cells were pelleted and washed three times in cold D-PBS.

Cells were resuspended at a density of $10^8$ cells/ml in cold lysis Buffer (1% NP40; 50 mM Tris-HCl, pH 8.0; 150 mM NaCl; 2 mM CaCl; 2 mM MgCl; 1:100 solution of pepstain, leupeptine, and aprotinin, added just before adding to cells; and 0.0001 g PMSF crystals, added just before adding to cells). Lysates were vortexed for approximately 30 seconds, incubated for 5 minute at room temperature, and further incubated for 15 minutes on ice. Lysates were centrifuged for 10 minutes at 10,000× g to pellet the insoluble material. Supernatant was collected into a new tube and stored at between 4° C. and −20° C.

One ml cell lysate was precleared by incubation with 200 μl of a protein A sepharose slurry (Zymed) overnight at 4° C. Precleared lysate was aliquoted into Eppendorf tubes at 50 μl/tube for each antibody to be tested. Twenty-five μl of polyclonal serum or 100 to 500 μl of monoclonal antibody supernatant were added to the precleared lysates and the resulting mixture incubated for 2 hours at 4° C. with rotation. One hundred μl rabbit anti-mouse IgG (Jackson) bound to protein A sepharose beads in a PBS slurry was then added and incubation continued for 30 minutes at room temperature with rotation. Beads were pelleted with gentle centrifugation, and washed three times with cold Wash Buffer (10 mM HEPES; 0.2M NaCl; 1% Trition X-100). Supernatant was removed by aspiration, and 20 μl 2× SDS sample buffer containing 10% β-mercaptoethanol was added. The sample was boiled for 2 minutes in a water bath, and the sample loaded onto a 5% SDS PAGE gel. Following separation, the proteins were transferred to nitrocellulose at constant current overnight. The nitrocellulose filters were blocked with 3% BSA in TBS-T for 1 hour at room temperature and the blocking buffer was removed. A 1:6000 dilution of Strepavidin-HRP conjugate (Jackson) in 0.1% BSA TBS-T was added and incubation continued for 30 minutes at room temperature. Filters were washed three times for 15 minutes each with TBS-T and autoradiographed using Amersham's ECL kit according to manufacturer's suggested protocol.

EXAMPLE 19

Isolation of Mouse cDNA Clones

Isolation of a mouse $\alpha_d$ homolog was attempted.

Cross-species hybridization was performed using two PCR-generated probes: a 1.5 kb fragment corresponding to bases 522 to 2047 from human clone 19A2 (SEQ ID NO: 1), and a 1.0 kb rat fragment which corresponds to bases 1900 to 2900 in human clone 19A2 (SEQ ID NO: 1). The human probe was generated by PCR using primer pairs designated ATM-2 and 9–10.1 set out in SEQ ID NOS: 38 and 39, respectively; the rat probe was generated using primer pairs 434L and 434R, set out in SEQ ID NOS: 34 and 35, respectively. Samples were incubated at 94° C. for 4 minutes and subjected to 30 cycles of the temperature step sequence: 94° C.; 50° C. 2 minutes; 72° C., 4 minutes.

| | |
|---|---|
| 5'-GTCCAAGCTGTCATGGGCCAG-3' | (SEQ ID NO: 38) |
| 5'-GTCCAGCAGACTGAAGAGCACGG-3' | (SEQ ID NO: 39) |

The PCR products were purified using the Qiagen Quick Spin kit according to manufacturer's suggested protocol, and approximately 180 ng DNA was labeled with 200 µCi [$^{32}$P]-dCTP using a Boehringer Mannheim Random Primer Labeling kit according to manufacturer's suggested protocol. Unincorporated isotope was removed using a Centri-sep Spin Column (Princeton Separations, Adelphia, N.J.) according to manufacturer's suggested protocol. The probes were denatured with 0.2N NaOH and neutralized with 0.4M Tris-HCl, pH 8.0, before use.

A mouse thymic oligo dT-primed cDNA library in lambda ZAP II (Stratagene) was plated at approximately 30,000 plaques per 15 cm plate. Plaque lifts on nitrocellulose filters (Schleicher & Schuell, Keene, N.H.) were incubated at 50° C. with agitation for 1 hour in a prehybridization solution (8 ml/lift) containing 30% formamide. Labeled human and rat probes were added to the prehybridization solution and incubation continued overnight at 50° C. Filters were washed twice in 2× SSC/0.1% at room temperature, once in 2× SSC/0.1% SDS at 37° C., and once in 2× SSC/0.1% SDS at 42° C. Filters were exposed on Kodak X-Omat AR film at −80° C. for 27 hours with an intensifying screen.

Four plaques giving positive signals on duplicate lifts were restreaked on LB medium with magnesium (LBM)/carbenicillin (100 mg/ml) plates and incubated overnight at 37° C. The phage plaques were lifted with Hybond filters (Amersham), probed as in the initial screen, and exposed on Kodak X-Omat AR film for 24 hours at −80° C. with an intensifying screen.

Twelve plaques giving positive signals were transferred into low Mg$^{++}$ phage diluent containing 10 mM Tris-HCl and 1 mM MgCl$_2$. Insert size was determined by PCR amplification using T3 and T7 primers (SEQ ID NOS: 13 and 14, respectively) and the following reaction conditions. Samples were incubated at 94° C. for 4 minutes and subjected to 30 cycles of the temperature step sequence: 94° C., for 15 seconds; 50° C., for 30 seconds; and 72° C. for 1 minute.

Six samples produced distinct bands that ranged in size from 300 bases to 1 kb. Phagemids were released via co-infection with helper phage and recircularized to generate Bluescript SK$^-$ (Stratagene). The resulting colonies were cultured in LRM/carbenicillin (100 mg/ml) overnight. DNA was isolated with a Promega Wizard miniprep kit (Madison, Wis.) according to manufacturer's suggested protocol. EcoRI restriction analysis of purified DNA confirmed the molecular weights which were detected using PCR. Insert DNA was sequenced with M13 and M13 reverse. 1 primers set out in SEQ ID NOS: 40 and 41, respectively.

| | |
|---|---|
| 5'-TGTAAAACGACGGCCAGT-3' | (SEQ ID NO: 40) |
| 5'-GGAAACAGCTATGACCATG-3' | (SEQ ID NO: 41) |

Sequencing was performed as described in Example 4.

Of the six clones, only two, designated 10.3-1 and 10.5-2, provided sequence information and were identical 600 bp fragments. The 600 bp sequence was 68% identical to a corresponding region of human $\alpha_d$, 40% identical to human CD11a, 58% identical to human CD11c, and 54% identical to mouse CD11b. This 600 bp fragment was then utilized to isolate a more complete cDNA encoding a putative mouse $\alpha_d$ homolog.

A mouse splenic cDNA library (oligo dT and random-primed) in lambda Zap II (Stratagene) was plated at 2.5×10$^4$ phage/15 cm LBM plate. Plaques were lifted on Hybond nylon transfer membranes (Amersham), denatured with 0.5M NaOH/1.5M NaCl, neutralized with 0.5M Tris Base/ 1.5M NaCl/11.6 HCl, and washed in 2× SSC. The DNA was cross-linked to filters by ultraviolet irradiation.

Approximately 500,000 plaques were screened using probes 10.3-1 and 10.5-2 previously labeled as described supra. Probes were added to a prehybridization solution and incubated overnight at 50° C. The filters were washed twice in 2× SSC/0.1% SDS at room temperature, once in 2× SSC/0.1% SDS at 37° C., and once in 2× SSC/0.1% SDS at 42° C. Filters were exposed on Kodak X-Omat AR film for 24 hours at −80° C. with an intensifying screen. Fourteen plaques giving positive signals on duplicate lifts were subjected to a secondary screen identical to that for the initial screen except for additional final high stringency washes in 2× SSC/0.1% SDS at 50° C., in 0.5× SSC/0.1% SDS at 50° C., and at 55° C. in 0.2× SSC/0.1% SDS. The filters were exposed on Kodak X-Omat AR film at −80° C. for 13 hours with an intensifying screen.

Eighteen positive plaques were transferred into low Mg$^{++}$ phage diluent and insert size determined by PCR amplification as described above. Seven of the samples gave single bands that ranged in size from 600 bp to 4 kb. EcoRI restriction analysis of purified DNA confirmed the sizes observed from PCR and the DNA was sequenced with primers M13 and M13 reverse.1 (SEQ ID NOS: 40 and 41, respectively).

One clone designated B3800 contained a 4 kb insert which corresponded to a region 200 bases downstream of the 5' end of the human $\alpha_d$ 19A2 clone and includes 553 bases of a 3' untranslated region. Clone B3800 showed 77% identity to a corresponding region of human $\alpha_d$, 44% identity to a corresponding region of human CD11a, 59% identity to a corresponding region of human CD11c, and 51% identity to a corresponding region of mouse CD11b. The second clone A1160 was a 1.2 kb insert which aligned to the 5' end of the coding region of human $\alpha_d$ approximately 12 nucleic acids downstream of the initiating methionine. Clone A1160 showed 75% identity to a corresponding region of human $\alpha_d$, 46% identity to a corresponding region of human CD11a, 62% identity to a corresponding region of human CD11c, and 66% identity to a corresponding region of mouse CD11b.

Clone A1160, the fragment closer to the 5' end of human clone 19A2, is 1160 bases in length, and shares a region of overlap with clone B3800 starting at base 205 and continuing to base 1134. Clone A1160 has a 110-base insertion (bases 704–814 of clone A1160) not present in the overlapping region of clone B3800. This insertion occurs at a probable exon-intron boundary [Fleming, et al., *J. Immunol.* 150:480–490 (1993)] and was removed before subsequent ligation of clones A1160 and B3800.

Rapid Amplification of 5' cDNA End of the Putative Mouse $\alpha_d$ Clone

RACE PCR [Frohman, "RACE: Rapid Amplification of cDNA Ends," in *PCR Protocols: A Guide to Methods and Applications*, Innis, et al. (eds.) pp. 28–38, Academic Press-:New York (1990)] was used to obtain missing 5' sequences of the putative mouse $\alpha_d$ clone, including 5' untranslated sequence and initiating methionine. A mouse splenic RACE-Ready kit (Clontech, Palo Alto, Calif.) was used according to the manufacturer's suggested protocol. Two antisense, gene-specific primers, A1160 RACE1-primary and A1160 RACE2-nested (SEQ ID NOS: 42 and 43), were designed to perform primary and nested PCR.

5'-GGACATGTTCACTGCCTCTAGG-3'  (SEQ ID NO: 42)

5'-GGCGGACAGTCAGACGACTGTCCTG-3'  (SEQ ID NO: 43)

The primers, SEQ ID NOS: 42 and 43, correspond to regions starting 302 and 247 bases from the 5' end, respectively. PCR was performed as described, supra, using the 5' anchor primer (SEQ ID NO: 44) and mouse spleen cDNA supplied with the kit.

5'-CTGGTTCGGCCCACCTCTGAAGGTTCCA-
GAATCGATAG-3'  (SEQ ID NO: 44)

Electrophoresis of the PCR product revealed a band approximately 280 bases in size, which was subcloned using a TA cloning kit (Invitrogen) according to manufacturer's suggested protocol. Ten resulting colonies were cultured, and the DNA isolated and sequenced. An additional 60 bases of 5' sequence were identified by this method, which correspond to bases 1 to 60 in SEQ ID NO: 45.

Characteristics of the Mouse cDNA and Predicted Amino Acid Sequence

A composite sequence of the mouse cDNA encoding a putative homolog of human $\alpha_d$ is set out in SEQ ID NO: 45. Although homology between the external domains of the human and mouse clones is high, homology between the cytoplasmic domains is only 30%. The observed variation may indicate C-terminal functional differences between the human and mouse proteins. Alternatively, the variation in the cytoplasmic domains may result from splice variation, or may indicate the existence of an additional $\beta_2$ integrin gene(s).

At the amino acid level, the mouse cDNA predicts a protein (SEQ ID NO: 46) with 28% identity to mouse CD11a, 53% identity to mouse CD11b, 28% identity to human CD11a, 55% identity to human CD11b, 59% identity to human CD11c, and 70% identity to human $\alpha_d$. Comparison of the amino acid sequences of the cytoplasmic domains of human $\alpha_d$ and the putative mouse homolog indicates regions of the same length, but having divergent primary structure. Similar sequence length in these regions suggests species variation rather than splice variant forms. When compared to the predicted rat polypeptide, Example 16, supra, mouse and rat cytoplasmic domains show greater than 60% identity.

EXAMPLE 20

Isolation of additional mouse αd cDNA clones for sequence verification

In order to verify the nucleic and amino acids sequences describe in Example 19 for mouse $\alpha_d$, additional mouse sequences were isolated for the purposes of confirmation.

Isolation of mouse cDNA by hybridization with two homologous $\alpha_d$ probes (3' and 5') was performed using both a mouse splenic random primed library and an oligo dT-primed cDNA library in lambda ZAP II (Strategene). The library was plated at $5 \times 10^5$ phage per 15 cm LBM plate. Plaques were lifted on Hybond nylon membranes (Amersham), and the membranes were denatured (0.5M NaOH/1.5M NaCl), neutralized (0.5M Tris Base/1.5M NaCl/11.6M HCl) and washed (2× SSC salt solution). DNA was cross-lined to filters by ultraviolet irradiation.

Probes were generated using primers described below in a PCR reaction under the following conditions. Samples were held at 94° C. for 4 minutes and then run through 30 cycles of the temperature step sequence (94° C. for 15 seconds; 50° C. for 30 seconds; 72° C. for 1 minute in a Perkin-Elmer 9600 thermocycler).

The 3' probe was approximately 900 bases long and spanned a region from nucleotides 2752 to 3651 (in SEQ ID NO: 1) (5'→3') and was produced with primers 11.b-1/2FOR11 and 11.b-1/2REV2 as shown in SEQ ID NOS: 69 and 74, respectively). This probe was used in a first set of lifts.

The 5' probe was approximately 800 bases long and spanned a region from nucleotides 149 to 946 (in SEQ ID NO: 1) (5'→3') and was produced with primers 11.b-1/2FOR1 and 11.a-1/1REV1 as shown in SEQ ID NOS: 50 and 85, respectively). This probe was used in a second set of lifts.

In a third set of lifts, both probes described above were used together on the same plates.

Approximately 500,000 plaques were screened using the two probes from above which were labeled in the same way as described in Example 17. Labeled probes were added to a prehybridization solution, containing 45% formamide, and incubated overnight at 50° C. Filters were washed twice in 2× SSC/0.1% SDS at room temperature (22° C.). A final wash was carried out in 2× SSC/0.1% SDS at 50° C. Autoradiography was for 19 hours at −80° C. on Kodak X-Omat AR film with an intensifying screen.

Thirteen plaques giving positive signals on at least duplicate lifts were subjected to a secondary screen performed as described for the initial screen except that both the 3' and 5' labeled probes were used for hybridization and an additional final wash was incorporated using 2× SSC/0.1% SDS at 65° C. Autoradiography was performed as described above for 2.5 hours.

Thirteen plaques (designated MS2P1 through MS2P13) giving positive signals were transferred into low $Mg^{++}$ phage diluent. Insert size was determined by PCR amplification (Perkin-Elmer 9600 thermocycler) using T3 and T7 primers which anneal to Bluescript phagemid in ZAP II (sequence previously described) under the same conditions shown above. Band sizes ranged from 500 bases to 4Kb. Phagemids were isolated, prepared, and sequenced with M13 and M13 reverse. 1 primers (SEQ ID NOS: 40 and 41, respectively). Five of the thirteen clones; MS2P-3, MS2P-6, MS2P-9, MS2P-12, and MS2P-13, were sequenced, and together, represented a region from approximately base 200 at the 5' end to about 300 bases past a first stop codon at the 3' end.

Automated sequencing was performed as described in Example 4 by first using M13 and M13 reverse.1 primers (SEQ ID NOS: 40 and 41, respectively) to sequence the ends of each clone and to determine its position relative to construct #17 (SEQ ID NO: 45). Each clone was then completely sequenced using the appropriate primers (listed below) for that particular region.

| | |
|---|---|
| 11.b-1/2FOR1 5'-GCAGCCAGCTTCGGACAG-AC-3' | (SEQ ID NO: 50) |
| 11.a-1/1FOR2 5'-CCGCCTGCCACTGGCGTGT-GC-3' | (SEQ ID NO: 60) |
| 11.a-1/1FOR3 5'-CCCAGATGAAGGACTTCGT-CAA-3' | (SEQ ID NO: 61) |
| 11.b-1/2FOR4 5'-GCTGGGATCATTCG-CTATGC-3' | (SEQ ID NO: 62) |
| 11.b-1/2FOR5 5'-CAATGGATGGACCA-GTTCTGG-3' | (SEQ ID NO: 63) |
| 11.b-1/2FOR6 5'-CAGATCGGCTCCTA-CTTTGG-3' | (SEQ ID NO: 64) |
| 11.b-1/2FOR7 5'-CATGGAGCCTCGAGACAG-G-3' | (SEQ ID NO: 65) |
| 11.b-1/2FOR8 5'-CCACTGTCCTCGAAGCTG-GAG-3' | (SEQ ID NO: 66) |
| 11.b-1/2FOR9 5'-CTTCGTCCTGTGCTGGCTG-TGGGCTC-3' | (SEQ ID NO: 67) |
| 11.b-1/2FOR10 5'-CGCCTGGCATGTGAGGC-TGAG-3' | (SEQ ID NO: 68) |
| 11.b-1/2FOR11 5'-CCGTGATCAGTAGGCAGG-AAG-3' | (SEQ ID NO: 69) |
| 11.b-1/2FOR12 5'-GTCACAGAGGGAACCT-CC-3' | (SEQ ID NO: 70) |
| 11.b-1/2FOR13 5'-GCTCCTGAGTGAGGCTG-AAATCA-3' | (SEQ ID NO: 71) |
| 11.b-1/2FOR14 5'-GAGATGCTGGATCTACCA-TCTGC-3' | (SEQ ID NO: 72) |
| 11.b-1/2FOR15 5'-CTGAGCTGGGAGATTTTT-ATGG-3' | (SEQ ID NO: 73) |
| 11.b-1/2REV2 5'-GTGGATCAGCACTGAAAT-CTG-3' | (SEQ ID NO: 74) |
| 11.b-1/2REV3 5'-CGTTTGAAGAAGCCAAG-CTTG-3' | (SEQ ID NO: 75) |
| 11.b-1/2REV4 5'-CACAGCGGAGGTGCAGG-CAG-3' | (SEQ ID NO: 76) |
| 11.b-1/2REV5 5'-CTCACTGCTTGCGCT-GGC-3' | (SEQ ID NO: 77) |
| 11.b-1/2REV6 5'-CGGTAAGATAGCTCT-GCTGG-3' | (SEQ ID NO: 78) |
| 11.b-1/2REV7 5'-GAGCCCACAGCCAG-CACAGG-3' | (SEQ ID NO: 79) |
| 11.b-1/2REV8 5'-GATCCAACGCCAGAT-CATACC-3' | (SEQ ID NO: 80) |
| 11.b-1/2REV9 5'-CACGGCCAGGTCCA-CCAGGC-3' | (SEQ ID NO: 81) |
| 11.b-1/2REV10 5'-CACGTCCCCTAGCA-CTGTCAG-3' | (SEQ ID NO: 82) |
| 11.b-1/2REV11 5'-CCATGTCCACAGAA-CAGAGAG-3' | (SEQ ID NO: 51) |
| 11.b-1/2REV12 5'-TTGACGAAGTCCTT-CATCTGGG-3' | (SEQ ID NO: 83) |
| 11.b-1/2REV13 5'-GAACTGCAAGCTGG-AGCCCAG-3' | (SEQ ID NO: 84) |
| 11.a-1/1REV1 5'-CTGGATGCTGCGAAG-TGCTAC-3' | (SEQ ID NO: 85) |
| 11.a-1/1REV2 5'-GCCTTGGAGCTGGACG-ATGGC-3' | (SEQ ID NO: 86) |

Sequences were edited, aligned, and compared to a previously isolated mouse $\alpha_d$ sequence (construct #17, SEQ ID NO: 45).

Alignment of the new sequences revealed an 18 base deletion in construct #17 beginning at nucleotide 2308; the deletion did not cause a shift in the reading frame. Clone MS2P-9, sequenced as described above, also revealed the same 18 base deletion. The deletion has been observed to occur in 50% of mouse clones that include the region but has not been detected in rat or human $\alpha_d$ clones. The eighteen base deletion is characterized by a 12 base palindromic sequence AAGCAGGAGCTCCTGTGT (SEQ ID NO: 91). This inverted repeat in the nucleic acid sequence is self-complementary and may form a loop out, causing cleavage during reverse transcription. The mouse $\alpha_d$ sequence which includes the additional 18 bases is set forth in SEQ ID NO: 52; the deduced amino acid sequence is set forth in SEQ ID NO: 53.

EXAMPLE 21

In situ hybridizations in Mouse

Tissue distribution was then determined for mouse $\alpha_d$ in order to provide a comparison to that in humans, described in Example 6.

A single stranded 200 bp mRNA probe was generated from a DNA template, corresponding to nucleotides 3460 to 3707 in the cytoplasmic tail region of the murine cDNA, by in vitro RNA transcription incorporating $^{35}$S-UTP (Amersham).

Whole mouse embryos (harvested at days 11-18 after fertilization) and various mouse tissues, including spleen, kidney, liver, intestine, and thymus, were hybridized in situ with the radiolabeled single-stranded mRNA probe.

Tissues were sectioned at 6 µm thickness, adhered to Vectabond (Vector Laboratories, Inc., Burlingame, Calif.) coated slides, and stored at −70° C. Prior to use, slides were removed from −70° C. and placed at 50° C. for approximately 5 minutes. Sections were fixed in 4% paraformaldehyde for 20 minutes at 4° C., dehydrated with an increasing ethanol gradient (70–95–100%) for 1 minute at 4° C. at each concentration, and air dried for 30 minutes at room temperature. Sections were denatured for 2 minutes at 70° C. in 70% formamide/2× SSC, rinsed twice in 2× SSC, dehydrated with the ethanol gradient described supra and air dried for 30 minutes. Hybridization was carried out overnight (12–16 hours) at 55 ° C. in a solution containing $^{35}$S-labeled riboprobes at 6×10$^5$ cpm/section and diethylpyrocarbonate (DEPC)-treated water to give a final concentration of 50% formamide, 0.3M NaCl, 20 mM Tris-HCl, pH 7.5, 10% dextran sulfate, 1× Denhardt's solution, 100 mM dithiothreitol (DTT) and 5 mM EDTA. After hybridization, sections were washed for 1 hour at room temperature in 4× SSC/10 mM DTT, 40 minutes at 60° C. in 50% formamide/ 2× SSC/10 mM DTT, 30 minutes at room temperature in 2× SSC, and 30 minutes at room temperature in 0.1× SSC. The sections were dehydrated, air dried for 2 hours, coated with Kodak NTB2 photographic emulsion, air dried for 2 hours, developed (after storage at 4° C. in complete darkness) and counterstained with hematoxylin/eosin.

Spleen tissue showed a strong signal primarily in the red pulp. This pattern is consistent with that of tissue macrophage distribution in the spleen, but does not exclude other cell types.

EXAMPLE 22

Generation of Mouse Expression Constructs

In order to construct an expression plasmid including mouse cDNA sequences exhibiting homology to human $\alpha_d$, inserts from clones A1160 and B3800 were ligated. Prior to this ligation, however, a 5' leader sequence, including an initiating methionine, was added to clone A1160. A primer designated "5' PCR leader" (SEQ ID NO: 47) was designed to contain: (1) identical nonspecific bases at positions 1–6 allowing for digestion; (2) a BamHI site (underlined in SEQ ID NO: 47) from positions 7–12 to facilitate subcloning into an expression vector; (3) a consensus Kozak sequence from positions 13–18, (4) a signal sequence including a codon for an initiating methionine (bold in SEQ ID NO: 47), and (5) an additional 31 bases of specifically overlapping 5' sequence from clone A1160 to allow primer annealing. A second primer designated "3' end frag" (SEQ ID NO: 48) was used with primer "5' PCR leader" to amplify the insert from clone A1160.

5'-AGTTAC<u>GGATCC</u>GGCACCATGACCTTCGGCACT-
GTGATCCTCCTGTGTG-3'     (SEQ ID NO: 47)

5'-GCTGGACGATGGCATCCAC-3'     (SEQ ID NO: 48)

The resulting PCR product did not digest with BamHI, suggesting that an insufficient number of bases preceded the restriction site, prohibiting recognition by the enzyme. The length of the "tail" sequence preceding the BamHI site in the 5' primer (SEQ ID NO: 47) was increased and PCR was repeated on the amplification product from the first PCR. A 5' primer, designated mAD.5'.2 (SEQ ID NO: 49), was designed with additional nonspecific bases at positions 1–4 and an additional 20 bases specifically overlapping the previously employed "5' PCR leader" primer sequences.

5'-GTAGAGTTAC<u>GGATCC</u>GGCACCAT-3'     (SEQ ID NO: 49)

Primers "mAD.5'.2" and "3' end frag" were used together in PCR with the product from the first amplification as template. A resulting secondary PCR product was subcloned into plasmid pCRtmII (Invitrogen) according to manufacturer's suggested protocol and transformed into competent One shot cells (Invitrogen). One clone containing the PCR product was identified by restriction enzyme analysis using BamHI and EcoRI and sequenced. After the sequence was verified, the insert was isolated by digestion with BamHI and EcoRI and gel purified.

The insert from clone B3800 was isolated by digestion with EcoRI and NotI, gel purified, and added to a ligation reaction which included the augmented A1160 BamHI/EcoRI fragment. Ligation was allowed to proceed for 14 hours at 14° C. Vector pcDNA.3 (Invitrogen), digested with BamHI and NoaI, was added to the ligation reaction with additional ligase and the reaction was continued for another 12 hours. An aliquot of the reaction mixture was transformed into competent E. coli cells, the resulting colonies cultured, and one positive clone identified by PCR analysis with the primers 11.b-1/2FOR1 and 11.b-1/2REV11 (SEQ ID NOS: 50 and 51, respectively). These primers bridge the A1160 and B3800 fragments, therefore detection of an amplification product indicates the two fragments were ligated. The sequence of the positive clone was verified with the primers set out in SEQ ID NOS: 50 and 51, which amplify from base 100 to 1405 after the initiating methionine.

EXAMPLE 23

Construction of a Knock-out Mouse

In order to more accurately assess the immunological role of the protein encoded by the putative mouse $\alpha_d$ cDNA, a "knock-out" mouse is designed wherein the genomic DNA sequence encoding the putative $\alpha_d$ homolog is disrupted by homologous recombination. The significance of the protein encoded by the disrupted gene is thereby assessed by the absence of the encoded protein. Generation of "knock-out" mice is described in Deng, et al., *Mol. Cell. Biol.* 13:2134–2140 (1993).

Design of such a mouse begins with construction of a plasmid containing sequences to be "knocked out" by homologous recombination events. A 750 base pair fragment of the mouse cDNA (corresponding to nucleotides 1985 to 2733 in SEQ ID NO: 45) was used to identify a mouse genomic sequence encoding the putative mouse $\alpha_d$ homolog from a λFIXII genomic library. Primary screening resulted in 14 positive plaques, seven of which were confirmed by secondary screening. Liquid lysates were obtained from two of the plaques giving the strongest signal and the λ DNA was isolated by conventional methods. Restriction mapping and Southern analysis confirmed the authenticity of one clone, designated 14-1, and the insert DNA was isolated by digestion with NotI. This fragment was cloned into Bluescript SKII⁺.

In order to identify a restriction fragment of approximately 9 to 14 kb, a length reported to optimize the probability of homologous recombination events, Southern hybridization was performed with the 750 bp cDNA probe. Prior to hybridization, a restriction map was constructed for clone 14-1. A 12 kb fragment was identified as a possible candidate and this fragment was subcloned into pBluescript SKII⁺ in a position wherein the mouse DNA is flanked by thymidine kinase encoding cassettes. Further analysis of this clone with an I domain probe (corresponding to nucleotides 454–1064 in SEQ ID NO: 45) indicated that the clone did not contain I domain encoding sequences.

Using the same I domain probe, the λFIXII genomic library was rescreened. Initially, six positive clones were detected, one of which remained positive upon secondary screening. DNA isolated from this clone reacted strongly in Southern analysis with an I domain probe. No reactivity was detected using the original 750 bp probe, however, indicating that this clone included regions 5' to nucleotides 1985–2773 of SEQ ID NO: 45.

Alternatively, the lack of hybridization to the 750 bp probe may have suggested that the clone was another member of the integrin family of proteins. To determine if this explanation was plausible, the 13 kb insert was subcloned into pBluescript SKII⁺. Purified DNA was sequenced using primers corresponding to $\alpha_d$ I domain nucleic acid sequences 441–461, 591–612, 717–739, and reverse 898–918 in SEQ ID NO: 52. Sequence information was obtained using only the first 4441–4461 primer, and only the 5'-most exon of the I domain was efficiently amplified. The remainder of the I domain was not amplified. The resulting clone therefore comprised exon 6 of the mouse $\alpha_d$ gene, and intronic sequences to the 3' and 5' end of the exon. Exon 7 was not represented in the clone. After sequencing, a construct is generated containing neomycin resistance and thymidine kinase genes.

The neomycin resistance (neo<sup>r</sup>) gene is inserted into the resulting plasmid in a manner that interrupts the protein coding sequence of the genomic mouse DNA. The resulting plasmid therefore contains a neo<sup>r</sup> gene within the mouse genomic DNA sequences, all of which are positioned within a thymidine kinase encoding region. Plasmid construction in

EXAMPLE 24

Cloning of Rabbit $\alpha_d$—Construction and Screening of the Rabbit cDNA Library Identification of human $\alpha_d$ homologs in rats and mice led to the investigation of the existence of a rabbit homolog which would be useful in rabbit models of human disease states described infra.

Poly A⁺ RNA was prepared from a whole rabbit spleen using an Invitrogen FastTrack kit (San Diego, Calif.) according to manufacturer's suggested protocol and reagents supplied with the kit. From 1.65 g tissue, 73 μg poly A⁺RNA were isolated. The rabbit spleen RNA was used to construct a ZAP Express cDNA library using a kit from Stratagene (La Jolla, Calif.). Resulting cDNA was directionally cloned into EcoRI and XhoI sites in the lambda arms of a pBK-CMV phagemid vector. Gigapack II Gold (Stratagene) was used to package the lambda arms into phage particles. The resulting library titer was estimated to be approximately 8×10⁵ particles, with an average insert size of 1.2 kb.

The library was amplified once by plating for confluent plaque growth and cell lysate was collected. The amplified library was plated at approximately 30,000 plaque forming units (pfu) per 150 mm plate with *E. coli* and the resulting mixture incubated for 12–16 hrs at 37° C. to allow plaque formation. Phage DNA was transferred onto Hybond N⁺ nylon membranes (Amersham, Arlington Heights, Ill.). The membranes were hybridized with a mixture of two random primed radiolabeled mouse $\alpha_d$ PCR DNA probes. The first probe was generated from a PCR product spanning nucleotides 149–946 in SEQ ID NO: 52. The second probe was from a PCR product spanning nucleotides 2752–3651 in SEQ ID NO: 52. Probes were labeled by random priming (Boehringer Mannheim Random Primed DNA Labeling Kit) and the reaction mixture was passed over a Sephadex G-50 column to remove unincorporated nucleotides. The hybridization solution was composed of 5× SSPE, 5× Denhardts, 1% SDS, 40% Formamide and the labeled probes at 1×10⁶ dpm/ml. Hybridization was carried out at 42° C. for 16–18 hours. Filters were washed extensively in 2× SSPE/0.1% SDS at room temperature and exposed to X-ray film to visualize any hybridizing plaques.

Two clones with significant sequence homology to human $\alpha_d$ were identified. Clone #2 was approximately 800 bp in length and mapped to the 5' end of human $\alpha_d$. Clone #2 includes an initiating methionine and complete leader sequence. Clone #7 was approximately 1.5 kb and includes an initiating methionine. The 5' end of clone #7 overlapped that of clone #2, while the 3' sequences terminated at a point beyond the I domain sequences. Clone #7 was completely sequenced by the primer walking method. The nucleotide and deduced amino acid sequences for clone #7 are set out in SEQ ID NOs: 100 and 101, respectively.

The predicted N terminal amino acid sequence for rabbit $\alpha_d$ as determined from clones #2 and #7 indicated a protein with 73% identity with human $\alpha_d$, 65% identity with mouse ad, and 58% identity with mouse CD11b, human CD11b, and human CD11c. The nucleic acid sequence for clone #2 is set out in SEQ ID NO: 92; the predicted amino acid sequence is set out in SEQ ID NO: 93

Isolation of a full length rabbit $\alpha_d$ cDNA was attempted using labeled rabbit clone #7 and rescreening the cDNA library from which the fragment was derived. Twenty-five additional clones were identified with one, designated clone 49, determined to be the largest. Clone 49 was completely sequenced using the nested deletions technique. The nucleotide and amino acid sequences for clone 49 are set out in SEQ ID NOs: 102 and 103, respectively. Since clones #7 and #49 did not overlap, oligonucleotides were designed to be used as primers in a PCR with first strand rabbit spleen cDNA to isolate the missing sequence.

The relationship of the putative amino acid sequence of these two partial clones with that of other leukointegrins is described in Table 1.

TABLE 1

Percent identity of $\beta_2$ integrin family members on the amino acid level.

| | Human $\alpha_d$ | Rabbit #7 | Rabbit #49 |
|---|---|---|---|
| Human $\alpha_d$ | 100 | 74 | 80 |
| Mouse $\alpha_d$ | 70 | 67 | 74 |
| Rat $\alpha_d$ | 70 | 66 | 73 |
| Mouse CD11a | random* | 28 | 28 |
| Mouse CD11b | 55 | 59 | 53 |
| Human CD11a | 36 | 28 | 28 |
| Human CD11b | 60 | 58 | 55 |
| Human CD11c | 66 | 59 | 62 |

*If <25% identity, it is just random alingment and not significant.

Isolation of a rabbit $\alpha_d$ clone allows expression of the protein, either on the surface of transfectants or as a soluble full length or truncated form. This protein is then used as an immunogen for the production of monoclonal antibodies for use in rabbit models of human disease states.

EXAMPLE 25

Animal Models For Determining $\alpha_d$ Therapeutic Utility

Immunohistologic data in dog and in situ hybridization in rats and mice has determined that in spleen $\alpha_d$ is expressed primarily by macrophages present in red pulp and in lymph nodes. $\alpha_d$ is found in medullary cords and sinuses. The expression pattern is remarkably similar to what has been reported for two murine antigens defined by the monoclonal antibodies F4/80 and SK39. While biochemical characterization of these murine antigens has demonstrated that they are distinct from $\alpha_d$, it is highly probably that $\alpha_d$ defines the same macrophage subset as the murine F4/80 and SK39 antigens.

In mouse, SK39-positive macrophages have been identified in splenic red pulp where they may participate in the clearance of foreign materials from circulation, and in medulla of lymph nodes [Jutila, et al., *J. Leukocyte Biol.* 54:30–39 (1993)]. SK39-positive macrophages have also been reported at sites of both acute and chronic inflammation. Furthermore, monocytes recruited to thioglycolate-inflamed peritoneal cavities also express the SK39 antigen. Collectively, these findings suggest that, if SK39⁺ cells are also $\alpha_d^+$, then these cells are responsible for the clearance of foreign materials in the spleen and participate in inflammation where macrophages play a significant role.

While the function of $\alpha_d$ remains unclear, other more well characterized $\beta_2$ integrins have been shown to participate in a wide variety of adhesion events that facilitate cell migration, enhance phagocytosis, and promote cell-cell interactions, events which all lead to upregulation of inflammatory processes. Therefore, it is highly plausible that interfering with the normal $\alpha_d$ function may also interfere with inflammation where macrophages play a significant role. Such an anti-inflammatory effect could result from: i)

blocking macrophage recruitment to sites of inflammation, ii) preventing macrophage activation at the site of inflammation or iii) interfering with macrophage effector functions which damage normal host tissue through either specific autoimmune responses or as a result of bystander cell damage.

Disease states in which there is evidence of macrophages playing a significant role in the disease process include multiple sclerosis, arthritis, graft atherosclerosis, some forms of diabetes and inflammatory bowel disease. Animal models, discussed below, have been shown to reproduce many of the aspects of these human disorders. Inhibitors of $\alpha_d$ function are tested in these model systems to determine if the potential exists for treating the corresponding human diseases.

A. Graft Arteriosclerosis

Cardiac transplantation is now the accepted form of therapeutic intervention for some types of end-state heart disease. As the use of cyclosporin A has increased one year survival rates to 80%, the development of progressive graft arteriosclerosis has emerged as the leading cause of death in cardiac transplants surviving beyond the first year. Recent studies have found that the incidence of significant graft arteriosclerosis 3 years following a cardiac transplant is in the range of 36–44% [Adams, et al., *Transplantation* 53:1115–1119 (1992); Adams, et al., *Transplantation* 56:794–799 (1993)].

Graft arteriosclerosis typically consists of diffuse, occlusive, intimal lesions which affect the entire coronary vessel wall, and are often accompanied by lipid deposition. While the pathogenesis of graft arteriosclerosis remains unknown, it is presumably linked to histocompatibility differences between donor and recipient, and is immunologic in nature. Histologically, the areas of intimal thickening are composed primarily of macrophages, although T cells are occasionally seen. It is therefore possible that macrophages expressing $\alpha_d$ may play a significant role in the induction and/or development of graft arteriosclerosis. In such a case, monoclonal antibodies or small molecule inhibitors (for example, soluble ICAM-R) of $\alpha_d$ function could be given prophylactically to individuals who received heart transplants and are at risk of developing graft arteriosclerosis.

Although atherosclerosis in heart transplants presents the greatest threat to life, graft arteriosclerosis is also seen in other solid organ transplants, including kidneys and livers. Therapeutic use of $\alpha_d$ blocking agents could prevent graft arteriosclerosis in other organ transplants and reduce complications resulting from graft failure.

One model for graft arteriosclerosis in the rat involves heterotopic cardiac allografts transplanted across minor histocompatibility barriers. When Lewis cardiac allografts are transplanted into MHC class I and II compatible F-344 recipients, 80% of the allografts survive at least 3 weeks, while 25% of the grafts survive indefinitely. During this low-grade graft rejection, arteriosclerosis lesions form in the donor heart. Arterial lesions in 120 day old allografts typically have diffuse fibrotic intimal thickening indistinguishable in appearance from graft arteriosclerosis lesions found in rejecting human cardiac allografts.

Rats are transplanted with hearts mismatched at minor histocompatibility antigens, for example Lewis into F-344. Monoclonal antibodies specific for rat $\alpha_d$ or small molecule inhibitors of $\alpha_d$ are given periodically to transplant recipients. Treatment is expected to reduce the incidence of graft arteriosclerosis in non-rejecting donor hearts. Treatment of rats with $\alpha_d$ monoclonal antibodies or small molecule inhibitors may not be limited to prophylactic treatments. Blocking $\alpha_d$ function is also be expected to reduce macrophage mediated inflammation and allow reversal of arterial damage in the graft.

B. Atherosclerosis in Rabbits Fed Cholesterol

Rabbits fed an atherogenic diet containing a cholesterol supplement for approximately 12–16 weeks develop intimal lesions that cover most of the lumenal surface of the ascending aorta [Rosenfeld, et al., *Arteriosclerosis* 7:9–23 (1987); Rosenfeld, et al., *Arteriosclerosis* 7:24–34 (1987)]. The atherosclerotic lesions seen in these rabbits are simmer to those in humans. Lesions contain large numbers of T cells, most of which express CD45RO, a marker associated with memory T cells. Approximately half of the infiltrating T cells also express MHC class II antigen and some express the IL-2 receptor suggesting that many of the cells are in an activated state.

One feature of the atherosclerotic lesions found in cholesterol fed rabbits, but apparently absent in rodent models, is the accumulation of foam cell-rich lesions. Foam cell macrophages are believed to result from the uptake of oxidized low-density lipoprotein (LDL) by specific receptors. Oxidized LDL particles have been found to be toxic for some cell types including endothelial cells and smooth muscle cells. The uptake of potentially toxic, oxidized LDL particles by macrophages serves as an irritant and drives macrophage activation, contributing to the inflammation associated with atherosclerotic lesions.

Once monoclonal antibodies have been generated to rabbit $\alpha_d$, cholesterol fed rabbits are treated. Treatments include prophylactic administration of $\alpha_d$ monoclonal antibodies or small molecule inhibitors, to demonstrate that $\alpha_d^+$ macrophages are involved in the disease process. Additional studies would demonstrate that monoclonal antibodies to $\alpha_d$ or small molecule inhibitors are capable of reversing vessel damage detected in rabbits fed an atherogenic diet.

C. Insulin-dependent Diabetes

BB rats spontaneously develop insulin-dependent diabetes at 70–150 days of age. Using immunohistochemistry, MHC class II$^+$, ED1$^+$ macrophages can be detected infiltrating the islets early in the disease. Many of the macrophages appear to be engaged in phagocytosis of cell debris or normal cells. As the disease progresses, larger numbers of macrophages are found infiltrating the islets, although significant numbers of T cells, and later B cells, also appear to be recruited to the site [Hanenberg, et al., *Diabetologia* 32:126–134 (1989)].

Development of diabetes in BB rats appears to depend on both early macrophage infiltration and subsequent T cells recruitment. Treatment of BB rats with silica particles, which are toxic to macrophages, has been effective in blocking the early macrophage infiltration of the islets. In the absence of early macrophage infiltration, subsequent tissue damage by an autoaggressive lymphocyte population falls to occur. Administration of monoclonal antibody OX-19 (specific for rat CD5) or monoclonal antibody OX-8 (specific for rat CD8), which block the T cell-associated phase of the disease, is also effective in suppressing the development of diabetes.

The central role of macrophages in the pathology of this model makes it attractive for testing inhibitors of $\alpha_d$ function. Rats genetically predisposed to the development of insulin-dependent diabetes are treated with monoclonal antibodies to $\alpha_d$ or small molecule inhibitors and evaluated for the development of the disease. Preventing or delaying clinical onset is evidence that $\alpha_d$ plays a pivotal role in macrophage damage to the islet cells.

D. Inflammatory Bowel Disease (Crohn's Disease, Ulcerative Colitis)

Animal models used in the study of inflammatory bowel disease (IBD) are generally elicited by intrarectal administration of noxious irritants (e.g. acetic acid or trinitrobenzene sulfonic acid/ethanol). Colonic inflammation induced by these agents is the result of chemical or metabolic injury and lacks the chronic and spontaneously relapsing inflammation associated with human IBD. However, a recently described model using subserosal injections of purified peptidoglycan-polysaccharide (PG-PS) polymers from either group A or group D streptococci appears to be a more physiologically relevant model for human IBD [Yamada, et al., *Gastroenterology* 104:759–771 (1993)].

In this model PG-PS is injected into the subserosal layer of the distal colon. The resulting inflammatory response is biphasic with an initial acute episode three days after injection, which is followed by a spontaneous chronic phase three to four weeks later. The late phase response is granulomatous in nature, and results in colonic thickening, adhesions, colonic nodules and mucosal lesions. In addition to mucosal injury, PG-PS colitis frequently leads to arthritis, anemia and granulomatous hepatitis. The extraintestinal manifestations of the disease make the model attractive for studying Crohn's colitis in that a significant number of patients with active Crohn's disease suffer from arthritic joint disease and hepatobiliary inflammation.

Granulomatous lesions are the result of chronic inflammation which leads to the recruitment and subsequent activation of cells of the monocyte/macrophage lineage. Presence of granulomatous lesions in Crohn's disease and the above animal model make this an attractive clinical target for $\alpha_d$ monoclonal antibodies or other inhibitors of $\alpha_d$ function. Inhibitors of $\alpha_d$ function are expected to block the formation of lesions associated with IBD or even reverse tissue damage seen in the disease.

E. Arthritis

Arthritis appears to be a multi-factorial disease process involving a variety of inflammatory cell types including neutrophils, T lymphocytes and phagocytic macrophages. Although a variety of arthritis models exist, preparations of streptococcal cell wall proteoglycan produce a disorder most similar to the human disease.

In rats, streptococcal cell wall induces inflammation of peripheral joints characterized by repeated episodes of disease progression followed by remission and eventually resulting in joint destruction over a period of several months [Cromartie, et al., *J. Exp. Med.* 146:1585–1602 (1977); Schwab et al., *Infection and Immunity* 59:4436–4442 (1991)]. During the chronic phase of the disease, mononuclear phagocytes or macrophages are believed to play a major role in destruction of the synovium. Furthermore, agents which suppress the recruitment of macrophages into the synovium effectively reduce the inflammation and pathology characteristic of arthritis.

A central role for the macrophage in synovium destruction that leads to arthritis predicts that monoclonal antibodies to $\alpha_d$ or inhibitors of $\alpha_d$ function may have therapeutic potential in the treatment of this disease. As in other models previously described, $\alpha_d$ monoclonal antibodies or small molecule inhibitors administered prophylactically are expected to block or moderate joint inflammation and prevent destruction of the synovium. Agents that interfere with $\alpha_d$ function may also moderate ongoing inflammation by preventing the recruitment of additional macrophages to the joint or blocking macrophage activation. The net result would be to reverse ongoing destruction of the joint and facilitate tissue repair.

F. Multiple Sclerosis

Although pathogenesis of multiple sclerosis (MS) remains unclear, it is generally accepted that the disease is mediated by $CD4^+$ T cells which recognize autoantigens in the central nervous system and initiate an inflammatory cascade. The resulting immune response results in the recruitment of additional inflammatory cells, including activated macrophages which contribute to the disease. Experimental autoimmune encephalomyelitis (EAE) is an animal model which reproduces some aspects of MS. Recently, monoclonal antibodies reactive with CD11b/CD18 [Huitinga, et al., *Eur. J. Immunol.* 23:709–715 (1993)] present on inflammatory macrophages have been shown to block both clinical and histologic disease. The results suggest that monoclonal antibodies or small molecule inhibitors to $\alpha_d$ are likely to be effective in blocking the inflammatory response in EAE. Such agents also have important therapeutic applications in the treatment of MS.

G. Immune Complex Alveolitis

Alveolar macrophages located in the alveolar ducts, airways, connective tissue, and pleural spaces of the lung represent the lung's first line of defense against inhaled environmental agents. In response to stimulation by agents, including bacterial-derived LPS, IFN-$\lambda$ and immune complexes, alveolar macrophages release a variety of potent inflammatory mediators, including highly reactive oxygen radicals and nitrogen intermediates. While superoxide anions, hydrogen peroxide and nitric oxide (NO.) have important functions in eradicating pathogens and lysing tumor targets, these agents can have injurious effects on normal tissues.

In a rat model of immune complex alveolitis, NO. release from alveolar macrophages has been shown to mediate much of the lung damage [Mulligan, et al., *Proc. Natl. Acad. Sci. (USA)* 88:638–6342 (1991)]. NO. has also been implicated as a mediator in other immune complex mediated injuries including dermal vasculitis [Mulligan, et al., supra] and could potentially play a role in diseases such as glomerulonephritis.

NO. mediated tissue damage is not limited to inflammation involving immune complexes. For example, microglial cell stimulated, by agents such as PMA, LPS or IFN-$\gamma$, produce NO. at levels capable of killing oligodendrocytes [Merrill, et al., *Immunol.* 151:2132 (1993)]. Pancreatic islet cells have also been found to be sensitive to NO., and macrophage release of this mediator has been implicated in the tissue damage which leads to diabetes [Kroncke, et al., BBRC 175:752–758 (1991)]. More recently, it was conclusively demonstrated that NO. release plays a role in endotoxic shock [MacMicking, et al., *Cell* 81:641–650 (1995)]. When administered lipopolysaccharide (LPS), normal wild-type mice experience a severe, progressive decline in arterial pressure resulting in death. Mice deficient in inducible nitric oxide, however, experience a much less severe decline in arterial pressure in response to LPS, and all survive the treatment.

In vitro assays indicate that blockage of $\alpha_d$ is effective at blocking some aspects of macrophage (or leukocyte which express $\alpha_d$, in general) activation, including NO. release. Alveolar macrophages stimulated with IFN-$\gamma$ in the presence of anti-$\alpha_d$ polyclonal anti-serum (generated in rabbits against a rat $\alpha_d$ I domain polypeptide) were found to produce significantly less nitrite/nitrate—breakdown products of NO. than macrophages treated with control antiserum. This finding indicates that monoclonal antibodies to $\alpha_d$, particularly to the I-domain, may be potent anti-inflammatory agents with potential uses in MS, diabetes, lung inflammation and endotoxic shock. Furthermore, in contrast to CD18, which effects the function of a wide variety of leukocyte types, the limited distribution of $\alpha_d$ may make this a more attractive target than CD18 for preventing macrophage (or leukocyte which express $\alpha_d$, in general) activation.

Rat IgG immune complex-induced alveolitis is a widely used experimental model important in understanding acute lung injury. The injury is elicited by instilling anti-bovine serum albumin (BSA) antibodies into lungs via tracheal cannulation, followed by an intravenous injection of BSA. The formation of immune complexes in the microvasculature of the lung leads to complement activation and the recruitment of neutrophils into the lung. Presumably, formation of immune complexes in the lung following extravasation of leukocytes from the blood and subsequent leukocyte movement across lung epithelium. The subsequent release of mediators, including radicals, TNF-α and nitric oxide (NO.), from activated endothelial cells, neutrophils and macrophages which participate in progression of the disease. Pathologic features of the disease include increased vascular permeability leading to edema and the presence of large numbers of erythrocytes and PMNs present in the alveolar spaces.

Polyclonal anti-serum specific for the I domain of $\alpha_d$ was tested in a rat model of immune complex-induced alveolitis. The anti-$\alpha_d$ polyclonal serum was administered via tracheal cannulation at the same time anti-BSA was introduced into the lungs. Lung injury was subsequently elicited by intravenous administration of BSA along with a trace amount of $^{125}$I-labeled BSA (approximately 800,000 cpm) to quantitate edema resulting from lung injury. Lung injury was allowed to proceed for four hours and damage was assessed using a lung permeability value, is defined as the ratio of $^{125}$I-labeled BSA in the lung compared to the amount of label present in the 1.0 ml of blood. Typically lung permeability values for positive control rates range between 0.6 and 0.8, while negative controls (rats not receiving BSA) have permeability index values in the range of 0.1–0.2.

Initial studies indicated that treatment with anti-$\alpha_d$ polyclonal anti-serum reduced lung permeability values by greater that 50%, representing a dramatic moderation of lung injury. Historically, treatments with anti-CD18 have reduced permeability values by 60%. These findings indicate that $\alpha_d$ may be the most important $\beta_2$ integrin during acute lung injury, however it cannot be precisely determined if the effect of the anti-sera prohibits leukocyte extravasation from the blood, or movement across lung epithelia.

As additional proof that $\alpha_d$ moderates lung injury, TNF-alpha levels in the bronchoalveolar lavage fluid were evaluated. Treatment with the anti-$\alpha_d$ anti-serum was found to reduce TNF-alpha levels approximately four-fold. TNF-alpha has long been viewed as an important mediator in acute lung inflammation, and responsible for the recruitment of inflammatory cells into sites of inflammation, cell activation and tissue damage. Presumably, anti-$\alpha_d$ anti-serum blocks activation of resident alveolar macrophages during the formation of immune complex alveolitis, and thereby moderates the release of TNF-α and NO., and reduces subsequent tissue damage caused by these agents and the recruitment of neutrophils.

Numerous modifications and variations in the invention as set forth in the above illustrative examples are expected to occur to those skilled in the art. Consequently only such limitations as appear in the appended claims should be placed on the invention.

What is claimed is:

1. A method for identifying a compound capable of reacting specifically with $\alpha_d$ and of modulating the interaction of $\alpha_d$ and a binding partner of $\alpha_d$ comprising the steps of:

a) immobilizing $\alpha_d$ or a fragment thereof, or a binding partner of $\alpha_d$, on a solid support, said fragment selected from the group consisting of a fragment comprising the cytoplasmic domain of $\alpha_d$, a fragment comprising the transmembrane domain of $\alpha_d$, and a fragment comprising the extracellular domain of $\alpha_d$;

b) labelling the non-immobilized binding partner with a detectable agent;

c) contacting said immobilized binding partner with said labelled binding partner in the presence and absence of a putative modulator compound capable of specifically reacting with $\alpha_d$;

d) detecting binding between said immobilized binding partner and said labelled binding partner; and e) identifying modulating compounds as those compounds that affect binding between said immobilized binding partner and said labelled binding partner.

2. The method of claim 1 wherein $\alpha_d$ or the binding partner of $\alpha_d$ is immobilized on a solid support coated or impregnated with a fluorescent agent; said non-immobilized binding partner is labelled with a compound capable of exciting said fluorescent agent; and $\alpha_d$ interaction with the binding partner of $\alpha_d$ is detected by light emission from said fluorescent agent.

3. The method of claim 1 or 2 wherein said binding partner of $\alpha_d$ is ICAM-R.

* * * * *

UNITED STATES PATENT AND TRADEMARK OFFICE
CERTIFICATE OF CORRECTION

PATENT NO. : 5,728,533  
DATED : March 17, 1998  
INVENTOR(S) : W. Michael Gallatin and Monica VanderVieren Page 1 of 2

It is certified that error appears in the above-identified patent and that said Letters Patent is hereby corrected as shown below:

In the specification:

Column 11, line 65, delete "(DTF)." and insert therefor -- (DTT). --

Column 18, line 44, delete "6underlined" and insert therefor -- underlined --

Column 23, line 13, delete "dam" and insert therefor -- data --

Column 24, line 34 after "recovery" delete "in" and insert -- is --

Column 26, line 40, after "then" delete "be"

Column 28, line 40, after "100" please delete "$\mu$from" and insert -- $\mu$l from --

Column 28, line 50, after "washed" delete "3xX" and insert -- 3X --

Column 28, line 67, after "other" delete "$\alpha_2$" and insert -- $\beta_2$ --

Column 29, line 12, after "St. Louis" delete "Me." and insert -- MO --

Column 32, line 32, after "antibodies;" delete "hint" and insert -- faint --

Column 39, line 63, after "cultured in" delete "LRM/" and insert -- LBM/ --

UNITED STATES PATENT AND TRADEMARK OFFICE
CERTIFICATE OF CORRECTION

PATENT NO. : 5,728,533
DATED : Mar. 17, 1998
INVENTOR(S) : W. Michael Gallatin, et al It is certified that error appears in the above-identified patent and that said Letters Patent is hereby corrected as shown below:

Column 41, line 66, delete "describe" and insert --described--

Signed and Sealed this

Third Day of November, 1998

Attest:

BRUCE LEHMAN

*Attesting Officer*          *Commissioner of Patents and Trademarks*

SEQUENCE LISTING ( 1 ) GENERAL INFORMATION:

( i i i ) NUMBER OF SEQUENCES: 103

( 2 ) INFORMATION FOR SEQ ID NO:1:

( i ) SEQUENCE CHARACTERISTICS:
( A ) LENGTH: 3726 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 3..3485

( x i ) SEQUENCE DESCRIPTION: SEQ ID NO:1:

```
TG ACC TTC GGC ACT GTG CTT CTT CTG AGT GTC CTG GCT TCT TAT CAT        47
   Thr Phe Gly Thr Val Leu Leu Leu Ser Val Leu Ala Ser Tyr His
   1               5                   10                  15

GGA TTC AAC CTG GAT GTG GAG GAG CCT ACG ATC TTC CAG GAG GAT GCA        95
Gly Phe Asn Leu Asp Val Glu Glu Pro Thr Ile Phe Gln Glu Asp Ala
                20                  25                  30

GGC GGC TTT GGG CAG AGC GTG GTG CAG TTC GGT GGA TCT CGA CTC GTG       143
Gly Gly Phe Gly Gln Ser Val Val Gln Phe Gly Gly Ser Arg Leu Val
```

|  |  |  |  |  |  |  |  |  |  |  |  |  |  |  |  |
|---|---|---|---|---|---|---|---|---|---|---|---|---|---|---|---|
|  |  | 35 |  |  |  |  | 40 |  |  |  |  | 45 |  |  |  |
| GTG | GGA | GCA | CCC | CTG | GAG | GTG | GTG | GCG | GCC | AAC | CAG | ACG | GGA | CGG | CTG |
| Val | Gly | Ala | Pro | Leu | Glu | Val | Val | Ala | Ala | Asn | Gln | Thr | Gly | Arg | Leu |
|  |  | 50 |  |  |  |  | 55 |  |  |  |  | 60 |  |  |  |
| TAT | GAC | TGC | GCA | GCT | GCC | ACC | GGC | ATG | TGC | CAG | CCC | ATC | CCG | CTG | CAC |
| Tyr | Asp | Cys | Ala | Ala | Ala | Thr | Gly | Met | Cys | Gln | Pro | Ile | Pro | Leu | His |
|  | 65 |  |  |  |  | 70 |  |  |  |  | 75 |  |  |  |  |
| ATC | CGC | CCT | GAG | GCC | GTG | AAC | ATG | TCC | TTG | GGC | CTG | ACC | CTG | GCA | GCC |
| Ile | Arg | Pro | Glu | Ala | Val | Asn | Met | Ser | Leu | Gly | Leu | Thr | Leu | Ala | Ala |
| 80 |  |  |  |  | 85 |  |  |  |  | 90 |  |  |  |  | 95 |
| TCC | ACC | AAC | GGC | TCC | CGG | CTC | CTG | GCC | TGT | GGC | CCG | ACC | CTG | CAC | AGA |
| Ser | Thr | Asn | Gly | Ser | Arg | Leu | Leu | Ala | Cys | Gly | Pro | Thr | Leu | His | Arg |
|  |  |  |  | 100 |  |  |  |  | 105 |  |  |  |  | 110 |  |
| GTC | TGT | GGG | GAG | AAC | TCA | TAC | TCA | AAG | GGT | TCC | TGC | CTC | CTG | CTG | GGC |
| Val | Cys | Gly | Glu | Asn | Ser | Tyr | Ser | Lys | Gly | Ser | Cys | Leu | Leu | Leu | Gly |
|  |  |  | 115 |  |  |  |  | 120 |  |  |  |  | 125 |  |  |
| TCG | CGC | TGG | GAG | ATC | ATC | CAG | ACA | GTC | CCC | GAC | GCC | ACG | CCA | GAG | TGT |
| Ser | Arg | Trp | Glu | Ile | Ile | Gln | Thr | Val | Pro | Asp | Ala | Thr | Pro | Glu | Cys |
|  |  | 130 |  |  |  |  | 135 |  |  |  |  | 140 |  |  |  |
| CCA | CAT | CAA | GAG | ATG | GAC | ATC | GTC | TTC | CTG | ATT | GAC | GGC | TCT | GGA | AGC |
| Pro | His | Gln | Glu | Met | Asp | Ile | Val | Phe | Leu | Ile | Asp | Gly | Ser | Gly | Ser |
|  | 145 |  |  |  |  | 150 |  |  |  |  | 155 |  |  |  |  |
| ATT | GAC | CAA | AAT | GAC | TTT | AAC | CAG | ATG | AAG | GGC | TTT | GTC | CAA | GCT | GTC |
| Ile | Asp | Gln | Asn | Asp | Phe | Asn | Gln | Met | Lys | Gly | Phe | Val | Gln | Ala | Val |
| 160 |  |  |  |  | 165 |  |  |  |  | 170 |  |  |  |  | 175 |
| ATG | GGC | CAG | TTT | GAG | GGC | ACT | GAC | ACC | CTG | TTT | GCA | CTG | ATG | CAG | TAC |
| Met | Gly | Gln | Phe | Glu | Gly | Thr | Asp | Thr | Leu | Phe | Ala | Leu | Met | Gln | Tyr |
|  |  |  | 180 |  |  |  |  | 185 |  |  |  |  | 190 |  |  |
| TCA | AAC | CTC | CTG | AAG | ATC | CAC | TTC | ACC | TTC | ACC | CAA | TTC | CGG | ACC | AGC |
| Ser | Asn | Leu | Leu | Lys | Ile | His | Phe | Thr | Phe | Thr | Gln | Phe | Arg | Thr | Ser |
|  |  | 195 |  |  |  |  | 200 |  |  |  |  | 205 |  |  |  |
| CCG | AGC | CAG | CAG | AGC | CTG | GTG | GAT | CCC | ATC | GTC | CAA | CTG | AAA | GGC | CTG |
| Pro | Ser | Gln | Gln | Ser | Leu | Val | Asp | Pro | Ile | Val | Gln | Leu | Lys | Gly | Leu |
|  |  | 210 |  |  |  |  | 215 |  |  |  |  | 220 |  |  |  |
| ACG | TTC | ACG | GCC | ACG | GGC | ATC | CTG | ACA | GTG | GTG | ACA | CAG | CTA | TTT | CAT |
| Thr | Phe | Thr | Ala | Thr | Gly | Ile | Leu | Thr | Val | Val | Thr | Gln | Leu | Phe | His |
| 225 |  |  |  |  | 230 |  |  |  |  | 235 |  |  |  |  |  |
| CAT | AAG | AAT | GGG | GCC | CGA | AAA | AGT | GCC | AAG | AAG | ATC | CTC | ATT | GTC | ATC |
| His | Lys | Asn | Gly | Ala | Arg | Lys | Ser | Ala | Lys | Lys | Ile | Leu | Ile | Val | Ile |
| 240 |  |  |  |  | 245 |  |  |  |  | 250 |  |  |  |  | 255 |
| ACA | GAT | GGG | CAG | AAG | TAC | AAA | GAC | CCC | CTG | GAA | TAC | AGT | GAT | GTC | ATC |
| Thr | Asp | Gly | Gln | Lys | Tyr | Lys | Asp | Pro | Leu | Glu | Tyr | Ser | Asp | Val | Ile |
|  |  |  |  | 260 |  |  |  |  | 265 |  |  |  |  | 270 |  |
| CCC | CAG | GCA | GAG | AAG | GCT | GGC | ATC | ATC | CGC | TAC | GCT | ATC | GGG | GTG | GGA |
| Pro | Gln | Ala | Glu | Lys | Ala | Gly | Ile | Ile | Arg | Tyr | Ala | Ile | Gly | Val | Gly |
|  |  |  | 275 |  |  |  |  | 280 |  |  |  |  | 285 |  |  |
| CAC | GCT | TTC | CAG | GGA | CCC | ACT | GCC | AGG | CAG | GAG | CTG | AAT | ACC | ATC | AGC |
| His | Ala | Phe | Gln | Gly | Pro | Thr | Ala | Arg | Gln | Glu | Leu | Asn | Thr | Ile | Ser |
|  |  | 290 |  |  |  |  | 295 |  |  |  |  | 300 |  |  |  |
| TCA | GCG | CCT | CCG | CAG | GAC | CAC | GTG | TTC | AAG | GTG | GAC | AAC | TTT | GCA | GCC |
| Ser | Ala | Pro | Pro | Gln | Asp | His | Val | Phe | Lys | Val | Asp | Asn | Phe | Ala | Ala |
|  | 305 |  |  |  |  | 310 |  |  |  |  | 315 |  |  |  |  |
| CTT | GGC | AGC | ATC | CAG | AAG | CAG | CTG | CAG | GAG | AAG | ATC | TAT | GCA | GTT | GAG |
| Leu | Gly | Ser | Ile | Gln | Lys | Gln | Leu | Gln | Glu | Lys | Ile | Tyr | Ala | Val | Glu |
| 320 |  |  |  |  | 325 |  |  |  |  | 330 |  |  |  |  | 335 |
| GGA | ACC | CAG | TCC | AGG | GCA | AGC | AGC | TCC | TTC | CAG | CAC | GAG | ATG | TCC | CAA |
| Gly | Thr | Gln | Ser | Arg | Ala | Ser | Ser | Ser | Phe | Gln | His | Glu | Met | Ser | Gln |
|  |  |  |  | 340 |  |  |  |  | 345 |  |  |  |  | 350 |  |
| GAA | GGC | TTC | AGC | ACA | GCC | CTC | ACA | ATG | GAT | GGC | CTC | TTC | CTG | GGG | GCT |
| Glu | Gly | Phe | Ser | Thr | Ala | Leu | Thr | Met | Asp | Gly | Leu | Phe | Leu | Gly | Ala |

191
239
287
335
383
431
479
527
575
623
671
719
767
815
863
911
959
1007
1055
1103

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 355 |     |     |     |     | 360 |     |     |     |     | 365 |     |     |      |
| GTG | GGG | AGC | TTT | AGC | TGG | TCT | GGA | GGT | GCC | TTC | CTG | TAT | CCC | CCA | AAT | 1151 |
| Val | Gly | Ser | Phe | Ser | Trp | Ser | Gly | Gly | Ala | Phe | Leu | Tyr | Pro | Pro | Asn |      |
|     |     | 370 |     |     |     |     | 375 |     |     |     |     | 380 |     |     |     |      |
| ATG | AGC | CCC | ACC | TTC | ATC | AAC | ATG | TCT | CAG | GAG | AAT | GTG | GAC | ATG | AGG | 1199 |
| Met | Ser | Pro | Thr | Phe | Ile | Asn | Met | Ser | Gln | Glu | Asn | Val | Asp | Met | Arg |      |
|     | 385 |     |     |     |     | 390 |     |     |     |     | 395 |     |     |     |     |      |
| GAC | TCT | TAC | CTG | GGT | TAC | TCC | ACC | GAG | CTA | GCC | CTG | TGG | AAG | GGG | GTA | 1247 |
| Asp | Ser | Tyr | Leu | Gly | Tyr | Ser | Thr | Glu | Leu | Ala | Leu | Trp | Lys | Gly | Val |      |
| 400 |     |     |     |     | 405 |     |     |     |     | 410 |     |     |     |     | 415 |      |
| CAG | AAC | CTG | GTC | CTG | GGG | GCC | CCC | CGC | TAC | CAG | CAT | ACC | GGG | AAG | GCT | 1295 |
| Gln | Asn | Leu | Val | Leu | Gly | Ala | Pro | Arg | Tyr | Gln | His | Thr | Gly | Lys | Ala |      |
|     |     |     |     | 420 |     |     |     |     | 425 |     |     |     |     | 430 |     |      |
| GTC | ATC | TTC | ACC | CAG | GTG | TCC | AGG | CAA | TGG | AGG | AAG | AAG | GCC | GAA | GTC | 1343 |
| Val | Ile | Phe | Thr | Gln | Val | Ser | Arg | Gln | Trp | Arg | Lys | Lys | Ala | Glu | Val |      |
|     |     |     | 435 |     |     |     |     | 440 |     |     |     |     | 445 |     |     |      |
| ACA | GGG | ACG | CAG | ATC | GGC | TCC | TAC | TTC | GGG | GCC | TCC | CTC | TGC | TCC | GTG | 1391 |
| Thr | Gly | Thr | Gln | Ile | Gly | Ser | Tyr | Phe | Gly | Ala | Ser | Leu | Cys | Ser | Val |      |
|     |     | 450 |     |     |     |     | 455 |     |     |     |     | 460 |     |     |     |      |
| GAT | GTG | GAC | AGC | GAT | GGC | AGC | ACC | GAC | CTG | ATC | CTC | ATT | GGG | GCC | CCC | 1439 |
| Asp | Val | Asp | Ser | Asp | Gly | Ser | Thr | Asp | Leu | Ile | Leu | Ile | Gly | Ala | Pro |      |
| 465 |     |     |     |     | 470 |     |     |     |     | 475 |     |     |     |     |     |      |
| CAT | TAC | TAT | GAG | CAG | ACC | CGA | GGG | GGC | CAG | GTG | TCC | GTG | TGT | CCC | TTG | 1487 |
| His | Tyr | Tyr | Glu | Gln | Thr | Arg | Gly | Gly | Gln | Val | Ser | Val | Cys | Pro | Leu |      |
| 480 |     |     |     |     | 485 |     |     |     |     | 490 |     |     |     |     | 495 |      |
| CCT | AGG | GGG | CAG | AGG | GTG | CAG | TGG | CAG | TGT | GAC | GCT | GTT | CTC | CGT | GGT | 1535 |
| Pro | Arg | Gly | Gln | Arg | Val | Gln | Trp | Gln | Cys | Asp | Ala | Val | Leu | Arg | Gly |      |
|     |     |     |     | 500 |     |     |     |     | 505 |     |     |     |     | 510 |     |      |
| GAG | CAG | GGC | CAC | CCC | TGG | GGC | CGC | TTT | GGG | GCA | GCC | CTG | ACA | GTG | TTG | 1583 |
| Glu | Gln | Gly | His | Pro | Trp | Gly | Arg | Phe | Gly | Ala | Ala | Leu | Thr | Val | Leu |      |
|     |     |     | 515 |     |     |     |     | 520 |     |     |     |     | 525 |     |     |      |
| GGG | GAT | GTG | AAT | GAG | GAC | AAG | CTG | ATA | GAC | GTG | GCC | ATT | GGG | GCC | CCG | 1631 |
| Gly | Asp | Val | Asn | Glu | Asp | Lys | Leu | Ile | Asp | Val | Ala | Ile | Gly | Ala | Pro |      |
|     |     | 530 |     |     |     |     | 535 |     |     |     |     | 540 |     |     |     |      |
| GGA | GAG | CAG | GAG | AAC | CGG | GGT | GCT | GTC | TAC | CTG | TTT | CAC | GGA | GCC | TCA | 1679 |
| Gly | Glu | Gln | Glu | Asn | Arg | Gly | Ala | Val | Tyr | Leu | Phe | His | Gly | Ala | Ser |      |
| 545 |     |     |     |     | 550 |     |     |     |     | 555 |     |     |     |     |     |      |
| GAA | TCC | GGC | ATC | AGC | CCC | TCC | CAC | AGC | CAG | CGG | ATT | GCC | AGC | TCC | CAG | 1727 |
| Glu | Ser | Gly | Ile | Ser | Pro | Ser | His | Ser | Gln | Arg | Ile | Ala | Ser | Ser | Gln |      |
| 560 |     |     |     |     | 565 |     |     |     |     | 570 |     |     |     |     | 575 |      |
| CTC | TCC | CCC | AGG | CTG | CAG | TAT | TTT | GGG | CAG | GCG | CTG | AGT | GGG | GGT | CAG | 1775 |
| Leu | Ser | Pro | Arg | Leu | Gln | Tyr | Phe | Gly | Gln | Ala | Leu | Ser | Gly | Gly | Gln |      |
|     |     |     |     | 580 |     |     |     |     | 585 |     |     |     |     | 590 |     |      |
| GAC | CTC | ACC | CAG | GAT | GGA | CTG | ATG | GAC | CTG | GCC | GTG | GGG | GCC | CGG | GGC | 1823 |
| Asp | Leu | Thr | Gln | Asp | Gly | Leu | Met | Asp | Leu | Ala | Val | Gly | Ala | Arg | Gly |      |
|     |     |     | 595 |     |     |     |     | 600 |     |     |     |     | 605 |     |     |      |
| CAG | GTG | CTC | CTG | CTC | AGG | AGT | CTG | CCG | GTG | CTG | AAA | GTG | GGG | GTG | GCC | 1871 |
| Gln | Val | Leu | Leu | Leu | Arg | Ser | Leu | Pro | Val | Leu | Lys | Val | Gly | Val | Ala |      |
|     |     | 610 |     |     |     |     | 615 |     |     |     |     | 620 |     |     |     |      |
| ATG | AGA | TTC | AGC | CCT | GTG | GAG | GTG | GCC | AAG | GCT | GTG | TAC | CGG | TGC | TGG | 1919 |
| Met | Arg | Phe | Ser | Pro | Val | Glu | Val | Ala | Lys | Ala | Val | Tyr | Arg | Cys | Trp |      |
|     | 625 |     |     |     |     | 630 |     |     |     |     | 635 |     |     |     |     |      |
| GAA | GAG | AAG | CCC | AGT | GCC | CTG | GAA | GCT | GGG | GAC | GCC | ACC | GTC | TGT | CTC | 1967 |
| Glu | Glu | Lys | Pro | Ser | Ala | Leu | Glu | Ala | Gly | Asp | Ala | Thr | Val | Cys | Leu |      |
| 640 |     |     |     |     | 645 |     |     |     |     | 650 |     |     |     |     | 655 |      |
| ACC | ATC | CAG | AAA | AGC | TCA | CTG | GAC | CAG | CTA | GGT | GAC | ATC | CAA | AGC | TCT | 2015 |
| Thr | Ile | Gln | Lys | Ser | Ser | Leu | Asp | Gln | Leu | Gly | Asp | Ile | Gln | Ser | Ser |      |
|     |     |     |     | 660 |     |     |     |     | 665 |     |     |     |     | 670 |     |      |
| GTC | AGG | TTT | GAT | CTG | GCA | CTG | GAC | CCA | GGT | CGT | CTG | ACT | TCT | CGT | GCC | 2063 |
| Val | Arg | Phe | Asp | Leu | Ala | Leu | Asp | Pro | Gly | Arg | Leu | Thr | Ser | Arg | Ala |      |

```
                675                         680                         685
ATT TTC AAT GAA ACC AAG AAC CCC ACT TTG ACT CGA AGA AAA ACC CTG             2111
Ile Phe Asn Glu Thr Lys Asn Pro Thr Leu Thr Arg Arg Lys Thr Leu
            690                         695                         700

GGA CTG GGG ATT CAC TGT GAA ACC CTG AAG CTG CTT TTG CCA GAT TGT             2159
Gly Leu Gly Ile His Cys Glu Thr Leu Lys Leu Leu Leu Pro Asp Cys
        705                         710                         715

GTG GAG GAT GTG GTG AGC CCC ATC ATT CTG CAC CTC AAC TTC TCA CTG             2207
Val Glu Asp Val Val Ser Pro Ile Ile Leu His Leu Asn Phe Ser Leu
720                         725                         730                         735

GTG AGA GAG CCC ATC CCC TCC CCC CAG AAC CTG CGT CCT GTG CTG GCC             2255
Val Arg Glu Pro Ile Pro Ser Pro Gln Asn Leu Arg Pro Val Leu Ala
                740                         745                         750

GTG GGC TCA CAA GAC CTC TTC ACT GCT TCT CTC CCC TTC GAG AAG AAC             2303
Val Gly Ser Gln Asp Leu Phe Thr Ala Ser Leu Pro Phe Glu Lys Asn
            755                         760                         765

TGT GGG CAA GAT GGC CTC TGT GAA GGG GAC CTG GGT GTC ACC CTC AGC             2351
Cys Gly Gln Asp Gly Leu Cys Glu Gly Asp Leu Gly Val Thr Leu Ser
        770                         775                         780

TTC TCA GGC CTG CAG ACC CTG ACC GTG GGG AGC TCC CTG GAG CTC AAC             2399
Phe Ser Gly Leu Gln Thr Leu Thr Val Gly Ser Ser Leu Glu Leu Asn
785                         790                         795

GTG ATT GTG ACT GTG TGG AAC GCA GGT GAG GAT TCC TAC GGA ACC GTG             2447
Val Ile Val Thr Val Trp Asn Ala Gly Glu Asp Ser Tyr Gly Thr Val
800                         805                         810                         815

GTC AGC CTC TAC TAT CCA GCA GGG CTG TCG CAC CGA CGG GTG TCA GGA             2495
Val Ser Leu Tyr Tyr Pro Ala Gly Leu Ser His Arg Arg Val Ser Gly
                820                         825                         830

GCC CAG AAG CAG CCC CAT CAG AGT GCC CTG CGC CTG GCA TGT GAG ACA             2543
Ala Gln Lys Gln Pro His Gln Ser Ala Leu Arg Leu Ala Cys Glu Thr
            835                         840                         845

GTG CCC ACT GAG GAT GAG GGC CTA AGA AGC AGC CGC TGC AGT GTC AAC             2591
Val Pro Thr Glu Asp Glu Gly Leu Arg Ser Ser Arg Cys Ser Val Asn
        850                         855                         860

CAC CCC ATC TTC CAT GAG GGC TCT AAC GGC ACC TTC ATA GTC ACA TTC             2639
His Pro Ile Phe His Glu Gly Ser Asn Gly Thr Phe Ile Val Thr Phe
865                         870                         875

GAT GTC TCC TAC AAG GCC ACC CTG GGA GAC AGG ATG CTT ATG AGG GCC             2687
Asp Val Ser Tyr Lys Ala Thr Leu Gly Asp Arg Met Leu Met Arg Ala
880                         885                         890                         895

AGT GCA AGC AGT GAG AAC AAT AAG GCT TCA AGC AGC AAG GCC ACC TTC             2735
Ser Ala Ser Ser Glu Asn Asn Lys Ala Ser Ser Ser Lys Ala Thr Phe
                900                         905                         910

CAG CTG GAG CTC CCG GTG AAG TAT GCA GTC TAC ACC ATG ATC AGC AGG             2783
Gln Leu Glu Leu Pro Val Lys Tyr Ala Val Tyr Thr Met Ile Ser Arg
            915                         920                         925

CAG GAA GAA TCC ACC AAG TAC TTC AAC TTT GCA ACC TCC GAT GAG AAG             2831
Gln Glu Glu Ser Thr Lys Tyr Phe Asn Phe Ala Thr Ser Asp Glu Lys
        930                         935                         940

AAA ATG AAA GAG GCT GAG CAT CGA TAC CGT GTG AAT AAC CTC AGC CAG             2879
Lys Met Lys Glu Ala Glu His Arg Tyr Arg Val Asn Asn Leu Ser Gln
945                         950                         955

CGA GAT CTG GCC ATC AGC ATT AAC TTC TGG GTT CCT GTC CTG CTG AAC             2927
Arg Asp Leu Ala Ile Ser Ile Asn Phe Trp Val Pro Val Leu Leu Asn
960                         965                         970                         975

GGG GTG GCT GTG TGG GAT GTG GTC ATG GAG GCC CCA TCT CAG AGT CTC             2975
Gly Val Ala Val Trp Asp Val Val Met Glu Ala Pro Ser Gln Ser Leu
                980                         985                         990

CCC TGT GTT TCA GAG AGA AAA CCT CCC CAG CAT TCT GAC TTC CTG ACC             3023
Pro Cys Val Ser Glu Arg Lys Pro Pro Gln His Ser Asp Phe Leu Thr
```

```
                         995                    1000                    1005
CAG  ATT  TCA  AGA  AGT  CCC  ATG  CTG  GAC  TGC  TCC  ATT  GCT  GAC  TGC  CTG        3071
Gln  Ile  Ser  Arg  Ser  Pro  Met  Leu  Asp  Cys  Ser  Ile  Ala  Asp  Cys  Leu
          1010                    1015                    1020

CAG  TTC  CGC  TGT  GAC  GTC  CCC  TCC  TTC  AGC  GTC  CAG  GAG  GAG  CTG  GAT        3119
Gln  Phe  Arg  Cys  Asp  Val  Pro  Ser  Phe  Ser  Val  Gln  Glu  Glu  Leu  Asp
          1025                    1030                    1035

TTC  ACC  CTG  AAG  GGC  AAT  CTC  AGT  TTC  GGC  TGG  GTC  CGC  GAG  ACA  TTG        3167
Phe  Thr  Leu  Lys  Gly  Asn  Leu  Ser  Phe  Gly  Trp  Val  Arg  Glu  Thr  Leu
1040                    1045                    1050                    1055

CAG  AAG  AAG  GTG  TTG  GTC  GTG  AGT  GTG  GCT  GAA  ATT  ACG  TTC  GAC  ACA        3215
Gln  Lys  Lys  Val  Leu  Val  Val  Ser  Val  Ala  Glu  Ile  Thr  Phe  Asp  Thr
                    1060                    1065                    1070

TCC  GTG  TAC  TCC  CAG  CTT  CCA  GGA  CAG  GAG  GCA  TTT  ATG  AGA  GCT  CAG        3263
Ser  Val  Tyr  Ser  Gln  Leu  Pro  Gly  Gln  Glu  Ala  Phe  Met  Arg  Ala  Gln
               1075                    1080                    1085

ATG  GAG  ATG  GTG  CTA  GAA  GAA  GAC  GAG  GTC  TAC  AAT  GCC  ATT  CCC  ATC        3311
Met  Glu  Met  Val  Leu  Glu  Glu  Asp  Glu  Val  Tyr  Asn  Ala  Ile  Pro  Ile
          1090                    1095                    1100

ATC  ATG  GGC  AGC  TCT  GTG  GGG  GCT  CTG  CTA  CTG  CTG  GCG  CTC  ATC  ACA        3359
Ile  Met  Gly  Ser  Ser  Val  Gly  Ala  Leu  Leu  Leu  Leu  Ala  Leu  Ile  Thr
     1105                    1110                    1115

GCC  ACA  CTG  TAC  AAG  CTT  GGC  TTC  TTC  AAA  CGC  CAC  TAC  AAG  GAA  ATG        3407
Ala  Thr  Leu  Tyr  Lys  Leu  Gly  Phe  Phe  Lys  Arg  His  Tyr  Lys  Glu  Met
1120                    1125                    1130                    1135

CTG  GAG  GAC  AAG  CCT  GAA  GAC  ACT  GCC  ACA  TTC  AGT  GGG  GAC  GAT  TTC        3455
Leu  Glu  Asp  Lys  Pro  Glu  Asp  Thr  Ala  Thr  Phe  Ser  Gly  Asp  Asp  Phe
               1140                    1145                    1150

AGC  TGT  GTG  GCC  CCA  AAT  GTG  CCT  TTG  TCC  TAATAATCCA  CTTTCCTGTT            3505
Ser  Cys  Val  Ala  Pro  Asn  Val  Pro  Leu  Ser
               1155                    1160

TATCTCTACC  ACTGTGGGCT  GGACTTGCTT  GCAACCATAA  ATCAACTTAC  ATGGAAACAA            3565

CTTCTGCATA  GATCTGCACT  GGCCTAAGCA  ACCTACCAGG  TGCTAAGCAC  CTTCTCGGAG            3625

AGATAGAGAT  TGTAATGTTT  TTACATATCT  GTCCATCTTT  TTCAGCAATG  ACCCACTTTT            3685

TACAGAAGCA  GGCATGGTGC  CAGCATAAAT  TTTCATATGC  T                                3726
```

( 2 ) INFORMATION FOR SEQ ID NO:2:

( i ) SEQUENCE CHARACTERISTICS:
        ( A ) LENGTH: 1161 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Thr  Phe  Gly  Thr  Val  Leu  Leu  Leu  Ser  Val  Leu  Ala  Ser  Tyr  His  Gly
 1              5                        10                       15

Phe  Asn  Leu  Asp  Val  Glu  Glu  Pro  Thr  Ile  Phe  Gln  Glu  Asp  Ala  Gly
               20                        25                       30

Gly  Phe  Gly  Gln  Ser  Val  Val  Gln  Phe  Gly  Gly  Ser  Arg  Leu  Val  Val
          35                        40                       45

Gly  Ala  Pro  Leu  Glu  Val  Val  Ala  Ala  Asn  Gln  Thr  Gly  Arg  Leu  Tyr
     50                        55                       60

Asp  Cys  Ala  Ala  Ala  Thr  Gly  Met  Cys  Gln  Pro  Ile  Pro  Leu  His  Ile
65                       70                        75                       80

Arg  Pro  Glu  Ala  Val  Asn  Met  Ser  Leu  Gly  Leu  Thr  Leu  Ala  Ala  Ser
               85                        90                       95
```

| | | | | | | | | | | | | | |
|---|---|---|---|---|---|---|---|---|---|---|---|---|---|
| Thr | Asn | Gly | Ser 100 | Arg | Leu | Leu | Ala | Cys 105 | Gly | Pro | Thr | Leu | His 110 | Arg | Val |
| Cys | Gly 115 | Glu | Asn | Ser | Tyr | Ser | Lys 120 | Gly | Ser | Cys | Leu | Leu 125 | Leu | Gly | Ser |
| Arg | Trp 130 | Glu | Ile | Ile | Gln | Thr 135 | Val | Pro | Asp | Ala | Thr 140 | Pro | Glu | Cys | Pro |
| His 145 | Gln | Glu | Met | Asp | Ile 150 | Val | Phe | Leu | Ile | Asp 155 | Gly | Ser | Gly | Ser | Ile 160 |
| Asp | Gln | Asn | Asp | Phe 165 | Asn | Gln | Met | Lys | Gly 170 | Phe | Val | Gln | Ala | Val 175 | Met |
| Gly | Gln | Phe | Glu 180 | Gly | Thr | Asp | Thr | Leu 185 | Phe | Ala | Leu | Met | Gln 190 | Tyr | Ser |
| Asn | Leu | Leu 195 | Lys | Ile | His | Phe | Thr 200 | Phe | Thr | Gln | Phe | Arg 205 | Thr | Ser | Pro |
| Ser | Gln 210 | Gln | Ser | Leu | Val | Asp 215 | Pro | Ile | Val | Gln | Leu 220 | Lys | Gly | Leu | Thr |
| Phe 225 | Thr | Ala | Thr | Gly | Ile 230 | Leu | Thr | Val | Val | Thr 235 | Gln | Leu | Phe | His | His 240 |
| Lys | Asn | Gly | Ala | Arg 245 | Lys | Ser | Ala | Lys | Lys 250 | Ile | Leu | Ile | Val | Ile 255 | Thr |
| Asp | Gly | Gln | Lys 260 | Tyr | Lys | Asp | Pro | Leu 265 | Glu | Tyr | Ser | Asp | Val 270 | Ile | Pro |
| Gln | Ala | Glu 275 | Lys | Ala | Gly | Ile | Ile 280 | Arg | Tyr | Ala | Ile | Gly 285 | Val | Gly | His |
| Ala | Phe 290 | Gln | Gly | Pro | Thr | Ala 295 | Arg | Gln | Glu | Leu | Asn 300 | Thr | Ile | Ser | Ser |
| Ala 305 | Pro | Pro | Gln | Asp | His 310 | Val | Phe | Lys | Val | Asp 315 | Asn | Phe | Ala | Ala | Leu 320 |
| Gly | Ser | Ile | Gln | Lys 325 | Gln | Leu | Gln | Glu | Lys 330 | Ile | Tyr | Ala | Val | Glu 335 | Gly |
| Thr | Gln | Ser | Arg 340 | Ala | Ser | Ser | Ser | Phe 345 | Gln | His | Glu | Met | Ser 350 | Gln | Glu |
| Gly | Phe | Ser 355 | Thr | Ala | Leu | Thr | Met 360 | Asp | Gly | Leu | Phe | Leu 365 | Gly | Ala | Val |
| Gly | Ser 370 | Phe | Ser | Trp | Ser | Gly 375 | Gly | Ala | Phe | Leu | Tyr 380 | Pro | Pro | Asn | Met |
| Ser 385 | Pro | Thr | Phe | Ile | Asn 390 | Met | Ser | Gln | Glu | Asn 395 | Val | Asp | Met | Arg | Asp 400 |
| Ser | Tyr | Leu | Gly | Tyr 405 | Ser | Thr | Glu | Leu | Ala 410 | Leu | Trp | Lys | Gly | Val 415 | Gln |
| Asn | Leu | Val | Leu 420 | Gly | Ala | Pro | Arg | Tyr 425 | Gln | His | Thr | Gly | Lys 430 | Ala | Val |
| Ile | Phe | Thr 435 | Gln | Val | Ser | Arg | Gln 440 | Trp | Arg | Lys | Lys | Ala 445 | Glu | Val | Thr |
| Gly | Thr | Gln 450 | Ile | Gly | Ser | Tyr | Phe 455 | Gly | Ala | Ser | Leu | Cys 460 | Ser | Val | Asp |
| Val 465 | Asp | Ser | Asp | Gly | Ser 470 | Thr | Asp | Leu | Ile | Leu 475 | Ile | Gly | Ala | Pro | His 480 |
| Tyr | Tyr | Glu | Gln | Thr 485 | Arg | Gly | Gly | Gln | Val 490 | Ser | Val | Cys | Pro | Leu 495 | Pro |
| Arg | Gly | Gln | Arg 500 | Val | Gln | Trp | Gln | Cys 505 | Asp | Ala | Val | Leu | Arg 510 | Gly | Glu |
| Gln | Gly | His 515 | Pro | Trp | Gly | Arg | Phe 520 | Gly | Ala | Ala | Leu | Thr 525 | Val | Leu | Gly |

Asp Val Asn Glu Asp Lys Leu Ile Asp Val Ala Ile Gly Ala Pro Gly
530                535                540

Glu Gln Glu Asn Arg Gly Ala Val Tyr Leu Phe His Gly Ala Ser Glu
545                550                555                560

Ser Gly Ile Ser Pro Ser His Ser Gln Arg Ile Ala Ser Ser Gln Leu
565                570                575

Ser Pro Arg Leu Gln Tyr Phe Gly Gln Ala Leu Ser Gly Gly Gln Asp
580                585                590

Leu Thr Gln Asp Gly Leu Met Asp Leu Ala Val Gly Ala Arg Gly Gln
595                600                605

Val Leu Leu Leu Arg Ser Leu Pro Val Leu Lys Val Gly Val Ala Met
610                615                620

Arg Phe Ser Pro Val Glu Val Ala Lys Ala Val Tyr Arg Cys Trp Glu
625                630                635                640

Glu Lys Pro Ser Ala Leu Glu Ala Gly Asp Ala Thr Val Cys Leu Thr
645                650                655

Ile Gln Lys Ser Ser Leu Asp Gln Leu Gly Asp Ile Gln Ser Ser Val
660                665                670

Arg Phe Asp Leu Ala Leu Asp Pro Gly Arg Leu Thr Ser Arg Ala Ile
675                680                685

Phe Asn Glu Thr Lys Asn Pro Thr Leu Thr Arg Arg Lys Thr Leu Gly
690                695                700

Leu Gly Ile His Cys Glu Thr Leu Lys Leu Leu Leu Pro Asp Cys Val
705                710                715                720

Glu Asp Val Val Ser Pro Ile Ile Leu His Leu Asn Phe Ser Leu Val
725                730                735

Arg Glu Pro Ile Pro Ser Pro Gln Asn Leu Arg Pro Val Leu Ala Val
740                745                750

Gly Ser Gln Asp Leu Phe Thr Ala Ser Leu Pro Phe Glu Lys Asn Cys
755                760                765

Gly Gln Asp Gly Leu Cys Glu Gly Asp Leu Gly Val Thr Leu Ser Phe
770                775                780

Ser Gly Leu Gln Thr Leu Thr Val Gly Ser Ser Leu Glu Leu Asn Val
785                790                795                800

Ile Val Thr Val Trp Asn Ala Gly Glu Asp Ser Tyr Gly Thr Val Val
805                810                815

Ser Leu Tyr Tyr Pro Ala Gly Leu Ser His Arg Arg Val Ser Gly Ala
820                825                830

Gln Lys Gln Pro His Gln Ser Ala Leu Arg Leu Ala Cys Glu Thr Val
835                840                845

Pro Thr Glu Asp Glu Gly Leu Arg Ser Ser Arg Cys Ser Val Asn His
850                855                860

Pro Ile Phe His Glu Gly Ser Asn Gly Thr Phe Ile Val Thr Phe Asp
865                870                875                880

Val Ser Tyr Lys Ala Thr Leu Gly Asp Arg Met Leu Met Arg Ala Ser
885                890                895

Ala Ser Ser Glu Asn Asn Lys Ala Ser Ser Ser Lys Ala Thr Phe Gln
900                905                910

Leu Glu Leu Pro Val Lys Tyr Ala Val Tyr Thr Met Ile Ser Arg Gln
915                920                925

Glu Glu Ser Thr Lys Tyr Phe Asn Phe Ala Thr Ser Asp Glu Lys Lys
930                935                940

Met Lys Glu Ala Glu His Arg Tyr Arg Val Asn Asn Leu Ser Gln Arg

```
945                       950                       955                       960
Asp  Leu  Ala  Ile  Ser  Ile  Asn  Phe  Trp  Val  Pro  Val  Leu  Leu  Asn  Gly
                    965                       970                       975
Val  Ala  Val  Trp  Asp  Val  Val  Met  Glu  Ala  Pro  Ser  Gln  Ser  Leu  Pro
                    980                       985                       990
Cys  Val  Ser  Glu  Arg  Lys  Pro  Pro  Gln  His  Ser  Asp  Phe  Leu  Thr  Gln
                    995                      1000                      1005
Ile  Ser  Arg  Ser  Pro  Met  Leu  Asp  Cys  Ser  Ile  Ala  Asp  Cys  Leu  Gln
               1010                      1015                      1020
Phe  Arg  Cys  Asp  Val  Pro  Ser  Phe  Ser  Val  Gln  Glu  Glu  Leu  Asp  Phe
1025                     1030                      1035                      1040
Thr  Leu  Lys  Gly  Asn  Leu  Ser  Phe  Gly  Trp  Val  Arg  Glu  Thr  Leu  Gln
                    1045                     1050                      1055
Lys  Lys  Val  Leu  Val  Val  Ser  Val  Ala  Glu  Ile  Thr  Phe  Asp  Thr  Ser
                    1060                     1065                      1070
Val  Tyr  Ser  Gln  Leu  Pro  Gly  Gln  Glu  Ala  Phe  Met  Arg  Ala  Gln  Met
                    1075                     1080                      1085
Glu  Met  Val  Leu  Glu  Glu  Asp  Glu  Val  Tyr  Asn  Ala  Ile  Pro  Ile  Ile
          1090                      1095                      1100
Met  Gly  Ser  Ser  Val  Gly  Ala  Leu  Leu  Leu  Ala  Leu  Ile  Thr  Ala
1105                     1110                      1115                      1120
Thr  Leu  Tyr  Lys  Leu  Gly  Phe  Phe  Lys  Arg  His  Tyr  Lys  Glu  Met  Leu
                    1125                     1130                      1135
Glu  Asp  Lys  Pro  Glu  Asp  Thr  Ala  Thr  Phe  Ser  Gly  Asp  Asp  Phe  Ser
                    1140                     1145                      1150
Cys  Val  Ala  Pro  Asn  Val  Pro  Lys  Ser
                    1155                     1160
```

( 2 ) INFORMATION FOR SEQ ID NO:3:

( i ) SEQUENCE CHARACTERISTICS:
       ( A ) LENGTH: 1153 amino acids
       ( B ) TYPE: amino acid
       ( C ) STRANDEDNESS: single
       ( D ) TOPOLOGY: linear ( i i ) MOLECULE TYPE: protein ( x i ) SEQUENCE DESCRIPTION: SEQ ID NO:3:

```
Met  Ala  Leu  Arg  Val  Leu  Leu  Leu  Thr  Ala  Leu  Thr  Leu  Cys  His  Gly
 1                     5                        10                       15
Phe  Asn  Leu  Asp  Thr  Glu  Asn  Ala  Met  Thr  Phe  Gln  Glu  Asn  Ala  Arg
                    20                       25                       30
Gly  Phe  Gly  Gln  Ser  Val  Val  Gln  Leu  Gln  Gly  Ser  Arg  Val  Val  Val
                    35                       40                       45
Gly  Ala  Pro  Gln  Glu  Ile  Val  Ala  Ala  Asn  Gln  Arg  Gly  Ser  Leu  Tyr
                    50                       55                       60
Gln  Cys  Asp  Tyr  Ser  Thr  Gly  Ser  Cys  Glu  Pro  Ile  Arg  Leu  Gln  Val
 65                         70                       75                        80
Pro  Val  Glu  Ala  Val  Asn  Met  Ser  Leu  Gly  Leu  Ser  Leu  Ala  Ala  Thr
                    85                       90                       95
Thr  Ser  Pro  Pro  Gln  Leu  Leu  Ala  Cys  Gly  Pro  Thr  Val  His  Gln  Thr
                    100                      105                      110
Cys  Ser  Glu  Asn  Thr  Tyr  Val  Lys  Gly  Leu  Cys  Phe  Leu  Phe  Gly  Ser
                    115                      120                      125
Asn  Leu  Arg  Gln  Gln  Pro  Gln  Lys  Phe  Pro  Glu  Ala  Leu  Arg  Gly  Cys
                    130                      135                      140
```

```
Pro Gln Glu Asp Ser Asp Ile Ala Phe Leu Ile Asp Gly Ser Gly Ser
145                 150                 155                 160

Ile Ile Pro His Asp Phe Arg Arg Met Lys Glu Phe Val Ser Thr Val
                165                 170                 175

Met Glu Gln Leu Lys Lys Ser Lys Thr Leu Phe Ser Leu Met Gln Tyr
            180                 185                 190

Ser Glu Glu Phe Arg Ile His Phe Thr Phe Lys Glu Phe Gln Asn Asn
        195                 200                 205

Pro Asn Pro Arg Ser Leu Val Lys Pro Ile Thr Gln Leu Leu Gly Arg
    210                 215                 220

Thr His Thr Ala Thr Gly Ile Arg Lys Val Val Arg Glu Leu Phe Asn
225                 230                 235                 240

Ile Thr Asn Gly Ala Arg Lys Asn Ala Phe Lys Ile Leu Val Val Ile
                245                 250                 255

Thr Asp Gly Glu Lys Phe Gly Asp Pro Leu Gly Tyr Glu Asp Val Ile
            260                 265                 270

Pro Glu Ala Asp Arg Glu Gly Val Ile Arg Tyr Val Ile Gly Val Gly
        275                 280                 285

Asp Ala Phe Arg Ser Glu Lys Ser Arg Gln Glu Leu Asn Thr Ile Ala
    290                 295                 300

Ser Lys Pro Pro Arg Asp His Val Phe Gln Val Asn Asn Phe Glu Ala
305                 310                 315                 320

Leu Lys Thr Ile Gln Asn Gln Leu Arg Glu Lys Ile Phe Ala Ile Glu
                325                 330                 335

Gly Thr Gln Thr Gly Ser Ser Ser Phe Glu His Glu Met Ser Gln
            340                 345                 350

Glu Gly Phe Ser Ala Ala Ile Thr Ser Asn Gly Pro Leu Leu Ser Thr
        355                 360                 365

Val Gly Ser Tyr Asp Trp Ala Gly Gly Val Phe Leu Tyr Thr Ser Lys
    370                 375                 380

Glu Lys Ser Thr Phe Ile Asn Met Thr Arg Val Asp Ser Asp Met Asn
385                 390                 395                 400

Asp Ala Tyr Leu Gly Tyr Ala Ala Ala Ile Ile Leu Arg Asn Arg Val
                405                 410                 415

Gln Ser Leu Val Leu Gly Ala Pro Arg Tyr Gln His Ile Gly Leu Val
            420                 425                 430

Ala Met Phe Arg Gln Asn Thr Gly Met Trp Glu Ser Asn Ala Asn Val
        435                 440                 445

Lys Gly Thr Gln Ile Gly Ala Tyr Phe Gly Ala Ser Leu Cys Ser Val
    450                 455                 460

Asp Val Asp Ser Asn Gly Ser Thr Asp Leu Val Leu Ile Gly Ala Pro
465                 470                 475                 480

His Tyr Tyr Glu Gln Thr Arg Gly Gly Gln Val Ser Val Cys Pro Leu
                485                 490                 495

Pro Arg Gly Gln Arg Ala Arg Trp Gln Cys Asp Ala Val Leu Tyr Gly
            500                 505                 510

Glu Gln Gly Gln Pro Trp Gly Arg Phe Gly Ala Ala Leu Thr Val Leu
        515                 520                 525

Gly Asp Val Asn Gly Asp Lys Leu Thr Asp Val Ala Ile Gly Ala Pro
    530                 535                 540

Gly Glu Glu Asp Asn Arg Gly Ala Val Tyr Leu Phe His Gly Thr Ser
545                 550                 555                 560

Gly Ser Gly Ile Ser Pro Ser His Ser Gln Arg Ile Ala Gly Ser Lys
```

-continued

|     |     |     |     | 565 |     |     |     | 570 |     |     |     | 575 |     |     |
|-----|-----|-----|-----|-----|-----|-----|-----|-----|-----|-----|-----|-----|-----|-----|
| Leu | Ser | Pro | Arg | Leu | Gln | Tyr | Phe | Gly | Gln | Ser | Leu | Ser | Gly | Gln |
|     |     |     | 580 |     |     |     |     | 585 |     |     |     | 590 |     |     |
| Asp | Leu | Thr | Met | Asp | Gly | Leu | Val | Asp | Leu | Thr | Val | Gly | Ala | Gln | Gly |
|     |     | 595 |     |     |     |     | 600 |     |     |     |     | 605 |     |     |
| His | Val | Leu | Leu | Leu | Arg | Ser | Gln | Pro | Val | Leu | Arg | Val | Lys | Ala | Ile |
|     | 610 |     |     |     |     | 615 |     |     |     |     | 620 |     |     |     |
| Met | Glu | Phe | Asn | Pro | Arg | Glu | Val | Ala | Arg | Asn | Val | Phe | Glu | Cys | Asn |
| 625 |     |     |     |     | 630 |     |     |     |     | 635 |     |     |     |     | 640 |
| Asp | Gln | Val | Val | Lys | Gly | Lys | Glu | Ala | Gly | Glu | Val | Arg | Val | Cys | Leu |
|     |     |     |     | 645 |     |     |     |     | 650 |     |     |     |     | 655 |     |
| His | Val | Gln | Lys | Ser | Thr | Arg | Asp | Arg | Leu | Arg | Glu | Gly | Gln | Ile | Gln |
|     |     |     | 660 |     |     |     |     | 665 |     |     |     |     | 670 |     |     |
| Ser | Val | Val | Thr | Tyr | Asp | Leu | Ala | Leu | Asp | Ser | Gly | Arg | Pro | His | Ser |
|     |     | 675 |     |     |     |     | 680 |     |     |     |     | 685 |     |     |     |
| Arg | Ala | Val | Phe | Asn | Glu | Thr | Lys | Asn | Ser | Thr | Arg | Arg | Gln | Thr | Gln |
|     | 690 |     |     |     |     | 695 |     |     |     |     | 700 |     |     |     |     |
| Val | Leu | Gly | Leu | Thr | Gln | Thr | Cys | Glu | Thr | Leu | Lys | Leu | Gln | Leu | Pro |
| 705 |     |     |     |     | 710 |     |     |     |     | 715 |     |     |     |     | 720 |
| Asn | Cys | Ile | Glu | Asp | Pro | Val | Ser | Pro | Ile | Val | Leu | Arg | Leu | Asn | Phe |
|     |     |     |     | 725 |     |     |     |     | 730 |     |     |     |     | 735 |     |
| Ser | Leu | Val | Gly | Thr | Pro | Leu | Ser | Ala | Phe | Gly | Asn | Leu | Arg | Pro | Val |
|     |     |     | 740 |     |     |     |     | 745 |     |     |     |     | 750 |     |     |
| Leu | Ala | Glu | Asp | Ala | Gln | Arg | Leu | Phe | Thr | Ala | Leu | Phe | Pro | Phe | Glu |
|     |     | 755 |     |     |     |     | 760 |     |     |     |     | 765 |     |     |     |
| Lys | Asn | Cys | Gly | Asn | Asp | Asn | Ile | Cys | Gln | Asp | Asp | Leu | Ser | Ile | Thr |
| 770 |     |     |     |     | 775 |     |     |     |     | 780 |     |     |     |     |     |
| Phe | Ser | Phe | Met | Ser | Leu | Asp | Cys | Leu | Val | Val | Gly | Gly | Pro | Arg | Glu |
| 785 |     |     |     |     | 790 |     |     |     |     | 795 |     |     |     |     | 800 |
| Phe | Asn | Val | Thr | Val | Thr | Val | Arg | Asn | Asp | Gly | Glu | Asp | Ser | Tyr | Arg |
|     |     |     |     | 805 |     |     |     |     | 810 |     |     |     |     | 815 |     |
| Thr | Gln | Val | Thr | Phe | Phe | Phe | Pro | Leu | Asp | Leu | Ser | Tyr | Arg | Lys | Val |
|     |     |     | 820 |     |     |     |     | 825 |     |     |     |     | 830 |     |     |
| Ser | Thr | Leu | Gln | Asn | Gln | Arg | Ser | Gln | Arg | Ser | Trp | Arg | Leu | Ala | Cys |
|     |     | 835 |     |     |     |     | 840 |     |     |     |     | 845 |     |     |     |
| Glu | Ser | Ala | Ser | Ser | Thr | Glu | Val | Ser | Gly | Ala | Leu | Lys | Ser | Thr | Ser |
| 850 |     |     |     |     | 855 |     |     |     |     | 860 |     |     |     |     |     |
| Cys | Ser | Ile | Asn | His | Pro | Ile | Phe | Pro | Glu | Asn | Ser | Glu | Val | Thr | Phe |
| 865 |     |     |     |     | 870 |     |     |     |     | 875 |     |     |     |     | 880 |
| Asn | Ile | Thr | Phe | Asp | Val | Asp | Ser | Lys | Ala | Ser | Leu | Gly | Asn | Lys | Leu |
|     |     |     |     | 885 |     |     |     |     | 890 |     |     |     |     | 895 |     |
| Leu | Leu | Lys | Ala | Asn | Val | Thr | Ser | Glu | Asn | Asn | Met | Pro | Arg | Thr | Asn |
|     |     |     | 900 |     |     |     |     | 905 |     |     |     |     | 910 |     |     |
| Lys | Thr | Glu | Phe | Gln | Leu | Glu | Leu | Pro | Val | Lys | Tyr | Ala | Val | Tyr | Met |
|     |     | 915 |     |     |     |     | 920 |     |     |     |     | 925 |     |     |     |
| Val | Val | Thr | Ser | His | Gly | Val | Ser | Thr | Lys | Tyr | Leu | Asn | Phe | Thr | Ala |
|     |     | 930 |     |     |     |     | 935 |     |     |     |     | 940 |     |     |     |
| Ser | Glu | Asn | Thr | Ser | Arg | Val | Met | Gln | His | Gln | Tyr | Gln | Val | Ser | Asn |
| 945 |     |     |     |     | 950 |     |     |     |     | 955 |     |     |     |     | 960 |
| Leu | Gly | Gln | Arg | Ser | Leu | Pro | Ile | Ser | Leu | Val | Phe | Leu | Val | Pro | Val |
|     |     |     |     | 965 |     |     |     |     | 970 |     |     |     |     | 975 |     |
| Arg | Leu | Asn | Gln | Thr | Val | Ile | Trp | Asp | Arg | Pro | Gln | Val | Thr | Phe | Ser |
|     |     |     | 980 |     |     |     |     | 985 |     |     |     |     | 990 |     |     |

|   |   |   |   |   |   |   |   |   |   |   |   |   |   |   |
|---|---|---|---|---|---|---|---|---|---|---|---|---|---|---|
| Glu | Asn | Leu | Ser | Ser | Thr | Cys | His | Thr | Lys | Glu | Arg | Leu | Pro | Ser | His |
|  |  | 995 |  |  |  |  |  | 1000 |  |  |  | 1005 |  |  |

Ser Asp Phe Leu Ala Glu Leu Arg Lys Ala Pro Val Val Asn Cys Ser
        1010                1015            1020

Ile Ala Val Cys Gln Arg Ile Gln Cys Asp Ile Pro Phe Phe Gly Ile
1025            1030                1035                    1040

Gln Glu Glu Phe Asn Ala Thr Leu Lys Gly Asn Leu Ser Phe Asp Trp
                1045                1050                1055

Tyr Ile Lys Thr Ser His Asn His Leu Leu Ile Val Ser Thr Ala Glu
            1060            1065                    1070

Ile Leu Phe Asn Asp Ser Val Phe Thr Leu Leu Pro Gly Gln Gly Ala
            1075                1080                1085

Phe Val Arg Ser Gln Thr Glu Thr Lys Val Glu Pro Phe Glu Val Pro
        1090                1095                1100

Asn Pro Leu Pro Leu Ile Val Gly Ser Ser Val Gly Gly Leu Leu Leu
1105                1110                1115                1120

Leu Ala Leu Ile Thr Ala Ala Leu Tyr Lys Leu Gly Phe Phe Lys Arg
                1125            1130                    1135

Gln Tyr Lys Asp Met Met Ser Glu Gly Gly Pro Pro Gly Ala Glu Pro
            1140            1145                1150

Gln (2) INFORMATION FOR SEQ ID NO:4:

(i) SEQUENCE CHARACTERISTICS:
      (A) LENGTH: 1163 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:4:

Met Thr Arg Thr Arg Ala Ala Leu Leu Leu Phe Thr Ala Leu Ala Thr
1               5                   10                  15

Ser Leu Gly Phe Asn Leu Asp Thr Glu Glu Leu Thr Ala Phe Arg Val
            20                  25                  30

Asp Ser Ala Gly Phe Gly Asp Ser Val Val Gln Tyr Ala Asn Ser Trp
        35              40                  45

Val Val Val Gly Ala Pro Gln Lys Ile Ile Ala Ala Asn Gln Ile Gly
    50              55                  60

Gly Leu Tyr Gln Cys Gly Tyr Ser Thr Gly Ala Cys Glu Pro Ile Gly
65              70              75                      80

Leu Gln Val Pro Pro Glu Ala Val Asn Met Ser Leu Gly Leu Ser Leu
                85                  90                  95

Ala Ser Thr Thr Ser Pro Ser Gln Leu Leu Ala Cys Gly Pro Thr Val
            100             105                 110

His His Glu Cys Gly Arg Asn Met Tyr Leu Thr Gly Leu Cys Phe Leu
        115             120                 125

Leu Gly Pro Thr Gln Leu Thr Gln Arg Leu Pro Val Ser Arg Gln Glu
    130             135                 140

Cys Pro Arg Gln Glu Gln Asp Ile Val Phe Leu Ile Asp Gly Ser Gly
145             150                 155                 160

Ser Ile Ser Ser Arg Asn Phe Ala Thr Met Met Asn Phe Val Arg Ala
                165                 170                 175

Val Ile Ser Gln Phe Gln Arg Pro Ser Thr Gln Phe Ser Leu Met Gln
            180                 185                 190

| | | | | | | | | | | | | | |
|---|---|---|---|---|---|---|---|---|---|---|---|---|---|
|Phe|Ser|Asn 195|Lys|Phe|Gln|Thr 200|His|Phe|Thr|Phe|Glu 205|Phe|Arg|Arg|
|Thr|Ser|Asn 210|Pro|Leu|Ser|Leu 215|Leu|Ala|Ser|Val|His 220|Gln|Leu|Gln|Gly|
|Phe 225|Thr|Tyr|Thr|Ala|Thr 230|Ala|Ile|Gln|Asn|Val 235|Val|His|Arg|Leu|Phe 240|
|His|Ala|Ser|Tyr|Gly 245|Ala|Arg|Arg|Asp|Ala 250|Ile|Lys|Ile|Leu|Ile 255|Val|
|Ile|Thr|Asp|Gly 260|Lys|Lys|Glu|Gly|Asp 265|Ser|Leu|Asp|Tyr|Lys 270|Asp|Val|
|Ile|Pro|Met 275|Ala|Asp|Ala|Ala|Gly 280|Ile|Ile|Arg|Tyr|Ala 285|Ile|Gly|Val|
|Gly|Leu 290|Ala|Phe|Gln|Asn|Arg 295|Asn|Ser|Trp|Lys|Glu 300|Leu|Asn|Asp|Ile|
|Ala 305|Ser|Lys|Pro|Ser|Gln 310|Glu|His|Ile|Phe|Lys 315|Val|Glu|Asp|Phe|Asp 320|
|Ala|Leu|Lys|Asp|Ile 325|Gln|Asn|Gln|Leu|Lys 330|Glu|Lys|Ile|Phe|Ala 335|Ile|
|Glu|Gly|Thr|Glu 340|Thr|Ile|Ser|Ser|Ser 345|Ser|Phe|Glu|Leu|Glu 350|Met|Ala|
|Gln|Glu|Gly 355|Phe|Ser|Ala|Val|Phe 360|Thr|Pro|Asp|Gly|Pro 365|Val|Leu|Gly|
|Ala|Val 370|Gly|Ser|Phe|Thr|Trp 375|Ser|Gly|Gly|Ala|Phe 380|Leu|Tyr|Pro|Pro|
|Asn 385|Met|Ser|Pro|Thr|Phe 390|Ile|Asn|Met|Ser|Gln 395|Glu|Asn|Val|Asp|Met 400|
|Arg|Asp|Ser|Tyr|Leu 405|Gly|Tyr|Ser|Thr|Glu 410|Leu|Ala|Leu|Trp|Lys 415|Gly|
|Val|Gln|Ser|Leu 420|Val|Leu|Gly|Ala|Pro 425|Arg|Tyr|Gln|His|Ile 430|Gly|Lys|
|Ala|Val|Ile 435|Phe|Ile|Gln|Val|Ser 440|Arg|Gln|Trp|Arg|Met 445|Lys|Ala|Glu|
|Val|Ile|Gly 450|Thr|Gln|Ile|Gly|Ser 455|Tyr|Phe|Gly|Ala|Ser 460|Leu|Cys|Ser|
|Val 465|Asp|Val|Asp|Thr|Asp 470|Gly|Ser|Thr|Asp|Leu 475|Val|Leu|Ile|Gly|Ala 480|
|Pro|His|Tyr|Tyr|Glu 485|Gln|Thr|Arg|Gly|Gly 490|Gln|Val|Ser|Val|Cys 495|Pro|
|Leu|Pro|Arg|Gly 500|Trp|Arg|Arg|Trp|Trp 505|Cys|Asp|Ala|Val|Leu 510|Tyr|Gly|
|Glu|Gln|Gly 515|His|Pro|Trp|Gly|Arg 520|Phe|Gly|Ala|Ala|Leu 525|Thr|Val|Leu|
|Gly|Asp 530|Val|Asn|Gly|Asp|Lys 535|Leu|Thr|Asp|Val|Val 540|Ile|Gly|Ala|Pro|
|Gly 545|Glu|Glu|Glu|Asn|Arg 550|Gly|Ala|Val|Tyr|Leu 555|Phe|His|Gly|Val|Leu 560|
|Gly|Pro|Ser|Ile|Ser 565|Pro|Ser|His|Ser|Gln 570|Arg|Ile|Ala|Gly|Ser 575|Gln|
|Leu|Ser|Ser|Arg 580|Leu|Gln|Tyr|Phe|Gly 585|Gln|Ala|Leu|Ser|Gly 590|Gly|Gln|
|Asp|Leu|Thr 595|Gln|Asp|Gly|Leu|Val 600|Asp|Leu|Ala|Val|Gly 605|Ala|Arg|Gly|
|Gln|Val|Leu|Leu|Leu|Arg|Thr|Arg|Pro|Val|Leu|Trp|Val|Gly|Val|Ser|

-continued

```
              610                    615                    620
Met Gln Phe Ile Pro Ala Glu Ile Pro Arg Ser Ala Phe Glu Cys Arg
625                     630                    635                    640

Glu Gln Val Val Ser Glu Gln Thr Leu Val Gln Ser Asn Ile Cys Leu
                    645                    650                    655

Tyr Ile Asp Lys Arg Ser Lys Asn Leu Leu Gly Ser Arg Asp Leu Gln
                660                    665                    670

Ser Ser Val Thr Leu Asp Leu Ala Leu Ala Pro Gly Arg Leu Ser Pro
            675                    680                    685

Arg Ala Ile Phe Gln Glu Thr Lys Asn Arg Ser Leu Ser Arg Val Arg
690                    695                    700

Val Leu Gly Leu Lys Ala His Cys Glu Asn Phe Asn Leu Leu Leu Pro
705                    710                    715                    720

Ser Cys Val Glu Asp Ser Val Ile Pro Ile Ile Leu Arg Leu Asn Phe
                725                    730                    735

Thr Leu Val Gly Lys Pro Leu Leu Ala Phe Arg Asn Leu Arg Pro Met
            740                    745                    750

Leu Ala Ala Leu Ala Gln Arg Tyr Phe Thr Ala Ser Leu Pro Phe Glu
            755                    760                    765

Lys Asn Cys Gly Ala Asp His Ile Cys Gln Asp Asn Leu Gly Ile Ser
770                    775                    780

Phe Ser Phe Pro Gly Leu Lys Ser Leu Leu Val Gly Ser Asn Leu Glu
785                    790                    795                    800

Leu Asn Ala Glu Val Met Val Trp Asn Asp Gly Glu Asp Ser Tyr Gly
                805                    810                    815

Thr Thr Ile Thr Phe Ser His Pro Ala Gly Leu Ser Tyr Arg Tyr Val
            820                    825                    830

Ala Glu Gly Gln Lys Gln Gly Gln Leu Arg Ser Leu His Leu Thr Cys
            835                    840                    845

Cys Ser Ala Pro Val Gly Ser Gln Gly Thr Trp Ser Thr Ser Cys Arg
850                    855                    860

Ile Asn His Leu Ile Phe Arg Gly Gly Ala Gln Ile Thr Phe Leu Ala
865                    870                    875                    880

Thr Phe Asp Val Ser Pro Lys Ala Val Gly Leu Asp Arg Leu Leu Leu
                885                    890                    895

Ile Ala Asn Val Ser Ser Glu Asn Asn Ile Pro Arg Thr Ser Lys Thr
            900                    905                    910

Ile Phe Gln Leu Glu Leu Pro Val Lys Tyr Ala Val Tyr Ile Val Val
        915                    920                    925

Ser Ser His Glu Gln Phe Thr Lys Tyr Leu Asn Phe Ser Glu Ser Glu
    930                    935                    940

Glu Lys Glu Ser His Val Ala Met His Arg Tyr Gln Val Asn Asn Leu
945                    950                    955                    960

Gly Gln Arg Asp Leu Pro Val Ser Ile Asn Phe Trp Val Pro Val Glu
                965                    970                    975

Leu Asn Gln Glu Ala Val Trp Met Asp Val Glu Val Ser His Pro Gln
            980                    985                    990

Asn Pro Ser Leu Arg Cys Ser Ser Glu Lys Ile Ala Pro Pro Ala Ser
        995                    1000                   1005

Asp Phe Leu Ala His Ile Gln Lys Asn Pro Val Leu Asp Cys Ser Ile
    1010                   1015                   1020

Ala Gly Cys Leu Arg Phe Arg Cys Asp Val Pro Ser Phe Ser Val Gln
1025                   1030                   1035                   1040
```

```
Glu Glu Leu Asp Phe Thr Leu Lys Gly Asn Leu Ser Phe Gly Trp Val
            1045                1050                1055
Arg Gln Ile Leu Gln Lys Lys Val Ser Val Val Ser Val Ala Glu Ile
            1060                1065                1070
Ile Phe Asp Thr Ser Val Tyr Ser Gln Leu Pro Gly Gln Glu Ala Phe
            1075                1080                1085
Met Arg Ala Gln Thr Ile Thr Val Leu Glu Lys Tyr Lys Val His Asn
            1090                1095                1100
Pro Ile Pro Leu Ile Val Gly Ser Ser Ile Gly Gly Leu Leu Leu Leu
1105                1110                1115                1120
Ala Leu Ile Thr Ala Val Leu Tyr Lys Val Gly Phe Phe Lys Arg Gln
                1125                1130                1135
Tyr Lys Glu Met Met Glu Glu Ala Asn Gly Gln Ile Ala Pro Glu Asn
            1140                1145                1150
Gly Thr Gln Thr Pro Ser Pro Pro Ser Glu Lys
            1155                1160
```

( 2 ) INFORMATION FOR SEQ ID NO:5:

( i ) SEQUENCE CHARACTERISTICS:
       ( A ) LENGTH: 12 amino acids
       ( B ) TYPE: amino acid
       ( D ) TOPOLOGY: linear ( i i ) MOLECULE TYPE: peptide ( x i ) SEQUENCE DESCRIPTION: SEQ ID NO:5:

```
Phe Asn Leu Asp Val Glu Glu Pro Met Val Phe Gln
1               5                   10
```

( 2 ) INFORMATION FOR SEQ ID NO:6:

( i ) SEQUENCE CHARACTERISTICS:
       ( A ) LENGTH: 35 base pairs
       ( B ) TYPE: nucleic acid
       ( C ) STRANDEDNESS: single
       ( D ) TOPOLOGY: linear ( i i ) MOLECULE TYPE: DNA ( x i ) SEQUENCE DESCRIPTION: SEQ ID NO:6:

TTYAAYYTGG AYGTNGARGA RCCNATGGTN TTYCA                35

( 2 ) INFORMATION FOR SEQ ID NO:7:

( i ) SEQUENCE CHARACTERISTICS:
       ( A ) LENGTH: 36 base pairs
       ( B ) TYPE: nucleic acid
       ( C ) STRANDEDNESS: single
       ( D ) TOPOLOGY: linear ( i i ) MOLECULE TYPE: DNA ( x i ) SEQUENCE DESCRIPTION: SEQ ID NO:7:

TTCAACCTGG ACGTGGAGGA GCCCATGGTG TTCCAA              36

( 2 ) INFORMATION FOR SEQ ID NO:8:

( i ) SEQUENCE CHARACTERISTICS:
       ( A ) LENGTH: 36 base pairs
       ( B ) TYPE: nucleic acid
       ( C ) STRANDEDNESS: single
       ( D ) TOPOLOGY: linear ( i i ) MOLECULE TYPE: DNA ( x i ) SEQUENCE DESCRIPTION: SEQ ID NO:8:

TTCAACCTGG ACGTNGAASA NCCATGGTC TTCCAA    36

( 2 ) INFORMATION FOR SEQ ID NO:9:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

TTYAAYYTNG AYGTNGARGA RCC    23

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

TTYAAYYTGG ACGTNGAAGA    20

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

TGRAANACCA TNGGYTC    17

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

TTGGAAGACC ATNGGYTC    18

( 2 ) INFORMATION FOR SEQ ID NO:13:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

ATTAACCCTC ACTAAAG    17

( 2 ) INFORMATION FOR SEQ ID NO:14:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

AATACGACTC ACTATAG                            17

( 2 ) INFORMATION FOR SEQ ID NO:15:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

Val Phe Gln Glu Xaa Gly Ala Gly Phe Gly Gln
1               5                          10

( 2 ) INFORMATION FOR SEQ ID NO:16:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

Leu Tyr Asp Xaa Val Ala Ala Thr Gly Leu Xaa Gln Pro Ile
1              5                         10

( 2 ) INFORMATION FOR SEQ ID NO:17:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

Pro Leu Glu Tyr Xaa Asp Val Ile Pro Gln Ala Glu
1              5                      10

( 2 ) INFORMATION FOR SEQ ID NO:18:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

Phe Gln Glu Gly Phe Ser Xaa Val Leu Xaa
1              5                      10

( 2 ) INFORMATION FOR SEQ ID NO:19:

( i ) SEQUENCE CHARACTERISTICS:
        ( A ) LENGTH: 14 amino acids
        ( B ) TYPE: amino acid ( D ) TOPOLOGY: linear ( i i ) MOLECULE TYPE: peptide ( x i ) SEQUENCE DESCRIPTION: SEQ ID NO:19:

Thr Ser Pro Thr Phe Ile Xaa Met Ser Gln Glu Asn Val Asp
1               5                   10

( 2 ) INFORMATION FOR SEQ ID NO:20:

( i ) SEQUENCE CHARACTERISTICS:
      ( A ) LENGTH: 17 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:20:

Leu Val Val Gly Ala Pro Leu Glu Val Val Ala Val Xaa Gln Thr Gly
1               5                   10                  15

Arg ( 2 ) INFORMATION FOR SEQ ID NO:21:

( i ) SEQUENCE CHARACTERISTICS:
      ( A ) LENGTH: 9 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:21:

Leu Asp Xaa Lys Pro Xaa Asp Thr Ala
1               5

( 2 ) INFORMATION FOR SEQ ID NO:22:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:22:

Phe Gly Glu Gln Phe Ser Glu
1               5

( 2 ) INFORMATION FOR SEQ ID NO:23:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:23:

RAANCCYTCY TGRAAACTYT C     21

( 2 ) INFORMATION FOR SEQ ID NO:24:

( i ) SEQUENCE CHARACTERISTICS:
      ( A ) LENGTH: 1006 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:24:

| | | | | | |
|---|---|---|---|---|---|
| TTCAACCTGG | ACGTGGAGGA | GCCCATGGTG | TTCAAGAGGA | TGGAGCTGGC | TTTGGACAGA | 60 |
| GCGTGGCCCA | GCTTGGCGGA | TCTAGACTCG | TGGTGGGAGC | CCCCCTGGAG | GTGGTGGCGG | 120 |
| TCAACCAAAC | AGGAAGGTTG | TATGACTGTG | TGGCTGCCAC | TGGCCTTGTC | AACCCATACC | 180 |
| CCTGCACACA | CCCCCAGATG | CTGTGAACAT | GTCCCTGGGT | CTGTCCCTGT | CAGCCGCCGC | 240 |
| CAGTCGCCCC | TGGCTGCTGG | CCTGTGGCCC | AACCATGCAC | AGAGCCTGTG | GGGAGAATAT | 300 |
| GTATGCAGAA | GGCTTTTGCC | TCCTGTTGGA | CTCCCATCTG | CAGACCATTT | GGACAGTACC | 360 |
| TGCTGCCCTA | CCAGAGTGTC | CAAGTCAAGA | GATGGACATT | GTCTTCCTGA | TTGATGGTTC | 420 |
| TGGCAGTATG | AGCAAAGTGA | CTTTAAACAA | ATGAAGGATT | TGTGAGAGCT | GTGATGGGAC | 480 |
| AGTTTGAGGG | CACCCAAACC | CTGTTCTCAC | TGATACAGTA | TCCCACCTCC | CTGAAGATCC | 540 |
| ACTTCACCTT | CACGCAATTC | CAGAGCAGCT | GGAACCCTCT | GAGCCTGGTG | GATCCCATTG | 600 |
| TCCAACTGGA | CGGCCTGACA | TATACAGCCA | CGGGCATCCG | GAAAGTGGTG | GAGGAACTGT | 660 |
| TTCATAGTAA | GAATGGGGCC | CGTAAAAGTG | CCAAGAAGAT | CCTCATTGTC | ATCACAGATG | 720 |
| GCAAAAATAC | AAAGACCCCC | TGGAGTACGA | GGACGTATCC | CCAGGCAGAG | AGAGCGGATC | 780 |
| ATCCGCTATG | CCATTGGGGT | GGGAGATGCT | TTCTGGAAAC | CCAGTGCCAA | GCAGGAGCTG | 840 |
| GACAACATTG | GCTCAGAGCC | GGCTCAGGAC | CATGTGTTCA | GGGTGGACAA | CTTTGCAGCA | 900 |
| CTCAGCAGCA | TCCAGGAGCA | GCTGCAGGAG | AAGATCTTTG | CACTCGAAGG | AACCCAGTCG | 960 |
| ACGACAAGTA | GCTCTTTCCA | ACATGAGATG | TTCCAAGAAG | GGTTCA | | 1006 |

( 2 ) INFORMATION FOR SEQ ID NO:25:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:25:

GTNTTYCARG ARGAYGG                                                  17

( 2 ) INFORMATION FOR SEQ ID NO:26:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:26:

CCACTGTCAG GATGCCCGTG                                          20

( 2 ) INFORMATION FOR SEQ ID NO:27:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:27:

AGTTACGAAT TCGCCACCAT GGCTCTACGG GTGCTTCTTC TG        42

( 2 ) INFORMATION FOR SEQ ID NO:28:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:28:

AGTTACGAAT TCGCCACCAT GACTCGGACT GTGCTTCTTC TG        42

( 2 ) INFORMATION FOR SEQ ID NO:29:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:29:

AGTTACGAAT TCGCCACCAT GACCTTCGGC ACTGTG        36

( 2 ) INFORMATION FOR SEQ ID NO:30:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:30:

TTGCTGACTG CCTGCAGTTC        20

( 2 ) INFORMATION FOR SEQ ID NO:31:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:31:

GTTCTGACGC GTAATGGCAT TGTAGACCTC GTCTTC        36

( 2 ) INFORMATION FOR SEQ ID NO:32:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:32:

ACGTATGCAG GATCCCATCA AGAGATGGAC ATCGCT        36

( 2 ) INFORMATION FOR SEQ ID NO:33:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:33:

ACTGCATGTC TCGAGGCTGA AGCCTTCTTG GGACATC　　　　　　　　　　　　　　　　37

( 2 ) INFORMATION FOR SEQ ID NO:34:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:34:

TATAGACTGC TGGGTAGTCC CCAC　　　　　　　　　　　　　　　　　　　　　　24

( 2 ) INFORMATION FOR SEQ ID NO:35:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:35:

TGAAGATTGG GGGTAAATAA CAGA　　　　　　　　　　　　　　　　　　　　　24

( 2 ) INFORMATION FOR SEQ ID NO:36:

( i ) SEQUENCE CHARACTERISTICS:
        ( A ) LENGTH: 3528 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..3456

( x i ) SEQUENCE DESCRIPTION: SEQ ID NO:36:

```
GGC  TGG  GCC  CTG  GCT  TCC  TGT  CAT  GGG  TCT  AAC  CTG  GAT  GTG  GAG  GAA        48
Gly  Trp  Ala  Leu  Ala  Ser  Cys  His  Gly  Ser  Asn  Leu  Asp  Val  Glu  Glu
 1              5                        10                       15

CCC  ATC  GTG  TTC  AGA  GAG  GAT  GCA  GCC  AGC  TTT  GGA  CAG  ACT  GTG  GTG        96
Pro  Ile  Val  Phe  Arg  Glu  Asp  Ala  Ala  Ser  Phe  Gly  Gln  Thr  Val  Val
             20                       25                       30

CAG  TTT  GGT  GGA  TCT  CGA  CTC  GTG  GTG  GGA  GCC  CCT  CTG  GAG  GCG  GTG       144
Gln  Phe  Gly  Gly  Ser  Arg  Leu  Val  Val  Gly  Ala  Pro  Leu  Glu  Ala  Val
         35                       40                       45

GCA  GTC  AAC  CAA  ACA  GGA  CGG  TTG  TAT  GAC  TGT  GCA  CCT  GCC  ACT  GGC       192
Ala  Val  Asn  Gln  Thr  Gly  Arg  Leu  Tyr  Asp  Cys  Ala  Pro  Ala  Thr  Gly
     50                       55                       60

ATG  TGC  CAG  CCC  ATC  GTA  CTG  CGC  AGT  CCC  CTA  GAG  GCA  GTG  AAC  ATG       240
Met  Cys  Gln  Pro  Ile  Val  Leu  Arg  Ser  Pro  Leu  Glu  Ala  Val  Asn  Met
 65                       70                       75                       80
```

| | | | | | | | | | | | | | | | | |
|---|---|---|---|---|---|---|---|---|---|---|---|---|---|---|---|---|
| TCC | CTG | GGC | CTG | TCT | CTG | GTG | ACT | GCC | ACC | AAT | AAC | GCC | CAG | TTG | CTG | 288 |
| Ser | Leu | Gly | Leu | Ser 85 | Leu | Val | Thr | Ala | Thr 90 | Asn | Asn | Ala | Gln | Leu 95 | Leu | |
| GCT | TGT | GGT | CCA | ACT | GCA | CAG | AGA | GCT | TGT | GTG | AAG | AAC | ATG | TAT | GCG | 336 |
| Ala | Cys | Gly | Pro 100 | Thr | Ala | Gln | Arg | Ala 105 | Cys | Val | Lys | Asn | Met 110 | Tyr | Ala | |
| AAA | GGT | TCC | TGC | CTC | CTT | CTC | GGC | TCC | AGC | TTG | CAG | TTC | ATC | CAG | GCA | 384 |
| Lys | Gly | Ser 115 | Cys | Leu | Leu | Leu | Gly | Ser 120 | Ser | Leu | Gln | Phe | Ile 125 | Gln | Ala | |
| GTC | CCT | GCC | TCC | ATG | CCA | GAG | TGT | CCA | AGA | CAA | GAG | ATG | GAC | ATT | GCT | 432 |
| Val | Pro 130 | Ala | Ser | Met | Pro 135 | Glu | Cys | Pro | Arg | Gln 140 | Glu | Met | Asp | Ile | Ala | |
| TTC | CTG | ATT | GAT | GGT | TCT | GGC | AGC | ATT | AAC | CAA | AGG | GAC | TTT | GCC | CAG | 480 |
| Phe 145 | Leu | Ile | Asp | Gly | Ser 150 | Gly | Ser | Ile | Asn | Gln 155 | Arg | Asp | Phe | Ala | Gln 160 | |
| ATG | AAG | GAC | TTT | GTC | AAA | GCT | TTG | ATG | GGA | GAG | TTT | GCG | AGC | ACC | AGC | 528 |
| Met | Lys | Asp | Phe | Val 165 | Lys | Ala | Leu | Met | Gly 170 | Glu | Phe | Ala | Ser | Thr 175 | Ser | |
| ACC | TTG | TTC | TCC | CTG | ATG | CAA | TAC | TCG | AAC | ATC | CTG | AAG | ACC | CAT | TTT | 576 |
| Thr | Leu | Phe | Ser 180 | Leu | Met | Gln | Tyr | Ser 185 | Asn | Ile | Leu | Lys | Thr 190 | His | Phe | |
| ACC | TTC | ACT | GAA | TTC | AAG | AAC | ATC | CTG | GAC | CCT | CAG | AGC | CTG | GTG | GAT | 624 |
| Thr | Phe | Thr 195 | Glu | Phe | Lys | Asn | Ile 200 | Leu | Asp | Pro | Gln | Ser 205 | Leu | Val | Asp | |
| CCC | ATT | GTC | CAG | CTG | CAA | GGC | CTG | ACC | TAC | ACA | GCC | ACA | GGC | ATC | CGG | 672 |
| Pro | Ile | Val | Gln 210 | Leu | Gln | Gly | Leu | Thr 215 | Tyr | Thr | Ala | Thr | Gly 220 | Ile | Arg | |
| ACA | GTG | ATG | GAA | GAG | CTA | TTT | CAT | AGC | AAG | AAT | GGG | TCC | CGT | AAA | AGT | 720 |
| Thr 225 | Val | Met | Glu | Glu | Leu 230 | Phe | His | Ser | Lys | Asn 235 | Gly | Ser | Arg | Lys | Ser 240 | |
| GCC | AAG | AAG | ATC | CTC | CTT | GTC | ATC | ACA | GAT | GGG | CAG | AAA | TAC | AGA | GAC | 768 |
| Ala | Lys | Lys | Ile | Leu 245 | Leu | Val | Ile | Thr | Asp 250 | Gly | Gln | Lys | Tyr | Arg 255 | Asp | |
| CCC | CTG | GAG | TAT | AGT | GAT | GTC | ATT | CCC | GCC | GCA | GAC | AAA | GCT | GGC | ATC | 816 |
| Pro | Leu | Glu | Tyr 260 | Ser | Asp | Val | Ile | Pro 265 | Ala | Ala | Asp | Lys | Ala 270 | Gly | Ile | |
| ATT | CGT | TAT | GCT | ATT | GGG | GTG | GGA | GAT | GCC | TTC | CAG | GAG | CCC | ACT | GCC | 864 |
| Ile | Arg | Tyr 275 | Ala | Ile | Gly | Val | Gly 280 | Asp | Ala | Phe | Gln | Glu 285 | Pro | Thr | Ala | |
| CTG | AAG | GAG | CTG | AAC | ACC | ATT | GGC | TCA | GCT | CCC | CCA | CAG | GAC | CAC | GTG | 912 |
| Leu | Lys | Glu 290 | Leu | Asn | Thr | Ile | Gly 295 | Ser | Ala | Pro | Pro | Gln 300 | Asp | His | Val | |
| TTC | AAG | GTA | GGC | AAC | TTT | GCA | GCA | CTT | CGC | AGC | ATC | CAG | AGG | CAA | CTT | 960 |
| Phe 305 | Lys | Val | Gly | Asn | Phe 310 | Ala | Ala | Leu | Arg | Ser 315 | Ile | Gln | Arg | Gln | Leu 320 | |
| CAG | GAG | AAA | ATC | TTC | GCC | ATT | GAG | GGA | ACT | CAA | TCA | AGG | TCA | AGT | AGT | 1008 |
| Gln | Glu | Lys | Ile | Phe 325 | Ala | Ile | Glu | Gly | Thr 330 | Gln | Ser | Arg | Ser | Ser 335 | Ser | |
| TCC | TTT | CAG | CAC | GAG | ATG | TCA | CAA | GAA | GGT | TTC | AGT | TCA | GCT | CTC | ACA | 1056 |
| Ser | Phe | Gln | His 340 | Glu | Met | Ser | Gln | Glu 345 | Gly | Phe | Ser | Ser | Ala 350 | Leu | Thr | |
| TCG | GAT | GGA | CCC | GTT | CTG | GGG | GCC | GYG | GGA | AGC | TTC | AGC | TGG | TCC | GGA | 1104 |
| Ser | Asp | Gly 355 | Pro | Val | Leu | Gly | Ala 360 | Xaa | Gly | Ser | Phe | Ser 365 | Trp | Ser | Gly | |
| GGT | GCC | TTC | TTA | TAT | CCC | CCA | AAT | ACG | AGA | CCC | ACC | TTT | ATC | AAC | ATG | 1152 |
| Gly | Ala | Phe 370 | Leu | Tyr | Pro | Pro 375 | Asn | Thr | Arg | Pro | Thr 380 | Phe | Ile | Asn | Met | |
| TCT | CAG | GAG | AAT | GTG | GAC | ATG | AGA | GAC | TCC | TAC | CTG | GGT | TAC | TCC | ACC | 1200 |
| Ser | Gln 385 | Glu | Asn | Val | Asp | Met 390 | Arg | Asp | Ser | Tyr | Leu 395 | Gly | Tyr | Ser | Thr 400 | |

```
GCA GTG GCC TTT TGG AAG GGG GTT CAC AGC CTG ATC CTG GGG GCC CCG      1248
Ala Val Ala Phe Trp Lys Gly Val His Ser Leu Ile Leu Gly Ala Pro
            405                 410                 415

CGT CAC CAG CAC ACG GGG AAG GTT GTC ATC TTT ACC CAG GAA GCC AGG      1296
Arg His Gln His Thr Gly Lys Val Val Ile Phe Thr Gln Glu Ala Arg
        420                 425                 430

CAT TGG AGG CCC AAG TCT GAA GTC AGA GGG ACA CAG ATC GGC TCC TAC      1344
His Trp Arg Pro Lys Ser Glu Val Arg Gly Thr Gln Ile Gly Ser Tyr
            435                 440                 445

TTC GGG GCC TCT CTC TGT TCT GTG GAC GTG GAT AGA GAT GGC AGC ACY      1392
Phe Gly Ala Ser Leu Cys Ser Val Asp Val Asp Arg Asp Gly Ser Xaa
        450                 455                 460

GAC CTG GTC CTG ATC GGA GCC CCC CAT TAC TAT GAG CAG ACC CGA GGG      1440
Asp Leu Val Leu Ile Gly Ala Pro His Tyr Tyr Glu Gln Thr Arg Gly
465                 470                 475                 480

GGG CAG GTC TCA GTG TKC CCC GTG CCC GGT GTG AGG GGC AGG TGG CAG      1488
Gly Gln Val Ser Val Xaa Pro Val Pro Gly Val Arg Gly Arg Trp Gln
                485                 490                 495

TGT GAG GCC ACC CTC CAC GGG GAG CAG GRC CAT CCT TGG GGC CGC TTT      1536
Cys Glu Ala Thr Leu His Gly Glu Gln Xaa His Pro Trp Gly Arg Phe
            500                 505                 510

GGG GTG GCT CTG ACA GTG CTG GGG GAC GTA AAC GGG GAC AAT CTG GCA      1584
Gly Val Ala Leu Thr Val Leu Gly Asp Val Asn Gly Asp Asn Leu Ala
        515                 520                 525

GAC GTG GCT ATT GGT GCC CCT GGA GAG GAG GAG AGC AGA GGT GCT GTC      1632
Asp Val Ala Ile Gly Ala Pro Gly Glu Glu Glu Ser Arg Gly Ala Val
530                 535                 540

TAC ATA TTT CAT GGA GCC TCG AGA CTG GAG ATC ATG CCC TCA CCC AGC      1680
Tyr Ile Phe His Gly Ala Ser Arg Leu Glu Ile Met Pro Ser Pro Ser
545                 550                 555                 560

CAG CGG GTC ACT GGC TCC CAG CTC TCC CTG AGA CTG CAG TAT TTT GGG      1728
Gln Arg Val Thr Gly Ser Gln Leu Ser Leu Arg Leu Gln Tyr Phe Gly
            565                 570                 575

CAG TCA TTG AGT GGG GGT CAG GAC CTT ACA CAG GAT GGC CTG GTG GAC      1776
Gln Ser Leu Ser Gly Gly Gln Asp Leu Thr Gln Asp Gly Leu Val Asp
        580                 585                 590

CTG GCC GTG GGA GCC CAG GGG CAC GTA CTG CTG CTC AGG AGT CTG CCT      1824
Leu Ala Val Gly Ala Gln Gly His Val Leu Leu Leu Arg Ser Leu Pro
            595                 600                 605

CTG CTG AAA GTG GAG CTC TCC ATA AGA TTC GCC CCC ATG GAG GTG GCA      1872
Leu Leu Lys Val Glu Leu Ser Ile Arg Phe Ala Pro Met Glu Val Ala
610                 615                 620

AAG GCT GTG TAC CAG TGC TGG GAA AGG ACT CCC ACT GTC CTC GAA GCT      1920
Lys Ala Val Tyr Gln Cys Trp Glu Arg Thr Pro Thr Val Leu Glu Ala
625                 630                 635                 640

GGA GAG GCC ACT GTC TGT CTC ACT GTC CAC AAA GGC TCA CCT GAC CTG      1968
Gly Glu Ala Thr Val Cys Leu Thr Val His Lys Gly Ser Pro Asp Leu
            645                 650                 655

TTA GGT AAT GTC CAA GGC TCT GTC AGG TAT GAT CTG GCG TTA GAT CCG      2016
Leu Gly Asn Val Gln Gly Ser Val Arg Tyr Asp Leu Ala Leu Asp Pro
        660                 665                 670

GGC CGC CTG ATT TCT CGT GCC ATT TTT GAT GAG ACT AAG AAC TGC ACT      2064
Gly Arg Leu Ile Ser Arg Ala Ile Phe Asp Glu Thr Lys Asn Cys Thr
            675                 680                 685

TTG ACG GGA AGG AAG ACT CTG GGG CTT GGT GAT CAC TGC GAA ACA GTG      2112
Leu Thr Gly Arg Lys Thr Leu Gly Leu Gly Asp His Cys Glu Thr Val
        690                 695                 700

AAG CTG CTT TTG CCG GAC TGT GTG GAA GAT GCA GTG AGC CCT ATC ATC      2160
Lys Leu Leu Leu Pro Asp Cys Val Glu Asp Ala Val Ser Pro Ile Ile
705                 710                 715                 720
```

| | | | | | | | | | | | | | | | | |
|---|---|---|---|---|---|---|---|---|---|---|---|---|---|---|---|---|
| CTG | CGC | CTC | AAC | TTT | TCC | CTG | GTG | AGA | GAC | TCT | GCT | TCA | CCC | AGG | AAC | 2208 |
| Leu | Arg | Leu | Asn | Phe | Ser | Leu | Val | Arg | Asp | Ser | Ala | Ser | Pro | Arg | Asn | |
| | | | | 725 | | | | 730 | | | | | | 735 | | |
| CTG | CAT | CCT | GTG | CTG | GCT | GTG | GGC | TCA | CAA | GAC | CAC | ATA | ACT | GCT | TCT | 2256 |
| Leu | His | Pro | Val | Leu | Ala | Val | Gly | Ser | Gln | Asp | His | Ile | Thr | Ala | Ser | |
| | | | 740 | | | | | 745 | | | | | 750 | | | |
| CTG | CCG | TTT | GAG | AAG | AAC | TGT | AAG | CAA | GAA | CTC | CTG | TGT | GAG | GGG | GAC | 2304 |
| Leu | Pro | Phe | Glu | Lys | Asn | Cys | Lys | Gln | Glu | Leu | Leu | Cys | Glu | Gly | Asp | |
| | | 755 | | | | | 760 | | | | | 765 | | | | |
| CTG | GGC | ATC | AGC | TTT | AAC | TTC | TCA | GGC | CTG | CAG | GTC | TTG | GTG | GTG | GGA | 2352 |
| Leu | Gly | Ile | Ser | Phe | Asn | Phe | Ser | Gly | Leu | Gln | Val | Leu | Val | Val | Gly | |
| | 770 | | | | | 775 | | | | | 780 | | | | | |
| GGC | TCC | CCA | GAG | CTC | ACT | GTG | ACA | GTC | ACT | GTG | TGG | AAT | GAG | GGT | GAG | 2400 |
| Gly | Ser | Pro | Glu | Leu | Thr | Val | Thr | Val | Thr | Val | Trp | Asn | Glu | Gly | Glu | |
| 785 | | | | | 790 | | | | | 795 | | | | | 800 | |
| GAC | AGC | TAT | GGA | ACT | TTA | GTC | AAG | TTC | TAC | TAC | CCA | GCA | GGG | CTA | TCT | 2448 |
| Asp | Ser | Tyr | Gly | Thr | Leu | Val | Lys | Phe | Tyr | Tyr | Pro | Ala | Gly | Leu | Ser | |
| | | | | 805 | | | | | 810 | | | | | 815 | | |
| TAC | CGA | CGG | GTA | ACA | GGG | ACT | CAG | CAA | CCT | CAT | CAG | TAC | CCA | CTA | CGC | 2496 |
| Tyr | Arg | Arg | Val | Thr | Gly | Thr | Gln | Gln | Pro | His | Gln | Tyr | Pro | Leu | Arg | |
| | | | 820 | | | | | 825 | | | | | 830 | | | |
| TTG | GCC | TGT | GAG | GCT | GAG | CCC | GCT | GCC | CAG | GAG | GAC | CTG | AGG | AGC | AGC | 2544 |
| Leu | Ala | Cys | Glu | Ala | Glu | Pro | Ala | Ala | Gln | Glu | Asp | Leu | Arg | Ser | Ser | |
| | | 835 | | | | | 840 | | | | | 845 | | | | |
| AGC | TGT | AGC | ATT | AAT | CAC | CCC | ATC | TTC | CGA | GAA | GGT | GCA | AAG | ACC | ACC | 2592 |
| Ser | Cys | Ser | Ile | Asn | His | Pro | Ile | Phe | Arg | Glu | Gly | Ala | Lys | Thr | Thr | |
| | 850 | | | | | 855 | | | | | 860 | | | | | |
| TTC | ATG | ATC | ACA | TTC | GAT | GTC | TCC | TAC | AAG | GCC | TTC | CTA | GGA | GAC | AGG | 2640 |
| Phe | Met | Ile | Thr | Phe | Asp | Val | Ser | Tyr | Lys | Ala | Phe | Leu | Gly | Asp | Arg | |
| 865 | | | | | 870 | | | | | 875 | | | | | 880 | |
| TTG | CTT | CTG | AGG | GCC | AAA | GCC | AGC | AGT | GAG | AAT | AAT | AAG | CCT | GAT | ACC | 2688 |
| Leu | Leu | Leu | Arg | Ala | Lys | Ala | Ser | Ser | Glu | Asn | Asn | Lys | Pro | Asp | Thr | |
| | | | | 885 | | | | | 890 | | | | | 895 | | |
| AAC | AAG | ACT | GCC | TTC | CAG | CTG | GAG | CTC | CCA | GTG | AAG | TAC | ACC | GTC | TAT | 2736 |
| Asn | Lys | Thr | Ala | Phe | Gln | Leu | Glu | Leu | Pro | Val | Lys | Tyr | Thr | Val | Tyr | |
| | | | 900 | | | | | 905 | | | | | 910 | | | |
| ACC | CTG | ATC | AGT | AGG | CAA | GAA | GAT | TCC | ACC | AAC | CAT | GTC | AAC | TTT | TCA | 2784 |
| Thr | Leu | Ile | Ser | Arg | Gln | Glu | Asp | Ser | Thr | Asn | His | Val | Asn | Phe | Ser | |
| | | 915 | | | | | 920 | | | | | 925 | | | | |
| TCT | TCC | CAC | GGG | GGG | AGA | AGG | CAA | GAA | GCC | GCA | CAT | CGC | TAT | CGT | GTG | 2832 |
| Ser | Ser | His | Gly | Gly | Arg | Arg | Gln | Glu | Ala | Ala | His | Arg | Tyr | Arg | Val | |
| | 930 | | | | | 935 | | | | | 940 | | | | | |
| AAT | AAC | CTG | AGT | CCA | CTG | AAG | CTG | GCC | GTC | AGA | GTT | AAC | TTC | TGG | GTC | 2880 |
| Asn | Asn | Leu | Ser | Pro | Leu | Lys | Leu | Ala | Val | Arg | Val | Asn | Phe | Trp | Val | |
| 945 | | | | | 950 | | | | | 955 | | | | | 960 | |
| CCT | GTC | CTT | CTG | AAC | GGT | GTG | GCT | GTG | TGG | GAC | GTG | ACT | CTG | AGC | AGC | 2928 |
| Pro | Val | Leu | Leu | Asn | Gly | Val | Ala | Val | Trp | Asp | Val | Thr | Leu | Ser | Ser | |
| | | | | 965 | | | | | 970 | | | | | 975 | | |
| CCA | GCA | CAG | GGT | GTC | TCC | TGC | GTG | TCC | CAG | ATG | AAA | CCT | CCT | CAG | AAT | 2976 |
| Pro | Ala | Gln | Gly | Val | Ser | Cys | Val | Ser | Gln | Met | Lys | Pro | Pro | Gln | Asn | |
| | | | 980 | | | | | 985 | | | | | 990 | | | |
| CCC | GAC | TTT | CTG | ACC | CAG | ATT | CAG | AGA | CGT | TCT | GTG | CTG | GAC | TGC | TCC | 3024 |
| Pro | Asp | Phe | Leu | Thr | Gln | Ile | Gln | Arg | Arg | Ser | Val | Leu | Asp | Cys | Ser | |
| | | 995 | | | | | 1000 | | | | | 1005 | | | | |
| ATT | GCT | GAC | TGC | CTG | CAC | TCC | CGC | TGT | GAC | ATC | CCC | TCC | TTG | GAC | ATC | 3072 |
| Ile | Ala | Asp | Cys | Leu | His | Ser | Arg | Cys | Asp | Ile | Pro | Ser | Leu | Asp | Ile | |
| | 1010 | | | | | 1015 | | | | | 1020 | | | | | |
| CAG | GAT | GAA | CTT | GAC | TTC | ATT | CTG | AGG | GGC | AAC | CTC | AGC | TTC | GGC | TGG | 3120 |
| Gln | Asp | Glu | Leu | Asp | Phe | Ile | Leu | Arg | Gly | Asn | Leu | Ser | Phe | Gly | Trp | |
| 1025 | | | | | 1030 | | | | | 1035 | | | | | 1040 | |

```
GTC  AGT  CAG  ACA  TTG  CAG  GAA  AAG  GTG  TTG  CTT  GTG  AGT  GAG  GCT  GAA         3168
Val  Ser  Gln  Thr  Leu  Gln  Glu  Lys  Val  Leu  Leu  Val  Ser  Glu  Ala  Glu
               1045                    1050                    1055

ATC  ACT  TTC  GAC  ACA  TCT  GTG  TAC  TCC  CAG  CTG  CCA  GGA  CAG  GAG  GCA         3216
Ile  Thr  Phe  Asp  Thr  Ser  Val  Tyr  Ser  Gln  Leu  Pro  Gly  Gln  Glu  Ala
               1060                    1065                    1070

TTT  CTG  AGA  GCC  CAG  GTG  GAG  ACA  ACG  TTA  GAA  GAA  TAC  GTG  GTC  TAT         3264
Phe  Leu  Arg  Ala  Gln  Val  Glu  Thr  Thr  Leu  Glu  Glu  Tyr  Val  Val  Tyr
               1075                    1080                    1085

GAG  CCC  ATC  TTC  CTC  GTG  GCG  GGC  AGC  TCG  GTG  GGA  GGT  CTG  CTG  TTA         3312
Glu  Pro  Ile  Phe  Leu  Val  Ala  Gly  Ser  Ser  Val  Gly  Gly  Leu  Leu  Leu
               1090                    1095                    1100

CTG  GCT  CTC  ATC  ACA  GTG  GTA  CTG  TAC  AAG  CTT  GGC  TYC  TYC  AAA  CGT         3360
Leu  Ala  Leu  Ile  Thr  Val  Val  Leu  Tyr  Lys  Leu  Gly  Xaa  Xaa  Lys  Arg
1105                    1110                    1115                    1120

CAG  TAC  AAA  GAA  ATG  CTG  GAC  GGC  AAG  GCT  GCA  GAT  CCT  GTC  ACA  GCC         3408
Gln  Tyr  Lys  Glu  Met  Leu  Asp  Gly  Lys  Ala  Ala  Asp  Pro  Val  Thr  Ala
               1125                    1130                    1135

GGC  CAG  GCA  GAT  TTC  GGC  TGT  GAG  ACT  CCT  CCA  TAT  CTC  GTG  AGC  TAGGAATC3463
Gly  Gln  Ala  Asp  Phe  Gly  Cys  Glu  Thr  Pro  Pro  Tyr  Leu  Val  Ser
               1140                    1145                    1150

CTCTCCTGCC  TATCTCTGNA  ATGAAGATTG  GTCCTGCCTA  TGAGTCTACT  GGCATGGGAA         3523

CGAGT                                                                                   3528
```

( 2 ) INFORMATION FOR SEQ ID NO:37:

( i ) SEQUENCE CHARACTERISTICS:
        ( A ) LENGTH: 1151 amino acids
        ( B ) TYPE: amino acid
        ( D ) TOPOLOGY: linear ( i i ) MOLECULE TYPE: protein ( x i ) SEQUENCE DESCRIPTION: SEQ ID NO:37:

```
Gly  Trp  Ala  Leu  Ala  Ser  Cys  His  Gly  Ser  Asn  Leu  Asp  Val  Glu  Glu
 1                    5                    10                        15

Pro  Ile  Val  Phe  Arg  Glu  Asp  Ala  Ala  Ser  Phe  Gly  Gln  Thr  Val  Val
               20                    25                    30

Gln  Phe  Gly  Gly  Ser  Arg  Leu  Val  Val  Gly  Ala  Pro  Leu  Glu  Ala  Val
          35                        40                    45

Ala  Val  Asn  Gln  Thr  Gly  Arg  Leu  Tyr  Asp  Cys  Ala  Pro  Ala  Thr  Gly
          50                    55                    60

Met  Cys  Gln  Pro  Ile  Val  Leu  Arg  Ser  Pro  Leu  Glu  Ala  Val  Asn  Met
 65                   70                    75                        80

Ser  Leu  Gly  Leu  Ser  Leu  Val  Thr  Ala  Thr  Asn  Asn  Ala  Gln  Leu  Leu
               85                    90                        95

Ala  Cys  Gly  Pro  Thr  Ala  Gln  Arg  Ala  Cys  Val  Lys  Asn  Met  Tyr  Ala
               100                   105                   110

Lys  Gly  Ser  Cys  Leu  Leu  Leu  Gly  Ser  Ser  Leu  Gln  Phe  Ile  Gln  Ala
          115                       120                   125

Val  Pro  Ala  Ser  Met  Pro  Glu  Cys  Pro  Arg  Gln  Glu  Met  Asp  Ile  Ala
     130                       135                   140

Phe  Leu  Ile  Asp  Gly  Ser  Gly  Ser  Ile  Asn  Gln  Arg  Asp  Phe  Ala  Gln
145                       150                   155                       160

Met  Lys  Asp  Phe  Val  Lys  Ala  Leu  Met  Gly  Glu  Phe  Ala  Ser  Thr  Ser
               165                   170                   175

Thr  Leu  Phe  Ser  Leu  Met  Gln  Tyr  Ser  Asn  Ile  Leu  Lys  Thr  His  Phe
               180                   185                   190
```

```
Thr Phe Thr Glu Phe Lys Asn Ile Leu Asp Pro Gln Ser Leu Val Asp
        195             200             205

Pro Ile Val Gln Leu Gln Gly Leu Thr Tyr Thr Ala Thr Gly Ile Arg
    210             215             220

Thr Val Met Glu Glu Leu Phe His Ser Lys Asn Gly Ser Arg Lys Ser
225             230             235                         240

Ala Lys Lys Ile Leu Leu Val Ile Thr Asp Gly Gln Lys Tyr Arg Asp
                245             250                 255

Pro Leu Glu Tyr Ser Asp Val Ile Pro Ala Ala Asp Lys Ala Gly Ile
            260             265             270

Ile Arg Tyr Ala Ile Gly Val Gly Asp Ala Phe Gln Glu Pro Thr Ala
        275             280             285

Leu Lys Glu Leu Asn Thr Ile Gly Ser Ala Pro Pro Gln Asp His Val
    290             295             300

Phe Lys Val Gly Asn Phe Ala Ala Leu Arg Ser Ile Gln Arg Gln Leu
305             310             315                         320

Gln Glu Lys Ile Phe Ala Ile Glu Gly Thr Gln Ser Arg Ser Ser Ser
                325             330                 335

Ser Phe Gln His Glu Met Ser Gln Glu Gly Phe Ser Ser Ala Leu Thr
            340             345             350

Ser Asp Gly Pro Val Leu Gly Ala Xaa Gly Ser Phe Ser Trp Ser Gly
        355             360             365

Gly Ala Phe Leu Tyr Pro Pro Asn Thr Arg Pro Thr Phe Ile Asn Met
    370             375             380

Ser Gln Glu Asn Val Asp Met Arg Asp Ser Tyr Leu Gly Tyr Ser Thr
385             390             395                         400

Ala Val Ala Phe Trp Lys Gly Val His Ser Leu Ile Leu Gly Ala Pro
                405             410                 415

Arg His Gln His Thr Gly Lys Val Val Ile Phe Thr Gln Glu Ala Arg
            420             425             430

His Trp Arg Pro Lys Ser Glu Val Arg Gly Thr Gln Ile Gly Ser Tyr
        435             440             445

Phe Gly Ala Ser Leu Cys Ser Val Asp Val Asp Arg Asp Gly Ser Xaa
    450             455             460

Asp Leu Val Leu Ile Gly Ala Pro His Tyr Tyr Glu Gln Thr Arg Gly
465             470             475                         480

Gly Gln Val Ser Val Xaa Pro Val Pro Gly Val Arg Gly Arg Trp Gln
                485             490                 495

Cys Glu Ala Thr Leu His Gly Glu Gln Xaa His Pro Trp Gly Arg Phe
            500             505             510

Gly Val Ala Leu Thr Val Leu Gly Asp Val Asn Gly Asp Asn Leu Ala
        515             520             525

Asp Val Ala Ile Gly Ala Pro Gly Glu Glu Glu Ser Arg Gly Ala Val
    530             535             540

Tyr Ile Phe His Gly Ala Ser Arg Leu Glu Ile Met Pro Ser Pro Ser
545             550             555                         560

Gln Arg Val Thr Gly Ser Gln Leu Ser Leu Arg Leu Gln Tyr Phe Gly
                565             570                 575

Gln Ser Leu Ser Gly Gly Gln Asp Leu Thr Gln Asp Gly Leu Val Asp
            580             585             590

Leu Ala Val Gly Ala Gln Gly His Val Leu Leu Leu Arg Ser Leu Pro
        595             600             605

Leu Leu Lys Val Glu Leu Ser Ile Arg Phe Ala Pro Met Glu Val Ala
```

```
          610                      615                      620
Lys  Ala  Val  Tyr  Gln  Cys  Trp  Glu  Arg  Thr  Pro  Thr  Val  Leu  Glu  Ala
625                      630                 635                           640

Gly  Glu  Ala  Thr  Val  Cys  Leu  Thr  Val  His  Lys  Gly  Ser  Pro  Asp  Leu
                    645                      650                 655

Leu  Gly  Asn  Val  Gln  Gly  Ser  Val  Arg  Tyr  Asp  Leu  Ala  Leu  Asp  Pro
               660                      665                      670

Gly  Arg  Leu  Ile  Ser  Arg  Ala  Ile  Phe  Asp  Glu  Thr  Lys  Asn  Cys  Thr
          675                      680                 685

Leu  Thr  Gly  Arg  Lys  Thr  Leu  Gly  Leu  Gly  Asp  His  Cys  Glu  Thr  Val
     690                      695                 700

Lys  Leu  Leu  Leu  Pro  Asp  Cys  Val  Glu  Asp  Ala  Val  Ser  Pro  Ile  Ile
705                 710                      715                      720

Leu  Arg  Leu  Asn  Phe  Ser  Leu  Val  Arg  Asp  Ser  Ala  Ser  Pro  Arg  Asn
                    725                      730                      735

Leu  His  Pro  Val  Leu  Ala  Val  Gly  Ser  Gln  Asp  His  Ile  Thr  Ala  Ser
               740                      745                      750

Leu  Pro  Phe  Glu  Lys  Asn  Cys  Lys  Gln  Glu  Leu  Leu  Cys  Glu  Gly  Asp
          755                      760                      765

Leu  Gly  Ile  Ser  Phe  Asn  Phe  Ser  Gly  Leu  Gln  Val  Leu  Val  Val  Gly
     770                      775                      780

Gly  Ser  Pro  Glu  Leu  Thr  Val  Thr  Val  Thr  Val  Trp  Asn  Glu  Gly  Glu
785                      790                      795                      800

Asp  Ser  Tyr  Gly  Thr  Leu  Val  Lys  Phe  Tyr  Tyr  Pro  Ala  Gly  Leu  Ser
                    805                      810                      815

Tyr  Arg  Arg  Val  Thr  Gly  Thr  Gln  Gln  Pro  His  Gln  Tyr  Pro  Leu  Arg
               820                      825                      830

Leu  Ala  Cys  Glu  Ala  Glu  Pro  Ala  Ala  Gln  Glu  Asp  Leu  Arg  Ser  Ser
          835                      840                      845

Ser  Cys  Ser  Ile  Asn  His  Pro  Ile  Phe  Arg  Glu  Gly  Ala  Lys  Thr  Thr
     850                      855                      860

Phe  Met  Ile  Thr  Phe  Asp  Val  Ser  Tyr  Lys  Ala  Phe  Leu  Gly  Asp  Arg
865                      870                      875                      880

Leu  Leu  Leu  Arg  Ala  Lys  Ala  Ser  Ser  Glu  Asn  Asn  Lys  Pro  Asp  Thr
                    885                      890                      895

Asn  Lys  Thr  Ala  Phe  Gln  Leu  Glu  Leu  Pro  Val  Lys  Tyr  Thr  Val  Tyr
               900                      905                      910

Thr  Leu  Ile  Ser  Arg  Gln  Glu  Asp  Ser  Thr  Asn  His  Val  Asn  Phe  Ser
          915                      920                      925

Ser  Ser  His  Gly  Gly  Arg  Arg  Gln  Glu  Ala  Ala  His  Arg  Tyr  Arg  Val
     930                      935                      940

Asn  Asn  Leu  Ser  Pro  Leu  Lys  Leu  Ala  Val  Arg  Val  Asn  Phe  Trp  Val
945                      950                      955                      960

Pro  Val  Leu  Leu  Asn  Gly  Val  Ala  Val  Trp  Asp  Val  Thr  Leu  Ser  Ser
                    965                      970                      975

Pro  Ala  Gln  Gly  Val  Ser  Cys  Val  Ser  Gln  Met  Lys  Pro  Pro  Gln  Asn
               980                      985                      990

Pro  Asp  Phe  Leu  Thr  Gln  Ile  Gln  Arg  Arg  Ser  Val  Leu  Asp  Cys  Ser
          995                      1000                     1005

Ile  Ala  Asp  Cys  Leu  His  Ser  Arg  Cys  Asp  Ile  Pro  Ser  Leu  Asp  Ile
     1010                     1015                     1020

Gln  Asp  Glu  Leu  Asp  Phe  Ile  Leu  Arg  Gly  Asn  Leu  Ser  Phe  Gly  Trp
1025                     1030                     1035                     1040
```

| | | | | | | | | | | | | | | |
|---|---|---|---|---|---|---|---|---|---|---|---|---|---|---|
|Val|Ser|Gln|Thr|Leu|Gln|Glu|Lys|Val|Leu|Leu|Val|Ser|Glu|Ala|Glu|
| | | | |1045| | | |1050| | | |1055| | |
|Ile|Thr|Phe|Asp|Thr|Ser|Val|Tyr|Ser|Gln|Leu|Pro|Gly|Gln|Glu|Ala|
| | | |1060| | | |1065| | | |1070| | | |
|Phe|Leu|Arg|Ala|Gln|Val|Glu|Thr|Thr|Leu|Glu|Glu|Tyr|Val|Val|Tyr|
| | |1075| | | |1080| | | |1085| | | | |
|Glu|Pro|Ile|Phe|Leu|Val|Ala|Gly|Ser|Ser|Val|Gly|Gly|Leu|Leu|Leu|
| |1090| | | |1095| | | |1100| | | | | |
|Leu|Ala|Leu|Ile|Thr|Val|Val|Leu|Tyr|Lys|Leu|Gly|Xaa|Xaa|Lys|Arg|
|1105| | | |1110| | | |1115| | | | | |1120| |
|Gln|Tyr|Lys|Glu|Met|Leu|Asp|Gly|Lys|Ala|Ala|Asp|Pro|Val|Thr|Ala|
| | | |1125| | | |1130| | | |1135| | | |
|Gly|Gln|Ala|Asp|Phe|Gly|Cys|Glu|Thr|Pro|Pro|Tyr|Leu|Val|Ser| |
| | |1140| | | |1145| | | |1150| | | | |

( 2 ) INFORMATION FOR SEQ ID NO:38:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:38:

GTCCAAGCTG TCATGGGCCA G                                      21

( 2 ) INFORMATION FOR SEQ ID NO:39:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:39:

GTCCAGCAGA CTGAAGAGCA CGG                                  23

( 2 ) INFORMATION FOR SEQ ID NO:40:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:40:

TGTAAAACGA CGGCCAGT                                            18

( 2 ) INFORMATION FOR SEQ ID NO:41:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:41:

GGAAACAGCT ATGACCATG                                         19

( 2 ) INFORMATION FOR SEQ ID NO:42:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:42:

```
GGACATGTTC ACTGCCTCTA GG                                              22
```

( 2 ) INFORMATION FOR SEQ ID NO:43:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:43:

```
GGCGGACAGT CAGACGACTG TCCTG                                           25
```

( 2 ) INFORMATION FOR SEQ ID NO:44:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:44:

```
CTGGTTCGGC CCACCTCTGA AGGTTCCAGA ATCGATAG                             38
```

( 2 ) INFORMATION FOR SEQ ID NO:45:

( i ) SEQUENCE CHARACTERISTICS:
        ( A ) LENGTH: 3519 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 52..3519

( x i ) SEQUENCE DESCRIPTION: SEQ ID NO:45:

```
GCTTTCTGAA GGTTCCAGAA TCGATAGTGA ATTCGTGGGC ACTGCTCAGA T ATG GTC      57
                                                        Met Val
                                                         1

CGT GGA GTT GTG ATC CTC CTG TGT GGC TGG GCC CTG GCT TCC TGT CAT      105
Arg Gly Val Val Ile Leu Leu Cys Gly Trp Ala Leu Ala Ser Cys His
         5                  10                  15

GGG TCT AAC CTG GAT GTG GAG AAG CCC GTC GTG TTC AAA GAG GAT GCA      153
Gly Ser Asn Leu Asp Val Glu Lys Pro Val Val Phe Lys Glu Asp Ala
     20                  25                  30

GCC AGC TTC GGA CAG ACT GTG GTG CAG TTT GGT GGA TCT CGA CTC GTG      201
Ala Ser Phe Gly Gln Thr Val Val Gln Phe Gly Gly Ser Arg Leu Val
 35                  40                  45                  50

GTG GGA GCC CCT CTG GAG GCG GTG GCA GTC AAC CAA ACA GGA CAG TCG      249
```

|  |  |  |  |  |  |  |  |  |  |  |  |  |  |  |  |
|---|---|---|---|---|---|---|---|---|---|---|---|---|---|---|---|
| Val | Gly | Ala | Pro | Leu | Glu | Ala | Val | Ala | Val | Asn | Gln | Thr | Gly | Gln | Ser |
|  |  |  |  | 55 |  |  |  | 60 |  |  |  |  |  | 65 |  |

| TCT | GAC | TGT | CCG | CCT | GCC | ACT | GGC | GTG | TGC | CAG | CCC | ATC | TTA | CTG | CAC | 297 |
|---|---|---|---|---|---|---|---|---|---|---|---|---|---|---|---|---|
| Ser | Asp | Cys | Pro | Pro | Ala | Thr | Gly | Val | Cys | Gln | Pro | Ile | Leu | Leu | His |  |
|  |  |  | 70 |  |  |  |  | 75 |  |  |  |  |  | 80 |  |  |

| ATT | CCC | CTA | GAG | GCA | GTG | AAC | ATG | TCC | CTG | GGC | CTG | TCT | CTG | GTG | GCT | 345 |
|---|---|---|---|---|---|---|---|---|---|---|---|---|---|---|---|---|
| Ile | Pro | Leu | Glu | Ala | Val | Asn | Met | Ser | Leu | Gly | Leu | Ser | Leu | Val | Ala |  |
|  |  |  | 85 |  |  |  |  | 90 |  |  |  |  | 95 |  |  |  |

| GAC | ACC | AAT | AAC | TCC | CAG | TTG | CTG | GCT | TGT | GGT | CCA | ACT | GCA | CAG | AGA | 393 |
|---|---|---|---|---|---|---|---|---|---|---|---|---|---|---|---|---|
| Asp | Thr | Asn | Asn | Ser | Gln | Leu | Leu | Ala | Cys | Gly | Pro | Thr | Ala | Gln | Arg |  |
|  |  |  | 100 |  |  |  |  | 105 |  |  |  |  | 110 |  |  |  |

| GCT | TGT | GCA | AAG | AAC | ATG | TAT | GCA | AAA | GGT | TCC | TGC | CTC | CTT | CTG | GGC | 441 |
|---|---|---|---|---|---|---|---|---|---|---|---|---|---|---|---|---|
| Ala | Cys | Ala | Lys | Asn | Met | Tyr | Ala | Lys | Gly | Ser | Cys | Leu | Leu | Leu | Gly |  |
| 115 |  |  |  |  | 120 |  |  |  |  | 125 |  |  |  |  | 130 |  |

| TCC | AGC | TTG | CAG | TTC | ATC | CAG | GCA | ATC | CCT | GCT | ACC | ATG | CCA | GAG | TGT | 489 |
|---|---|---|---|---|---|---|---|---|---|---|---|---|---|---|---|---|
| Ser | Ser | Leu | Gln | Phe | Ile | Gln | Ala | Ile | Pro | Ala | Thr | Met | Pro | Glu | Cys |  |
|  |  |  |  | 135 |  |  |  |  | 140 |  |  |  |  | 145 |  |  |

| CCA | GGA | CAA | GAG | ATG | GAC | ATT | GCT | TTC | CTG | ATT | GAT | GGC | TCC | GGC | AGC | 537 |
|---|---|---|---|---|---|---|---|---|---|---|---|---|---|---|---|---|
| Pro | Gly | Gln | Glu | Met | Asp | Ile | Ala | Phe | Leu | Ile | Asp | Gly | Ser | Gly | Ser |  |
|  |  |  | 150 |  |  |  |  | 155 |  |  |  |  | 160 |  |  |  |

| ATT | GAT | CAA | AGT | GAC | TTT | ACC | CAG | ATG | AAG | GAC | TTC | GTC | AAA | GCT | TTG | 585 |
|---|---|---|---|---|---|---|---|---|---|---|---|---|---|---|---|---|
| Ile | Asp | Gln | Ser | Asp | Phe | Thr | Gln | Met | Lys | Asp | Phe | Val | Lys | Ala | Leu |  |
|  |  |  | 165 |  |  |  |  | 170 |  |  |  |  | 175 |  |  |  |

| ATG | GGC | CAG | TTG | GCG | AGC | ACC | AGC | ACC | TCG | TTC | TCC | CTG | ATG | CAA | TAC | 633 |
|---|---|---|---|---|---|---|---|---|---|---|---|---|---|---|---|---|
| Met | Gly | Gln | Leu | Ala | Ser | Thr | Ser | Thr | Ser | Phe | Ser | Leu | Met | Gln | Tyr |  |
|  |  | 180 |  |  |  |  | 185 |  |  |  |  | 190 |  |  |  |  |

| TCA | AAC | ATC | CTG | AAG | ACT | CAT | TTT | ACC | TTC | ACG | GAA | TTC | AAG | AGC | AGC | 681 |
|---|---|---|---|---|---|---|---|---|---|---|---|---|---|---|---|---|
| Ser | Asn | Ile | Leu | Lys | Thr | His | Phe | Thr | Phe | Thr | Glu | Phe | Lys | Ser | Ser |  |
| 195 |  |  |  |  | 200 |  |  |  |  | 205 |  |  |  |  | 210 |  |

| CTG | AGC | CCT | CAG | AGC | CTG | GTG | GAT | GCC | ATC | GTC | CAG | CTC | CAA | GGC | CTG | 729 |
|---|---|---|---|---|---|---|---|---|---|---|---|---|---|---|---|---|
| Leu | Ser | Pro | Gln | Ser | Leu | Val | Asp | Ala | Ile | Val | Gln | Leu | Gln | Gly | Leu |  |
|  |  |  |  | 215 |  |  |  |  | 220 |  |  |  |  | 225 |  |  |

| ACG | TAC | ACA | GCC | TCG | GGC | ATC | CAG | AAA | GTG | GTG | AAA | GAG | CTA | TTT | CAT | 777 |
|---|---|---|---|---|---|---|---|---|---|---|---|---|---|---|---|---|
| Thr | Tyr | Thr | Ala | Ser | Gly | Ile | Gln | Lys | Val | Val | Lys | Glu | Leu | Phe | His |  |
|  |  |  | 230 |  |  |  |  | 235 |  |  |  |  | 240 |  |  |  |

| AGC | AAG | AAT | GGG | GCC | CGA | AAA | AGT | GCC | AAG | AAG | ATA | CTA | ATT | GTC | ATC | 825 |
|---|---|---|---|---|---|---|---|---|---|---|---|---|---|---|---|---|
| Ser | Lys | Asn | Gly | Ala | Arg | Lys | Ser | Ala | Lys | Lys | Ile | Leu | Ile | Val | Ile |  |
|  |  | 245 |  |  |  |  | 250 |  |  |  |  | 255 |  |  |  |  |

| ACA | GAT | GGG | CAG | AAA | TTC | AGA | GAC | CCC | CTG | GAG | TAT | AGA | CAT | GTC | ATC | 873 |
|---|---|---|---|---|---|---|---|---|---|---|---|---|---|---|---|---|
| Thr | Asp | Gly | Gln | Lys | Phe | Arg | Asp | Pro | Leu | Glu | Tyr | Arg | His | Val | Ile |  |
|  | 260 |  |  |  |  | 265 |  |  |  |  | 270 |  |  |  |  |  |

| CCT | GAA | GCA | GAG | AAA | GCT | GGG | ATC | ATT | CGC | TAT | GCT | ATA | GGG | GTG | GGA | 921 |
|---|---|---|---|---|---|---|---|---|---|---|---|---|---|---|---|---|
| Pro | Glu | Ala | Glu | Lys | Ala | Gly | Ile | Ile | Arg | Tyr | Ala | Ile | Gly | Val | Gly |  |
| 275 |  |  |  |  | 280 |  |  |  |  | 285 |  |  |  |  | 290 |  |

| GAT | GCC | TTC | CGG | GAA | CCC | ACT | GCC | CTA | CAG | GAG | CTG | AAC | ACC | ATT | GGC | 969 |
|---|---|---|---|---|---|---|---|---|---|---|---|---|---|---|---|---|
| Asp | Ala | Phe | Arg | Glu | Pro | Thr | Ala | Leu | Gln | Glu | Leu | Asn | Thr | Ile | Gly |  |
|  |  |  | 295 |  |  |  |  | 300 |  |  |  |  | 305 |  |  |  |

| TCA | GCT | CCC | TCG | CAG | GAC | CAC | GTG | TTC | AAG | GTG | GGC | AAT | TTT | GTA | GCA | 1017 |
|---|---|---|---|---|---|---|---|---|---|---|---|---|---|---|---|---|
| Ser | Ala | Pro | Ser | Gln | Asp | His | Val | Phe | Lys | Val | Gly | Asn | Phe | Val | Ala |  |
|  |  |  | 310 |  |  |  |  | 315 |  |  |  |  | 320 |  |  |  |

| CTT | CGC | AGC | ATC | CAG | CGG | CAA | ATT | CAG | GAG | AAA | ATC | TTT | GCC | ATT | GAA | 1065 |
|---|---|---|---|---|---|---|---|---|---|---|---|---|---|---|---|---|
| Leu | Arg | Ser | Ile | Gln | Arg | Gln | Ile | Gln | Glu | Lys | Ile | Phe | Ala | Ile | Glu |  |
|  |  | 325 |  |  |  |  | 330 |  |  |  |  | 335 |  |  |  |  |

| GGA | ACC | GAA | TCA | AGG | TCA | AGT | TCC | TTT | CAG | CAC | GAG | ATG | TCA | CAA | | 1113 |
|---|---|---|---|---|---|---|---|---|---|---|---|---|---|---|---|---|
| Gly | Thr | Glu | Ser | Arg | Ser | Ser | Ser | Phe | Gln | His | Glu | Met | Ser | Gln |  |  |
| 340 |  |  |  |  | 345 |  |  |  |  | 350 |  |  |  |  |  |  |

| GAA | GGT | TTC | AGC | TCA | GCT | CTC | TCA | ATG | GAT | GGA | CCA | GTT | CTG | GGG | GCT | 1161 |
|---|---|---|---|---|---|---|---|---|---|---|---|---|---|---|---|---|
| Glu | Gly | Phe | Ser | Ser | Ala | Leu | Ser | Met | Asp | Gly | Pro | Val | Leu | Gly | Ala |  |
| 355 |  |  |  |  | 360 |  |  |  |  | 365 |  |  |  |  | 370 |  |

| GTG | GGA | GGC | TTC | AGC | TGG | TCT | GGA | GGT | GCC | TTC | TTG | TAC | CCC | TCA | AAT | 1209 |

```
                Val Gly Gly Phe Ser Trp Ser Gly Gly Ala Phe Leu Tyr Pro Ser Asn
                            375             380                 385

ATG AGA TCC ACC TTC ATC AAC ATG TCT CAG GAG AAC GAG GAT ATG AGG        1257
Met Arg Ser Thr Phe Ile Asn Met Ser Gln Glu Asn Glu Asp Met Arg
            390             395                 400

GAC GCT TAC CTG GGT TAC TCC ACC GCA CTG GCC TTT TGG AAG GGG GTC        1305
Asp Ala Tyr Leu Gly Tyr Ser Thr Ala Leu Ala Phe Trp Lys Gly Val
            405             410                 415

CAC AGC CTG ATC CTG GGG GCC CCT CGC CAC CAG CAC ACG GGG AAG GTT        1353
His Ser Leu Ile Leu Gly Ala Pro Arg His Gln His Thr Gly Lys Val
        420             425                 430

GTC ATC TTT ACC CAG GAA TCC AGG CAC TGG AGG CCC AAG TCT GAA GTC        1401
Val Ile Phe Thr Gln Glu Ser Arg His Trp Arg Pro Lys Ser Glu Val
435                 440             445                 450

AGA GGG ACA CAG ATC GGC TCC TAC TTT GGG GCA TCT CTC TGT TCT GTG        1449
Arg Gly Thr Gln Ile Gly Ser Tyr Phe Gly Ala Ser Leu Cys Ser Val
                455             460                 465

GAC ATG GAT AGA GAT GGC AGC ACT GAC CTG GTC CTG ATT GGA GTC CCC        1497
Asp Met Asp Arg Asp Gly Ser Thr Asp Leu Val Leu Ile Gly Val Pro
            470             475                 480

CAT TAC TAT GAG CAC ACC CGA GGG GGG CAG GTG TCG GTG TGC CCC ATG        1545
His Tyr Tyr Glu His Thr Arg Gly Gly Gln Val Ser Val Cys Pro Met
            485             490                 495

CCT GGT GTG AGG AGC AGG TGG CAT TGT GGG ACC ACC CTC CAT GGG GAG        1593
Pro Gly Val Arg Ser Arg Trp His Cys Gly Thr Thr Leu His Gly Glu
        500             505                 510

CAG GGC CAT CCT TGG GGC CGC TTT GGG GCG GCT CTG ACA GTG CTA GGG        1641
Gln Gly His Pro Trp Gly Arg Phe Gly Ala Ala Leu Thr Val Leu Gly
515             520                 525                 530

GAC GTG AAT GGG GAC AGT CTG GCG GAT GTG GCT ATT GGT GCA CCC GGA        1689
Asp Val Asn Gly Asp Ser Leu Ala Asp Val Ala Ile Gly Ala Pro Gly
                535             540                 545

GAG GAG GAG AAC AGA GGT GCT GTC TAC ATA TTT CAT GGA GCC TCG AGA        1737
Glu Glu Glu Asn Arg Gly Ala Val Tyr Ile Phe His Gly Ala Ser Arg
            550             555                 560

CAG GAC ATC GCT CCC TCG CCT AGC CAG CGG GTC ACT GGC TCC CAG CTC        1785
Gln Asp Ile Ala Pro Ser Pro Ser Gln Arg Val Thr Gly Ser Gln Leu
            565             570                 575

TTC CTG AGG CTC CAA TAT TTT GGG CAG TCA TTA AGT GGG GGT CAG GAC        1833
Phe Leu Arg Leu Gln Tyr Phe Gly Gln Ser Leu Ser Gly Gly Gln Asp
        580             585                 590

CTT ACA CAG GAT GGC CTG GTG GAC CTG GCC GTG GGA GCC CAG GGG CAC        1881
Leu Thr Gln Asp Gly Leu Val Asp Leu Ala Val Gly Ala Gln Gly His
595             600             605                 610

GTG CTG CTG CTT AGG AGT CTG CCT TTG CTG AAA GTG GGG ATC TCC ATT        1929
Val Leu Leu Leu Arg Ser Leu Pro Leu Leu Lys Val Gly Ile Ser Ile
                615             620                 625

AGA TTT GCC CCC TCA GAG GTG GCA AAG ACT GTG TAC CAG TGC TGG GGA        1977
Arg Phe Ala Pro Ser Glu Val Ala Lys Thr Val Tyr Gln Cys Trp Gly
            630             635                 640

AGG ACT CCC ACT GTC CTC GAA GCT GGA GAG GCC ACC GTC TGT CTC ACT        2025
Arg Thr Pro Thr Val Leu Glu Ala Gly Glu Ala Thr Val Cys Leu Thr
            645             650                 655

GTC CGC AAA GGT TCA CCT GAC CTG TTA GGT GAT GTC CAA AGC TCT GTC        2073
Val Arg Lys Gly Ser Pro Asp Leu Leu Gly Asp Val Gln Ser Ser Val
        660             665                 670

AGG TAT GAT CTG GCG TTG GAT CCG GGC CGT CTG ATT TCT CGT GCC ATT        2121
Arg Tyr Asp Leu Ala Leu Asp Pro Gly Arg Leu Ile Ser Arg Ala Ile
675             680             685                 690

TTT GAT GAG ACG AAG AAC TGC ACT TTG ACC CGA AGG AAG ACT CTG GGG        2169
```

|     |     |     |     |     |     |     |     |     |     |     |     |     |     |     |      |
| --- | --- | --- | --- | --- | --- | --- | --- | --- | --- | --- | --- | --- | --- | --- | ---- |
| Phe | Asp | Glu | Thr | Lys<br>695 | Asn | Cys | Thr | Leu | Thr<br>700 | Arg | Arg | Lys | Thr | Leu<br>705 | Gly |
| CTT | GGT | GAT | CAC | TGC | GAA | ACA | ATG | AAG | CTG | CTT | TTG | CCA | GAC | TGT | GTG | 2217 |
| Leu | Gly | Asp | His<br>710 | Cys | Glu | Thr | Met | Lys<br>715 | Leu | Leu | Leu | Pro | Asp<br>720 | Cys | Val |
| GAG | GAT | GCA | GTG | ACC | CCT | ATC | ATC | CTG | CGC | CTT | AAC | TTA | TCC | CTG | GCA | 2265 |
| Glu | Asp | Ala<br>725 | Val | Thr | Pro | Ile | Ile<br>730 | Leu | Arg | Leu | Asn | Leu<br>735 | Ser | Leu | Ala |
| GGG | GAC | TCT | GCT | CCA | TCC | AGG | AAC | CTT | CGT | CCT | GTG | CTG | GCT | GTG | GGC | 2313 |
| Gly | Asp<br>740 | Ser | Ala | Pro | Ser | Arg<br>745 | Asn | Leu | Arg | Pro | Val<br>750 | Leu | Ala | Val | Gly |
| TCA | CAA | GAC | CAT | GTA | ACA | GCT | TCT | TTC | CCG | TTT | GAG | AAG | AAC | TGT | GAG | 2361 |
| Ser<br>755 | Gln | Asp | His | Val | Thr<br>760 | Ala | Ser | Phe | Pro | Phe<br>765 | Glu | Lys | Asn | Cys | Glu<br>770 |
| GGG | AAC | CTG | GGC | GTC | AGC | TTC | AAC | TTC | TCA | GGC | CTG | CAG | GTC | TTG | GAG | 2409 |
| Gly | Asn | Leu | Gly | Val<br>775 | Ser | Phe | Asn | Phe | Ser<br>780 | Gly | Leu | Gln | Val | Leu<br>785 | Glu |
| GTA | GGA | AGC | TCC | CCA | GAG | CTC | ACT | GTG | ACA | GTA | ACA | GTT | TGG | AAT | GAG | 2457 |
| Val | Gly | Ser | Ser<br>790 | Pro | Glu | Leu | Thr | Val<br>795 | Thr | Val | Thr | Val | Trp<br>800 | Asn | Glu |
| GGT | GAG | GAC | AGC | TAT | GGA | ACC | TTA | ATC | AAG | TTC | TAC | TAC | CCA | GCA | GAG | 2505 |
| Gly | Glu | Asp<br>805 | Ser | Tyr | Gly | Thr | Leu<br>810 | Ile | Lys | Phe | Tyr | Tyr<br>815 | Pro | Ala | Glu |
| CTA | TCT | TAC | CGA | CGG | GTG | ACA | AGA | GCC | CAG | CAA | CCT | CAT | CCG | TAC | CCA | 2553 |
| Leu | Ser<br>820 | Tyr | Arg | Arg | Val | Thr<br>825 | Arg | Ala | Gln | Gln | Pro<br>830 | His | Pro | Tyr | Pro |
| CTA | CGC | CTG | GCA | TGT | GAG | GCT | GAG | CCC | ACG | GGC | CAG | GAG | AGC | CTG | AGG | 2601 |
| Leu | Arg<br>835 | Leu | Ala | Cys | Glu | Ala<br>840 | Glu | Pro | Thr | Gly | Gln<br>845 | Glu | Ser | Leu | Arg<br>850 |
| AGC | AGC | AGC | TGT | AGC | ATC | AAT | CAC | CCC | ATC | TTC | CGA | GAA | GGT | GCC | AAG | 2649 |
| Ser | Ser | Ser | Cys | Ser<br>855 | Ile | Asn | His | Pro | Ile<br>860 | Phe | Arg | Glu | Gly | Ala<br>865 | Lys |
| GCC | ACC | TTC | ATG | ATC | ACA | TTT | GAT | GTC | TCC | TAC | AAG | GCC | TTC | CTG | GGA | 2697 |
| Ala | Thr | Phe | Met<br>870 | Ile | Thr | Phe | Asp | Val<br>875 | Ser | Tyr | Lys | Ala | Phe<br>880 | Leu | Gly |
| GAC | AGG | TTG | CTT | CTG | AGG | GCC | AGC | GCA | AGC | AGT | GAG | AAT | AAT | AAG | CCT | 2745 |
| Asp | Arg | Leu<br>885 | Leu | Leu | Arg | Ala | Ser<br>890 | Ala | Ser | Ser | Glu | Asn<br>895 | Asn | Lys | Pro |
| GAA | ACC | AGC | AAG | ACT | GCC | TTC | CAG | CTG | GAG | CTT | CCG | GTG | AAG | TAC | ACG | 2793 |
| Glu | Thr | Ser<br>900 | Lys | Thr | Ala | Phe | Gln<br>905 | Leu | Glu | Leu | Pro | Val<br>910 | Lys | Tyr | Thr |
| GTC | TAT | ACC | GTG | ATC | AGT | AGG | CAG | GAA | GAT | TCT | ACC | AAG | CAT | TTC | AAC | 2841 |
| Val<br>915 | Tyr | Thr | Val | Ile | Ser<br>920 | Arg | Gln | Glu | Asp | Ser<br>925 | Thr | Lys | His | Phe | Asn<br>930 |
| TTC | TCA | TCT | TCC | CAC | GGG | GAG | AGA | CAG | AAA | GAG | GCC | GAA | CAT | CGA | TAT | 2889 |
| Phe | Ser | Ser | Ser | His<br>935 | Gly | Glu | Arg | Gln | Lys<br>940 | Glu | Ala | Glu | His | Arg<br>945 | Tyr |
| CGT | GTG | AAT | AAC | CTG | AGT | CCA | TTG | ACG | CTG | GCC | ATC | AGC | GTT | AAC | TTC | 2937 |
| Arg | Val | Asn | Asn | Leu<br>950 | Ser | Pro | Leu | Thr | Leu<br>955 | Ala | Ile | Ser | Val<br>960 | Asn | Phe |
| TGG | GTC | CCC | ATC | CTT | CTG | AAT | GGT | GTG | GCC | GTG | TGG | GAT | GTG | ACT | CTG | 2985 |
| Trp | Val | Pro<br>965 | Ile | Leu | Leu | Asn | Gly<br>970 | Val | Ala | Val | Trp | Asp<br>975 | Val | Thr | Leu |
| AGG | AGC | CCA | GCA | CAG | GGT | GTC | TCC | TGT | GTG | TCA | CAG | AGG | GAA | CCT | CCT | 3033 |
| Arg | Ser | Pro<br>980 | Ala | Gln | Gly | Val | Ser<br>985 | Cys | Val | Ser | Gln | Arg<br>990 | Glu | Pro | Pro |
| CAA | CAT | TCC | GAC | CTT | CTG | ACC | CAG | ATC | CAA | GGA | CGC | TCT | GTG | CTG | GAC | 3081 |
| Gln<br>995 | His | Ser | Asp | Leu | Leu<br>1000 | Thr | Gln | Ile | Gln | Gly<br>1005 | Arg | Ser | Val | Leu | Asp<br>1010 |
| TGC | GCC | ATC | GCC | GAC | TGC | CTG | CAC | CTC | CGC | TGT | GAC | ATC | CCC | TCC | TTG | 3129 |

```
                                           -continued

Cys Ala Ile Ala Asp Cys Leu His Leu Arg Cys Asp Ile Pro Ser Leu
            1015                1020                1025

GGC ACC CTG GAT GAG CTT GAC TTC ATT CTG AAG GGC AAC CTC AGC TTC            3177
Gly Thr Leu Asp Glu Leu Asp Phe Ile Leu Lys Gly Asn Leu Ser Phe
            1030                1035                1040

GGC TGG ATC AGT CAG ACA TTG CAG AAA AAG GTG TTG CTC CTG AGT GAG            3225
Gly Trp Ile Ser Gln Thr Leu Gln Lys Lys Val Leu Leu Leu Ser Glu
            1045                1050                1055

GCT GAA ATC ACA TTC AAC ACA TCT GTG TAT TCC CAG CTG CCG GGA CAG            3273
Ala Glu Ile Thr Phe Asn Thr Ser Val Tyr Ser Gln Leu Pro Gly Gln
            1060                1065                1070

GAG GCA TTT CTG AGA GCC CAG GTG TCA ACG ATG CTA GAA GAA TAC GTG            3321
Glu Ala Phe Leu Arg Ala Gln Val Ser Thr Met Leu Glu Glu Tyr Val
1075                1080                1085                1090

GTC TAT GAG CCC GTC TTC CTC ATG GTG TTC AGC TCA GTG GGA GGT CTG            3369
Val Tyr Glu Pro Val Phe Leu Met Val Phe Ser Ser Val Gly Gly Leu
                1095                1100                1105

CTG TTA CTG GCT CTC ATC ACT GTG GCG CTG TAC AAG CTT GGC TTC TTC            3417
Leu Leu Leu Ala Leu Ile Thr Val Ala Leu Tyr Lys Leu Gly Phe Phe
                1110                1115                1120

AAA CGT CAG TAT AAA GAG ATG CTG GAT CTA CCA TCT GCA GAT CCT GAC            3465
Lys Arg Gln Tyr Lys Glu Met Leu Asp Leu Pro Ser Ala Asp Pro Asp
            1125                1130                1135

CCA GCC GGC CAG GCA GAT TCC AAC CAT GAG ACT CCT CCA CAT CTC ACG            3513
Pro Ala Gly Gln Ala Asp Ser Asn His Glu Thr Pro Pro His Leu Thr
            1140                1145                1150

TCC TAG                                                                     3519
Ser
1155

( 2 ) INFORMATION FOR SEQ ID NO:46:

( i ) SEQUENCE CHARACTERISTICS:
            ( A ) LENGTH: 1155 amino acids
            ( B ) TYPE: amino acid
            ( D ) TOPOLOGY: linear ( i i ) MOLECULE TYPE: protein ( x i ) SEQUENCE DESCRIPTION: SEQ ID NO:46:

Met Val Arg Gly Val Val Ile Leu Leu Cys Gly Trp Ala Leu Ala Ser
1               5                   10                  15

Cys His Gly Ser Asn Leu Asp Val Glu Lys Pro Val Val Phe Lys Glu
                20                  25                  30

Asp Ala Ala Ser Phe Gly Gln Thr Val Val Gln Phe Gly Gly Ser Arg
            35                  40                  45

Leu Val Val Gly Ala Pro Leu Glu Ala Val Ala Val Asn Gln Thr Gly
    50                  55                  60

Gln Ser Ser Asp Cys Pro Pro Ala Thr Gly Val Cys Gln Pro Ile Leu
65                  70                  75                  80

Leu His Ile Pro Leu Glu Ala Val Asn Met Ser Leu Gly Leu Ser Leu
                85                  90                  95

Val Ala Asp Thr Asn Asn Ser Gln Leu Leu Ala Cys Gly Pro Thr Ala
                100                 105                 110

Gln Arg Ala Cys Ala Lys Asn Met Tyr Ala Lys Gly Ser Cys Leu Leu
            115                 120                 125

Leu Gly Ser Ser Leu Gln Phe Ile Gln Ala Ile Pro Ala Thr Met Pro
    130                 135                 140

Glu Cys Pro Gly Gln Glu Met Asp Ile Ala Phe Leu Ile Asp Gly Ser
145                 150                 155                 160
```

-continued

| | | | | | | | | | | | | | | |
|---|---|---|---|---|---|---|---|---|---|---|---|---|---|---|
| Gly | Ser | Ile | Asp | Gln | Ser | Asp | Phe | Thr | Gln | Met | Lys | Asp | Phe | Val | Lys |
| | | | | 165 | | | | | 170 | | | | 175 | | |
| Ala | Leu | Met | Gly | Gln | Leu | Ala | Ser | Thr | Ser | Thr | Ser | Phe | Ser | Leu | Met |
| | | | 180 | | | | | 185 | | | | | 190 | | |
| Gln | Tyr | Ser | Asn | Ile | Leu | Lys | Thr | His | Phe | Thr | Phe | Thr | Glu | Phe | Lys |
| | | 195 | | | | | 200 | | | | | 205 | | | |
| Ser | Ser | Leu | Ser | Pro | Gln | Ser | Leu | Val | Asp | Ala | Ile | Val | Gln | Leu | Gln |
| | 210 | | | | | 215 | | | | | 220 | | | | |
| Gly | Leu | Thr | Tyr | Thr | Ala | Ser | Gly | Ile | Gln | Lys | Val | Val | Lys | Glu | Leu |
| 225 | | | | | 230 | | | | | 235 | | | | | 240 |
| Phe | His | Ser | Lys | Asn | Gly | Ala | Arg | Lys | Ser | Ala | Lys | Lys | Ile | Leu | Ile |
| | | | | 245 | | | | | 250 | | | | | 255 | |
| Val | Ile | Thr | Asp | Gly | Gln | Lys | Phe | Arg | Asp | Pro | Leu | Glu | Tyr | Arg | His |
| | | | 260 | | | | | 265 | | | | | 270 | | |
| Val | Ile | Pro | Glu | Ala | Glu | Lys | Ala | Gly | Ile | Ile | Arg | Tyr | Ala | Ile | Gly |
| | | | 275 | | | | | 280 | | | | 285 | | | |
| Val | Gly | Asp | Ala | Phe | Arg | Glu | Pro | Thr | Ala | Leu | Gln | Glu | Leu | Asn | Thr |
| | 290 | | | | | 295 | | | | | 300 | | | | |
| Ile | Gly | Ser | Ala | Pro | Ser | Gln | Asp | His | Val | Phe | Lys | Val | Gly | Asn | Phe |
| 305 | | | | | 310 | | | | | 315 | | | | | 320 |
| Val | Ala | Leu | Arg | Ser | Ile | Gln | Arg | Gln | Ile | Gln | Glu | Lys | Ile | Phe | Ala |
| | | | | 325 | | | | | 330 | | | | | 335 | |
| Ile | Glu | Gly | Thr | Glu | Ser | Arg | Ser | Ser | Ser | Phe | Gln | His | Glu | Met |
| | | | 340 | | | | | 345 | | | | 350 | | | |
| Ser | Gln | Glu | Gly | Phe | Ser | Ser | Ala | Leu | Ser | Met | Asp | Gly | Pro | Val | Leu |
| | | 355 | | | | | 360 | | | | | 365 | | | |
| Gly | Ala | Val | Gly | Gly | Phe | Ser | Trp | Ser | Gly | Gly | Ala | Phe | Leu | Tyr | Pro |
| | 370 | | | | | 375 | | | | | 380 | | | | |
| Ser | Asn | Met | Arg | Ser | Thr | Phe | Ile | Asn | Met | Ser | Gln | Glu | Asn | Glu | Asp |
| 385 | | | | | 390 | | | | | 395 | | | | | 400 |
| Met | Arg | Asp | Ala | Tyr | Leu | Gly | Tyr | Ser | Thr | Ala | Leu | Ala | Phe | Trp | Lys |
| | | | | 405 | | | | | 410 | | | | | 415 | |
| Gly | Val | His | Ser | Leu | Ile | Leu | Gly | Ala | Pro | Arg | His | Gln | His | Thr | Gly |
| | | | 420 | | | | | 425 | | | | | 430 | | |
| Lys | Val | Val | Ile | Phe | Thr | Gln | Glu | Ser | Arg | His | Trp | Arg | Pro | Lys | Ser |
| | | 435 | | | | | 440 | | | | | 445 | | | |
| Glu | Val | Arg | Gly | Thr | Gln | Ile | Gly | Ser | Tyr | Phe | Gly | Ala | Ser | Leu | Cys |
| | 450 | | | | | 455 | | | | | 460 | | | | |
| Ser | Val | Asp | Met | Asp | Arg | Asp | Gly | Ser | Thr | Asp | Leu | Val | Leu | Ile | Gly |
| 465 | | | | | 470 | | | | | 475 | | | | | 480 |
| Val | Pro | His | Tyr | Tyr | Glu | His | Thr | Arg | Gly | Gly | Gln | Val | Ser | Val | Cys |
| | | | | 485 | | | | | 490 | | | | | 495 | |
| Pro | Met | Pro | Gly | Val | Arg | Ser | Arg | Trp | His | Cys | Gly | Thr | Thr | Leu | His |
| | | | 500 | | | | | 505 | | | | | 510 | | |
| Gly | Glu | Gln | Gly | His | Pro | Trp | Gly | Arg | Phe | Gly | Ala | Ala | Leu | Thr | Val |
| | | 515 | | | | | 520 | | | | | 525 | | | |
| Leu | Gly | Asp | Val | Asn | Gly | Asp | Ser | Leu | Ala | Asp | Val | Ala | Ile | Gly | Ala |
| | 530 | | | | | 535 | | | | | 540 | | | | |
| Pro | Gly | Glu | Glu | Glu | Asn | Arg | Gly | Ala | Val | Tyr | Ile | Phe | His | Gly | Ala |
| 545 | | | | | 550 | | | | | 555 | | | | | 560 |
| Ser | Arg | Gln | Asp | Ile | Ala | Pro | Ser | Pro | Ser | Gln | Arg | Val | Thr | Gly | Ser |
| | | | | 565 | | | | | 570 | | | | | 575 | |
| Gln | Leu | Phe | Leu | Arg | Leu | Gln | Tyr | Phe | Gly | Gln | Ser | Leu | Ser | Gly | Gly |

|       |       |       | 580   |       |       |       | 585   |       |       |       | 590   |       |       |
|-------|-------|-------|-------|-------|-------|-------|-------|-------|-------|-------|-------|-------|-------|
| Gln   | Asp   | Leu   | Thr   | Gln   | Asp   | Gly   | Leu   | Val   | Asp   | Leu   | Ala   | Val   | Gly   | Ala | Gln |

Gln Asp Leu Thr Gln Asp Gly Leu Val Asp Leu Ala Val Gly Ala Gln
           595                 600                 605

Gly His Val Leu Leu Leu Arg Ser Leu Pro Leu Leu Lys Val Gly Ile
     610                 615                 620

Ser Ile Arg Phe Ala Pro Ser Glu Val Ala Lys Thr Val Tyr Gln Cys
625                 630                 635                 640

Trp Gly Arg Thr Pro Thr Val Leu Glu Ala Gly Glu Ala Thr Val Cys
                645                 650                 655

Leu Thr Val Arg Lys Gly Ser Pro Asp Leu Leu Gly Asp Val Gln Ser
            660                 665                 670

Ser Val Arg Tyr Asp Leu Ala Leu Asp Pro Gly Arg Leu Ile Ser Arg
            675                 680                 685

Ala Ile Phe Asp Glu Thr Lys Asn Cys Thr Leu Thr Arg Arg Lys Thr
    690                 695                 700

Leu Gly Leu Gly Asp His Cys Glu Thr Met Lys Leu Leu Leu Pro Asp
705                 710                 715                 720

Cys Val Glu Asp Ala Val Thr Pro Ile Ile Leu Arg Leu Asn Leu Ser
                725                 730                 735

Leu Ala Gly Asp Ser Ala Pro Ser Arg Asn Leu Arg Pro Val Leu Ala
            740                 745                 750

Val Gly Ser Gln Asp His Val Thr Ala Ser Phe Pro Phe Glu Lys Asn
            755                 760                 765

Cys Glu Gly Asn Leu Gly Val Ser Phe Asn Phe Ser Gly Leu Gln Val
    770                 775                 780

Leu Glu Val Gly Ser Ser Pro Glu Leu Thr Val Thr Val Thr Val Trp
785                 790                 795                 800

Asn Glu Gly Glu Asp Ser Tyr Gly Thr Leu Ile Lys Phe Tyr Tyr Pro
                805                 810                 815

Ala Glu Leu Ser Tyr Arg Arg Val Thr Arg Ala Gln Gln Pro His Pro
            820                 825                 830

Tyr Pro Leu Arg Leu Ala Cys Glu Ala Glu Pro Thr Gly Gln Glu Ser
            835                 840                 845

Leu Arg Ser Ser Ser Cys Ser Ile Asn His Pro Ile Phe Arg Glu Gly
    850                 855                 860

Ala Lys Ala Thr Phe Met Ile Thr Phe Asp Val Ser Tyr Lys Ala Phe
865                 870                 875                 880

Leu Gly Asp Arg Leu Leu Leu Arg Ala Ser Ala Ser Ser Glu Asn Asn
                885                 890                 895

Lys Pro Glu Thr Ser Lys Thr Ala Phe Gln Leu Glu Leu Pro Val Lys
            900                 905                 910

Tyr Thr Val Tyr Thr Val Ile Ser Arg Gln Glu Asp Ser Thr Lys His
            915                 920                 925

Phe Asn Phe Ser Ser Ser His Gly Glu Arg Gln Lys Glu Ala Glu His
    930                 935                 940

Arg Tyr Arg Val Asn Asn Leu Ser Pro Leu Thr Leu Ala Ile Ser Val
945                 950                 955                 960

Asn Phe Trp Val Pro Ile Leu Leu Asn Gly Val Ala Val Trp Asp Val
                965                 970                 975

Thr Leu Arg Ser Pro Ala Gln Gly Val Ser Cys Val Ser Gln Arg Glu
            980                 985                 990

Pro Pro Gln His Ser Asp Leu Leu Thr Gln Ile Gln Gly Arg Ser Val
            995                 1000                1005

| | | | | | | | | | | | | |
|---|---|---|---|---|---|---|---|---|---|---|---|---|
|Leu|Asp|Cys|Ala|Ile|Ala|Asp|Cys|Leu|His|Leu|Arg|Cys|Asp|Ile|Pro|
| |1010| | | |1015| | | | |1020| | | | | |

Leu Asp Cys Ala Ile Ala Asp Cys Leu His Leu Arg Cys Asp Ile Pro
    1010            1015                1020

Ser Leu Gly Thr Leu Asp Glu Leu Asp Phe Ile Leu Lys Gly Asn Leu
1025            1030            1035                    1040

Ser Phe Gly Trp Ile Ser Gln Thr Leu Gln Lys Lys Val Leu Leu Leu
                1045            1050                1055

Ser Glu Ala Glu Ile Thr Phe Asn Thr Ser Val Tyr Ser Gln Leu Pro
            1060            1065            1070

Gly Gln Glu Ala Phe Leu Arg Ala Gln Val Ser Thr Met Leu Glu Glu
        1075            1080            1085

Tyr Val Val Tyr Glu Pro Val Phe Leu Met Val Phe Ser Ser Val Gly
    1090            1095            1100

Gly Leu Leu Leu Leu Ala Leu Ile Thr Val Ala Leu Tyr Lys Leu Gly
1105            1110            1115            1120

Phe Phe Lys Arg Gln Tyr Lys Glu Met Leu Asp Leu Pro Ser Ala Asp
            1125            1130            1135

Pro Asp Pro Ala Gly Gln Ala Asp Ser Asn His Glu Thr Pro Pro His
        1140            1145            1150

Leu Thr Ser
    1155

(2) INFORMATION FOR SEQ ID NO:47:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:47:

AGTTACGGAT CCGGCACCAT GACCTTCGGC ACTGTGATCC TCCTGTGTG    49

(2) INFORMATION FOR SEQ ID NO:48:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:48:

GCTGGACGAT GGCATCCAC    19

(2) INFORMATION FOR SEQ ID NO:49:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:49:

GTAGAGTTAC GGATCCGGCA CCAT    24

(2) INFORMATION FOR SEQ ID NO:50:

(i) SEQUENCE CHARACTERISTICS:
        (A) LENGTH: 20 base pairs ( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:50:

GCAGCCAGCT TCGGACAGAC       20

( 2 ) INFORMATION FOR SEQ ID NO:51:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:51:

CCATGTCCAC AGAACAGAGA G       21

( 2 ) INFORMATION FOR SEQ ID NO:52:

( i ) SEQUENCE CHARACTERISTICS:
( A ) LENGTH: 3803 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 1..3486

( x i ) SEQUENCE DESCRIPTION: SEQ ID NO:52:

```
ATG GTC CGT GGA GTT GTG ATC CTC CTG TGT GGC TGG GCC CTG GCT TCC      48
Met Val Arg Gly Val Val Ile Leu Leu Cys Gly Trp Ala Leu Ala Ser
 1               5                  10                  15

TGT CAT GGG TCT AAC CTG GAT GTG GAG AAG CCC GTC GTG TTC AAA GAG      96
Cys His Gly Ser Asn Leu Asp Val Glu Lys Pro Val Val Phe Lys Glu
             20                  25                  30

GAT GCA GCC AGC TTC GGA CAG ACT GTG GTG CAG TTT GGT GGA TCT CGA     144
Asp Ala Ala Ser Phe Gly Gln Thr Val Val Gln Phe Gly Gly Ser Arg
         35                  40                  45

CTC GTG GTG GGA GCC CCT CTG GAG GCG GTG GCA GTC AAC CAA ACA GGA     192
Leu Val Val Gly Ala Pro Leu Glu Ala Val Ala Val Asn Gln Thr Gly
     50                  55                  60

CAG TCG TCT GAC TGT CCG CCT GCC ACT GGC GTG TGC CAG CCC ATC TTA     240
Gln Ser Ser Asp Cys Pro Pro Ala Thr Gly Val Cys Gln Pro Ile Leu
 65                  70                  75                  80

CTG CAC ATT CCC CTA GAG GCA GTG AAC ATG TCC CTG GGC CTG TCT CTG     288
Leu His Ile Pro Leu Glu Ala Val Asn Met Ser Leu Gly Leu Ser Leu
                 85                  90                  95

GTG GCT GAC ACC AAT AAC TCC CAG TTG CTG GCT TGT GGT CCA ACT GCA     336
Val Ala Asp Thr Asn Asn Ser Gln Leu Leu Ala Cys Gly Pro Thr Ala
            100                 105                 110

CAG AGA GCT TGT GCA AAG AAC ATG TAT GCA AAA GGT TCC TGC CTC CTT     384
Gln Arg Ala Cys Ala Lys Asn Met Tyr Ala Lys Gly Ser Cys Leu Leu
        115                 120                 125

CTG GGC TCC AGC TTG CAG TTC ATC CAG GCA ATC CCT GCT ACC ATG CCA     432
Leu Gly Ser Ser Leu Gln Phe Ile Gln Ala Ile Pro Ala Thr Met Pro
    130                 135                 140

GAG TGT CCA GGA CAA GAG ATG GAC ATT GCT TTC CTG ATT GAT GGC TCC     480
Glu Cys Pro Gly Gln Glu Met Asp Ile Ala Phe Leu Ile Asp Gly Ser
```

-continued

| 145 | | | | 150 | | | | 155 | | | | 160 | | | | |
|---|---|---|---|---|---|---|---|---|---|---|---|---|---|---|---|---|
| GGC | AGC | ATT | GAT | CAA | AGT | GAC | TTT | ACC | CAG | ATG | AAG | GAC | TTC | GTC | AAA | 528 |
| Gly | Ser | Ile | Asp | Gln | Ser | Asp | Phe | Thr | Gln | Met | Lys | Asp | Phe | Val | Lys | |
| | | | | 165 | | | | 170 | | | | 175 | | | | |
| GCT | TTG | ATG | GGC | CAG | TTG | GCG | AGC | ACC | AGC | ACC | TCG | TTC | TCC | CTG | ATG | 576 |
| Ala | Leu | Met | Gly | Gln | Leu | Ala | Ser | Thr | Ser | Thr | Ser | Phe | Ser | Leu | Met | |
| | | | 180 | | | | | 185 | | | | | 190 | | | |
| CAA | TAC | TCA | AAC | ATC | CTG | AAG | ACT | CAT | TTT | ACC | TTC | ACG | GAA | TTC | AAG | 624 |
| Gln | Tyr | Ser | Asn | Ile | Leu | Lys | Thr | His | Phe | Thr | Phe | Thr | Glu | Phe | Lys | |
| | | 195 | | | | | 200 | | | | | 205 | | | | |
| AGC | AGC | CTG | AGC | CCT | CAG | AGC | CTG | GTG | GAT | GCC | ATC | GTC | CAG | CTC | CAA | 672 |
| Ser | Ser | Leu | Ser | Pro | Gln | Ser | Leu | Val | Asp | Ala | Ile | Val | Gln | Leu | Gln | |
| | 210 | | | | | 215 | | | | | 220 | | | | | |
| GGC | CTG | ACG | TAC | ACA | GCC | TCG | GGC | ATC | CAG | AAA | GTG | GTG | AAA | GAG | CTA | 720 |
| Gly | Leu | Thr | Tyr | Thr | Ala | Ser | Gly | Ile | Gln | Lys | Val | Val | Lys | Glu | Leu | |
| 225 | | | | | 230 | | | | | 235 | | | | | 240 | |
| TTT | CAT | AGC | AAG | AAT | GGG | GCC | CGA | AAA | AGT | GCC | AAG | AAG | ATA | CTA | ATT | 768 |
| Phe | His | Ser | Lys | Asn | Gly | Ala | Arg | Lys | Ser | Ala | Lys | Lys | Ile | Leu | Ile | |
| | | | | 245 | | | | | 250 | | | | | 255 | | |
| GTC | ATC | ACA | GAT | GGG | CAG | AAA | TTC | AGA | GAC | CCC | CTG | GAG | TAT | AGA | CAT | 816 |
| Val | Ile | Thr | Asp | Gly | Gln | Lys | Phe | Arg | Asp | Pro | Leu | Glu | Tyr | Arg | His | |
| | | | 260 | | | | | 265 | | | | | 270 | | | |
| GTC | ATC | CCT | GAA | GCA | GAG | AAA | GCT | GGG | ATC | ATT | CGC | TAT | GCT | ATA | GGG | 864 |
| Val | Ile | Pro | Glu | Ala | Glu | Lys | Ala | Gly | Ile | Ile | Arg | Tyr | Ala | Ile | Gly | |
| | | 275 | | | | | 280 | | | | | 285 | | | | |
| GTG | GGA | GAT | GCC | TTC | CGG | GAA | CCC | ACT | GCC | CTA | CAG | GAG | CTG | AAC | ACC | 912 |
| Val | Gly | Asp | Ala | Phe | Arg | Glu | Pro | Thr | Ala | Leu | Gln | Glu | Leu | Asn | Thr | |
| | 290 | | | | | 295 | | | | | 300 | | | | | |
| ATT | GGC | TCA | GCT | CCC | TCG | CAG | GAC | CAC | GTG | TTC | AAG | GTG | GGC | AAT | TTT | 960 |
| Ile | Gly | Ser | Ala | Pro | Ser | Gln | Asp | His | Val | Phe | Lys | Val | Gly | Asn | Phe | |
| 305 | | | | | 310 | | | | | 315 | | | | | 320 | |
| GTA | GCA | CTT | CGC | AGC | ATC | CAG | CGG | CAA | ATT | CAG | GAG | AAA | ATC | TTT | GCC | 1008 |
| Val | Ala | Leu | Arg | Ser | Ile | Gln | Arg | Gln | Ile | Gln | Glu | Lys | Ile | Phe | Ala | |
| | | | | 325 | | | | | 330 | | | | | 335 | | |
| ATT | GAA | GGA | ACC | GAA | TCA | AGG | TCA | AGT | AGT | TCC | TTT | CAG | CAC | GAG | ATG | 1056 |
| Ile | Glu | Gly | Thr | Glu | Ser | Arg | Ser | Ser | Ser | Ser | Phe | Gln | His | Glu | Met | |
| | | | 340 | | | | | 345 | | | | | 350 | | | |
| TCA | CAA | GAA | GGT | TTC | AGC | TCA | GCT | CTC | TCA | ATG | GAT | GGA | CCA | GTT | CTG | 1104 |
| Ser | Gln | Glu | Gly | Phe | Ser | Ser | Ala | Leu | Ser | Met | Asp | Gly | Pro | Val | Leu | |
| | | 355 | | | | | 360 | | | | | 365 | | | | |
| GGG | GCT | GTG | GGA | GGC | TTC | AGC | TGG | TCT | GGA | GGT | GCC | TTC | TTG | TAC | CCC | 1152 |
| Gly | Ala | Val | Gly | Gly | Phe | Ser | Trp | Ser | Gly | Gly | Ala | Phe | Leu | Tyr | Pro | |
| | 370 | | | | | 375 | | | | | 380 | | | | | |
| TCA | AAT | ATG | AGA | TCC | ACC | TTC | ATC | AAC | ATG | TCT | CAG | GAG | AAC | GAG | GAT | 1200 |
| Ser | Asn | Met | Arg | Ser | Thr | Phe | Ile | Asn | Met | Ser | Gln | Glu | Asn | Glu | Asp | |
| 385 | | | | | 390 | | | | | 395 | | | | | 400 | |
| ATG | AGG | GAC | GCT | TAC | CTG | GGT | TAC | TCC | ACC | GCA | CTG | GCC | TTT | TGG | AAG | 1248 |
| Met | Arg | Asp | Ala | Tyr | Leu | Gly | Tyr | Ser | Thr | Ala | Leu | Ala | Phe | Trp | Lys | |
| | | | | 405 | | | | | 410 | | | | | 415 | | |
| GGG | GTC | CAC | AGC | CTG | ATC | CTG | GGG | GCC | CCT | CGC | CAC | CAG | CAC | ACG | GGG | 1296 |
| Gly | Val | His | Ser | Leu | Ile | Leu | Gly | Ala | Pro | Arg | His | Gln | His | Thr | Gly | |
| | | | 420 | | | | | 425 | | | | | 430 | | | |
| AAG | GTT | GTC | ATC | TTT | ACC | CAG | GAA | TCC | AGG | CAC | TGG | AGG | CCC | AAG | TCT | 1344 |
| Lys | Val | Val | Ile | Phe | Thr | Gln | Glu | Ser | Arg | His | Trp | Arg | Pro | Lys | Ser | |
| | | 435 | | | | | 440 | | | | | 445 | | | | |
| GAA | GTC | AGA | GGG | ACA | CAG | ATC | GGC | TCC | TAC | TTT | GGG | GCA | TCT | CTC | TGT | 1392 |
| Glu | Val | Arg | Gly | Thr | Gln | Ile | Gly | Ser | Tyr | Phe | Gly | Ala | Ser | Leu | Cys | |
| | 450 | | | | | 455 | | | | | 460 | | | | | |
| TCT | GTG | GAC | ATG | GAT | AGA | GAT | GGC | AGC | ACT | GAC | CTG | GTC | CTG | ATT | GGA | 1440 |
| Ser | Val | Asp | Met | Asp | Arg | Asp | Gly | Ser | Thr | Asp | Leu | Val | Leu | Ile | Gly | |

|  |  |  |  |  |  |  |  |  |  |  |  |  |  |  |  |
|---|---|---|---|---|---|---|---|---|---|---|---|---|---|---|---|
| 465 |  |  |  |  | 470 |  |  |  |  | 475 |  |  |  |  | 480 |

| GTC | CCC | CAT | TAC | TAT | GAG | CAC | ACC | CGA | GGG | GGG | CAG | GTG | TCG | GTG | TGC | 1488 |
|---|---|---|---|---|---|---|---|---|---|---|---|---|---|---|---|---|
| Val | Pro | His | Tyr | Tyr | Glu | His | Thr | Arg | Gly | Gly | Gln | Val | Ser | Val | Cys |  |
|  |  |  |  | 485 |  |  |  |  | 490 |  |  |  |  | 495 |  |  |

| CCC | ATG | CCT | GGT | GTG | AGG | AGC | AGG | TGG | CAT | TGT | GGG | ACC | ACC | CTC | CAT | 1536 |
|---|---|---|---|---|---|---|---|---|---|---|---|---|---|---|---|---|
| Pro | Met | Pro | Gly | Val | Arg | Ser | Arg | Trp | His | Cys | Gly | Thr | Thr | Leu | His |  |
|  |  |  | 500 |  |  |  |  | 505 |  |  |  |  | 510 |  |  |  |

| GGG | GAG | CAG | GGC | CAT | CCT | TGG | GGC | CGC | TTT | GGG | GCG | GCT | CTG | ACA | GTG | 1584 |
|---|---|---|---|---|---|---|---|---|---|---|---|---|---|---|---|---|
| Gly | Glu | Gln | Gly | His | Pro | Trp | Gly | Arg | Phe | Gly | Ala | Ala | Leu | Thr | Val |  |
|  |  | 515 |  |  |  |  | 520 |  |  |  |  | 525 |  |  |  |  |

| CTA | GGG | GAC | GTG | AAT | GGG | GAC | AGT | CTG | GCG | GAT | GTG | GCT | ATT | GGT | GCA | 1632 |
|---|---|---|---|---|---|---|---|---|---|---|---|---|---|---|---|---|
| Leu | Gly | Asp | Val | Asn | Gly | Asp | Ser | Leu | Ala | Asp | Val | Ala | Ile | Gly | Ala |  |
| 530 |  |  |  |  | 535 |  |  |  |  | 540 |  |  |  |  |  |  |

| CCC | GGA | GAG | GAG | GAG | AAC | AGA | GGT | GCT | GTC | TAC | ATA | TTT | CAT | GGA | GCC | 1680 |
|---|---|---|---|---|---|---|---|---|---|---|---|---|---|---|---|---|
| Pro | Gly | Glu | Glu | Glu | Asn | Arg | Gly | Ala | Val | Tyr | Ile | Phe | His | Gly | Ala |  |
| 545 |  |  |  |  | 550 |  |  |  |  | 555 |  |  |  |  | 560 |  |

| TCG | AGA | CAG | GAC | ATC | GCT | CCC | TCG | CCT | AGC | CAG | CGG | GTC | ACT | GGC | TCC | 1728 |
|---|---|---|---|---|---|---|---|---|---|---|---|---|---|---|---|---|
| Ser | Arg | Gln | Asp | Ile | Ala | Pro | Ser | Pro | Ser | Gln | Arg | Val | Thr | Gly | Ser |  |
|  |  |  |  | 565 |  |  |  |  | 570 |  |  |  |  | 575 |  |  |

| CAG | CTC | TTC | CTG | AGG | CTC | CAA | TAT | TTT | GGG | CAG | TCA | TTA | AGT | GGG | GGT | 1776 |
|---|---|---|---|---|---|---|---|---|---|---|---|---|---|---|---|---|
| Gln | Leu | Phe | Leu | Arg | Leu | Gln | Tyr | Phe | Gly | Gln | Ser | Leu | Ser | Gly | Gly |  |
|  |  |  | 580 |  |  |  |  | 585 |  |  |  |  | 590 |  |  |  |

| CAG | GAC | CTT | ACA | CAG | GAT | GGC | CTG | GTG | GAC | CTG | GCC | GTG | GGA | GCC | CAG | 1824 |
|---|---|---|---|---|---|---|---|---|---|---|---|---|---|---|---|---|
| Gln | Asp | Leu | Thr | Gln | Asp | Gly | Leu | Val | Asp | Leu | Ala | Val | Gly | Ala | Gln |  |
|  |  | 595 |  |  |  |  | 600 |  |  |  |  | 605 |  |  |  |  |

| GGG | CAC | GTG | CTG | CTG | CTT | AGG | AGT | CTG | CCT | TTG | CTG | AAA | GTG | GGG | ATC | 1872 |
|---|---|---|---|---|---|---|---|---|---|---|---|---|---|---|---|---|
| Gly | His | Val | Leu | Leu | Leu | Arg | Ser | Leu | Pro | Leu | Leu | Lys | Val | Gly | Ile |  |
| 610 |  |  |  |  | 615 |  |  |  |  | 620 |  |  |  |  |  |  |

| TCC | ATT | AGA | TTT | GCC | CCC | TCA | GAG | GTG | GCA | AAG | ACT | GTG | TAC | CAG | TGC | 1920 |
|---|---|---|---|---|---|---|---|---|---|---|---|---|---|---|---|---|
| Ser | Ile | Arg | Phe | Ala | Pro | Ser | Glu | Val | Ala | Lys | Thr | Val | Tyr | Gln | Cys |  |
| 625 |  |  |  |  | 630 |  |  |  |  | 635 |  |  |  |  | 640 |  |

| TGG | GGA | AGG | ACT | CCC | ACT | GTC | CTC | GAA | GCT | GGA | GAG | GCC | ACC | GTC | TGT | 1968 |
|---|---|---|---|---|---|---|---|---|---|---|---|---|---|---|---|---|
| Trp | Gly | Arg | Thr | Pro | Thr | Val | Leu | Glu | Ala | Gly | Glu | Ala | Thr | Val | Cys |  |
|  |  |  |  | 645 |  |  |  |  | 650 |  |  |  |  | 655 |  |  |

| CTC | ACT | GTC | CGC | AAA | GGT | TCA | CCT | GAC | CTG | TTA | GGT | GAT | GTC | CAA | AGC | 2016 |
|---|---|---|---|---|---|---|---|---|---|---|---|---|---|---|---|---|
| Leu | Thr | Val | Arg | Lys | Gly | Ser | Pro | Asp | Leu | Leu | Gly | Asp | Val | Gln | Ser |  |
|  |  |  | 660 |  |  |  |  | 665 |  |  |  |  | 670 |  |  |  |

| TCT | GTC | AGG | TAT | GAT | CTG | GCG | TTG | GAT | CCG | GGC | CGT | CTG | ATT | TCT | CGT | 2064 |
|---|---|---|---|---|---|---|---|---|---|---|---|---|---|---|---|---|
| Ser | Val | Arg | Tyr | Asp | Leu | Ala | Leu | Asp | Pro | Gly | Arg | Leu | Ile | Ser | Arg |  |
|  |  | 675 |  |  |  |  | 680 |  |  |  |  | 685 |  |  |  |  |

| GCC | ATT | TTT | GAT | GAG | ACG | AAG | AAC | TGC | ACT | TTG | ACC | CGA | AGG | AAG | ACT | 2112 |
|---|---|---|---|---|---|---|---|---|---|---|---|---|---|---|---|---|
| Ala | Ile | Phe | Asp | Glu | Thr | Lys | Asn | Cys | Thr | Leu | Thr | Arg | Arg | Lys | Thr |  |
| 690 |  |  |  |  | 695 |  |  |  |  | 700 |  |  |  |  |  |  |

| CTG | GGG | CTT | GGT | GAT | CAC | TGC | GAA | ACA | ATG | AAG | CTG | CTT | TTG | CCA | GAC | 2160 |
|---|---|---|---|---|---|---|---|---|---|---|---|---|---|---|---|---|
| Leu | Gly | Leu | Gly | Asp | His | Cys | Glu | Thr | Met | Lys | Leu | Leu | Leu | Pro | Asp |  |
| 705 |  |  |  |  | 710 |  |  |  |  | 715 |  |  |  |  | 720 |  |

| TGT | GTG | GAG | GAT | GCA | GTG | ACC | CCT | ATC | ATC | CTG | CGC | CTT | AAC | TTA | TCC | 2208 |
|---|---|---|---|---|---|---|---|---|---|---|---|---|---|---|---|---|
| Cys | Val | Glu | Asp | Ala | Val | Thr | Pro | Ile | Ile | Leu | Arg | Leu | Asn | Leu | Ser |  |
|  |  |  |  | 725 |  |  |  |  | 730 |  |  |  |  | 735 |  |  |

| CTG | GCA | GGG | GAC | TCT | GCT | CCA | TCC | AGG | AAC | CTT | CGT | CCT | GTG | CTG | GCT | 2256 |
|---|---|---|---|---|---|---|---|---|---|---|---|---|---|---|---|---|
| Leu | Ala | Gly | Asp | Ser | Ala | Pro | Ser | Arg | Asn | Leu | Arg | Pro | Val | Leu | Ala |  |
|  |  |  | 740 |  |  |  |  | 745 |  |  |  |  | 750 |  |  |  |

| GTG | GGC | TCA | CAA | GAC | CAT | GTA | ACA | GCT | TCT | TTC | CCG | TTT | GAG | AAG | AAC | 2304 |
|---|---|---|---|---|---|---|---|---|---|---|---|---|---|---|---|---|
| Val | Gly | Ser | Gln | Asp | His | Val | Thr | Ala | Ser | Phe | Pro | Phe | Glu | Lys | Asn |  |
|  |  | 755 |  |  |  |  | 760 |  |  |  |  | 765 |  |  |  |  |

| TGT | AAG | CAG | GAG | CTC | CTG | TGT | GAG | GGG | AAC | CTG | GGC | GTC | AGC | TTC | AAC | 2352 |
|---|---|---|---|---|---|---|---|---|---|---|---|---|---|---|---|---|
| Cys | Lys | Gln | Glu | Leu | Leu | Cys | Glu | Gly | Asn | Leu | Gly | Val | Ser | Phe | Asn |  |
| 770 |  |  |  |  | 775 |  |  |  |  | 780 |  |  |  |  |  |  |

| TTC | TCA | GGC | CTG | CAG | GTC | TTG | GAG | GTA | GGA | AGC | TCC | CCA | GAG | CTC | ACT | 2400 |
|---|---|---|---|---|---|---|---|---|---|---|---|---|---|---|---|---|
| Phe | Ser | Gly | Leu | Gln | Val | Leu | Glu | Val | Gly | Ser | Ser | Pro | Glu | Leu | Thr |  |

| | | | | |
|---|---|---|---|---|
| 785 | | 790 | 795 | 800 |

| | | | | | | | | | | | | | | | | |
|---|---|---|---|---|---|---|---|---|---|---|---|---|---|---|---|---|
| GTG | ACA | GTA | ACA | GTT | TGG | AAT | GAG | GGT | GAG | GAC | AGC | TAT | GGA | ACC | TTA | 2448 |
| Val | Thr | Val | Thr | Val 805 | Trp | Asn | Glu | Gly 810 | Glu | Asp | Ser | Tyr | Gly 815 | Thr | Leu | |
| ATC | AAG | TTC | TAC | TAC | CCA | GCA | GAG | CTA | TCT | TAC | CGA | CGG | GTG | ACA | AGA | 2496 |
| Ile | Lys | Phe | Tyr 820 | Tyr | Pro | Ala | Glu | Leu 825 | Ser | Tyr | Arg | Arg | Val 830 | Thr | Arg | |
| GCC | CAG | CAA | CCT | CAT | CCG | TAC | CCA | CTA | CGC | CTG | GCA | TGT | GAG | GCT | GAG | 2544 |
| Ala | Gln | Gln 835 | Pro | His | Pro | Tyr | Pro 840 | Leu | Arg | Leu | Ala | Cys 845 | Glu | Ala | Glu | |
| CCC | ACG | GGC | CAG | GAG | AGC | CTG | AGG | AGC | AGC | AGC | TGT | AGC | ATC | AAT | CAC | 2592 |
| Pro | Thr 850 | Gly | Gln | Glu | Ser | Leu 855 | Arg | Ser | Ser | Ser | Cys 860 | Ser | Ile | Asn | His | |
| CCC | ATC | TTC | CGA | GAA | GGT | GCC | AAG | GCC | ACC | TTC | ATG | ATC | ACA | TTT | GAT | 2640 |
| Pro 865 | Ile | Phe | Arg | Glu | Gly 870 | Ala | Lys | Ala | Thr | Phe 875 | Met | Ile | Thr | Phe | Asp 880 | |
| GTC | TCC | TAC | AAG | GCC | TTC | CTG | GGA | GAC | AGG | TTG | CTT | CTG | AGG | GCC | AGC | 2688 |
| Val | Ser | Tyr | Lys | Ala 885 | Phe | Leu | Gly | Asp | Arg 890 | Leu | Leu | Leu | Arg | Ala 895 | Ser | |
| GCA | AGC | AGT | GAG | AAT | AAT | AAG | CCT | GAA | ACC | AGC | AAG | ACT | GCC | TTC | CAG | 2736 |
| Ala | Ser | Ser | Glu 900 | Asn | Asn | Lys | Pro | Glu 905 | Thr | Ser | Lys | Thr | Ala 910 | Phe | Gln | |
| CTG | GAG | CTT | CCG | GTG | AAG | TAC | ACG | GTC | TAT | ACC | GTG | ATC | AGT | AGG | CAG | 2784 |
| Leu | Glu | Leu 915 | Pro | Val | Lys | Tyr | Thr 920 | Val | Tyr | Thr | Val | Ile 925 | Ser | Arg | Gln | |
| GAA | GAT | TCT | ACC | AAG | CAT | TTC | AAC | TTC | TCA | TCT | TCC | CAC | GGG | GAG | AGA | 2832 |
| Glu | Asp | Ser 930 | Thr | Lys | His | Phe | Asn 935 | Phe | Ser | Ser | Ser | His 940 | Gly | Glu | Arg | |
| CAG | AAA | GAG | GCC | GAA | CAT | CGA | TAT | CGT | GTG | AAT | AAC | CTG | AGT | CCA | TTG | 2880 |
| Gln 945 | Lys | Glu | Ala | Glu | His 950 | Arg | Tyr | Arg | Val | Asn 955 | Asn | Leu | Ser | Pro | Leu 960 | |
| ACG | CTG | GCC | ATC | AGC | GTT | AAC | TTC | TGG | GTC | CCC | ATC | CTT | CTG | AAT | GGT | 2928 |
| Thr | Leu | Ala | Ile | Ser 965 | Val | Asn | Phe | Trp | Val 970 | Pro | Ile | Leu | Leu | Asn 975 | Gly | |
| GTG | GCC | GTG | TGG | GAT | GTG | ACT | CTG | AGG | AGC | CCA | GCA | CAG | GGT | GTC | TCC | 2976 |
| Val | Ala | Val | Trp 980 | Asp | Val | Thr | Leu | Arg 985 | Ser | Pro | Ala | Gln | Gly 990 | Val | Ser | |
| TGT | GTG | TCA | CAG | AGG | GAA | CCT | CCT | CAA | CAT | TCC | GAC | CTT | CTG | ACC | CAG | 3024 |
| Cys | Val | Ser 995 | Gln | Arg | Glu | Pro | Pro 1000 | Gln | His | Ser | Asp | Leu 1005 | Leu | Thr | Gln | |
| ATC | CAA | GGA | CGC | TCT | GTG | CTG | GAC | TGC | GCC | ATC | GCC | GAC | TGC | CTG | CAC | 3072 |
| Ile | Gln | Gly 1010 | Arg | Ser | Val | Leu | Asp 1015 | Cys | Ala | Ile | Ala | Asp 1020 | Cys | Leu | His | |
| CTC | CGC | TGT | GAC | ATC | CCC | TCC | TTG | GGC | ACC | CTG | GAT | GAG | CTT | GAC | TTC | 3120 |
| Leu | Arg 1025 | Cys | Asp | Ile | Pro | Ser 1030 | Leu | Gly | Thr | Leu | Asp 1035 | Glu | Leu | Asp | Phe 1040 | |
| ATT | CTG | AAG | GGC | AAC | CTC | AGC | TTC | GGC | TGG | ATC | AGT | CAG | ACA | TTG | CAG | 3168 |
| Ile | Leu | Lys | Gly | Asn 1045 | Leu | Ser | Phe | Gly | Trp 1050 | Ile | Ser | Gln | Thr | Leu 1055 | Gln | |
| AAA | AAG | GTG | TTG | CTC | CTG | AGT | GAG | GCT | GAA | ATC | ACA | TTC | AAC | ACA | TCT | 3216 |
| Lys | Lys | Val | Leu 1060 | Leu | Leu | Ser | Glu | Ala 1065 | Glu | Ile | Thr | Phe | Asn 1070 | Thr | Ser | |
| GTG | TAT | TCC | CAG | CTG | CCG | GGA | CAG | GAG | GCA | TTT | CTG | AGA | GCC | CAG | GTG | 3264 |
| Val | Tyr | Ser 1075 | Gln | Leu | Pro | Gly | Gln 1080 | Glu | Ala | Phe | Leu | Arg 1085 | Ala | Gln | Val | |
| TCA | ACG | ATG | CTA | GAA | GAA | TAC | GTG | GTC | TAT | GAG | CCC | GTC | TTC | CTC | ATG | 3312 |
| Ser | Thr | Met 1090 | Leu | Glu | Glu | Tyr | Val 1095 | Val | Tyr | Glu | Pro | Val 1100 | Phe | Leu | Met | |
| GTG | TTC | AGC | TCA | GTG | GGA | GGT | CTG | CTG | TTA | CTG | GCT | CTC | ATC | ACT | GTG | 3360 |
| Val | Phe | Ser | Ser | Val | Gly | Gly | Leu | Leu | Leu | Leu | Ala | Leu | Ile | Thr | Val | |

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| 1105  |       |       |       |       | 1110  |       |       |       |       | 1115  |       |       |       |       | 1120  |      |
| GCG   | CTG   | TAC   | AAG   | CTT   | GGC   | TTC   | TTC   | AAA   | CGT   | CAG   | TAT   | AAA   | GAG   | ATG   | CTG   | 3408 |
| Ala   | Leu   | Tyr   | Lys   | Leu   | Gly   | Phe   | Phe   | Lys   | Arg   | Gln   | Tyr   | Lys   | Glu   | Met   | Leu   |      |
|       |       |       |       |       | 1125  |       |       |       |       | 1130  |       |       |       |       | 1135  |      |
| GAT   | CTA   | CCA   | TCT   | GCA   | GAT   | CCT   | GAC   | CCA   | GCC   | GGC   | CAG   | GCA   | GAT   | TCC   | AAC   | 3456 |
| Asp   | Leu   | Pro   | Ser   | Ala   | Asp   | Pro   | Asp   | Pro   | Ala   | Gly   | Gln   | Ala   | Asp   | Ser   | Asn   |      |
|       |       |       |       |       | 1140  |       |       |       |       | 1145  |       |       |       |       | 1150  |      |
| CAT   | GAG   | ACT   | CCT   | CCA   | CAT   | CTC   | ACG   | TCC   | TAGGAATCTA | CTTCCTGTA |       |       |       |       |       | 3503 |
| His   | Glu   | Thr   | Pro   | Pro   | His   | Leu   | Thr   | Ser   |       |       |       |       |       |       |       |      |
|       |       |       |       |       | 1155  |       |       |       | 1160  |       |       |       |       |       |       |      |

TATCTCCACA ATTACGAGAT TGGTTTTGCT TTTGCCTATG AATCTACTGG CATGGGAACA 3563

AGTTCTCTTC AGCTCTGGGC TAGCCTGGGA AACTTCCCAG AAATGATGCC CTACCTCCTG 3623

AGCTGGGAGA TTTTTATGGT TTGCCCATGT GTCAGATTTC AGTGCTGATC CACTTTTTTT 3683

GCAAGAGCAG GAATGGGGTC AGCATAAATT TACATATGGA TAAGAACTAA CACAAGACTG 3743

AGTAATATGC TCAATATTCA ATGTATTGCT TGTATAAATT TTTAAAAAAT AAAATGAAAN 3803

( 2 ) INFORMATION FOR SEQ ID NO:53:

( i ) SEQUENCE CHARACTERISTICS:
        ( A ) LENGTH: 1161 amino acids
        ( B ) TYPE: amino acid
        ( D ) TOPOLOGY: linear ( i i ) MOLECULE TYPE: protein ( x i ) SEQUENCE DESCRIPTION: SEQ ID NO:53:

| Met | Val | Arg | Gly | Val | Val | Ile | Leu | Leu | Cys | Gly | Trp | Ala | Leu | Ala | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Cys | His | Gly | Ser | Asn | Leu | Asp | Val | Glu | Lys | Pro | Val | Val | Phe | Lys | Glu |
|     |     |     | 20  |     |     |     |     | 25  |     |     |     |     | 30  |     |     |
| Asp | Ala | Ala | Ser | Phe | Gly | Gln | Thr | Val | Val | Gln | Phe | Gly | Gly | Ser | Arg |
|     |     | 35  |     |     |     |     | 40  |     |     |     |     | 45  |     |     |     |
| Leu | Val | Val | Gly | Ala | Pro | Leu | Glu | Ala | Val | Ala | Val | Asn | Gln | Thr | Gly |
|     | 50  |     |     |     |     | 55  |     |     |     |     | 60  |     |     |     |     |
| Gln | Ser | Ser | Asp | Cys | Pro | Pro | Ala | Thr | Gly | Val | Cys | Gln | Pro | Ile | Leu |
| 65  |     |     |     |     | 70  |     |     |     |     | 75  |     |     |     |     | 80  |
| Leu | His | Ile | Pro | Leu | Glu | Ala | Val | Asn | Met | Ser | Leu | Gly | Leu | Ser | Leu |
|     |     |     |     | 85  |     |     |     |     | 90  |     |     |     |     | 95  |     |
| Val | Ala | Asp | Thr | Asn | Asn | Ser | Gln | Leu | Leu | Ala | Cys | Gly | Pro | Thr | Ala |
|     |     |     | 100 |     |     |     |     | 105 |     |     |     |     | 110 |     |     |
| Gln | Arg | Ala | Cys | Ala | Lys | Asn | Met | Tyr | Ala | Lys | Gly | Ser | Cys | Leu | Leu |
|     |     | 115 |     |     |     |     | 120 |     |     |     |     | 125 |     |     |     |
| Leu | Gly | Ser | Ser | Leu | Gln | Phe | Ile | Gln | Ala | Ile | Pro | Ala | Thr | Met | Pro |
|     | 130 |     |     |     |     | 135 |     |     |     |     | 140 |     |     |     |     |
| Glu | Cys | Pro | Gly | Gln | Glu | Met | Asp | Ile | Ala | Phe | Leu | Ile | Asp | Gly | Ser |
| 145 |     |     |     |     | 150 |     |     |     |     | 155 |     |     |     |     | 160 |
| Gly | Ser | Ile | Asp | Gln | Ser | Asp | Phe | Thr | Gln | Met | Lys | Asp | Phe | Val | Lys |
|     |     |     | 165 |     |     |     |     | 170 |     |     |     |     | 175 |     |     |
| Ala | Leu | Met | Gly | Gln | Leu | Ala | Ser | Thr | Ser | Thr | Ser | Phe | Ser | Leu | Met |
|     |     |     | 180 |     |     |     |     | 185 |     |     |     |     | 190 |     |     |
| Gln | Tyr | Ser | Asn | Ile | Leu | Lys | Thr | His | Phe | Thr | Phe | Thr | Glu | Phe | Lys |
|     |     | 195 |     |     |     |     | 200 |     |     |     |     | 205 |     |     |     |
| Ser | Ser | Leu | Ser | Pro | Gln | Ser | Leu | Val | Asp | Ala | Ile | Val | Gln | Leu | Gln |
|     | 210 |     |     |     |     | 215 |     |     |     |     | 220 |     |     |     |     |
| Gly | Leu | Thr | Tyr | Thr | Ala | Ser | Gly | Ile | Gln | Lys | Val | Val | Lys | Glu | Leu |
| 225 |     |     |     |     | 230 |     |     |     |     | 235 |     |     |     |     | 240 |

-continued

```
Phe His Ser Lys Asn Gly Ala Arg Lys Ser Ala Lys Lys Ile Leu Ile
            245             250             255

Val Ile Thr Asp Gly Gln Lys Phe Arg Asp Pro Leu Glu Tyr Arg His
            260             265             270

Val Ile Pro Glu Ala Glu Lys Ala Gly Ile Ile Arg Tyr Ala Ile Gly
            275             280             285

Val Gly Asp Ala Phe Arg Glu Pro Thr Ala Leu Gln Glu Leu Asn Thr
    290             295             300

Ile Gly Ser Ala Pro Ser Gln Asp His Val Phe Lys Val Gly Asn Phe
305             310             315             320

Val Ala Leu Arg Ser Ile Gln Arg Gln Ile Gln Glu Lys Ile Phe Ala
            325             330             335

Ile Glu Gly Thr Glu Ser Arg Ser Ser Ser Phe Gln His Glu Met
            340             345             350

Ser Gln Glu Gly Phe Ser Ser Ala Leu Ser Met Asp Gly Pro Val Leu
            355             360             365

Gly Ala Val Gly Gly Phe Ser Trp Ser Gly Gly Ala Phe Leu Tyr Pro
    370             375             380

Ser Asn Met Arg Ser Thr Phe Ile Asn Met Ser Gln Glu Asn Glu Asp
385             390             395             400

Met Arg Asp Ala Tyr Leu Gly Tyr Ser Thr Ala Leu Ala Phe Trp Lys
            405             410             415

Gly Val His Ser Leu Ile Leu Gly Ala Pro Arg His Gln His Thr Gly
            420             425             430

Lys Val Val Ile Phe Thr Gln Glu Ser Arg His Trp Arg Pro Lys Ser
            435             440             445

Glu Val Arg Gly Thr Gln Ile Gly Ser Tyr Phe Gly Ala Ser Leu Cys
    450             455             460

Ser Val Asp Met Asp Arg Asp Gly Ser Thr Asp Leu Val Leu Ile Gly
465             470             475             480

Val Pro His Tyr Tyr Glu His Thr Arg Gly Gly Gln Val Ser Val Cys
            485             490             495

Pro Met Pro Gly Val Arg Ser Arg Trp His Cys Gly Thr Thr Leu His
            500             505             510

Gly Glu Gln Gly His Pro Trp Gly Arg Phe Gly Ala Ala Leu Thr Val
    515             520             525

Leu Gly Asp Val Asn Gly Asp Ser Leu Ala Asp Val Ala Ile Gly Ala
    530             535             540

Pro Gly Glu Glu Glu Asn Arg Gly Ala Val Tyr Ile Phe His Gly Ala
545             550             555             560

Ser Arg Gln Asp Ile Ala Pro Ser Pro Ser Gln Arg Val Thr Gly Ser
            565             570             575

Gln Leu Phe Leu Arg Leu Gln Tyr Phe Gly Gln Ser Leu Ser Gly Gly
            580             585             590

Gln Asp Leu Thr Gln Asp Gly Leu Val Asp Leu Ala Val Gly Ala Gln
            595             600             605

Gly His Val Leu Leu Leu Arg Ser Leu Pro Leu Leu Lys Val Gly Ile
    610             615             620

Ser Ile Arg Phe Ala Pro Ser Glu Val Ala Lys Thr Val Tyr Gln Cys
625             630             635             640

Trp Gly Arg Thr Pro Thr Val Leu Glu Ala Gly Glu Ala Thr Val Cys
            645             650             655

Leu Thr Val Arg Lys Gly Ser Pro Asp Leu Leu Gly Asp Val Gln Ser
```

-continued

```
                    660                        665                        670
Ser  Val  Arg  Tyr  Asp  Leu  Ala  Leu  Asp  Pro  Gly  Arg  Leu  Ile  Ser  Arg
          675                      680                      685
Ala  Ile  Phe  Asp  Glu  Thr  Lys  Asn  Cys  Thr  Leu  Thr  Arg  Arg  Lys  Thr
     690                      695                      700
Leu  Gly  Leu  Gly  Asp  His  Cys  Glu  Thr  Met  Lys  Leu  Leu  Leu  Pro  Asp
705                      710                      715                           720
Cys  Val  Glu  Asp  Ala  Val  Thr  Pro  Ile  Ile  Leu  Arg  Leu  Asn  Leu  Ser
               725                      730                           735
Leu  Ala  Gly  Asp  Ser  Ala  Pro  Ser  Arg  Asn  Leu  Arg  Pro  Val  Leu  Ala
               740                      745                      750
Val  Gly  Ser  Gln  Asp  His  Val  Thr  Ala  Ser  Phe  Pro  Phe  Glu  Lys  Asn
               755                      760                      765
Cys  Lys  Gln  Glu  Leu  Leu  Cys  Glu  Gly  Asn  Leu  Gly  Val  Ser  Phe  Asn
     770                      775                      780
Phe  Ser  Gly  Leu  Gln  Val  Leu  Glu  Val  Gly  Ser  Ser  Pro  Glu  Leu  Thr
785                      790                      795                           800
Val  Thr  Val  Thr  Val  Trp  Asn  Glu  Gly  Glu  Asp  Ser  Tyr  Gly  Thr  Leu
               805                      810                      815
Ile  Lys  Phe  Tyr  Tyr  Pro  Ala  Glu  Leu  Ser  Tyr  Arg  Arg  Val  Thr  Arg
               820                      825                      830
Ala  Gln  Gln  Pro  His  Pro  Tyr  Pro  Leu  Arg  Leu  Ala  Cys  Glu  Ala  Glu
               835                      840                      845
Pro  Thr  Gly  Gln  Glu  Ser  Leu  Arg  Ser  Ser  Ser  Cys  Ser  Ile  Asn  His
     850                      855                      860
Pro  Ile  Phe  Arg  Glu  Gly  Ala  Lys  Ala  Thr  Phe  Met  Ile  Thr  Phe  Asp
865                      870                      875                           880
Val  Ser  Tyr  Lys  Ala  Phe  Leu  Gly  Asp  Arg  Leu  Leu  Leu  Arg  Ala  Ser
               885                      890                      895
Ala  Ser  Ser  Glu  Asn  Asn  Lys  Pro  Glu  Thr  Ser  Lys  Thr  Ala  Phe  Gln
               900                      905                      910
Leu  Glu  Leu  Pro  Val  Lys  Tyr  Thr  Val  Tyr  Thr  Val  Ile  Ser  Arg  Gln
          915                      920                      925
Glu  Asp  Ser  Thr  Lys  His  Phe  Asn  Phe  Ser  Ser  Ser  His  Gly  Glu  Arg
     930                      935                      940
Gln  Lys  Glu  Ala  Glu  His  Arg  Tyr  Arg  Val  Asn  Asn  Leu  Ser  Pro  Leu
945                      950                      955                           960
Thr  Leu  Ala  Ile  Ser  Val  Asn  Phe  Trp  Val  Pro  Ile  Leu  Leu  Asn  Gly
               965                      970                           975
Val  Ala  Val  Trp  Asp  Val  Thr  Leu  Arg  Ser  Pro  Ala  Gln  Gly  Val  Ser
               980                      985                      990
Cys  Val  Ser  Gln  Arg  Glu  Pro  Pro  Gln  His  Ser  Asp  Leu  Leu  Thr  Gln
          995                      1000                     1005
Ile  Gln  Gly  Arg  Ser  Val  Leu  Asp  Cys  Ala  Ile  Ala  Asp  Cys  Leu  His
          1010                     1015                     1020
Leu  Arg  Cys  Asp  Ile  Pro  Ser  Leu  Gly  Thr  Leu  Asp  Glu  Leu  Asp  Phe
1025                     1030                     1035                          1040
Ile  Leu  Lys  Gly  Asn  Leu  Ser  Phe  Gly  Trp  Ile  Ser  Gln  Thr  Leu  Gln
               1045                     1050                     1055
Lys  Lys  Val  Leu  Leu  Leu  Ser  Glu  Ala  Glu  Ile  Thr  Phe  Asn  Thr  Ser
               1060                     1065                     1070
Val  Tyr  Ser  Gln  Leu  Pro  Gly  Gln  Glu  Ala  Phe  Leu  Arg  Ala  Gln  Val
               1075                     1080                     1085
```

```
Ser Thr Met Leu Glu Glu Tyr Val Val Tyr Glu Pro Val Phe Leu Met
     1090                1095                1100
Val Phe Ser Ser Val Gly Gly Leu Leu Leu Ala Leu Ile Thr Val
1105                1110                1115                1120
Ala Leu Tyr Lys Leu Gly Phe Phe Lys Arg Gln Tyr Lys Glu Met Leu
             1125                1130                1135
Asp Leu Pro Ser Ala Asp Pro Asp Pro Ala Gly Gln Ala Asp Ser Asn
             1140                1145                1150
His Glu Thr Pro Pro His Leu Thr Ser
         1155             1160
```

( 2 ) INFORMATION FOR SEQ ID NO:54:

( i ) SEQUENCE CHARACTERISTICS:
        ( A ) LENGTH: 3597 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 40..3525

( x i ) SEQUENCE DESCRIPTION: SEQ ID NO:54:

```
AGCTTTACAG CTCTCTACTT CTCAGTGCAC TGCTCAGTG ATG GCC GGT GGA GTT                54
                                           Met Ala Gly Gly Val
                                            1               5

GTG ATC CTC CTG TGT GGC TGG GTC CTG GCT TCC TGT CAT GGG TCT AAC              102
Val Ile Leu Leu Cys Gly Trp Val Leu Ala Ser Cys His Gly Ser Asn
             10                  15                  20

CTG GAT GTG GAG GAA CCC ATC GTG TTC AGA GAG GAT GCA GCC AGC TTT              150
Leu Asp Val Glu Glu Pro Ile Val Phe Arg Glu Asp Ala Ala Ser Phe
         25                  30                  35

GGA CAG ACT GTG GTG CAG TTT GGT GGA TCT CGA CTC GTG GTG GGA GCC              198
Gly Gln Thr Val Val Gln Phe Gly Gly Ser Arg Leu Val Val Gly Ala
     40                  45                  50

CCT CTG GAG GCG GTG GCA GTC AAC CAA ACA GGA CGG TTG TAT GAC TGT              246
Pro Leu Glu Ala Val Ala Val Asn Gln Thr Gly Arg Leu Tyr Asp Cys
 55                  60                  65

GCA CCT GCC ACT GGC ATG TGC CAG CCC ATC GTA CTG CGC AGT CCC CTA              294
Ala Pro Ala Thr Gly Met Cys Gln Pro Ile Val Leu Arg Ser Pro Leu
 70                  75                  80                  85

GAG GCA GTG AAC ATG TCC CTG GGC CTG TCT CTG GTG ACT GCC ACC AAT              342
Glu Ala Val Asn Met Ser Leu Gly Leu Ser Leu Val Thr Ala Thr Asn
                 90                  95                 100

AAC GCC CAG TTG CTG GCT TGT GGT CCA ACT GCA CAG AGA GCT TGT GTG              390
Asn Ala Gln Leu Leu Ala Cys Gly Pro Thr Ala Gln Arg Ala Cys Val
            105                 110                 115

AAG AAC ATG TAT GCG AAA GGT TCC TGC CTC CTT CTC GGC TCC AGC TTG              438
Lys Asn Met Tyr Ala Lys Gly Ser Cys Leu Leu Leu Gly Ser Ser Leu
        120                 125                 130

CAG TTC ATC CAG GCA GTC CCT GCC TCC ATG CCA GAG TGT CCA AGA CAA              486
Gln Phe Ile Gln Ala Val Pro Ala Ser Met Pro Glu Cys Pro Arg Gln
    135                 140                 145

GAG ATG GAC ATT GCT TTC CTG ATT GAT GGT TCT GGC AGC ATT AAC CAA              534
Glu Met Asp Ile Ala Phe Leu Ile Asp Gly Ser Gly Ser Ile Asn Gln
150                 155                 160                 165

AGG GAC TTT GCC CAG ATG AAG GAC TTT GTC AAA GCT TTG ATG GGA GAG              582
Arg Asp Phe Ala Gln Met Lys Asp Phe Val Lys Ala Leu Met Gly Glu
                170                 175                 180
```

| | | | | | | | | | | | | | | | | |
|---|---|---|---|---|---|---|---|---|---|---|---|---|---|---|---|---|
| TTT | GCG | AGC | ACC | AGC | ACC | TTG | TTC | TCC | CTG | ATG | CAA | TAC | TCG | AAC | ATC | 630 |
| Phe | Ala | Ser | Thr 185 | Ser | Thr | Leu | Phe | Ser 190 | Leu | Met | Gln | Tyr | Ser 195 | Asn | Ile | |
| CTG | AAG | ACC | CAT | TTT | ACC | TTC | ACT | GAA | TTC | AAG | AAC | ATC | CTG | GAC | CCT | 678 |
| Leu | Lys | Thr 200 | His | Phe | Thr | Phe | Thr 205 | Glu | Phe | Lys | Asn | Ile 210 | Leu | Asp | Pro | |
| CAG | AGC | CTG | GTG | GAT | CCC | ATT | GTC | CAG | CTG | CAA | GGC | CTG | ACC | TAC | ACA | 726 |
| Gln | Ser 215 | Leu | Val | Asp | Pro | Ile 220 | Val | Gln | Leu | Gln | Gly 225 | Leu | Thr | Tyr | Thr | |
| GCC | ACA | GGC | ATC | CGG | ACA | GTG | ATG | GAA | GAG | CTA | TTT | CAT | AGC | AAG | AAT | 774 |
| Ala 230 | Thr | Gly | Ile | Arg | Thr 235 | Val | Met | Glu | Glu | Leu 240 | Phe | His | Ser | Lys | Asn 245 | |
| GGG | TCC | CGT | AAA | AGT | GCC | AAG | AAG | ATC | CTC | CTT | GTC | ATC | ACA | GAT | GGG | 822 |
| Gly | Ser | Arg | Lys | Ser 250 | Ala | Lys | Lys | Ile | Leu 255 | Leu | Val | Ile | Thr | Asp 260 | Gly | |
| CAG | AAA | TAC | AGA | GAC | CCC | CTG | GAG | TAT | AGT | GAT | GTC | ATT | CCC | GCC | GCA | 870 |
| Gln | Lys | Tyr | Arg 265 | Asp | Pro | Leu | Glu | Tyr 270 | Ser | Asp | Val | Ile | Pro 275 | Ala | Ala | |
| GAC | AAA | GCT | GGC | ATC | ATT | CGT | TAT | GCT | ATT | GGG | GTG | GGA | GAT | GCC | TTC | 918 |
| Asp | Lys | Ala 280 | Gly | Ile | Ile | Arg | Tyr 285 | Ala | Ile | Gly | Val | Gly 290 | Asp | Ala | Phe | |
| CAG | GAG | CCC | ACT | GCC | CTG | AAG | GAG | CTG | AAC | ACC | ATT | GGC | TCA | GCT | CCC | 966 |
| Gln | Glu | Pro | Thr 295 | Ala | Leu | Lys | Glu 300 | Leu | Asn | Thr | Ile | Gly 305 | Ser | Ala | Pro | |
| CCA | CAG | GAC | CAC | GTG | TTC | AAG | GTA | GGC | AAC | TTT | GCA | GCA | CTT | CGC | AGC | 1014 |
| Pro 310 | Gln | Asp | His | Val | Phe 315 | Lys | Val | Gly | Asn | Phe 320 | Ala | Ala | Leu | Arg | Ser 325 | |
| ATC | CAG | AGG | CAA | CTT | CAG | GAG | AAA | ATC | TTC | GCC | ATT | GAG | GGA | ACT | CAA | 1062 |
| Ile | Gln | Arg | Gln | Leu 330 | Gln | Glu | Lys | Ile | Phe 335 | Ala | Ile | Glu | Gly | Thr 340 | Gln | |
| TCA | AGG | TCA | AGT | AGT | TCC | TTT | CAG | CAC | GAG | ATG | TCA | CAA | GAA | GGT | TTC | 1110 |
| Ser | Arg | Ser | Ser 345 | Ser | Ser | Phe | Gln | His 350 | Glu | Met | Ser | Gln | Glu 355 | Gly | Phe | |
| AGT | TCA | GCT | CTC | ACA | TCG | GAT | GGA | CCC | GTT | CTG | GGG | GCC | GTG | GGA | AGC | 1158 |
| Ser | Ser | Ala 360 | Leu | Thr | Ser | Asp | Gly 365 | Pro | Val | Leu | Gly | Ala 370 | Val | Gly | Ser | |
| TTC | AGC | TGG | TCC | GGA | GGT | GCC | TTC | TTA | TAT | CCC | CCA | AAT | ACG | AGA | CCC | 1206 |
| Phe | Ser 375 | Trp | Ser | Gly | Gly | Ala 380 | Phe | Leu | Tyr | Pro | Pro 385 | Asn | Thr | Arg | Pro | |
| ACC | TTT | ATC | AAC | ATG | TCT | CAG | GAG | AAT | GTG | GAC | ATG | AGA | GAC | TCC | TAC | 1254 |
| Thr 390 | Phe | Ile | Asn | Met | Ser 395 | Gln | Glu | Asn | Val | Asp 400 | Met | Arg | Asp | Ser | Tyr 405 | |
| CTG | GGT | TAC | TCC | ACC | GCA | GTG | GCC | TTT | TGG | AAG | GGG | GTT | CAC | AGC | CTG | 1302 |
| Leu | Gly | Tyr | Ser | Thr 410 | Ala | Val | Ala | Phe | Trp 415 | Lys | Gly | Val | His | Ser 420 | Leu | |
| ATC | CTG | GGG | GCC | CCG | CGT | CAC | CAG | CAC | ACG | GGG | AAG | GTT | GTC | ATC | TTT | 1350 |
| Ile | Leu | Gly | Ala 425 | Pro | Arg | His | Gln | His 430 | Thr | Gly | Lys | Val | Val 435 | Ile | Phe | |
| ACC | CAG | GAA | GCC | AGG | CAT | TGG | AGG | CCC | AAG | TCT | GAA | GTC | AGA | GGG | ACA | 1398 |
| Thr | Gln | Glu 440 | Ala | Arg | His | Trp | Arg 445 | Pro | Lys | Ser | Glu | Val 450 | Arg | Gly | Thr | |
| CAG | ATC | GGC | TCC | TAC | TTC | GGG | GCC | TCT | CTC | TGT | TCT | GTG | GAC | GTG | GAT | 1446 |
| Gln | Ile | Gly 455 | Ser | Tyr | Phe | Gly | Ala 460 | Ser | Leu | Cys | Ser | Val 465 | Asp | Val | Asp | |
| AGA | GAT | GGC | AGC | ACY | GAC | CTG | GTC | CTG | ATC | GGA | GCC | CCC | CAT | TAC | TAT | 1494 |
| Arg | Asp 470 | Gly | Ser | Xaa | Asp 475 | Leu | Val | Leu | Ile | Gly 480 | Ala | Pro | His | Tyr | Tyr 485 | |
| GAG | CAG | ACC | CGA | GGG | GGG | CAG | GTC | TCA | GTG | TTC | CCC | GTG | CCC | GGT | GTG | 1542 |
| Glu | Gln | Thr | Arg | Gly 490 | Gly | Gln | Val | Ser | Val 495 | Phe | Pro | Val | Pro 500 | Gly | Val | |

| | | | | | | | | | | | | | | | | |
|---|---|---|---|---|---|---|---|---|---|---|---|---|---|---|---|---|
|AGG|GGC|AGG|TGG|CAG|TGT|GAG|GCC|ACC|CTC|CAC|GGG|GAG|CAG|GGC|CAT|1590|
|Arg|Gly|Arg|Trp|Gln|Cys|Glu|Ala|Thr|Leu|His|Gly|Glu|Gln|Gly|His| |
| | | |505| | | |510| | | |  |515| | | | |

```
AGG GGC AGG TGG CAG TGT GAG GCC ACC CTC CAC GGG GAG CAG GGC CAT      1590
Arg Gly Arg Trp Gln Cys Glu Ala Thr Leu His Gly Glu Gln Gly His
            505             510                 515

CCT TGG GGC CGC TTT GGG GTG GCT CTG ACA GTG CTG GGG GAC GTA AAC      1638
Pro Trp Gly Arg Phe Gly Val Ala Leu Thr Val Leu Gly Asp Val Asn
            520             525                 530

GGG GAC AAT CTG GCA GAC GTG GCT ATT GGT GCC CCT GGA GAG GAG GAG      1686
Gly Asp Asn Leu Ala Asp Val Ala Ile Gly Ala Pro Gly Glu Glu Glu
            535             540                 545

AGC AGA GGT GCT GTC TAC ATA TTT CAT GGA GCC TCG AGA CTG GAG ATC      1734
Ser Arg Gly Ala Val Tyr Ile Phe His Gly Ala Ser Arg Leu Glu Ile
550             555             560                 565

ATG CCC TCA CCC AGC CAG CGG GTC ACT GGC TCC CAG CTC TCC CTG AGA      1782
Met Pro Ser Pro Ser Gln Arg Val Thr Gly Ser Gln Leu Ser Leu Arg
                570             575                 580

CTG CAG TAT TTT GGG CAG TCA TTG AGT GGG GGT CAG GAC CTT ACA CAG      1830
Leu Gln Tyr Phe Gly Gln Ser Leu Ser Gly Gly Gln Asp Leu Thr Gln
            585             590                 595

GAT GGC CTG GTG GAC CTG GCC GTG GGA GCC CAG GGG CAC GTA CTG CTG      1878
Asp Gly Leu Val Asp Leu Ala Val Gly Ala Gln Gly His Val Leu Leu
            600             605                 610

CTC AGG AGT CTG CCT CTG CTG AAA GTG GAG CTC TCC ATA AGA TTC GCC      1926
Leu Arg Ser Leu Pro Leu Leu Lys Val Glu Leu Ser Ile Arg Phe Ala
615             620             625

CCC ATG GAG GTG GCA AAG GCT GTG TAC CAG TGC TGG GAA AGG ACT CCC      1974
Pro Met Glu Val Ala Lys Ala Val Tyr Gln Cys Trp Glu Arg Thr Pro
630             635             640                 645

ACT GTC CTC GAA GCT GGA GAG GCC ACT GTC TGT CTC ACT GTC CAC AAA      2022
Thr Val Leu Glu Ala Gly Glu Ala Thr Val Cys Leu Thr Val His Lys
            650             655                 660

GGC TCA CCT GAC CTG TTA GGT AAT GTC CAA GGC TCT GTC AGG TAT GAT      2070
Gly Ser Pro Asp Leu Leu Gly Asn Val Gln Gly Ser Val Arg Tyr Asp
            665             670                 675

CTG GCG TTA GAT CCG GGC CGC CTG ATT TCT CGT GCC ATT TTT GAT GAG      2118
Leu Ala Leu Asp Pro Gly Arg Leu Ile Ser Arg Ala Ile Phe Asp Glu
            680             685                 690

ACT AAG AAC TGC ACT TTG ACG GGA AGG AAG ACT CTG GGG CTT GGT GAT      2166
Thr Lys Asn Cys Thr Leu Thr Gly Arg Lys Thr Leu Gly Leu Gly Asp
695             700             705

CAC TGC GAA ACA GTG AAG CTG CTT TTG CCG GAC TGT GTG GAA GAT GCA      2214
His Cys Glu Thr Val Lys Leu Leu Leu Pro Asp Cys Val Glu Asp Ala
710             715             720                 725

GTG AGC CCT ATC ATC CTG CGC CTC AAC TTT TCC CTG GTG AGA GAC TCT      2262
Val Ser Pro Ile Ile Leu Arg Leu Asn Phe Ser Leu Val Arg Asp Ser
                730             735                 740

GCT TCA CCC AGG AAC CTG CAT CCT GTG CTG GCT GTG GGC TCA CAA GAC      2310
Ala Ser Pro Arg Asn Leu His Pro Val Leu Ala Val Gly Ser Gln Asp
            745             750                 755

CAC ATA ACT GCT TCT CTG CCG TTT GAG AAG AAC TGT AAG CAA GAA CTC      2358
His Ile Thr Ala Ser Leu Pro Phe Glu Lys Asn Cys Lys Gln Glu Leu
            760             765                 770

CTG TGT GAG GGG GAC CTG GGC ATC AGC TTT AAC TTC TCA GGC CTG CAG      2406
Leu Cys Glu Gly Asp Leu Gly Ile Ser Phe Asn Phe Ser Gly Leu Gln
775             780             785

GTC TTG GTG GTG GGA GGC TCC CCA GAG CTC ACT GTG ACA GTC ACT GTG      2454
Val Leu Val Val Gly Gly Ser Pro Glu Leu Thr Val Thr Val Thr Val
790             795             800                 805

TGG AAT GAG GGT GAG GAC AGC TAT GGA ACT TTA GTC AAG TTC TAC TAC      2502
Trp Asn Glu Gly Glu Asp Ser Tyr Gly Thr Leu Val Lys Phe Tyr Tyr
            810             815                 820
```

```
CCA GCA GGG CTA TCT TAC CGA CGG GTA ACA GGG ACT CAG CAA CCT CAT    2550
Pro Ala Gly Leu Ser Tyr Arg Arg Val Thr Gly Thr Gln Gln Pro His
            825             830                 835

CAG TAC CCA CTA CGC TTG GCC TGT GAG GCT GAG CCC GCT GCC CAG GAG    2598
Gln Tyr Pro Leu Arg Leu Ala Cys Glu Ala Glu Pro Ala Ala Gln Glu
            840             845                 850

GAC CTG AGG AGC AGC AGC TGT AGC ATT AAT CAC CCC ATC TTC CGA GAA    2646
Asp Leu Arg Ser Ser Ser Cys Ser Ile Asn His Pro Ile Phe Arg Glu
            855             860                 865

GGT GCA AAG ACC ACC TTC ATG ATC ACA TTC GAT GTC TCC TAC AAG GCC    2694
Gly Ala Lys Thr Thr Phe Met Ile Thr Phe Asp Val Ser Tyr Lys Ala
870             875             880                 885

TTC CTA GGA GAC AGG TTG CTT CTG AGG GCC AAA GCC AGC AGT GAG AAT    2742
Phe Leu Gly Asp Arg Leu Leu Leu Arg Ala Lys Ala Ser Ser Glu Asn
                890             895                 900

AAT AAG CCT GAT ACC AAC AAG ACT GCC TTC CAG CTG GAG CTC CCA GTG    2790
Asn Lys Pro Asp Thr Asn Lys Thr Ala Phe Gln Leu Glu Leu Pro Val
            905             910                 915

AAG TAC ACC GTC TAT ACC CTG ATC AGT AGG CAA GAA GAT TCC ACC AAC    2838
Lys Tyr Thr Val Tyr Thr Leu Ile Ser Arg Gln Glu Asp Ser Thr Asn
            920             925                 930

CAT GTC AAC TTT TCA TCT TCC CAC GGG GGG AGA AGG CAA GAA GCC GCA    2886
His Val Asn Phe Ser Ser Ser His Gly Gly Arg Arg Gln Glu Ala Ala
935             940             945

CAT CGC TAT CGT GTG AAT AAC CTG AGT CCA CTG AAG CTG GCC GTC AGA    2934
His Arg Tyr Arg Val Asn Asn Leu Ser Pro Leu Lys Leu Ala Val Arg
950             955             960                 965

GTT AAC TTC TGG GTC CCT GTC CTT CTG AAC GGT GTG GCT GTG TGG GAC    2982
Val Asn Phe Trp Val Pro Val Leu Leu Asn Gly Val Ala Val Trp Asp
                970             975                 980

GTG ACT CTG AGC AGC CCA GCA CAG GGT GTC TCC TGC GTG TCC CAG ATG    3030
Val Thr Leu Ser Ser Pro Ala Gln Gly Val Ser Cys Val Ser Gln Met
            985             990                 995

AAA CCT CCT CAG AAT CCC GAC TTT CTG ACC CAG ATT CAG AGA CGT TCT    3078
Lys Pro Pro Gln Asn Pro Asp Phe Leu Thr Gln Ile Gln Arg Arg Ser
        1000            1005                1010

GTG CTG GAC TGC TCC ATT GCT GAC TGC CTG CAC TTC CGC TGT GAC ATC    3126
Val Leu Asp Cys Ser Ile Ala Asp Cys Leu His Phe Arg Cys Asp Ile
        1015            1020                1025

CCC TCC TTG GAC ATC CAG GAT GAA CTT GAC TTC ATT CTG AGG GGC AAC    3174
Pro Ser Leu Asp Ile Gln Asp Glu Leu Asp Phe Ile Leu Arg Gly Asn
1030            1035            1040                1045

CTC AGC TTC GGC TGG GTC AGT CAG ACA TTG CAG GAA AAG GTG TTG CTT    3222
Leu Ser Phe Gly Trp Val Ser Gln Thr Leu Gln Glu Lys Val Leu Leu
                1050            1055                1060

GTG AGT GAG GCT GAA ATC ACT TTC GAC ACA TCT GTG TAC TCC CAG CTG    3270
Val Ser Glu Ala Glu Ile Thr Phe Asp Thr Ser Val Tyr Ser Gln Leu
            1065            1070                1075

CCA GGA CAG GAG GCA TTT CTG AGA GCC CAG GTG GAG ACA ACG TTA GAA    3318
Pro Gly Gln Glu Ala Phe Leu Arg Ala Gln Val Glu Thr Thr Leu Glu
            1080            1085                1090

GAA TAC GTG GTC TAT GAG CCC ATC TTC CTC GTG GCG GGC AGC TCG GTG    3366
Glu Tyr Val Val Tyr Glu Pro Ile Phe Leu Val Ala Gly Ser Ser Val
            1095            1100                1105

GGA GGT CTG CTG TTA CTG GCT CTC ATC ACA GTG GTA CTG TAC AAG CTT    3414
Gly Gly Leu Leu Leu Leu Ala Leu Ile Thr Val Val Leu Tyr Lys Leu
1110            1115            1120                1125

GGC TTC TYC AAA CGT CAG TAC AAA GAA ATG CTG GAC GGC AAG GCT GCA    3462
Gly Phe Xaa Lys Arg Gln Tyr Lys Glu Met Leu Asp Gly Lys Ala Ala
            1130            1135                1140
```

-continued

```
GAT CCT GTC ACA GCC GGC CAG GCA GAT TTC GGC TGT GAG ACT CCT CCA        3510
Asp Pro Val Thr Ala Gly Gln Ala Asp Phe Gly Cys Glu Thr Pro Pro
        1145                1150                1155

TAT CTC GTG AGC TAGGAATCCA CTCTCCTGCC TATCTCTGCA ATGAAGATTG             3562
Tyr Leu Val Ser
        1160

GTCCTGCCTA TGAGTCTACT GGCATGGGAA CGAGT                                  3597
```

(2) INFORMATION FOR SEQ ID NO:55:

(i) SEQUENCE CHARACTERISTICS:
        (A) LENGTH: 1161 amino acids
        (B) TYPE: amino acid
        (D) TOPOLOGY: linear (ii) MOLECULE TYPE: protein (xi) SEQUENCE DESCRIPTION: SEQ ID NO:55:

```
Met Ala Gly Gly Val Val Ile Leu Leu Cys Gly Trp Val Leu Ala Ser
 1               5                  10                  15

Cys His Gly Ser Asn Leu Asp Val Glu Glu Pro Ile Val Phe Arg Glu
            20                  25                  30

Asp Ala Ala Ser Phe Gly Gln Thr Val Val Gln Phe Gly Gly Ser Arg
        35                  40                  45

Leu Val Val Gly Ala Pro Leu Glu Ala Val Ala Val Asn Gln Thr Gly
    50                  55                  60

Arg Leu Tyr Asp Cys Ala Pro Ala Thr Gly Met Cys Gln Pro Ile Val
 65                  70                  75                  80

Leu Arg Ser Pro Leu Glu Ala Val Asn Met Ser Leu Gly Leu Ser Leu
                85                  90                  95

Val Thr Ala Thr Asn Asn Ala Gln Leu Leu Ala Cys Gly Pro Thr Ala
                100                 105                 110

Gln Arg Ala Cys Val Lys Asn Met Tyr Ala Lys Gly Ser Cys Leu Leu
            115                 120                 125

Leu Gly Ser Ser Leu Gln Phe Ile Gln Ala Val Pro Ala Ser Met Pro
    130                 135                 140

Glu Cys Pro Arg Gln Glu Met Asp Ile Ala Phe Leu Ile Asp Gly Ser
145                 150                 155                 160

Gly Ser Ile Asn Gln Arg Asp Phe Ala Gln Met Lys Asp Phe Val Lys
                165                 170                 175

Ala Leu Met Gly Glu Phe Ala Ser Thr Ser Thr Leu Phe Ser Leu Met
                180                 185                 190

Gln Tyr Ser Asn Ile Leu Lys Thr His Phe Thr Phe Thr Glu Phe Lys
            195                 200                 205

Asn Ile Leu Asp Pro Gln Ser Leu Val Asp Pro Ile Val Gln Leu Gln
    210                 215                 220

Gly Leu Thr Tyr Thr Ala Thr Gly Ile Arg Thr Val Met Glu Glu Leu
225                 230                 235                 240

Phe His Ser Lys Asn Gly Ser Arg Lys Ser Ala Lys Lys Ile Leu Leu
                245                 250                 255

Val Ile Thr Asp Gly Gln Lys Tyr Arg Asp Pro Leu Glu Tyr Ser Asp
            260                 265                 270

Val Ile Pro Ala Ala Asp Lys Ala Gly Ile Ile Arg Tyr Ala Ile Gly
        275                 280                 285

Val Gly Asp Ala Phe Gln Glu Pro Thr Ala Leu Lys Glu Leu Asn Thr
    290                 295                 300

Ile Gly Ser Ala Pro Pro Gln Asp His Val Phe Lys Val Gly Asn Phe
```

```
305                 310                 315                 320
Ala Ala Leu Arg Ser Ile Gln Arg Gln Leu Gln Glu Lys Ile Phe Ala
                325                 330                 335
Ile Glu Gly Thr Gln Ser Arg Ser Ser Ser Phe Gln His Glu Met
                340                 345                 350
Ser Gln Glu Gly Phe Ser Ser Ala Leu Thr Ser Asp Gly Pro Val Leu
                355                 360                 365
Gly Ala Val Gly Ser Phe Ser Trp Ser Gly Gly Ala Phe Leu Tyr Pro
        370                 375                 380
Pro Asn Thr Arg Pro Thr Phe Ile Asn Met Ser Gln Glu Asn Val Asp
385                 390                 395                 400
Met Arg Asp Ser Tyr Leu Gly Tyr Ser Thr Ala Val Ala Phe Trp Lys
                405                 410                 415
Gly Val His Ser Leu Ile Leu Gly Ala Pro Arg His Gln His Thr Gly
                420                 425                 430
Lys Val Val Ile Phe Thr Gln Glu Ala Arg His Trp Arg Pro Lys Ser
                435                 440                 445
Glu Val Arg Gly Thr Gln Ile Gly Ser Tyr Phe Gly Ala Ser Leu Cys
        450                 455                 460
Ser Val Asp Val Asp Arg Asp Gly Ser Xaa Asp Leu Val Leu Ile Gly
465                 470                 475                 480
Ala Pro His Tyr Tyr Glu Gln Thr Arg Gly Gly Gln Val Ser Val Phe
                485                 490                 495
Pro Val Pro Gly Val Arg Gly Arg Trp Gln Cys Glu Ala Thr Leu His
                500                 505                 510
Gly Glu Gln Gly His Pro Trp Gly Arg Phe Gly Val Ala Leu Thr Val
                515                 520                 525
Leu Gly Asp Val Asn Gly Asp Asn Leu Ala Asp Val Ala Ile Gly Ala
        530                 535                 540
Pro Gly Glu Glu Glu Ser Arg Gly Ala Val Tyr Ile Phe His Gly Ala
545                 550                 555                 560
Ser Arg Leu Glu Ile Met Pro Ser Pro Ser Gln Arg Val Thr Gly Ser
                565                 570                 575
Gln Leu Ser Leu Arg Leu Gln Tyr Phe Gly Gln Ser Leu Ser Gly Gly
                580                 585                 590
Gln Asp Leu Thr Gln Asp Gly Leu Val Asp Leu Ala Val Gly Ala Gln
                595                 600                 605
Gly His Val Leu Leu Leu Arg Ser Leu Pro Leu Leu Lys Val Glu Leu
        610                 615                 620
Ser Ile Arg Phe Ala Pro Met Glu Val Ala Lys Ala Val Tyr Gln Cys
625                 630                 635                 640
Trp Glu Arg Thr Pro Thr Val Leu Glu Ala Gly Glu Ala Thr Val Cys
                645                 650                 655
Leu Thr Val His Lys Gly Ser Pro Asp Leu Leu Gly Asn Val Gln Gly
                660                 665                 670
Ser Val Arg Tyr Asp Leu Ala Leu Asp Pro Gly Arg Leu Ile Ser Arg
                675                 680                 685
Ala Ile Phe Asp Glu Thr Lys Asn Cys Thr Leu Thr Gly Arg Lys Thr
        690                 695                 700
Leu Gly Leu Gly Asp His Cys Glu Thr Val Lys Leu Leu Leu Pro Asp
705                 710                 715                 720
Cys Val Glu Asp Ala Val Ser Pro Ile Ile Leu Arg Leu Asn Phe Ser
                725                 730                 735
```

| | | | | | | | | | | | | | | |
|---|---|---|---|---|---|---|---|---|---|---|---|---|---|---|
| Leu | Val | Arg | Asp 740 | Ser | Ala | Ser | Pro 745 | Arg | Asn | Leu | His | Pro 750 | Val | Leu | Ala |
| Val | Gly | Ser 755 | Gln | Asp | His | Ile | Thr 760 | Ala | Ser | Leu | Pro | Phe 765 | Glu | Lys | Asn |
| Cys | Lys 770 | Gln | Glu | Leu | Leu | Cys 775 | Glu | Gly | Asp | Leu | Gly 780 | Ile | Ser | Phe | Asn |
| Phe 785 | Ser | Gly | Leu | Gln | Val 790 | Leu | Val | Val | Gly | Gly 795 | Ser | Pro | Glu | Leu | Thr 800 |
| Val | Thr | Val | Thr | Val 805 | Trp | Asn | Glu | Gly | Glu 810 | Asp | Ser | Tyr | Gly | Thr 815 | Leu |
| Val | Lys | Phe | Tyr 820 | Tyr | Pro | Ala | Gly | Leu 825 | Ser | Tyr | Arg | Arg | Val 830 | Thr | Gly |
| Thr | Gln | Gln 835 | Pro | His | Gln | Tyr | Pro 840 | Leu | Arg | Leu | Ala | Cys 845 | Glu | Ala | Glu |
| Pro | Ala 850 | Ala | Gln | Glu | Asp | Leu 855 | Arg | Ser | Ser | Ser | Cys 860 | Ser | Ile | Asn | His |
| Pro 865 | Ile | Phe | Arg | Glu | Gly 870 | Ala | Lys | Thr | Thr | Phe 875 | Met | Ile | Thr | Phe | Asp 880 |
| Val | Ser | Tyr | Lys | Ala 885 | Phe | Leu | Gly | Asp | Arg 890 | Leu | Leu | Leu | Arg | Ala 895 | Lys |
| Ala | Ser | Ser | Glu 900 | Asn | Asn | Lys | Pro | Asp 905 | Thr | Asn | Lys | Thr | Ala 910 | Phe | Gln |
| Leu | Glu | Leu 915 | Pro | Val | Lys | Tyr | Thr 920 | Val | Tyr | Thr | Leu | Ile 925 | Ser | Arg | Gln |
| Glu | Asp 930 | Ser | Thr | Asn | His | Val 935 | Asn | Phe | Ser | Ser | Ser 940 | His | Gly | Gly | Arg |
| Arg 945 | Gln | Glu | Ala | Ala | His 950 | Arg | Tyr | Arg | Val | Asn 955 | Asn | Leu | Ser | Pro | Leu 960 |
| Lys | Leu | Ala | Val | Arg 965 | Val | Asn | Phe | Trp | Val 970 | Pro | Val | Leu | Leu | Asn 975 | Gly |
| Val | Ala | Val | Trp 980 | Asp | Val | Thr | Leu | Ser 985 | Ser | Pro | Ala | Gln | Gly 990 | Val | Ser |
| Cys | Val | Ser 995 | Gln | Met | Lys | Pro | Pro 1000 | Gln | Asn | Pro | Asp | Phe 1005 | Leu | Thr | Gln |
| Ile | Gln | Arg 1010 | Arg | Ser | Val | Leu | Asp 1015 | Cys | Ser | Ile | Ala | Asp 1020 | Cys | Leu | His |
| Phe | Arg 1025 | Cys | Asp | Ile | Pro | Ser 1030 | Leu | Asp | Ile | Gln | Asp 1035 | Glu | Leu | Asp | Phe 1040 |
| Ile | Leu | Arg | Gly | Asn 1045 | Leu | Ser | Phe | Gly | Trp 1050 | Val | Ser | Gln | Thr | Leu 1055 | Gln |
| Glu | Lys | Val | Leu | Leu 1060 | Val | Ser | Glu | Ala | Glu 1065 | Ile | Thr | Phe | Asp | Thr 1070 | Ser |
| Val | Tyr | Ser 1075 | Gln | Leu | Pro | Gly | Gln 1080 | Glu | Ala | Phe | Leu | Arg 1085 | Ala | Gln | Val |
| Glu | Thr 1090 | Thr | Leu | Glu | Glu | Tyr 1095 | Val | Val | Tyr | Glu | Pro 1100 | Ile | Phe | Leu | Val |
| Ala | Gly 1105 | Ser | Ser | Val | Gly | Gly 1110 | Leu | Leu | Leu | Leu | Ala 1115 | Leu | Ile | Thr | Val 1120 |
| Val | Leu | Tyr | Lys | Leu 1125 | Gly | Xaa | Xaa | Lys | Arg 1130 | Gln | Tyr | Lys | Glu 1135 | Met | Leu |
| Asp | Gly | Lys 1140 | Ala | Ala | Asp | Pro | Val 1145 | Thr | Xaa | Gly | Gln | Ala 1150 | Asp | Phe | Gly |
| Cys | Glu 1155 | Thr | Pro | Pro | Tyr | Leu 1160 | Val | Ser | | | | | | | |

( 2 ) INFORMATION FOR SEQ ID NO:56:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:56:

CCTGTCATGG GTCTAACCTG    20

( 2 ) INFORMATION FOR SEQ ID NO:57:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:57:

AGGTTAGACC CATGACAGG    19

( 2 ) INFORMATION FOR SEQ ID NO:58:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:58:

GGCCTTGCAG CTGGACAATG    20

( 2 ) INFORMATION FOR SEQ ID NO:59:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:59:

CCAAAGCTGG CTGCATCCTC TC    22

( 2 ) INFORMATION FOR SEQ ID NO:60:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:60:

CCGCCTGCCA CTGGCGTGTG C    21

( 2 ) INFORMATION FOR SEQ ID NO:61:

( i ) SEQUENCE CHARACTERISTICS:

(A) LENGTH: 22 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:61:

CCCAGATGAA GGACTTCGTC AA                                                        22

(2) INFORMATION FOR SEQ ID NO:62:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:62:

GCTGGGATCA TTCGCTATGC                                                           20

(2) INFORMATION FOR SEQ ID NO:63:

(i) SEQUENCE CHARACTERISTICS:
                (A) LENGTH: 21 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:63:

CAATGGATGG ACCAGTTCTG G                                                         21

(2) INFORMATION FOR SEQ ID NO:64:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:64:

CAGATCGGCT CCTACTTTGG                                                           20

(2) INFORMATION FOR SEQ ID NO:65:

(i) SEQUENCE CHARACTERISTICS:
                (A) LENGTH: 19 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:65:

CATGGAGCCT CGAGACAGG                                                            19

(2) INFORMATION FOR SEQ ID NO:66:

(i) SEQUENCE CHARACTERISTICS:
                (A) LENGTH: 21 base pairs
                (B) TYPE: nucleic acid
                (C) STRANDEDNESS: single
                (D) TOPOLOGY: linear ( i i ) MOLECULE TYPE: DNA ( x i ) SEQUENCE DESCRIPTION: SEQ ID NO:66:

CCACTGTCCT CGAAGCTGGA G                                                                    21

( 2 ) INFORMATION FOR SEQ ID NO:67:

( i ) SEQUENCE CHARACTERISTICS:
                ( A ) LENGTH: 26 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:67:

CTTCGTCCTG TGCTGGCTGT GGGCTC                                                               26

( 2 ) INFORMATION FOR SEQ ID NO:68:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:68:

CGCCTGGCAT GTGAGGCTGA G                                                                    21

( 2 ) INFORMATION FOR SEQ ID NO:69:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:69:

CCGTGATCAG TAGGCAGGAA G                                                                    21

( 2 ) INFORMATION FOR SEQ ID NO:70:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:70:

GTCACAGAGG GAACCTCC                                                                        18

( 2 ) INFORMATION FOR SEQ ID NO:71:

( i ) SEQUENCE CHARACTERISTICS:
                ( A ) LENGTH: 23 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:71:

GCTCCTGAGT GAGGCTGAAA TCA                                                                  23

( 2 ) INFORMATION FOR SEQ ID NO:72:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:72:

GAGATGCTGG ATCTACCATC TGC    23

( 2 ) INFORMATION FOR SEQ ID NO:73:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:73:

CTGAGCTGGG AGATTTTTAT GG    22

( 2 ) INFORMATION FOR SEQ ID NO:74:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:74:

GTGGATCAGC ACTGAAATCT G    21

( 2 ) INFORMATION FOR SEQ ID NO:75:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:75:

CGTTTGAAGA AGCCAAGCTT G    21

( 2 ) INFORMATION FOR SEQ ID NO:76:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:76:

CACAGCGGAG GTGCAGGCAG    20

( 2 ) INFORMATION FOR SEQ ID NO:77:

( i ) SEQUENCE CHARACTERISTICS:

(A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:77:

CTCACTGCTT GCGCTGGC 18

(2) INFORMATION FOR SEQ ID NO:78:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:78:

CGGTAAGATA GCTCTGCTGG 20

(2) INFORMATION FOR SEQ ID NO:79:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:79:

GAGCCCACAG CCAGCACAGG 20

(2) INFORMATION FOR SEQ ID NO:80:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:80:

GATCCAACGC CAGATCATAC C 21

(2) INFORMATION FOR SEQ ID NO:81:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:81:

CACGGCCAGG TCCACCAGGC 20

(2) INFORMATION FOR SEQ ID NO:82:

(i) SEQUENCE CHARACTERISTICS:
            (A) LENGTH: 21 base pairs
            (B) TYPE: nucleic acid
            (C) STRANDEDNESS: single
            (D) TOPOLOGY: linear ( i i ) MOLECULE TYPE: DNA ( x i ) SEQUENCE DESCRIPTION: SEQ ID NO:82:

CACGTCCCCT AGCACTGTCA G 21

( 2 ) INFORMATION FOR SEQ ID NO:83:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:83:

TTGACGAAGT CCTTCATCTG GG 22

( 2 ) INFORMATION FOR SEQ ID NO:84:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:84:

GAACTGCAAG CTGGAGCCCA G 21

( 2 ) INFORMATION FOR SEQ ID NO:85:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:85:

CTGGATGCTG CGAAGTGCTA C 21

( 2 ) INFORMATION FOR SEQ ID NO:86:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:86:

GCCTTGGAGC TGGACGATGG C 21

( 2 ) INFORMATION FOR SEQ ID NO:87:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:87:

GTAAGATCTC CAGAGTGTCC AAGACAAGAG ATG 33

( 2 ) INFORMATION FOR SEQ ID NO:88:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:88:

```
CTTCTCGAGT GTGAGAGCTG AACTGAAACC TTC                         33
```

( 2 ) INFORMATION FOR SEQ ID NO:89:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:89:

```
CGCTGTGACG TCAGAGTTGA GTCCAAATAT GG                          32
```

( 2 ) INFORMATION FOR SEQ ID NO:90:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:90:

```
GGTGACACTA TAGAATAGGG C                                      21
```

( 2 ) INFORMATION FOR SEQ ID NO:91:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:91:

```
AAGCAGGAGCTCCTGTGT                                           18
```

( 2 ) INFORMATION FOR SEQ ID NO:92:

( i ) SEQUENCE CHARACTERISTICS:
        ( A ) LENGTH: 852 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 61..852

( x i ) SEQUENCE DESCRIPTION: SEQ ID NO:92:

```
TGATCTCCCT CCAGGCCACT GTTCCCTCTC CACTTCCCCT CACCGCTGCA CTGCTCAGAG    60
```

| | | | | | | | | | | | | | | | | |
|---|---|---|---|---|---|---|---|---|---|---|---|---|---|---|---|---|
| ATG | GCC | CTT | GGG | GCT | GTG | GTC | CTC | CTT | GGG | GTC | CTG | GCT | TCT | TAC | CAC | 108 |
| Met | Ala | Leu | Gly | Ala | Val | Val | Leu | Leu | Gly | Val | Leu | Ala | Ser | Tyr | His | |
| 1 | | | | 5 | | | | | 10 | | | | | 15 | | |
| GGA | TTC | AAC | TTG | GAC | GTG | ATG | AGC | GGT | GAT | CTT | CCA | GGA | AGA | CGC | AGC | 156 |
| Gly | Phe | Asn | Leu | Asp | Val | Met | Ser | Gly | Asp | Leu | Pro | Gly | Arg | Arg | Ser | |
| | | | 20 | | | | 25 | | | | | 30 | | | | |
| GGG | CTT | CGG | GCA | GAG | CGT | GAT | GCA | GTT | TGG | GGA | TCT | CGA | CTC | GTG | GTG | 204 |
| Gly | Leu | Arg | Ala | Glu | Arg | Asp | Ala | Val | Trp | Gly | Ser | Arg | Leu | Val | Val | |
| | | 35 | | | | 40 | | | | | 45 | | | | | |
| GGA | GCC | CCC | CTG | GCG | GTG | GTG | TCG | GCC | AAC | CAC | ACA | GGA | CGG | CTG | TAC | 252 |
| Gly | Ala | Pro | Leu | Ala | Val | Val | Ser | Ala | Asn | His | Thr | Gly | Arg | Leu | Tyr | |
| | 50 | | | | 55 | | | | | 60 | | | | | | |
| GAG | TGT | GCG | CCT | GCC | TCC | GGC | ACC | TGC | ACG | CCC | ATT | TTC | CCA | TTC | ATG | 300 |
| Glu | Cys | Ala | Pro | Ala | Ser | Gly | Thr | Cys | Thr | Pro | Ile | Phe | Pro | Phe | Met | |
| 65 | | | | | 70 | | | | | 75 | | | | | 80 | |
| CCC | CCC | GAA | GCC | GTG | AAC | ATG | TCC | CTG | GGC | CTG | TCC | CTG | GCA | GCC | TCC | 348 |
| Pro | Pro | Glu | Ala | Val | Asn | Met | Ser | Leu | Gly | Leu | Ser | Leu | Ala | Ala | Ser | |
| | | | | 85 | | | | | 90 | | | | | 95 | | |
| CCC | AAC | CAT | TCC | CAG | CTG | CTG | GCT | TGT | GGC | CCG | ACC | GTG | CAT | AGA | GCC | 396 |
| Pro | Asn | His | Ser | Gln | Leu | Leu | Ala | Cys | Gly | Pro | Thr | Val | His | Arg | Ala | |
| | | | 100 | | | | | 105 | | | | | 110 | | | |
| TGC | GGG | GAG | GAC | GTG | TAC | GCC | CAG | GGT | TTC | TGT | GTG | CTG | CTG | GAT | GCC | 444 |
| Cys | Gly | Glu | Asp | Val | Tyr | Ala | Gln | Gly | Phe | Cys | Val | Leu | Leu | Asp | Ala | |
| | | 115 | | | | | 120 | | | | | 125 | | | | |
| CAC | GCA | CAG | CCC | ATC | GGG | ACT | GTG | CCA | GCT | GCC | CTG | CCC | GAG | TGC | CCA | 492 |
| His | Ala | Gln | Pro | Ile | Gly | Thr | Val | Pro | Ala | Ala | Leu | Pro | Glu | Cys | Pro | |
| | 130 | | | | | 135 | | | | | 140 | | | | | |
| GAT | CAA | GAG | ATG | GAC | ATT | GTC | TTC | CTG | ATT | GAC | GGC | TCT | GGC | AGC | ATT | 540 |
| Asp | Gln | Glu | Met | Asp | Ile | Val | Phe | Leu | Ile | Asp | Gly | Ser | Gly | Ser | Ile | |
| 145 | | | | | 150 | | | | | 155 | | | | | 160 | |
| AGC | TCA | AAT | GAC | TTC | CGC | AAG | ATG | AAG | GAC | TTT | GTC | AGA | GCT | GTG | ATG | 588 |
| Ser | Ser | Asn | Asp | Phe | Arg | Lys | Met | Lys | Asp | Phe | Val | Arg | Ala | Val | Met | |
| | | | | 165 | | | | | 170 | | | | | 175 | | |
| GAC | CAG | TTC | AAG | GAC | ACC | AAC | ACC | CAG | TTC | TCG | CTG | ATG | CAG | TAC | TCC | 636 |
| Asp | Gln | Phe | Lys | Asp | Thr | Asn | Thr | Gln | Phe | Ser | Leu | Met | Gln | Tyr | Ser | |
| | | | 180 | | | | | 185 | | | | | 190 | | | |
| AAT | GTG | CTG | GTG | ACA | CAT | TTC | ACC | TTC | AGC | AGC | TTC | CGG | AAC | AGC | TCC | 684 |
| Asn | Val | Leu | Val | Thr | His | Phe | Thr | Phe | Ser | Ser | Phe | Arg | Asn | Ser | Ser | |
| | | 195 | | | | | 200 | | | | | 205 | | | | |
| AAT | CCT | CAG | GGC | CTA | GTG | GAG | CCC | ATT | GTG | CAG | CTG | ACA | GGC | CTC | ACG | 732 |
| Asn | Pro | Gln | Gly | Leu | Val | Glu | Pro | Ile | Val | Gln | Leu | Thr | Gly | Leu | Thr | |
| | 210 | | | | | 215 | | | | | 220 | | | | | |
| TTC | ACG | GCC | ACA | GGG | ATC | CTG | AAA | GTG | GTG | ACA | GAG | CTG | TTT | CAA | ACC | 780 |
| Phe | Thr | Ala | Thr | Gly | Ile | Leu | Lys | Val | Val | Thr | Glu | Leu | Phe | Gln | Thr | |
| 225 | | | | | 230 | | | | | 235 | | | | | 240 | |
| AAG | AAC | GGG | GCC | CGC | GAA | AGT | GCC | AAG | AAG | ATC | CTC | ATC | GTC | ATC | ACA | 828 |
| Lys | Asn | Gly | Ala | Arg | Glu | Ser | Ala | Lys | Lys | Ile | Leu | Ile | Val | Ile | Thr | |
| | | | | 245 | | | | | 250 | | | | | 255 | | |
| GAT | GGG | CAG | AAG | TAC | AAA | GCG | GCA | | | | | | | | | 852 |
| Asp | Gly | Gln | Lys | Tyr | Lys | Ala | Ala | | | | | | | | | |
| | | | | 260 | | | | | | | | | | | | |

( 2 ) INFORMATION FOR SEQ ID NO:93:

( i ) SEQUENCE CHARACTERISTICS:
        ( A ) LENGTH: 264 amino acids
        ( B ) TYPE: amino acid
        ( D ) TOPOLOGY: linear ( i i ) MOLECULE TYPE: protein ( x i ) SEQUENCE DESCRIPTION: SEQ ID NO:93:

| Met | Ala | Leu | Gly | Ala | Val | Val | Leu | Leu | Gly | Val | Leu | Ala | Ser | Tyr | His |
|1|||| 5 ||||| 10 ||||| 15 ||

| Gly | Phe | Asn | Leu | Asp | Val | Met | Ser | Gly | Asp | Leu | Pro | Gly | Arg | Arg | Ser |
||||20|||||25||||30|||

| Gly | Leu | Arg | Ala | Glu | Arg | Asp | Ala | Val | Trp | Gly | Ser | Arg | Leu | Val | Val |
|||35|||||40||||45|||

| Gly | Ala | Pro | Leu | Ala | Val | Val | Ser | Ala | Asn | His | Thr | Gly | Arg | Leu | Tyr |
||50||||55||||| 60 ||||

| Glu | Cys | Ala | Pro | Ala | Ser | Gly | Thr | Cys | Thr | Pro | Ile | Phe | Pro | Phe | Met |
|65||||70||||| 75 |||||80|

| Pro | Pro | Glu | Ala | Val | Asn | Met | Ser | Leu | Gly | Leu | Ser | Leu | Ala | Ala | Ser |
|||| 85 ||||| 90 ||||| 95 |

| Pro | Asn | His | Ser | Gln | Leu | Leu | Ala | Cys | Gly | Pro | Thr | Val | His | Arg | Ala |
||| 100 |||||105|||||110|||

| Cys | Gly | Glu | Asp | Val | Tyr | Ala | Gln | Gly | Phe | Cys | Val | Leu | Leu | Asp | Ala |
||| 115 |||||120|||||125|||

| His | Ala | Gln | Pro | Ile | Gly | Thr | Val | Pro | Ala | Ala | Leu | Pro | Glu | Cys | Pro |
||130|||||135|||||140||||

| Asp | Gln | Glu | Met | Asp | Ile | Val | Phe | Leu | Ile | Asp | Gly | Ser | Gly | Ser | Ile |
|145||||150|||||155|||||160|

| Ser | Ser | Asn | Asp | Phe | Arg | Lys | Met | Lys | Asp | Phe | Val | Arg | Ala | Val | Met |
|||| 165 |||||170|||||175||

| Asp | Gln | Phe | Lys | Asp | Thr | Asn | Thr | Gln | Phe | Ser | Leu | Met | Gln | Tyr | Ser |
||| 180 |||||185|||||190|||

| Asn | Val | Leu | Val | Thr | His | Phe | Thr | Phe | Ser | Ser | Phe | Arg | Asn | Ser | Ser |
|||195|||||200|||||205|||

| Asn | Pro | Gln | Gly | Leu | Val | Glu | Pro | Ile | Val | Gln | Leu | Thr | Gly | Leu | Thr |
||210||||215|||||220||||

| Phe | Thr | Ala | Thr | Gly | Ile | Leu | Lys | Val | Val | Thr | Glu | Leu | Phe | Gln | Thr |
|225||||230|||||235|||||240|

| Lys | Asn | Gly | Ala | Arg | Glu | Ser | Ala | Lys | Lys | Ile | Leu | Ile | Val | Ile | Thr |
||||245|||||250|||||255||

| Asp | Gly | Gln | Lys | Tyr | Lys | Ala | Ala |
||||260||||

(2) INFORMATION FOR SEQ ID NO:94:

(i) SEQUENCE CHARACTERISTICS:
  (A) LENGTH: 22 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:94:

CTGGTCTGGA GGTGCCTTCC TG    22

(2) INFORMATION FOR SEQ ID NO:95:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:95:

CCTGAGCAGG AGCACCTGGC C    21

( 2 ) INFORMATION FOR SEQ ID NO:96:

( i ) SEQUENCE CHARACTERISTICS:
        ( A ) LENGTH: 2499 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:96:

```
ATGACCTTCG GCACTGTGCT TCTTCTGAGT GTCCTGGCTT CTTATCATGG ATTCAACCTG      60
GATGTGGAGG AGCCTACGAT CTTCCAGGAG GATGCAGGCG GCTTTGGGCA GAGCGTGGTG     120
CAGTTCGGTG GATCTCGACT CGTGGTGGGA GCACCCCTGG AGGTGGTGGC GGCCAACCAG     180
ACGGGACGGC TGTATGACTG CGCAGCTGCC ACCGGCATGT GCCAGCCCAT CCCGCTGCAC     240
ATCCGCCCTG AGGCCGTGAA CATGTCCTTG GGCCTGACCC TGCAGCCTC CACCAACGGC      300
TCCCGGCTCC TGGCCTGTGG CCCGACCCTG CACAGAGTCT GTGGGGAGAA CTCATACTCA     360
AAGGGTTCCT GCCTCCTGCT GGGCTCGCGC TGGGAGATCA TCCAGACAGT CCCCGACGCC     420
ACGCCAGAGT GTCCACATCA AGAGATGGAC ATCGTCTTCC TGATTGACGG CTCTGGAAGC     480
ATTGACCAAA ATGACTTTAA CCAGATGAAG GGCTTTGTCC AAGCTGTCAT GGGCCAGTTT     540
GAGGGCACTG ACACCCTGTT TGCACTGATG CAGTACTCAA ACCTCCTGAA GATCCACTTC     600
ACCTTCACCC AATTCCGGAC CAGCCCGAGC CAGCAGAGCC TGGTGGATCC CATCGTCCAA     660
CTGAAAGGCC TGACGTTCAC GGCCACGGGC ATCCTGACAG TGGTGACACA GCTATTTCAT     720
CATAAGAATG GGCCCGAAA AAGTGCCAAG AAGATCCTCA TTGTCATCAC AGATGGGCAG     780
AAGTACAAAG ACCCCCTGGA ATACAGTGAT GTCATCCCCC AGGCAGAGAA GGCTGGCATC     840
ATCCGCTACG CTATCGGGGT GGGACACGCT TTCCAGGGAC CCACTGCCAG GCAGGAGCTG     900
AATACCATCA GCTCAGCGCC TCCGCAGGAC CACGTGTTCA AGGTGGACAA CTTTGCAGCC     960
CTTGGCAGCA TCCAGAAGCA GCTGCAGGAG AAGATCTATG CAGTTGAGGG AACCCAGTCC    1020
AGGGCAAGCA GCTCCTTCCA GCACGAGATG TCCCAAGAAG GCTTCAGCAC AGCCCTCACA    1080
ATGGATGGCC TCTTCCTGGG GGCTGTGGGG AGCTTTAGCT GGTCTGGAGG TGCCTTCCTG    1140
TATCCCCCAA ATATGAGCCC CACCTTCATC AACATGTCTC AGGAGAATGT GGACATGAGG    1200
GACTCTTACC TGGGTTACTC CACCGAGCTA GCCCTGTGGA AGGGGGTACA GAACCTGGTC    1260
CTGGGGGCCC CCCGCTACCA GCATACCGGG AAGGCTGTCA TCTTCACCCA GGTGTCCAGG    1320
CAATGGAGGA AGAAGGCCGA AGTCACAGGG ACGCAGATCG GCTCCTACTT CGGGGCCTCC    1380
CTCTGCTCCG TGGATGTGGA CAGCGATGGC AGCACCGACC TGATCCTCAT TGGGGCCCCC    1440
CATTACTATG AGCAGACCCG AGGGGGCCAG GTGTCCGTGT GTCCCTTGCC TAGGGGGAGG    1500
GTGCAGTGGC AGTGTGACGC TGTTCTCCGT GGTGAGCAGG GCCACCCCTG GGGCCGCTTT    1560
GGGGCAGCCC TGACAGTGTT GGGGGATGTG AATGAGGACA AGCTGATAGA CGTGGCCATT    1620
GGGGCCCCGG GAGAGCAGGA GAACCGGGGT GCTGTCTACC TGTTTCACGG AGCCTCAGAA    1680
TCCGGCATCA GCCCCTCCCA CAGCCAGCGG ATTGCCAGCT CCAGCTCTC CCCCAGGCTG    1740
CAGTATTTTG GCAGGCGCT GAGTGGGGGT CAGGACCTCA CCCAGGATGG ACTGATGGAC    1800
CTGGCCGTGG GGCCCGGGG CCAGGTGCTC CTGCTCAGGA GTCTGCCGGT GCTGAAAGTG    1860
GGGGTGGCCA TGAGATTCAG CCCTGTGGAG GTGGCCAAGG CTGTGTACCG GTGCTGGGAA    1920
GAGAAGCCCA GTGCCCTGGA AGCTGGGGAC GCCACCGTCT GTCTCACCAT CCAGAAAAGC    1980
```

-continued

```
TCACTGGACC AGCTAGGTGA CATCCAAAGC TCTGTCAGGT TTGATCTGGC ACTGGACCCA    2040
GGTCGTCTGA CTTCTCGTGC CATTTTCAAT GAAACCAAGA ACCCCACTTT GACTCGAAGA    2100
AAAACCCTGG GACTGGGGAT TCACTGTGAA ACCCTGAAGC TGCTTTTGCC AGTGAGGACT    2160
TTGGGTTCTG GGAAGGGGGA GAGAGGAGGA GCCCAAGGCT GGCCTGGAGC ACCCCGTTC     2220
TCTGCTGAGC GAGGTGGGAA GGGTTAGGAT GTTGGGGCTG GAGAGAGGGA CATTAGGGCA    2280
GGAGAACCTG GCTCCACGGC TTGGAGGGAG CACTGTCAGG GCAGTGGGGA GTGGATGCAG    2340
TGGAGGAGGA CTTGTGGTGG AGCGTAGAGA GGACAGCAGG TTCTTGAAAG CCTGTTCTCT    2400
CTCAGGATTG TGTGGAGGAT GTGGTGAGCC CCATCATTCT GCACCTCAAC TTCTCACTGG    2460
TGAGAGAGCC CATCCCCTCC CCCCAGAACC TGCGTCCTG                           2499
```

( 2 ) INFORMATION FOR SEQ ID NO:97:

( i ) SEQUENCE CHARACTERISTICS:
        ( A ) LENGTH: 3956 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:97:

```
TTTAACTGCA CCAACTTTAA AATACGCTAT TGGAGCTGGA ATTACCGCGG CTGCTGGCAC     60
CAGACTTGCC CTCCAATGGA TCCTCGTTAA AGGATTTAAA GTGGACTCAT TCCAATTACA    120
GGGCCTCGAA AGAGTCCTGT ATTGTTATTT TTCGTCACTA CCTCCCCGGG TCGGGAGTGG    180
GTAATTTGCG CGCCTGCTGC CTTCCTTGGA TGTGGTAGCC GTTTCTCAGG CTCCCTCTCC    240
GGAATCGAAC CCTGATTCCC CGTCACCCGT GGTCACCATG GTAGGCACGT GCAGTTCGGT    300
GGATCTCGAC TCGTGGTGGG AGCACCCCTG GAGGTGGTGG CGGCCAACCA GACGGGACGG    360
CTGTATGACT GCGCAGCTGC CACCGGCATG TGCCAGCCCA TCCCGCTGCA CATCCGCCCT    420
GAGGCCGTGA ACATGTCCTT GGGCCTGACC CTGGCAGCCT CCACCAACGG CTCCCGGCTC    480
CTGGCCTGTG GCCCGACCCT GCACAGAGTC TGTGGGGAGA ACTCATACTC AAAGGGTTCC    540
TGCCTCCTGC TGGGCTCGCG CTGGGAGATC ATCCAGACAG TCCCGACGC CACGCCAGAG     600
TGTCCACATC AAGAGATGGA CATCGTCTTC CTGATTGACG GCTCTGGAAG CATTGACCAA    660
AATGACTTTA ACCAGATGAA GGGCTTTGTC CAAGCTGTCA TGGGCCAGTT TGAGGGCACT    720
GACACCCTGT TTGCACTGAT GCAGTACTCA AACCTCCTGA AGATCCACTT CACCTTCACC    780
CAATTCCGGA CCAGCCCGAG CCAGCAGAGC CTGGTGGATC CCATCGTCCA ACTGAAAGGC    840
CTGACGTTCA CGGCCACGGG CATCCTGACA GTGGTGACAC AGCTATTTCA TCATAAGAAT    900
GGGGCCCGAA AAAGTGCCAA GAAGATCCTC ATTGTCATCA CAGATGGGCA GAAGTACAAA    960
GACCCCCTGG AATACAGTGA TGTCATCCCC CAGGCAGAGA AGGCTGGCAT CATCCGCTAC   1020
GCTATCGGGG TGGACACGC  TTTCCAGGGA CCCACTGCCA GGCAGGAGCT GAATACCATC   1080
AGCTCAGCGC CTCCGCAGGA CCACGTGTTC AAGGTGGACA ACTTTGCAGC CCTTGGCAGC   1140
ATCCAGAAGC AGCTGCAGGA GAAGATCTAT GCAGTTGAGG GAACCCAGTC CAGGGCAAGC   1200
AGCTCCTTCC AGCACGAGAT GTCCCAAGAA GGCTTCAGCA CAGCCCTCAC AATGGATGGC   1260
CTCTTCCTGG GGGCTGTGGG GAGCTTTAGC TGGTCTGGAG GTGCCTTCCT GTATCCCCCA   1320
AATATGAGCC CCACCTTCAT CAACATGTCT CAGGAGAATG TGGACATGAG GGACTCTTAC   1380
CTGGGTTACT CCACCGAGCT AGCCCTGTGG AAGGGGGTAC AGAACCTGGT CCTGGGGGCC   1440
CCCCGCTACC AGCATACCGG GAAGGCTGTC ATCTTCACCC AGGTGTCCAG GCAATGGAGG   1500
```

-continued

```
AAGAAGGCCG AAGTCACAGG GACGCAGATC GGCTCCTACT TCGGGGCCTC CCTCTGCTCC   1560
GTGGATGTGG ACAGCGATGG CAGCACCGAC CTGATCCTCA TTGGGGCCCC CCATTACTAT   1620
GAGCAGACCC GAGGGGGCCA GGTGTCCGTG TGTCCCTTGC CTAGGGGGAG GGTGCAGTGG   1680
CAGTGTGACG CTGTTCTCCG TGGTGAGCAG GGCCACCCCT GGGGCCGCTT TGGGGCAGCC   1740
CTGACAGTGT TGGGGGATGT GAATGAGGAC AAGCTGATAG ACGTGGCCAT TGGGCCCCG    1800
GGAGAGCAGG AGAACCGGGG TGCTGTCTAC CTGTTTCACG GAGCCTCAGA ATCCGGCATC   1860
AGCCCCTCCC ACAGCCAGCG GATTGCCAGC TCCCAGCTCT CCCCCAGGCT GCAGTATTTT   1920
GGGCAGGCGC TGAGTGGGGG TCAGGACCTC ACCCAGGATG GACTGATGGA CCTGGCCGTG   1980
GGGGCCCGGG GCCAGGTGCT CCTGCTCAGG AGTCTGCCGG TGCTGAAAGT GGGGGTGGCC   2040
ATGAGATTCA GCCCTGTGGA GGTGGCCAAG GCTGTGTACC GGTGCTGGGA AGAGAAGCCC   2100
AGTGCCCTGG AAGCTGGGGA CGCCACCGTC TGTCTCACCA TCCAGAAAAG CTCACTGGAC   2160
CAGCTAGGTG ACATCCAAAG CTCTGTCAGG TTTGATCTGG CACTGGACCC AGGTCGTCTG   2220
ACTTCTCGTG CCATTTTCAA TGAAACCAAG AACCCCACTT TGACTCGAAG AAAAACCCTG   2280
GGACTGGGGA TTCACTGTGA AACCCTGAAG CTGCTTTTGC CAGATTGTGT GGAGGATGTG   2340
GTGAGCCCCA TCATTCTGCA CCTCAACTTC TCACTGGTGA GAGAGCCCAT CCCCTCCCCC   2400
CAGAACCTGC GTCCTGTGCT GGCCGTGGGC TCACAAGACC TCTTCACTGC TTCTCTCCCC   2460
TTCGAGAAGA ACTGTGGGCA AGATGGCCTC TGTGAAGGGG ACCTGGGTGT CACCCTCAGC   2520
TTCTCAGGCC TGCAGACCCT GACCGTGGGG AGCTCCCTGG AGCTCAACGT GATTGTGACT   2580
GTGTGGAACG CAGGTGAGGA TTCCTACGGA ACCGTGGTCA GCCTCTACTA TCCAGCAGGG   2640
CTGTCGCACC GACGGGTGTC AGGAGCCCAG AAGCAGCCCC ATCAGAGTGC CCTGCGCCTG   2700
GCATGTGAGA CAGTGCCCAC TGAGGATGAG GGCCTAAGAA GCAGCCGCTG CAGTGTCAAC   2760
CACCCCATCT TCCATGAGGG CTCTAACGGC ACCTTCATAG TCACATTCGA TGTCTCCTAC   2820
AAGGCCACCC TGGGAGACAG GATGCTTATG AGGGCCAGTG CAAGCAGTGA GAACAATAAG   2880
GCTTCAAGCA GCAAGGCCAC CTTCCAGCTG GAGCTCCCGG TGAAGTATGC AGTCTACACC   2940
ATGATCAGCA GGCAGGAAGA ATCCACCAAG TACTTCAACT TGCAACCTC CGATGAGAAG    3000
AAAATGAAAG AGGCTGAGCA TCGATACCGT GTGAATAACC TCAGCCAGCG AGATCTGGCC   3060
ATCAGCATTA ACTTCTGGGT TCCTGTCCTG CTGAACGGGG TGGCTGTGTG GGATGTGGTC   3120
ATGGAGGCCC CATCTCAGAG TCTCCCCTGT GTTCAGAGA GAAAACCTCC CCAGCATTCT    3180
GACTTCCTGA CCCAGATTTC AAGAAGTCCC ATGCTGGACT GCTCCATTGC TGACTGCCTG   3240
CAGTTCCGCT GTGACGTCCC CTCCTTCAGC GTCCAGGAGG AGCTGGATTT CACCCTGAAG   3300
GGCAATCTCA GTTTCGGCTG GGTCCGCGAG ACATTGCAGA AGAAGGTGTT GGTCGTGAGT   3360
GTGGCTGAAA TTACGTTCGA CACATCCGTG TACTCCCAGC TTCCAGGACA GGAGGCATTT   3420
ATGAGAGCTC AGATGGAGAT GGTGCTAGAA GAAGACGAGG TCTACAATGC CATTCCCATC   3480
ATCATGGGCA GCTCTGTGGG GGCTCTGCTA CTGCTGGCGC TCATCACAGC CACACTGTAC   3540
AAGCTTGGCT TCTTCAAACG CCACTACAAG GAAATGCTGG AGGACAAGCC TGAAGACACT   3600
GCCACATTCA GTGGGGACGA TTTCAGCTGT GTGGCCCCAA ATGTGCCTTT GTCCTAATAA   3660
TCCACTTTCC TGTTTATCTC TACCACTGTG GGCTGGACTT GCTTGCAACC ATAAATCAAC   3720
TTACATGGAA ACAACTTCTG CATAGATCTG CACTGGCCTA AGCAACCTAC CAGGTGCTAA   3780
GCACCTTCTC GGAGAGATAG AGATTGTCAA TGTTTTTACA TATCTGTCCA TCTTTTTCAG   3840
CAATGACCCA CTTTTTACAG AAGCAGGCAT GGTGCCAGCA TAAATTTTCA TATGCTTAAG   3900
```

```
AATTGTCACA TGAAAAAAAA AAAAAAAAAA AAAAAAAAAA AAAAAAAAAA CTTTAG            3 9 5 6
```

( 2 ) INFORMATION FOR SEQ ID NO:98:

( i ) SEQUENCE CHARACTERISTICS:
        ( A ) LENGTH: 3785 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..3486

( x i ) SEQUENCE DESCRIPTION: SEQ ID NO:98:

```
ATG ACC TTC GGC ACT GTG CTT CTT CTG AGT GTC CTG GCT TCT TAT CAT          4 8
Met Thr Phe Gly Thr Val Leu Leu Leu Ser Val Leu Ala Ser Tyr His
  1           5                  10                  15

GGA TTC AAC CTG GAT GTG GAG GAG CCT ACG ATC TTC CAG GAG GAT GCA          9 6
Gly Phe Asn Leu Asp Val Glu Glu Pro Thr Ile Phe Gln Glu Asp Ala
             20                  25                  30

GGC GGC TTT GGG CAG AGC GTG GTG CAG TTC GGT GGA TCT CGA CTC GTG         1 4 4
Gly Gly Phe Gly Gln Ser Val Val Gln Phe Gly Gly Ser Arg Leu Val
         35                  40                  45

GTG GGA GCA CCC CTG GAG GTG GTG GCG GCC AAC CAG ACG GGA CGG CTG         1 9 2
Val Gly Ala Pro Leu Glu Val Val Ala Ala Asn Gln Thr Gly Arg Leu
     50                  55                  60

TAT GAC TGC GCA GCT GCC ACC GGC ATG TGC CAG CCC ATC CCG CTG CAC         2 4 0
Tyr Asp Cys Ala Ala Ala Thr Gly Met Cys Gln Pro Ile Pro Leu His
 65                  70                  75                  80

ATC CGC CCT GAG GCC GTG AAC ATG TCC TTG GGC CTG ACC CTG GCA GCC         2 8 8
Ile Arg Pro Glu Ala Val Asn Met Ser Leu Gly Leu Thr Leu Ala Ala
                 85                  90                  95

TCC ACC AAC GGC TCC CGG CTC CTG GCC TGT GGC CCG ACC CTG CAC AGA         3 3 6
Ser Thr Asn Gly Ser Arg Leu Leu Ala Cys Gly Pro Thr Leu His Arg
            100                 105                 110

GTC TGT GGG GAG AAC TCA TAC TCA AAG GGT TCC TGC CTC CTG CTG GGC         3 8 4
Val Cys Gly Glu Asn Ser Tyr Ser Lys Gly Ser Cys Leu Leu Leu Gly
        115                 120                 125

TCG CGC TGG GAG ATC ATC CAG ACA GTC CCC GAC GCC ACG CCA GAG TGT         4 3 2
Ser Arg Trp Glu Ile Ile Gln Thr Val Pro Asp Ala Thr Pro Glu Cys
    130                 135                 140

CCA CAT CAA GAG ATG GAC ATC GTC TTC CTG ATT GAC GGC TCT GGA AGC         4 8 0
Pro His Gln Glu Met Asp Ile Val Phe Leu Ile Asp Gly Ser Gly Ser
145                 150                 155                 160

ATT GAC CAA AAT GAC TTT AAC CAG ATG AAG GGC TTT GTC CAA GCT GTC         5 2 8
Ile Asp Gln Asn Asp Phe Asn Gln Met Lys Gly Phe Val Gln Ala Val
                165                 170                 175

ATG GGC CAG TTT GAG GGC ACT GAC ACC CTG TTT GCA CTG ATG CAG TAC         5 7 6
Met Gly Gln Phe Glu Gly Thr Asp Thr Leu Phe Ala Leu Met Gln Tyr
            180                 185                 190

TCA AAC CTC CTG AAG ATC CAC TTC ACC TTC ACC CAA TTC CGG ACC AGC         6 2 4
Ser Asn Leu Leu Lys Ile His Phe Thr Phe Thr Gln Phe Arg Thr Ser
        195                 200                 205

CCG AGC CAG CAG AGC CTG GTG GAT CCC ATC GTC CAA CTG AAA GGC CTG         6 7 2
Pro Ser Gln Gln Ser Leu Val Asp Pro Ile Val Gln Leu Lys Gly Leu
    210                 215                 220

ACG TTC ACG GCC ACG GGC ATC CTG ACA GTG GTG ACA CAG CTA TTT CAT         7 2 0
Thr Phe Thr Ala Thr Gly Ile Leu Thr Val Val Thr Gln Leu Phe His
225                 230                 235                 240
```

-continued

| | | | | | | | | | | | | | | | | |
|---|---|---|---|---|---|---|---|---|---|---|---|---|---|---|---|---|
| CAT | AAG | AAT | GGG | GCC | CGA | AAA | AGT | GCC | AAG | AAG | ATC | CTC | ATT | GTC | ATC | 768 |
| His | Lys | Asn | Gly | Ala | Arg | Lys | Ser | Ala | Lys | Lys | Ile | Leu | Ile | Val | Ile | |
| | | | | 245 | | | | 250 | | | | | 255 | | | |
| ACA | GAT | GGG | CAG | AAG | TAC | AAA | GAC | CCC | CTG | GAA | TAC | AGT | GAT | GTC | ATC | 816 |
| Thr | Asp | Gly | Gln | Lys | Tyr | Lys | Asp | Pro | Leu | Glu | Tyr | Ser | Asp | Val | Ile | |
| | | | 260 | | | | | 265 | | | | | 270 | | | |
| CCC | CAG | GCA | GAG | AAG | GCT | GGC | ATC | ATC | CGC | TAC | GCT | ATC | GGG | GTG | GGA | 864 |
| Pro | Gln | Ala | Glu | Lys | Ala | Gly | Ile | Ile | Arg | Tyr | Ala | Ile | Gly | Val | Gly | |
| | | 275 | | | | | 280 | | | | | 285 | | | | |
| CAC | GCT | TTC | CAG | GGA | CCC | ACT | GCC | AGG | CAG | GAG | CTG | AAT | ACC | ATC | AGC | 912 |
| His | Ala | Phe | Gln | Gly | Pro | Thr | Ala | Arg | Gln | Glu | Leu | Asn | Thr | Ile | Ser | |
| | 290 | | | | | 295 | | | | | 300 | | | | | |
| TCA | GCG | CCT | CCG | CAG | GAC | CAC | GTG | TTC | AAG | GTG | GAC | AAC | TTT | GCA | GCC | 960 |
| Ser | Ala | Pro | Pro | Gln | Asp | His | Val | Phe | Lys | Val | Asp | Asn | Phe | Ala | Ala | |
| 305 | | | | 310 | | | | | 315 | | | | | | 320 | |
| CTT | GGC | AGC | ATC | CAG | AAG | CAG | CTG | CAG | GAG | AAG | ATC | TAT | GCA | GTT | GAG | 1008 |
| Leu | Gly | Ser | Ile | Gln | Lys | Gln | Leu | Gln | Glu | Lys | Ile | Tyr | Ala | Val | Glu | |
| | | | | 325 | | | | | 330 | | | | | 335 | | |
| GGA | ACC | CAG | TCC | AGG | GCA | AGC | AGC | TCC | TTC | CAG | CAC | GAG | ATG | TCC | CAA | 1056 |
| Gly | Thr | Gln | Ser | Arg | Ala | Ser | Ser | Ser | Phe | Gln | His | Glu | Met | Ser | Gln | |
| | | | 340 | | | | | 345 | | | | | 350 | | | |
| GAA | GGC | TTC | AGC | ACA | GCC | CTC | ACA | ATG | GAT | GGC | CTC | TTC | CTG | GGG | GCT | 1104 |
| Glu | Gly | Phe | Ser | Thr | Ala | Leu | Thr | Met | Asp | Gly | Leu | Phe | Leu | Gly | Ala | |
| | | 355 | | | | | 360 | | | | | 365 | | | | |
| GTG | GGG | AGC | TTT | AGC | TGG | TCT | GGA | GGT | GCC | TTC | CTG | TAT | CCC | CCA | AAT | 1152 |
| Val | Gly | Ser | Phe | Ser | Trp | Ser | Gly | Gly | Ala | Phe | Leu | Tyr | Pro | Pro | Asn | |
| | 370 | | | | | 375 | | | | | 380 | | | | | |
| ATG | AGC | CCC | ACC | TTC | ATC | AAC | ATG | TCT | CAG | GAG | AAT | GTG | GAC | ATG | AGG | 1200 |
| Met | Ser | Pro | Thr | Phe | Ile | Asn | Met | Ser | Gln | Glu | Asn | Val | Asp | Met | Arg | |
| 385 | | | | | 390 | | | | | 395 | | | | | 400 | |
| GAC | TCT | TAC | CTG | GGT | TAC | TCC | ACC | GAG | CTA | GCC | CTG | TGG | AAG | GGG | GTA | 1248 |
| Asp | Ser | Tyr | Leu | Gly | Tyr | Ser | Thr | Glu | Leu | Ala | Leu | Trp | Lys | Gly | Val | |
| | | | | 405 | | | | | 410 | | | | | 415 | | |
| CAG | AAC | CTG | GTC | CTG | GGG | GCC | CCC | CGC | TAC | CAG | CAT | ACC | GGG | AAG | GCT | 1296 |
| Gln | Asn | Leu | Val | Leu | Gly | Ala | Pro | Arg | Tyr | Gln | His | Thr | Gly | Lys | Ala | |
| | | | 420 | | | | | 425 | | | | | 430 | | | |
| GTC | ATC | TTC | ACC | CAG | GTG | TCC | AGG | CAA | TGG | AGG | AAG | AAG | GCC | GAA | GTC | 1344 |
| Val | Ile | Phe | Thr | Gln | Val | Ser | Arg | Gln | Trp | Arg | Lys | Lys | Ala | Glu | Val | |
| | | 435 | | | | | 440 | | | | | 445 | | | | |
| ACA | GGG | ACG | CAG | ATC | GGC | TCC | TAC | TTC | GGG | GCC | TCC | CTC | TGC | TCC | GTG | 1392 |
| Thr | Gly | Thr | Gln | Ile | Gly | Ser | Tyr | Phe | Gly | Ala | Ser | Leu | Cys | Ser | Val | |
| | 450 | | | | | 455 | | | | | 460 | | | | | |
| GAT | GTG | GAC | AGC | GAT | GGC | AGC | ACC | GAC | CTG | ATC | CTC | ATT | GGG | GCC | CCC | 1440 |
| Asp | Val | Asp | Ser | Asp | Gly | Ser | Thr | Asp | Leu | Ile | Leu | Ile | Gly | Ala | Pro | |
| 465 | | | | | 470 | | | | | 475 | | | | | 480 | |
| CAT | TAC | TAT | GAG | CAG | ACC | CGA | GGG | GGC | CAG | GTG | TCC | GTG | TGT | CCC | TTG | 1488 |
| His | Tyr | Tyr | Glu | Gln | Thr | Arg | Gly | Gly | Gln | Val | Ser | Val | Cys | Pro | Leu | |
| | | | | 485 | | | | | 490 | | | | | 495 | | |
| CCT | AGG | GGG | AGG | GTG | CAG | TGG | CAG | TGT | GAC | GCT | GTT | CTC | CGT | GGT | GAG | 1536 |
| Pro | Arg | Gly | Arg | Val | Gln | Trp | Gln | Cys | Asp | Ala | Val | Leu | Arg | Gly | Glu | |
| | | | 500 | | | | | 505 | | | | | 510 | | | |
| CAG | GGC | CAC | CCC | TGG | GGC | CGC | TTT | GGG | GCA | GCC | CTG | ACA | GTG | TTG | GGG | 1584 |
| Gln | Gly | His | Pro | Trp | Gly | Arg | Phe | Gly | Ala | Ala | Leu | Thr | Val | Leu | Gly | |
| | | 515 | | | | | 520 | | | | | 525 | | | | |
| GAT | GTG | AAT | GAG | GAC | AAG | CTG | ATA | GAC | GTG | GCC | ATT | GGG | GCC | CCG | GGA | 1632 |
| Asp | Val | Asn | Glu | Asp | Lys | Leu | Ile | Asp | Val | Ala | Ile | Gly | Ala | Pro | Gly | |
| | 530 | | | | | 535 | | | | | 540 | | | | | |
| GAG | CAG | GAG | AAC | CGG | GGT | GCT | GTC | TAC | CTG | TTT | CAC | GGA | GCC | TCA | GAA | 1680 |
| Glu | Gln | Glu | Asn | Arg | Gly | Ala | Val | Tyr | Leu | Phe | His | Gly | Ala | Ser | Glu | |
| 545 | | | | | 550 | | | | | 555 | | | | | 560 | |

| | |
|---|---|
| TCC GGC ATC AGC CCC TCC CAC AGC CAG CGG ATT GCC AGC TCC CAG CTC<br>Ser Gly Ile Ser Pro Ser His Ser Gln Arg Ile Ala Ser Ser Gln Leu<br>565            570                575 | 1728 |
| TCC CCC AGG CTG CAG TAT TTT GGG CAG GCG CTG AGT GGG GGT CAG GAC<br>Ser Pro Arg Leu Gln Tyr Phe Gly Gln Ala Leu Ser Gly Gly Gln Asp<br>       580            585                590 | 1776 |
| CTC ACC CAG GAT GGA CTG ATG GAC CTG GCC GTG GGG GCC CGG GGC CAG<br>Leu Thr Gln Asp Gly Leu Met Asp Leu Ala Val Gly Ala Arg Gly Gln<br>       595            600                605 | 1824 |
| GTG CTC CTG CTC AGG AGT CTG CCG GTG CTG AAA GTG GGG GTG GCC ATG<br>Val Leu Leu Leu Arg Ser Leu Pro Val Leu Lys Val Gly Val Ala Met<br>610            615                620 | 1872 |
| AGA TTC AGC CCT GTG GAG GTG GCC AAG GCT GTG TAC CGG TGC TGG GAA<br>Arg Phe Ser Pro Val Glu Val Ala Lys Ala Val Tyr Arg Cys Trp Glu<br>625            630                635            640 | 1920 |
| GAG AAG CCC AGT GCC CTG GAA GCT GGG GAC GCC ACC GTC TGT CTC ACC<br>Glu Lys Pro Ser Ala Leu Glu Ala Gly Asp Ala Thr Val Cys Leu Thr<br>       645            650                655 | 1968 |
| ATC CAG AAA AGC TCA CTG GAC CAG CTA GGT GAC ATC CAA AGC TCT GTC<br>Ile Gln Lys Ser Ser Leu Asp Gln Leu Gly Asp Ile Gln Ser Ser Val<br>       660            665                670 | 2016 |
| AGG TTT GAT CTG GCA CTG GAC CCA GGT CGT CTG ACT TCT CGT GCC ATT<br>Arg Phe Asp Leu Ala Leu Asp Pro Gly Arg Leu Thr Ser Arg Ala Ile<br>       675            680                685 | 2064 |
| TTC AAT GAA ACC AAG AAC CCC ACT TTG ACT CGA AGA AAA ACC CTG GGA<br>Phe Asn Glu Thr Lys Asn Pro Thr Leu Thr Arg Arg Lys Thr Leu Gly<br>690            695                700 | 2112 |
| CTG GGG ATT CAC TGT GAA ACC CTG AAG CTG CTT TTG CCA GAT TGT GTG<br>Leu Gly Ile His Cys Glu Thr Leu Lys Leu Leu Leu Pro Asp Cys Val<br>705            710                715            720 | 2160 |
| GAG GAT GTG GTG AGC CCC ATC ATT CTG CAC CTC AAC TTC TCA CTG GTG<br>Glu Asp Val Val Ser Pro Ile Ile Leu His Leu Asn Phe Ser Leu Val<br>       725            730                735 | 2208 |
| AGA GAG CCC ATC CCC TCC CCC CAG AAC CTG CGT CCT GTG CTG GCC GTG<br>Arg Glu Pro Ile Pro Ser Pro Gln Asn Leu Arg Pro Val Leu Ala Val<br>       740            745                750 | 2256 |
| GGC TCA CAA GAC CTC TTC ACT GCT TCT CTC CCC TTC GAG AAG AAC TGT<br>Gly Ser Gln Asp Leu Phe Thr Ala Ser Leu Pro Phe Glu Lys Asn Cys<br>       755            760                765 | 2304 |
| GGG CAA GAT GGC CTC TGT GAA GGG GAC CTG GGT GTC ACC CTC AGC TTC<br>Gly Gln Asp Gly Leu Cys Glu Gly Asp Leu Gly Val Thr Leu Ser Phe<br>       770            775                780 | 2352 |
| TCA GGC CTG CAG ACC CTG ACC GTG GGG AGC TCC CTG GAG CTC AAC GTG<br>Ser Gly Leu Gln Thr Leu Thr Val Gly Ser Ser Leu Glu Leu Asn Val<br>785            790                795            800 | 2400 |
| ATT GTG ACT GTG TGG AAC GCA GGT GAG GAT TCC TAC GGA ACC GTG GTC<br>Ile Val Thr Val Trp Asn Ala Gly Glu Asp Ser Tyr Gly Thr Val Val<br>       805            810                815 | 2448 |
| AGC CTC TAC TAT CCA GCA GGG CTG TCG CAC CGA CGG GTG TCA GGA GCC<br>Ser Leu Tyr Tyr Pro Ala Gly Leu Ser His Arg Arg Val Ser Gly Ala<br>       820            825                830 | 2496 |
| CAG AAG CAG CCC CAT CAG AGT GCC CTG CGC CTG GCA TGT GAG ACA GTG<br>Gln Lys Gln Pro His Gln Ser Ala Leu Arg Leu Ala Cys Glu Thr Val<br>       835            840                845 | 2544 |
| CCC ACT GAG GAT GAG GGC CTA AGA AGC AGC CGC TGC AGT GTC AAC CAC<br>Pro Thr Glu Asp Glu Gly Leu Arg Ser Ser Arg Cys Ser Val Asn His<br>850            855                860 | 2592 |
| CCC ATC TTC CAT GAG GGC TCT AAC GGC ACC TTC ATA GTC ACA TTC GAT<br>Pro Ile Phe His Glu Gly Ser Asn Gly Thr Phe Ile Val Thr Phe Asp<br>865            870                875            880 | 2640 |

| | | | | | | | | | | | | | | | | |
|---|---|---|---|---|---|---|---|---|---|---|---|---|---|---|---|---|
| GTC | TCC | TAC | AAG | GCC | ACC | CTG | GGA | GAC | AGG | ATG | CTT | ATG | AGG | GCC | AGT | 2688 |
| Val | Ser | Tyr | Lys | Ala | Thr | Leu | Gly | Asp | Arg | Met | Leu | Met | Arg | Ala | Ser | |
| | | | 885 | | | | | 890 | | | | | | 895 | | |
| GCA | AGC | AGT | GAG | AAC | AAT | AAG | GCT | TCA | AGC | AGC | AAG | GCC | ACC | TTC | CAG | 2736 |
| Ala | Ser | Ser | Glu | Asn | Asn | Lys | Ala | Ser | Ser | Ser | Lys | Ala | Thr | Phe | Gln | |
| | | | 900 | | | | | 905 | | | | | 910 | | | |
| CTG | GAG | CTC | CCG | GTG | AAG | TAT | GCA | GTC | TAC | ACC | ATG | ATC | AGC | AGG | CAG | 2784 |
| Leu | Glu | Leu | Pro | Val | Lys | Tyr | Ala | Val | Tyr | Thr | Met | Ile | Ser | Arg | Gln | |
| | | | 915 | | | | | 920 | | | | | 925 | | | |
| GAA | GAA | TCC | ACC | AAG | TAC | TTC | AAC | TTT | GCA | ACC | TCC | GAT | GAG | AAG | AAA | 2832 |
| Glu | Glu | Ser | Thr | Lys | Tyr | Phe | Asn | Phe | Ala | Thr | Ser | Asp | Glu | Lys | Lys | |
| | | | 930 | | | | | 935 | | | | | 940 | | | |
| ATG | AAA | GAG | GCT | GAG | CAT | CGA | TAC | CGT | GTG | AAT | AAC | CTC | AGC | CAG | CGA | 2880 |
| Met | Lys | Glu | Ala | Glu | His | Arg | Tyr | Arg | Val | Asn | Asn | Leu | Ser | Gln | Arg | |
| 945 | | | | 950 | | | | | 955 | | | | | | 960 | |
| GAT | CTG | GCC | ATC | AGC | ATT | AAC | TTC | TGG | GTT | CCT | GTC | CTG | CTG | AAC | GGG | 2928 |
| Asp | Leu | Ala | Ile | Ser | Ile | Asn | Phe | Trp | Val | Pro | Val | Leu | Leu | Asn | Gly | |
| | | | | 965 | | | | | 970 | | | | | | 975 | |
| GTG | GCT | GTG | TGG | GAT | GTG | GTC | ATG | GAG | GCC | CCA | TCT | CAG | AGT | CTC | CCC | 2976 |
| Val | Ala | Val | Trp | Asp | Val | Val | Met | Glu | Ala | Pro | Ser | Gln | Ser | Leu | Pro | |
| | | | 980 | | | | | 985 | | | | | 990 | | | |
| TGT | GTT | TCA | GAG | AGA | AAA | CCT | CCC | CAG | CAT | TCT | GAC | TTC | CTG | ACC | CAG | 3024 |
| Cys | Val | Ser | Glu | Arg | Lys | Pro | Pro | Gln | His | Ser | Asp | Phe | Leu | Thr | Gln | |
| | | 995 | | | | | 1000 | | | | | 1005 | | | | |
| ATT | TCA | AGA | AGT | CCC | ATG | CTG | GAC | TGC | TCC | ATT | GCT | GAC | TGC | CTG | CAG | 3072 |
| Ile | Ser | Arg | Ser | Pro | Met | Leu | Asp | Cys | Ser | Ile | Ala | Asp | Cys | Leu | Gln | |
| | | | 1010 | | | | | 1015 | | | | | 1020 | | | |
| TTC | CGC | TGT | GAC | GTC | CCC | TCC | TTC | AGC | GTC | CAG | GAG | GAG | CTG | GAT | TTC | 3120 |
| Phe | Arg | Cys | Asp | Val | Pro | Ser | Phe | Ser | Val | Gln | Glu | Glu | Leu | Asp | Phe | |
| 1025 | | | | | 1030 | | | | | 1035 | | | | | 1040 | |
| ACC | CTG | AAG | GGC | AAT | CTC | AGT | TTC | GGC | TGG | GTC | CGC | GAG | ACA | TTG | CAG | 3168 |
| Thr | Leu | Lys | Gly | Asn | Leu | Ser | Phe | Gly | Trp | Val | Arg | Glu | Thr | Leu | Gln | |
| | | | | 1045 | | | | | 1050 | | | | | 1055 | | |
| AAG | AAG | GTG | TTG | GTC | GTG | AGT | GTG | GCT | GAA | ATT | ACG | TTC | GAC | ACA | TCC | 3216 |
| Lys | Lys | Val | Leu | Val | Val | Ser | Val | Ala | Glu | Ile | Thr | Phe | Asp | Thr | Ser | |
| | | | 1060 | | | | | 1065 | | | | | 1070 | | | |
| GTG | TAC | TCC | CAG | CTT | CCA | GGA | CAG | GAG | GCA | TTT | ATG | AGA | GCT | CAG | ATG | 3264 |
| Val | Tyr | Ser | Gln | Leu | Pro | Gly | Gln | Glu | Ala | Phe | Met | Arg | Ala | Gln | Met | |
| | | | 1075 | | | | | 1080 | | | | | 1085 | | | |
| GAG | ATG | GTG | CTA | GAA | GAA | GAC | GAG | GTC | TAC | AAT | GCC | ATT | CCC | ATC | ATC | 3312 |
| Glu | Met | Val | Leu | Glu | Glu | Asp | Glu | Val | Tyr | Asn | Ala | Ile | Pro | Ile | Ile | |
| | | | 1090 | | | | | 1095 | | | | | 1100 | | | |
| ATG | GGC | AGC | TCT | GTG | GGG | GCT | CTA | CTA | CTG | CTG | GCG | CTC | ATC | ACA | GCC | 3360 |
| Met | Gly | Ser | Ser | Val | Gly | Ala | Leu | Leu | Leu | Leu | Ala | Leu | Ile | Thr | Ala | |
| 1105 | | | | 1110 | | | | | 1115 | | | | | | 1120 | |
| ACA | CTG | TAC | AAG | CTT | GGC | TTC | TTC | AAA | CGC | CAC | TAC | AAG | GAA | ATG | CTG | 3408 |
| Thr | Leu | Tyr | Lys | Leu | Gly | Phe | Phe | Lys | Arg | His | Tyr | Lys | Glu | Met | Leu | |
| | | | | 1125 | | | | | 1130 | | | | | 1135 | | |
| GAG | GAC | AAG | CCT | GAA | GAC | ACT | GCC | ACA | TTC | AGT | GGG | GAC | GAT | TTC | AGC | 3456 |
| Glu | Asp | Lys | Pro | Glu | Asp | Thr | Ala | Thr | Phe | Ser | Gly | Asp | Asp | Phe | Ser | |
| | | | 1140 | | | | | 1145 | | | | | 1150 | | | |
| TGT | GTG | GCC | CCA | AAT | GTG | CCT | TTG | TCC | TAATAATCCA | CTTTCCTGTT | | | | | | 3503 |
| Cys | Val | Ala | Pro | Asn | Val | Pro | Leu | Ser | | | | | | | | |
| | | | 1155 | | | | | 1160 | | | | | | | | |

```
TATCTCTACC ACTGTGGGCT GGACTTGCTT GCAACCATAA ATCAACTTAC ATGGAAACAA    3563

CTTCTGCATA GATCTGCACT GGCCTAAGCA ACCTACCAGG TGCTAAGCAC CTTCTCGGAG    3623

AGATAGAGAT TGTCAATGTT TTACATATC  TGTCCATCTT TTTCAGCAAT GACCCACTTT    3683

TTACAGAAGC AGGCATGGTG CCAGCATAAA TTTTCATATG CTTAAGAATT GTCACATGAA    3743
```

```
AAAAAAAAAA AAAAAAAAA AAAAAAAAA AAAAAACTTT AG                3785
```

( 2 ) INFORMATION FOR SEQ ID NO:99:

( i ) SEQUENCE CHARACTERISTICS:
        ( A ) LENGTH: 1161 amino acids
        ( B ) TYPE: amino acid
        ( D ) TOPOLOGY: linear ( i i ) MOLECULE TYPE: protein ( x i ) SEQUENCE DESCRIPTION: SEQ ID NO:99:

```
Met Thr Phe Gly Thr Val Leu Leu Leu Ser Val Leu Ala Ser Tyr His
 1               5                  10                  15

Gly Phe Asn Leu Asp Val Glu Glu Pro Thr Ile Phe Gln Glu Asp Ala
                 20                  25                  30

Gly Gly Phe Gly Gln Ser Val Val Gln Phe Gly Gly Ser Arg Leu Val
             35                  40                  45

Val Gly Ala Pro Leu Glu Val Val Ala Ala Asn Gln Thr Gly Arg Leu
     50                  55                  60

Tyr Asp Cys Ala Ala Ala Thr Gly Met Cys Gln Pro Ile Pro Leu His
 65                  70                  75                  80

Ile Arg Pro Glu Ala Val Asn Met Ser Leu Gly Leu Thr Leu Ala Ala
                 85                  90                  95

Ser Thr Asn Gly Ser Arg Leu Leu Ala Cys Gly Pro Thr Leu His Arg
                100                 105                 110

Val Cys Gly Glu Asn Ser Tyr Ser Lys Gly Ser Cys Leu Leu Leu Gly
            115                 120                 125

Ser Arg Trp Glu Ile Ile Gln Thr Val Pro Asp Ala Thr Pro Glu Cys
    130                 135                 140

Pro His Gln Glu Met Asp Ile Val Phe Leu Ile Asp Gly Ser Gly Ser
145                 150                 155                 160

Ile Asp Gln Asn Asp Phe Asn Gln Met Lys Gly Phe Val Gln Ala Val
                165                 170                 175

Met Gly Gln Phe Glu Gly Thr Asp Thr Leu Phe Ala Leu Met Gln Tyr
            180                 185                 190

Ser Asn Leu Leu Lys Ile His Phe Thr Phe Thr Gln Phe Arg Thr Ser
            195                 200                 205

Pro Ser Gln Gln Ser Leu Val Asp Pro Ile Val Gln Leu Lys Gly Leu
    210                 215                 220

Thr Phe Thr Ala Thr Gly Ile Leu Thr Val Val Thr Gln Leu Phe His
225                 230                 235                 240

His Lys Asn Gly Ala Arg Lys Ser Ala Lys Lys Ile Leu Ile Val Ile
                245                 250                 255

Thr Asp Gly Gln Lys Tyr Lys Asp Pro Leu Glu Tyr Ser Asp Val Ile
            260                 265                 270

Pro Gln Ala Glu Lys Ala Gly Ile Ile Arg Tyr Ala Ile Gly Val Gly
    275                 280                 285

His Ala Phe Gln Gly Pro Thr Ala Arg Gln Glu Leu Asn Thr Ile Ser
    290                 295                 300

Ser Ala Pro Pro Gln Asp His Val Phe Lys Val Asp Asn Phe Ala Ala
305                 310                 315                 320

Leu Gly Ser Ile Gln Lys Gln Leu Gln Glu Lys Ile Tyr Ala Val Glu
                325                 330                 335

Gly Thr Gln Ser Arg Ala Ser Ser Ser Phe Gln His Glu Met Ser Gln
            340                 345                 350
```

-continued

| | | | | | | | | | | | | | |
|---|---|---|---|---|---|---|---|---|---|---|---|---|---|
| Glu | Gly | Phe 355 | Ser | Thr | Ala | Leu | Thr 360 | Met | Asp | Gly | Leu | Phe 365 | Leu | Gly | Ala |
| Val | Gly 370 | Ser | Phe | Ser | Trp | Ser 375 | Gly | Gly | Ala | Phe | Leu | Tyr 380 | Pro | Pro | Asn |
| Met 385 | Ser | Pro | Thr | Phe | Ile 390 | Asn | Met | Ser | Gln | Glu 395 | Asn | Val | Asp | Met | Arg 400 |
| Asp | Ser | Tyr | Leu | Gly 405 | Tyr | Ser | Thr | Glu | Leu 410 | Ala | Leu | Trp | Lys | Gly 415 | Val |
| Gln | Asn | Leu | Val 420 | Leu | Gly | Ala | Pro | Arg 425 | Tyr | Gln | His | Thr | Gly 430 | Lys | Ala |
| Val | Ile | Phe 435 | Thr | Gln | Val | Ser | Arg 440 | Gln | Trp | Arg | Lys | Lys 445 | Ala | Glu | Val |
| Thr | Gly 450 | Thr | Gln | Ile | Gly | Ser 455 | Tyr | Phe | Gly | Ala | Ser 460 | Leu | Cys | Ser | Val |
| Asp 465 | Val | Asp | Ser | Asp | Gly 470 | Ser | Thr | Asp | Leu | Ile 475 | Leu | Ile | Gly | Ala | Pro 480 |
| His | Tyr | Tyr | Glu | Gln 485 | Thr | Arg | Gly | Gly | Gln 490 | Val | Ser | Val | Cys | Pro 495 | Leu |
| Pro | Arg | Gly | Arg 500 | Val | Gln | Trp | Gln | Cys 505 | Asp | Ala | Val | Leu | Arg 510 | Gly | Glu |
| Gln | Gly | His 515 | Pro | Trp | Gly | Arg | Phe 520 | Gly | Ala | Ala | Leu | Thr 525 | Val | Leu | Gly |
| Asp | Val 530 | Asn | Glu | Asp | Lys | Leu 535 | Ile | Asp | Val | Ala | Ile 540 | Gly | Ala | Pro | Gly |
| Glu 545 | Gln | Glu | Asn | Arg | Gly 550 | Ala | Val | Tyr | Leu | Phe 555 | His | Gly | Ala | Ser | Glu 560 |
| Ser | Gly | Ile | Ser | Pro 565 | Ser | His | Ser | Gln | Arg 570 | Ile | Ala | Ser | Ser | Gln 575 | Leu |
| Ser | Pro | Arg | Leu 580 | Gln | Tyr | Phe | Gly | Gln 585 | Ala | Leu | Ser | Gly | Gly 590 | Gln | Asp |
| Leu | Thr | Gln 595 | Asp | Gly | Leu | Met | Asp 600 | Leu | Ala | Val | Gly | Ala 605 | Arg | Gly | Gln |
| Val | Leu 610 | Leu | Leu | Arg | Ser | Leu 615 | Pro | Val | Leu | Lys | Val 620 | Gly | Val | Ala | Met |
| Arg 625 | Phe | Ser | Pro | Val | Glu 630 | Val | Ala | Lys | Ala | Val 635 | Tyr | Arg | Cys | Trp | Glu 640 |
| Glu | Lys | Pro | Ser | Ala 645 | Leu | Glu | Ala | Gly | Asp 650 | Ala | Thr | Val | Cys | Leu 655 | Thr |
| Ile | Gln | Lys | Ser 660 | Ser | Leu | Asp | Gln | Leu 665 | Gly | Asp | Ile | Gln | Ser 670 | Ser | Val |
| Arg | Phe | Asp 675 | Leu | Ala | Leu | Asp | Pro 680 | Gly | Arg | Leu | Thr | Ser 685 | Arg | Ala | Ile |
| Phe | Asn 690 | Glu | Thr | Lys | Asn | Pro 695 | Thr | Leu | Thr | Arg | Arg 700 | Lys | Thr | Leu | Gly |
| Leu 705 | Gly | Ile | His | Cys | Glu 710 | Thr | Leu | Lys | Leu | Leu 715 | Leu | Pro | Asp | Cys | Val 720 |
| Glu | Asp | Val | Val | Ser 725 | Pro | Ile | Ile | Leu | His 730 | Leu | Asn | Phe | Ser | Leu 735 | Val |
| Arg | Glu | Pro | Ile 740 | Pro | Ser | Pro | Gln | Asn 745 | Leu | Arg | Pro | Val | Leu 750 | Ala | Val |
| Gly | Ser | Gln 755 | Asp | Leu | Phe | Thr | Ala 760 | Ser | Leu | Pro | Phe | Glu 765 | Lys | Asn | Cys |
| Gly | Gln 770 | Asp | Gly | Leu | Cys 775 | Glu | Gly | Asp | Leu | Gly 780 | Val | Thr | Leu | Ser | Phe |

Ser Gly Leu Gln Thr Leu Thr Val Gly Ser Ser Leu Glu Leu Asn Val
785                 790                 795                 800

Ile Val Thr Val Trp Asn Ala Gly Glu Asp Ser Tyr Gly Thr Val Val
                805                 810                 815

Ser Leu Tyr Tyr Pro Ala Gly Leu Ser His Arg Arg Val Ser Gly Ala
            820                 825                 830

Gln Lys Gln Pro His Gln Ser Ala Leu Arg Leu Ala Cys Glu Thr Val
        835                 840                 845

Pro Thr Glu Asp Glu Gly Leu Arg Ser Ser Arg Cys Ser Val Asn His
    850                 855                 860

Pro Ile Phe His Glu Gly Ser Asn Gly Thr Phe Ile Val Thr Phe Asp
865                 870                 875                 880

Val Ser Tyr Lys Ala Thr Leu Gly Asp Arg Met Leu Met Arg Ala Ser
                885                 890                 895

Ala Ser Ser Glu Asn Asn Lys Ala Ser Ser Lys Ala Thr Phe Gln
            900                 905                 910

Leu Glu Leu Pro Val Lys Tyr Ala Val Tyr Thr Met Ile Ser Arg Gln
        915                 920                 925

Glu Glu Ser Thr Lys Tyr Phe Asn Phe Ala Thr Ser Asp Glu Lys Lys
    930                 935                 940

Met Lys Glu Ala Glu His Arg Tyr Arg Val Asn Asn Leu Ser Gln Arg
945                 950                 955                 960

Asp Leu Ala Ile Ser Ile Asn Phe Trp Val Pro Val Leu Leu Asn Gly
                965                 970                 975

Val Ala Val Trp Asp Val Val Met Glu Ala Pro Ser Gln Ser Leu Pro
            980                 985                 990

Cys Val Ser Glu Arg Lys Pro Pro Gln His Ser Asp Phe Leu Thr Gln
        995                 1000                1005

Ile Ser Arg Ser Pro Met Leu Asp Cys Ser Ile Ala Asp Cys Leu Gln
    1010                1015                1020

Phe Arg Cys Asp Val Pro Ser Phe Ser Val Gln Glu Glu Leu Asp Phe
1025                1030                1035                1040

Thr Leu Lys Gly Asn Leu Ser Phe Gly Trp Val Arg Glu Thr Leu Gln
                1045                1050                1055

Lys Lys Val Leu Val Val Ser Val Ala Glu Ile Thr Phe Asp Thr Ser
            1060                1065                1070

Val Tyr Ser Gln Leu Pro Gly Gln Glu Ala Phe Met Arg Ala Gln Met
        1075                1080                1085

Glu Met Val Leu Glu Glu Asp Glu Val Tyr Asn Ala Ile Pro Ile Ile
    1090                1095                1100

Met Gly Ser Ser Val Gly Ala Leu Leu Leu Leu Ala Leu Ile Thr Ala
1105                1110                1115                1120

Thr Leu Tyr Lys Leu Gly Phe Phe Lys Arg His Tyr Lys Glu Met Leu
                1125                1130                1135

Glu Asp Lys Pro Glu Asp Thr Ala Thr Phe Ser Gly Asp Asp Phe Ser
            1140                1145                1150

Cys Val Ala Pro Asn Val Pro Leu Ser
        1155                1160

( 2 ) INFORMATION FOR SEQ ID NO:100:

( i ) SEQUENCE CHARACTERISTICS:
      ( A ) LENGTH: 1318 base pairs
      ( B ) TYPE: nucleic acid
      ( C ) STRANDEDNESS: single (D) TOPOLOGY: linear (ii) MOLECULE TYPE: cDNA (ix) FEATURE:
(A) NAME/KEY: CDS
(B) LOCATION: 17..1255

(xi) SEQUENCE DESCRIPTION: SEQ ID NO:100:

```
AATTCGGCAC GAGCTT GGG GCT GTG GTC CTC CTT GGG GTC CTG GCT TCT              49
                   Gly Ala Val Val Leu Leu Gly Val Leu Ala Ser
                    1               5                  10

TAC CAC GGA TTC AAC TTG GAC GTG GAT GAG CCG GTG ATC TTC CAG GAA            97
Tyr His Gly Phe Asn Leu Asp Val Asp Glu Pro Val Ile Phe Gln Glu
            15                  20                  25

GAC GCA GCG GGC TTC GGG CAG AGC GTG ATG CAG TTT GGA GGA TCT CGA           145
Asp Ala Ala Gly Phe Gly Gln Ser Val Met Gln Phe Gly Gly Ser Arg
        30                  35                  40

CTC GTG GTG GGA GCC CCC CTG GCG GTG GTG TCG GCC AAC CAC ACA GGA           193
Leu Val Val Gly Ala Pro Leu Ala Val Val Ser Ala Asn His Thr Gly
    45                  50                  55

CGG CTG TAC GAG TGT GCG CCT GCC TCC GGC ACC TGC ACG CCC ATT TTC           241
Arg Leu Tyr Glu Cys Ala Pro Ala Ser Gly Thr Cys Thr Pro Ile Phe
60                  65                  70                  75

CCA TTC ATG CCC CCC GAA GCC GTG AAC ATG TCC CTG GGC CTG TCC CTG           289
Pro Phe Met Pro Pro Glu Ala Val Asn Met Ser Leu Gly Leu Ser Leu
                80                  85                  90

GCA GCC TCC CCC AAC CAT TCC CAG CTG CTG GCT TGT GGC CCG ACC GTG           337
Ala Ala Ser Pro Asn His Ser Gln Leu Leu Ala Cys Gly Pro Thr Val
            95                  100                 105

CAT AGA GCC TGC GGG GAG GAC GTG TAC GCC CAG GGT TTC TGT GTG CTG           385
His Arg Ala Cys Gly Glu Asp Val Tyr Ala Gln Gly Phe Cys Val Leu
        110                 115                 120

CTG GAT GCC CAC GCA CAG CCC ATC GGG ACT GTG CCA GCT GCC CTG CCC           433
Leu Asp Ala His Ala Gln Pro Ile Gly Thr Val Pro Ala Ala Leu Pro
    125                 130                 135

GAG TGC CCA GAT CAA GAG ATG GAC ATT GTC TTC CTG ATT GAC GGC TCT           481
Glu Cys Pro Asp Gln Glu Met Asp Ile Val Phe Leu Ile Asp Gly Ser
140                 145                 150                 155

GGC AGC ATT AGC TCA AAT GAC TTC CGC AAG ATG AAG GAC TTT GTC AGA           529
Gly Ser Ile Ser Ser Asn Asp Phe Arg Lys Met Lys Asp Phe Val Arg
                160                 165                 170

GCT GTG ATG GAC CAG TTC AAG GAC ACC AAC ACC CAG TTC TCG CTG ATG           577
Ala Val Met Asp Gln Phe Lys Asp Thr Asn Thr Gln Phe Ser Leu Met
            175                 180                 185

CAG TAC TCC AAT GTG CTG GTG ACA CAT TTC ACC TTC AGC AGC TTC CGG           625
Gln Tyr Ser Asn Val Leu Val Thr His Phe Thr Phe Ser Ser Phe Arg
        190                 195                 200

AAC AGC TCC AAT CCT CAG GGC CTA GTG GAG CCC ATT GTG CAG CTG ACA           673
Asn Ser Ser Asn Pro Gln Gly Leu Val Glu Pro Ile Val Gln Leu Thr
    205                 210                 215

GGC CTC ACG TTC ACG GCC ACA GGG ATC CTG AAA GTG GTG ACA GAG CTG           721
Gly Leu Thr Phe Thr Ala Thr Gly Ile Leu Lys Val Val Thr Glu Leu
220                 225                 230                 235

TTT CAA ACC AAG AAC GGG GCC CGC GAA AGT GCC AAG AAG ATC CTC ATC           769
Phe Gln Thr Lys Asn Gly Ala Arg Glu Ser Ala Lys Lys Ile Leu Ile
                240                 245                 250

GTC ATC ACA GAT GGG CAG AAG TAC AAA GAC CCC CTG CAC TAC AGT GCT           817
Val Ile Thr Asp Gly Gln Lys Tyr Lys Asp Pro Leu His Tyr Ser Ala
            255                 260                 265

GTC ATC CCA CAG GCA GAG CAG GCG GGC ATC ATC CGC TAC GCC ATC GGG           865
Val Ile Pro Gln Ala Glu Gln Ala Gly Ile Ile Arg Tyr Ala Ile Gly
```

| | | | | | | | | | | | | | | | | |
|---|---|---|---|---|---|---|---|---|---|---|---|---|---|---|---|---|
| | | 270 | | | | 275 | | | | | 280 | | | | | |
| GTG | GGG | GAC | GCG | TTC | CAG | AAA | CCC | ACA | GCC | AGG | CAG | GAG | CTG | GAC | ACC | 913 |
| Val | Gly | Asp | Ala | Phe | Gln | Lys | Pro | Thr | Ala | Arg | Gln | Glu | Leu | Asp | Thr | |
| 285 | | | | | 290 | | | | | 295 | | | | | | |
| ATC | GCC | TCC | GAG | CCG | CCC | GAC | GCC | CAC | GTG | TTC | CAG | GTG | GAC | AAT | TTC | 961 |
| Ile | Ala | Ser | Glu | Pro | Pro | Asp | Ala | His | Val | Phe | Gln | Val | Asp | Asn | Phe | |
| 300 | | | | | 305 | | | | | 310 | | | | | 315 | |
| TCA | GCA | CTC | AGC | AGC | ATC | CAA | AAG | CAG | CTG | TAT | GAC | AGG | ATC | TTT | GCC | 1009 |
| Ser | Ala | Leu | Ser | Ser | Ile | Gln | Lys | Gln | Leu | Tyr | Asp | Arg | Ile | Phe | Ala | |
| | | | | 320 | | | | | 325 | | | | | 330 | | |
| GTC | GAG | GGA | ACC | CTG | TCA | TCG | GCA | AGC | ACC | TCC | TTC | CAG | CAT | GAG | ATG | 1057 |
| Val | Glu | Gly | Thr | Leu | Ser | Ser | Ala | Ser | Thr | Ser | Phe | Gln | His | Glu | Met | |
| | | | 335 | | | | | 340 | | | | | 345 | | | |
| TCC | CAA | GAG | GGC | TTC | AGC | TCA | CTT | CTC | ACC | ACG | GAA | GGA | CCG | GTG | CTG | 1105 |
| Ser | Gln | Glu | Gly | Phe | Ser | Ser | Leu | Leu | Thr | Thr | Glu | Gly | Pro | Val | Leu | |
| | | | 350 | | | | | 355 | | | | | 360 | | | |
| GGG | GCT | GTG | GGC | AGC | TTC | GAT | TGG | TCC | GGG | GGT | GCT | TTC | CTG | TAC | CCC | 1153 |
| Gly | Ala | Val | Gly | Ser | Phe | Asp | Trp | Ser | Gly | Gly | Ala | Phe | Leu | Tyr | Pro | |
| | 365 | | | | | 370 | | | | | 375 | | | | | |
| CCC | GGC | GGG | AGC | CCC | ACC | TTC | ATC | AAC | ATG | TCT | CAG | CAG | AAC | GTG | GAC | 1201 |
| Pro | Gly | Gly | Ser | Pro | Thr | Phe | Ile | Asn | Met | Ser | Gln | Gln | Asn | Val | Asp | |
| 380 | | | | | 385 | | | | | 390 | | | | | 395 | |
| ATG | AGG | GAC | TCC | TAC | CTG | GGT | GAG | GAA | GGG | GTG | GGG | GTG | GGG | ACA | GGT | 1249 |
| Met | Arg | Asp | Ser | Tyr | Leu | Gly | Glu | Glu | Gly | Val | Gly | Val | Gly | Thr | Gly | |
| | | | | 400 | | | | | 405 | | | | | 410 | | |
| GGG | AGC | TGAGGCTTGG | | GGTGGGGTGG | | GGCTGGGCTG | | GGAGGGGAGG | | GAAGAGGAGG | | | | | | 1305 |
| Gly | Ser | | | | | | | | | | | | | | | |
| GGAGAGGCAA | AGA | | | | | | | | | | | | | | | 1318 |

( 2 ) INFORMATION FOR SEQ ID NO:101:

( i ) SEQUENCE CHARACTERISTICS:
        ( A ) LENGTH: 413 amino acids
        ( B ) TYPE: amino acid
        ( D ) TOPOLOGY: linear ( i i ) MOLECULE TYPE: protein ( x i ) SEQUENCE DESCRIPTION: SEQ ID NO:101:

| | | | | | | | | | | | | | | |
|---|---|---|---|---|---|---|---|---|---|---|---|---|---|---|
| Gly | Ala | Val | Val | Leu | Leu | Gly | Val | Leu | Ala | Ser | Tyr | His | Gly | Phe | Asn |
| 1 | | | | 5 | | | | | 10 | | | | | 15 | |

| | | | | | | | | | | | | | | |
|---|---|---|---|---|---|---|---|---|---|---|---|---|---|---|
| Leu | Asp | Val | Asp | Glu | Pro | Val | Ile | Phe | Gln | Glu | Asp | Ala | Ala | Gly | Phe |
| | | | 20 | | | | | 25 | | | | | 30 | | |

| | | | | | | | | | | | | | | |
|---|---|---|---|---|---|---|---|---|---|---|---|---|---|---|
| Gly | Gln | Ser | Val | Met | Gln | Phe | Gly | Gly | Ser | Arg | Leu | Val | Val | Gly | Ala |
| | | 35 | | | | | 40 | | | | | 45 | | | |

| | | | | | | | | | | | | |
|---|---|---|---|---|---|---|---|---|---|---|---|---|
| Pro | Leu | Ala | Val | Val | Ser | Ala | Asn | His | Thr | Gly | Arg | Leu | Tyr | Glu | Cys |
| | 50 | | | | | 55 | | | | | 60 | | | | |

| | | | | | | | | | | | | |
|---|---|---|---|---|---|---|---|---|---|---|---|---|
| Ala | Pro | Ala | Ser | Gly | Thr | Cys | Thr | Pro | Ile | Phe | Pro | Phe | Met | Pro | Pro |
| 65 | | | | | 70 | | | | | 75 | | | | | 80 |

| | | | | | | | | | | | | |
|---|---|---|---|---|---|---|---|---|---|---|---|---|
| Glu | Ala | Val | Asn | Met | Ser | Leu | Gly | Leu | Ser | Leu | Ala | Ala | Ser | Pro | Asn |
| | | | | 85 | | | | | 90 | | | | | 95 | |

| | | | | | | | | | | | | |
|---|---|---|---|---|---|---|---|---|---|---|---|---|
| His | Ser | Gln | Leu | Leu | Ala | Cys | Gly | Pro | Thr | Val | His | Arg | Ala | Cys | Gly |
| | | | 100 | | | | | 105 | | | | | 110 | | |

| | | | | | | | | | | | | |
|---|---|---|---|---|---|---|---|---|---|---|---|---|
| Glu | Asp | Val | Tyr | Ala | Gln | Gly | Phe | Cys | Val | Leu | Leu | Asp | Ala | His | Ala |
| | | 115 | | | | | 120 | | | | | 125 | | | |

| | | | | | | | | | | | | |
|---|---|---|---|---|---|---|---|---|---|---|---|---|
| Gln | Pro | Ile | Gly | Thr | Val | Pro | Ala | Ala | Leu | Pro | Glu | Cys | Pro | Asp | Gln |
| | 130 | | | | | 135 | | | | | 140 | | | | |

| | | | | | | | | | | | | |
|---|---|---|---|---|---|---|---|---|---|---|---|---|
| Glu | Met | Asp | Ile | Val | Phe | Leu | Ile | Asp | Gly | Ser | Gly | Ser | Ile | Ser | Ser |
| 145 | | | | | 150 | | | | | 155 | | | | | 160 |

```
Asn  Asp  Phe  Arg  Lys  Met  Lys  Asp  Phe  Val  Arg  Ala  Val  Met  Asp  Gln
               165                 170                           175

Phe  Lys  Asp  Thr  Asn  Thr  Gln  Phe  Ser  Leu  Met  Gln  Tyr  Ser  Asn  Val
               180                 185                           190

Leu  Val  Thr  His  Phe  Thr  Phe  Ser  Ser  Phe  Arg  Asn  Ser  Ser  Asn  Pro
               195                 200                           205

Gln  Gly  Leu  Val  Glu  Pro  Ile  Val  Gln  Leu  Thr  Gly  Leu  Thr  Phe  Thr
     210                      215                 220

Ala  Thr  Gly  Ile  Leu  Lys  Val  Val  Thr  Glu  Leu  Phe  Gln  Thr  Lys  Asn
225                      230                 235                           240

Gly  Ala  Arg  Glu  Ser  Ala  Lys  Lys  Ile  Leu  Ile  Val  Ile  Thr  Asp  Gly
               245                 250                           255

Gln  Lys  Tyr  Lys  Asp  Pro  Leu  His  Tyr  Ser  Ala  Val  Ile  Pro  Gln  Ala
               260                 265                           270

Glu  Gln  Ala  Gly  Ile  Ile  Arg  Tyr  Ala  Ile  Gly  Val  Gly  Asp  Ala  Phe
               275                 280                           285

Gln  Lys  Pro  Thr  Ala  Arg  Gln  Glu  Leu  Asp  Thr  Ile  Ala  Ser  Glu  Pro
     290                      295                 300

Pro  Asp  Ala  His  Val  Phe  Gln  Val  Asp  Asn  Phe  Ser  Ala  Leu  Ser  Ser
305                      310                 315                           320

Ile  Gln  Lys  Gln  Leu  Tyr  Asp  Arg  Ile  Phe  Ala  Val  Glu  Gly  Thr  Leu
               325                 330                           335

Ser  Ser  Ala  Ser  Thr  Ser  Phe  Gln  His  Glu  Met  Ser  Gln  Glu  Gly  Phe
               340                 345                           350

Ser  Ser  Leu  Leu  Thr  Thr  Glu  Gly  Pro  Val  Leu  Gly  Ala  Val  Gly  Ser
               355                 360                           365

Phe  Asp  Trp  Ser  Gly  Gly  Ala  Phe  Leu  Tyr  Pro  Pro  Gly  Gly  Ser  Pro
     370                      375                 380

Thr  Phe  Ile  Asn  Met  Ser  Gln  Gln  Asn  Val  Asp  Met  Arg  Asp  Ser  Tyr
385                      390                 395                           400

Leu  Gly  Glu  Glu  Gly  Val  Gly  Val  Gly  Thr  Gly  Gly  Ser
               405                 410
```

( 2 ) INFORMATION FOR SEQ ID NO:102:

( i ) SEQUENCE CHARACTERISTICS:
        ( A ) LENGTH: 1484 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1482

( x i ) SEQUENCE DESCRIPTION: SEQ ID NO:102:

```
GAT  GTC  CAG  AGC  TCC  ATC  AGC  TAT  GAT  CTG  GCA  CTG  GAC  CCA  GGC  CGC    48
Asp  Val  Gln  Ser  Ser  Ile  Ser  Tyr  Asp  Leu  Ala  Leu  Asp  Pro  Gly  Arg
1                   5                   10                          15

CTG  GTC  TCT  CGG  GCC  ATT  TTT  CAA  GAG  ACC  CAG  AAC  CAG  ACT  TTA  ACT    96
Leu  Val  Ser  Arg  Ala  Ile  Phe  Gln  Glu  Thr  Gln  Asn  Gln  Thr  Leu  Thr
               20                   25                          30

CGA  AGG  AAG  ACC  CTG  GGG  CTG  GGG  CGT  CAC  TGT  GAA  ACC  ATG  AGG  CTA   144
Arg  Arg  Lys  Thr  Leu  Gly  Leu  Gly  Arg  His  Cys  Glu  Thr  Met  Arg  Leu
               35                   40                          45

CTT  TTG  CCA  GAC  TGC  GTA  GAG  GAC  GTG  GTG  AAC  CCC  ATC  GTC  CTG  CAC   192
Leu  Leu  Pro  Asp  Cys  Val  Glu  Asp  Val  Val  Asn  Pro  Ile  Val  Leu  His
```

|  |  |  |  |  |  |  |  |  |  |  |  |  |  |  |  |
|---|---|---|---|---|---|---|---|---|---|---|---|---|---|---|---|
|  |  | 50 |  |  |  |  | 55 |  |  |  |  | 60 |  |  |  |
| CTC | AAC | TTC | TCC | CTG | GAG | GGA | CAG | CCA | ATC | CTC | TCA | TCC | CAG | AAT | CTG | 240 |
| Leu | Asn | Phe | Ser | Leu | Glu | Gly | Gln | Pro | Ile | Leu | Ser | Ser | Gln | Asn | Leu |  |
| 65 |  |  |  |  | 70 |  |  |  |  | 75 |  |  |  |  | 80 |  |
| CGC | CCT | GTG | CTG | GCC | ACG | GGC | TCG | CAG | GAC | CAC | TTC | ATT | GCC | TCC | CTC | 288 |
| Arg | Pro | Val | Leu | Ala | Thr | Gly | Ser | Gln | Asp | His | Phe | Ile | Ala | Ser | Leu |  |
|  |  |  |  | 85 |  |  |  |  | 90 |  |  |  |  | 95 |  |  |
| CCC | TTT | GAG | AAG | AAC | TGC | GGA | CAA | GAT | CGC | CTG | TGT | GAG | GGG | GAC | CTG | 336 |
| Pro | Phe | Glu | Lys | Asn | Cys | Gly | Gln | Asp | Arg | Leu | Cys | Glu | Gly | Asp | Leu |  |
|  |  |  | 100 |  |  |  |  | 105 |  |  |  |  | 110 |  |  |  |
| AGC | ATC | AGC | TTC | AAC | TTC | TCG | GGC | TTG | AAT | ACC | CTG | CTG | GTG | GGG | CTC | 384 |
| Ser | Ile | Ser | Phe | Asn | Phe | Ser | Gly | Leu | Asn | Thr | Leu | Leu | Val | Gly | Leu |  |
|  |  | 115 |  |  |  |  | 120 |  |  |  |  | 125 |  |  |  |  |
| TCC | CTG | GAG | CTC | ACA | GTG | ACA | GTG | ACC | GTG | CGG | AAT | GAG | GGC | GAG | GAC | 432 |
| Ser | Leu | Glu | Leu | Thr | Val | Thr | Val | Thr | Val | Arg | Asn | Glu | Gly | Glu | Asp |  |
| 130 |  |  |  |  | 135 |  |  |  |  | 140 |  |  |  |  |  |  |
| TCC | TAT | GGG | ACC | GCC | ATC | ACC | CTC | TAC | TAC | CCA | GCA | GGG | CTA | TCC | TAC | 480 |
| Ser | Tyr | Gly | Thr | Ala | Ile | Thr | Leu | Tyr | Tyr | Pro | Ala | Gly | Leu | Ser | Tyr |  |
| 145 |  |  |  |  | 150 |  |  |  |  | 155 |  |  |  |  | 160 |  |
| AGG | CGG | GTG | TCG | GGC | CAG | ACA | CAA | CCC | TGG | CAG | CGC | CCC | CTG | CAC | CTC | 528 |
| Arg | Arg | Val | Ser | Gly | Gln | Thr | Gln | Pro | Trp | Gln | Arg | Pro | Leu | His | Leu |  |
|  |  |  |  | 165 |  |  |  |  | 170 |  |  |  |  | 175 |  |  |
| GCA | TGT | GAG | GCT | GTA | CCT | ACC | GAG | AGC | GAG | GGC | TTG | AGG | AGT | ACC | AGC | 576 |
| Ala | Cys | Glu | Ala | Val | Pro | Thr | Glu | Ser | Glu | Gly | Leu | Arg | Ser | Thr | Ser |  |
|  |  |  | 180 |  |  |  |  | 185 |  |  |  |  | 190 |  |  |  |
| TGC | AGC | GTC | AAC | CAC | CCC | ATC | TTC | CAA | GGG | GGT | GCT | CAG | GGC | ACT | TTC | 624 |
| Cys | Ser | Val | Asn | His | Pro | Ile | Phe | Gln | Gly | Gly | Ala | Gln | Gly | Thr | Phe |  |
|  |  | 195 |  |  |  |  | 200 |  |  |  |  | 205 |  |  |  |  |
| GTA | GTC | AAG | TTC | GAT | GTC | TCC | TCC | AAG | GCC | AGC | CTG | GGT | GAC | AGG | TTG | 672 |
| Val | Val | Lys | Phe | Asp | Val | Ser | Ser | Lys | Ala | Ser | Leu | Gly | Asp | Arg | Leu |  |
| 210 |  |  |  |  | 215 |  |  |  |  | 220 |  |  |  |  |  |  |
| CTC | ATG | GGG | GCC | AGT | GCC | AGC | AGT | GAG | AAT | AAT | AAG | CCT | GCG | AGC | AAC | 720 |
| Leu | Met | Gly | Ala | Ser | Ala | Ser | Ser | Glu | Asn | Asn | Lys | Pro | Ala | Ser | Asn |  |
| 225 |  |  |  |  | 230 |  |  |  |  | 235 |  |  |  |  | 240 |  |
| AAG | ACC | TCC | TTT | GAG | CTG | GAA | CTG | CCA | GTG | AAA | TAC | GCT | GTC | TAC | ATG | 768 |
| Lys | Thr | Ser | Phe | Glu | Leu | Glu | Leu | Pro | Val | Lys | Tyr | Ala | Val | Tyr | Met |  |
|  |  |  |  | 245 |  |  |  |  | 250 |  |  |  |  | 255 |  |  |
| ATG | ATC | ACA | AGG | CAC | GAA | GGC | TCC | ACC | AGG | TTC | TTC | AAC | TTT | TCC | ACT | 816 |
| Met | Ile | Thr | Arg | His | Glu | Gly | Ser | Thr | Arg | Phe | Phe | Asn | Phe | Ser | Thr |  |
|  |  |  | 260 |  |  |  |  | 265 |  |  |  |  | 270 |  |  |  |
| TCC | GCT | GAG | AAG | AGC | AGC | AAA | GAG | GCC | GAG | CAC | CGC | TAT | CGG | GTG | AAC | 864 |
| Ser | Ala | Glu | Lys | Ser | Ser | Lys | Glu | Ala | Glu | His | Arg | Tyr | Arg | Val | Asn |  |
|  |  | 275 |  |  |  |  | 280 |  |  |  |  | 285 |  |  |  |  |
| AAC | CTG | AGT | CTG | CGA | GAT | GTG | GCC | GTC | AGC | GTG | GAC | TTC | TGG | GCC | CCC | 912 |
| Asn | Leu | Ser | Leu | Arg | Asp | Val | Ala | Val | Ser | Val | Asp | Phe | Trp | Ala | Pro |  |
| 290 |  |  |  |  | 295 |  |  |  |  | 300 |  |  |  |  |  |  |
| GTG | CAG | CTG | AAC | GGA | GCA | GCT | GTG | TGG | GAC | GTG | GCG | GTG | GAG | GCC | CCT | 960 |
| Val | Gln | Leu | Asn | Gly | Ala | Ala | Val | Trp | Asp | Val | Ala | Val | Glu | Ala | Pro |  |
| 305 |  |  |  |  | 310 |  |  |  |  | 315 |  |  |  |  | 320 |  |
| GCC | CAG | AGC | CTG | CCC | TGT | GCG | CGG | GAG | AGG | GAA | CCT | CCG | AGG | ACC | TCT | 1008 |
| Ala | Gln | Ser | Leu | Pro | Cys | Ala | Arg | Glu | Arg | Glu | Pro | Pro | Arg | Thr | Ser |  |
|  |  |  |  | 325 |  |  |  |  | 330 |  |  |  |  | 335 |  |  |
| GAC | CTG | AGC | CGG | GTC | CCG | GGG | AGT | CCC | GTG | CTG | GAC | TGC | AGC | GTT | GCG | 1056 |
| Asp | Leu | Ser | Arg | Val | Pro | Gly | Ser | Pro | Val | Leu | Asp | Cys | Ser | Val | Ala |  |
|  |  |  | 340 |  |  |  |  | 345 |  |  |  |  | 350 |  |  |  |
| CAC | TGC | CTG | AGG | TTC | CGC | TGC | CAC | ATC | CCC | TCC | TTC | AGC | GCC | AAG | GAG | 1104 |
| His | Cys | Leu | Arg | Phe | Arg | Cys | His | Ile | Pro | Ser | Phe | Ser | Ala | Lys | Glu |  |
|  |  | 355 |  |  |  |  | 360 |  |  |  |  | 365 |  |  |  |  |
| GAG | CTC | CAC | TTC | ACC | CTG | AAG | GGC | AAC | CTC | AGC | TTC | GCC | TGG | GTC | AGC | 1152 |
| Glu | Leu | His | Phe | Thr | Leu | Lys | Gly | Asn | Leu | Ser | Phe | Ala | Trp | Val | Ser |  |

|  |  |  |  |  |  |  |  |  |  |  |  |  |  |  |  |  |
|---|---|---|---|---|---|---|---|---|---|---|---|---|---|---|---|---|
|  |  | 370 |  |  |  | 375 |  |  |  |  | 380 |  |  |  |  |  |
| CAG | ATG | CTG | CAA | AAG | AAG | GTG | TCG | GTG | GTG | AGT | GTG | GCC | GAG | ATC | ACC | 1200 |
| Gln | Met | Leu | Gln | Lys | Lys | Val | Ser | Val | Val | Ser | Val | Ala | Glu | Ile | Thr |  |
| 385 |  |  |  | 390 |  |  |  |  | 395 |  |  |  |  |  | 400 |  |
| TTC | AAC | AGG | GCC | GTG | TAC | TCC | CAA | GTT | CCG | GGC | GAG | GAG | CCC | TTT | ATG | 1248 |
| Phe | Asn | Arg | Ala | Val | Tyr | Ser | Gln | Val | Pro | Gly | Glu | Glu | Pro | Phe | Met |  |
|  |  |  |  | 405 |  |  |  |  | 410 |  |  |  |  | 415 |  |  |
| AGA | GCC | CAG | GTG | GAG | ACG | GTG | CTG | GAG | GAG | TAT | GAG | GAG | CAC | GAC | CCC | 1296 |
| Arg | Ala | Gln | Val | Glu | Thr | Val | Leu | Glu | Glu | Tyr | Glu | Glu | His | Asp | Pro |  |
|  |  |  | 420 |  |  |  |  | 425 |  |  |  |  | 430 |  |  |  |
| GTC | CCC | CTG | GTG | GTG | GGC | AGC | TGT | GTG | GGC | GGC | CTG | CTG | CTG | CTG | GCT | 1344 |
| Val | Pro | Leu | Val | Val | Gly | Ser | Cys | Val | Gly | Gly | Leu | Leu | Leu | Leu | Ala |  |
|  |  | 435 |  |  |  |  | 440 |  |  |  |  | 445 |  |  |  |  |
| CTC | ATC | TCA | GCC | ACC | CTG | TAC | AAG | CTT | GGC | TTC | TTC | AAG | CGC | CGG | TAC | 1392 |
| Leu | Ile | Ser | Ala | Thr | Leu | Tyr | Lys | Leu | Gly | Phe | Phe | Lys | Arg | Arg | Tyr |  |
| 450 |  |  |  |  | 455 |  |  |  |  | 460 |  |  |  |  |  |  |
| AAG | GAG | ATG | CTG | GGC | GAG | AAA | CCG | GGA | GAC | GCG | GCC | ACC | TTC | CCC | GGG | 1440 |
| Lys | Glu | Met | Leu | Gly | Glu | Lys | Pro | Gly | Asp | Ala | Ala | Thr | Phe | Pro | Gly |  |
| 465 |  |  |  |  | 470 |  |  |  |  | 475 |  |  |  |  | 480 |  |
| GAG | GAC | GCC | AGC | TGC | GGG | GCT | TCA | GAT | TTG | CCT | TTG | TCC | CAG |  |  | 1482 |
| Glu | Asp | Ala | Ser | Cys | Gly | Ala | Ser | Asp | Leu | Pro | Leu | Ser | Gln |  |  |  |
|  |  |  |  | 485 |  |  |  |  | 490 |  |  |  |  |  |  |  |
| TG |  |  |  |  |  |  |  |  |  |  |  |  |  |  |  | 1484 |

( 2 ) INFORMATION FOR SEQ ID NO:103:

( i ) SEQUENCE CHARACTERISTICS:
        ( A ) LENGTH: 494 amino acids
        ( B ) TYPE: amino acid
        ( D ) TOPOLOGY: linear ( i i ) MOLECULE TYPE: protein ( x i ) SEQUENCE DESCRIPTION: SEQ ID NO:103:

| Asp | Val | Gln | Ser | Ser | Ile | Ser | Tyr | Asp | Leu | Ala | Leu | Asp | Pro | Gly | Arg |
|---|---|---|---|---|---|---|---|---|---|---|---|---|---|---|---|
| 1 |  |  |  | 5 |  |  |  |  | 10 |  |  |  |  | 15 |  |
| Leu | Val | Ser | Arg | Ala | Ile | Phe | Gln | Glu | Thr | Gln | Asn | Gln | Thr | Leu | Thr |
|  |  |  | 20 |  |  |  |  | 25 |  |  |  |  | 30 |  |  |
| Arg | Arg | Lys | Thr | Leu | Gly | Leu | Gly | Arg | His | Cys | Glu | Thr | Met | Arg | Leu |
|  |  |  | 35 |  |  |  |  | 40 |  |  |  |  | 45 |  |  |
| Leu | Leu | Pro | Asp | Cys | Val | Glu | Asp | Val | Val | Asn | Pro | Ile | Val | Leu | His |
|  |  | 50 |  |  |  |  | 55 |  |  |  |  | 60 |  |  |  |
| Leu | Asn | Phe | Ser | Leu | Glu | Gly | Gln | Pro | Ile | Leu | Ser | Ser | Gln | Asn | Leu |
| 65 |  |  |  |  | 70 |  |  |  |  | 75 |  |  |  |  | 80 |
| Arg | Pro | Val | Leu | Ala | Thr | Gly | Ser | Gln | Asp | His | Phe | Ile | Ala | Ser | Leu |
|  |  |  |  | 85 |  |  |  |  | 90 |  |  |  |  | 95 |  |
| Pro | Phe | Glu | Lys | Asn | Cys | Gly | Gln | Asp | Arg | Leu | Cys | Glu | Gly | Asp | Leu |
|  |  |  | 100 |  |  |  |  | 105 |  |  |  |  | 110 |  |  |
| Ser | Ile | Ser | Phe | Asn | Phe | Ser | Gly | Leu | Asn | Thr | Leu | Leu | Val | Gly | Leu |
|  |  | 115 |  |  |  |  | 120 |  |  |  |  | 125 |  |  |  |
| Ser | Leu | Glu | Leu | Thr | Val | Thr | Val | Thr | Val | Arg | Asn | Glu | Gly | Glu | Asp |
|  | 130 |  |  |  |  | 135 |  |  |  |  | 140 |  |  |  |  |
| Ser | Tyr | Gly | Thr | Ala | Ile | Thr | Leu | Tyr | Tyr | Pro | Ala | Gly | Leu | Ser | Tyr |
| 145 |  |  |  |  | 150 |  |  |  |  | 155 |  |  |  |  | 160 |
| Arg | Arg | Val | Ser | Gly | Gln | Thr | Gln | Pro | Trp | Gln | Arg | Pro | Leu | His | Leu |
|  |  |  |  | 165 |  |  |  |  | 170 |  |  |  |  | 175 |  |
| Ala | Cys | Glu | Ala | Val | Pro | Thr | Glu | Ser | Glu | Gly | Leu | Arg | Ser | Thr | Ser |
|  |  |  | 180 |  |  |  |  | 185 |  |  |  |  | 190 |  |  |

-continued

```
Cys Ser Val Asn His Pro Ile Phe Gln Gly Gly Ala Gln Gly Thr Phe
        195             200                     205

Val Val Lys Phe Asp Val Ser Ser Lys Ala Ser Leu Gly Asp Arg Leu
    210             215                 220

Leu Met Gly Ala Ser Ala Ser Ser Glu Asn Asn Lys Pro Ala Ser Asn
225             230                 235                     240

Lys Thr Ser Phe Glu Leu Glu Leu Pro Val Lys Tyr Ala Val Tyr Met
                245                 250                 255

Met Ile Thr Arg His Glu Gly Ser Thr Arg Phe Phe Asn Phe Ser Thr
            260             265                     270

Ser Ala Glu Lys Ser Ser Lys Glu Ala Glu His Arg Tyr Arg Val Asn
        275             280                 285

Asn Leu Ser Leu Arg Asp Val Ala Val Ser Val Asp Phe Trp Ala Pro
    290             295                 300

Val Gln Leu Asn Gly Ala Ala Val Trp Asp Val Ala Val Glu Ala Pro
305             310                 315                     320

Ala Gln Ser Leu Pro Cys Ala Arg Glu Arg Glu Pro Pro Arg Thr Ser
            325                 330                 335

Asp Leu Ser Arg Val Pro Gly Ser Pro Val Leu Asp Cys Ser Val Ala
            340                 345                 350

His Cys Leu Arg Phe Arg Cys His Ile Pro Ser Phe Ser Ala Lys Glu
        355                 360                 365

Glu Leu His Phe Thr Leu Lys Gly Asn Leu Ser Phe Ala Trp Val Ser
    370             375                 380

Gln Met Leu Gln Lys Lys Val Ser Val Val Ser Val Ala Glu Ile Thr
385             390                 395                     400

Phe Asn Arg Ala Val Tyr Ser Gln Val Pro Gly Glu Glu Pro Phe Met
            405                 410                     415

Arg Ala Gln Val Glu Thr Val Leu Glu Glu Tyr Glu Glu His Asp Pro
        420                 425             430

Val Pro Leu Val Val Gly Ser Cys Val Gly Gly Leu Leu Leu Leu Ala
        435             440                 445

Leu Ile Ser Ala Thr Leu Tyr Lys Leu Gly Phe Phe Lys Arg Arg Tyr
    450             455                 460

Lys Glu Met Leu Gly Glu Lys Pro Gly Asp Ala Ala Thr Phe Pro Gly
465             470                 475                     480

Glu Asp Ala Ser Cys Gly Ala Ser Asp Leu Pro Leu Ser Gln
            485                 490
```